(12) United States Patent
Baynes et al.

(10) Patent No.: US 9,238,845 B2
(45) Date of Patent: *Jan. 19, 2016

(54) METHODS OF PRODUCING SUGARS FROM BIOMASS FEEDSTOCKS

(71) Applicant: Midori USA, Inc., Cambridge, MA (US)

(72) Inventors: Brian M. Baynes, Winchester, MA (US); John M. Geremia, Watertown, MA (US); Joseph Andoh, Nashua, NH (US); Ashish Dhawan, Naperville, IL (US)

(73) Assignee: Midori USA, Inc., Cambridge, MA (US)

( * ) Notice: Subject to any disclaimer, the term of this patent is extended or adjusted under 35 U.S.C. 154(b) by 49 days.

This patent is subject to a terminal disclaimer.

(21) Appl. No.: 13/831,495

(22) Filed: Mar. 14, 2013

(65) Prior Publication Data

US 2014/0060522 A1 Mar. 6, 2014

Related U.S. Application Data

(60) Provisional application No. 61/693,210, filed on Aug. 24, 2012.

(51) Int. Cl.
| | | |
|---|---|---|
| *C08B 15/00* | (2006.01) | |
| *C13K 1/02* | (2006.01) | |
| *C13K 13/00* | (2006.01) | |
| *C12P 7/10* | (2006.01) | |

(52) U.S. Cl.
CPC ............... *C13K 13/007* (2013.01); *C13K 1/02* (2013.01); *C13K 13/002* (2013.01); *C12P 7/10* (2013.01); *C12P 2203/00* (2013.01)

(58) Field of Classification Search
None
See application file for complete search history.

(56) References Cited

U.S. PATENT DOCUMENTS

| | | | |
|---|---|---|---|
| 2,764,563 | A | 9/1956 | McMaster et al. |
| 2,841,574 | A | 7/1958 | Foster |
| 3,681,021 | A | 8/1972 | Mikovsky et al. |
| 3,691,222 | A | 9/1972 | Wendel |
| 3,954,883 | A | 5/1976 | Haag et al. |
| 4,117,016 | A | 9/1978 | Hughes |
| 4,171,418 | A | 10/1979 | Barua et al. |
| 4,179,402 | A | 12/1979 | Kim et al. |
| 4,266,085 | A | 5/1981 | Kim et al. |
| 4,284,835 | A | 8/1981 | Kim et al. |

(Continued)

FOREIGN PATENT DOCUMENTS

| | | |
|---|---|---|
| AU | 737428 B2 | 8/2001 |
| AU | 2010250802 A1 | 12/2011 |

(Continued)

OTHER PUBLICATIONS

Figueiredo et al., "Characterization of Active Sites on Carbon Catalysts", Industrial & Engineering Chemistry Research, vol. 46, No. 2, 2007, pp. 4110-4115.

(Continued)

*Primary Examiner* — Melvin C Mayes
*Assistant Examiner* — Douglas Call
(74) *Attorney, Agent, or Firm* — Morrison & Foerster LLP

(57) ABSTRACT

Provided herein are catalysts useful in non-enzymatic saccharification processes. The catalysts can be polymeric catalysts or solid-supported catalysts with acidic and ionic moieties. Provided are also methods for hydrolyzing cellulosic materials into monosaccharides and/or oligosaccharides using the catalysts described herein.

18 Claims, 8 Drawing Sheets

(56) References Cited

U.S. PATENT DOCUMENTS

| | | | |
|---|---|---|---|
| 4,306,085 A | 12/1981 | Kim et al. | |
| 4,317,936 A | 3/1982 | Kim et al. | |
| 4,460,680 A | 7/1984 | Ogawa et al. | |
| 4,533,708 A | 8/1985 | Costello | |
| 4,623,522 A | 11/1986 | Rickelton | |
| 4,640,945 A | 2/1987 | Peiffer et al. | |
| 4,677,137 A | 6/1987 | Bany et al. | |
| 4,717,785 A | 1/1988 | Paxson | |
| 4,804,786 A | 2/1989 | Fischer et al. | |
| 4,835,237 A | 5/1989 | Burkhardt et al. | |
| 4,892,955 A | 1/1990 | Wada et al. | |
| 4,933,405 A | 6/1990 | Evani | |
| 5,093,297 A | 3/1992 | Woo et al. | |
| 5,214,182 A | 5/1993 | Knifton | |
| 5,342,892 A | 8/1994 | Vanderbilt et al. | |
| 6,261,757 B1 | 7/2001 | Irving et al. | |
| 6,280,913 B1 | 8/2001 | Irving et al. | |
| 6,316,173 B1 | 11/2001 | Irving et al. | |
| 6,379,876 B1 | 4/2002 | Irving et al. | |
| 7,491,672 B2 | 2/2009 | Carnahan et al. | |
| 8,013,130 B2 | 9/2011 | Yanagawa et al. | |
| 8,017,724 B2 | 9/2011 | Yanagawa et al. | |
| 8,466,242 B2 | 6/2013 | Geremia et al. | |
| 8,476,388 B2* | 7/2013 | Geremia et al. | 526/274 |
| 2002/0022676 A1 | 2/2002 | He et al. | |
| 2002/0164730 A1 | 11/2002 | Ballesteros Perdices et al. | |
| 2004/0089961 A1 | 5/2004 | Wulff et al. | |
| 2006/0247474 A1 | 11/2006 | Tsuda et al. | |
| 2007/0159069 A1 | 7/2007 | Tsuda et al. | |
| 2007/0197801 A1 | 8/2007 | Bolk et al. | |
| 2007/0232783 A1 | 10/2007 | Moad et al. | |
| 2007/0244024 A1 | 10/2007 | Barthel et al. | |
| 2008/0154051 A1 | 6/2008 | Bolk et al. | |
| 2008/0261006 A1 | 10/2008 | McCarty et al. | |
| 2009/0166295 A1 | 7/2009 | Chen et al. | |
| 2009/0197791 A1 | 8/2009 | Balastre et al. | |
| 2009/0263699 A1 | 10/2009 | Sadasue et al. | |
| 2010/0137548 A1 | 6/2010 | Moad et al. | |
| 2010/0211158 A1 | 8/2010 | Haverty et al. | |
| 2010/0261239 A1 | 10/2010 | Soucaille et al. | |
| 2010/0279361 A1 | 11/2010 | South et al. | |
| 2010/0285534 A1 | 11/2010 | South et al. | |
| 2010/0297721 A1 | 11/2010 | Hogsett et al. | |
| 2010/0304454 A1 | 12/2010 | De Bont | |
| 2011/0015387 A1 | 1/2011 | Schuth et al. | |
| 2011/0059485 A1 | 3/2011 | Caiazza et al. | |
| 2011/0171709 A1 | 7/2011 | Bardsley | |
| 2011/0178258 A1 | 7/2011 | El Kadib et al. | |
| 2011/0207189 A1 | 8/2011 | Burgard et al. | |
| 2011/0262669 A1 | 10/2011 | Kriegel et al. | |
| 2011/0269204 A1 | 11/2011 | Burk et al. | |
| 2011/0281362 A1 | 11/2011 | Olson | |
| 2011/0312049 A1 | 12/2011 | Osterhout et al. | |
| 2011/0312054 A1 | 12/2011 | Brevnova et al. | |
| 2012/0003701 A1 | 1/2012 | Brevnova et al. | |
| 2012/0040409 A1 | 2/2012 | Hau et al. | |
| 2012/0186446 A1 | 7/2012 | Bara et al. | |
| 2012/0220740 A1 | 8/2012 | Geremia et al. | |
| 2012/0252957 A1 | 10/2012 | Geremia et al. | |
| 2013/0178617 A1* | 7/2013 | Raines et al. | 536/124 |
| 2013/0233308 A1 | 9/2013 | Geremia et al. | |

FOREIGN PATENT DOCUMENTS

| | | |
|---|---|---|
| CA | 867405 A | 3/1971 |
| CA | 874429 A | 6/1971 |
| CA | 874430 A | 6/1971 |
| CA | 1198475 A | 12/1985 |
| CA | 1285219 C | 6/1991 |
| CA | 2251700 A1 | 11/1997 |
| CA | 2209066 A1 | 2/1998 |
| CA | 2310274 A1 | 6/1999 |
| CA | 2572026 A1 | 6/2007 |
| CA | 2186860 C | 3/2008 |
| CA | 2702737 A1 | 4/2009 |
| DE | 2501032 A1 | 4/1976 |
| DE | 2719606 A1 | 11/1978 |
| EP | 0002557 A2 | 6/1979 |
| EP | 283817 A2 | 9/1988 |
| EP | 0824111 A1 | 2/1998 |
| EP | 0757586 B1 | 6/2004 |
| FR | 2147330 A1 | 3/1973 |
| FR | 2752238 B1 | 9/1998 |
| GB | 950501 A | 2/1964 |
| GB | 1236615 A | 6/1971 |
| GB | 1236616 A | 6/1971 |
| JP | 49-3917 B | 1/1974 |
| JP | 62-187424 A | 8/1987 |
| JP | 64-25771 A | 1/1989 |
| JP | 3-86704 A | 4/1991 |
| JP | 10-197831 A | 7/1998 |
| JP | 10-253931 A | 9/1998 |
| JP | 2000-95789 A | 4/2000 |
| JP | 2006-45149 A | 2/2006 |
| JP | 2009-163914 A | 7/2009 |
| WO | 95/29005 A1 | 11/1995 |
| WO | 97/42230 A1 | 11/1997 |
| WO | 00/07966 A1 | 2/2000 |
| WO | 00/39055 A1 | 7/2000 |
| WO | 2005/047233 A1 | 5/2005 |
| WO | 2006/011899 A1 | 2/2006 |
| WO | 2006/011900 A2 | 2/2006 |
| WO | 2006/032282 A1 | 3/2006 |
| WO | 2006/110891 A2 | 10/2006 |
| WO | 2006/110901 A2 | 10/2006 |
| WO | 2007027832 A2 | 3/2007 |
| WO | 2009/050251 A2 | 4/2009 |
| WO | 2010/110998 A1 | 9/2010 |
| WO | 2010/134027 A1 | 11/2010 |
| WO | 2011029166 A1 | 3/2011 |
| WO | 2012011962 A2 | 1/2012 |
| WO | 2014/032004 A1 | 2/2014 |

OTHER PUBLICATIONS

Gao et al., "Chemical Structure and Catalytic Activity of Quaternary Onium Salt-Type Triphase Catalysts Based on CPS Microspheres", Journal of Applied Polymer Science, vol. 123, 2012, pp. 824-832.

Gelbard, Georges, "Organic Synthesis by Catalysis with Ion-Exchange Resins", Industrial & Engineering Chemistry Research, vol. 44, 2005, pp. 8468-8498.

Greene et al., "Purification and Characterization of an Extracellular Endoglucanase from the Marine Shipworm Bacterium", Archives of Biochemistry and Biophysics, vol. 267, No. 1, Nov. 15, 1988, pp. 334-341.

Itsuno et al., "Main-Chain Ionic Chiral Polymers: Synthesis of Optically Active Quaternary Ammonium Sulfonate Polymers and Their Application in Asymmetric Catalysis", Journal of the American Chemical Society, vol. 132, 2010, pp. 2864-2865.

Gusakov et al., "Enhancement of Enzymatic Cellulose Hydrolysis Using a Novel Type of Bioreactor with Intensive Stirring Induced by Electromagnetic Field", Applied Biochemistry and Biotechnology, vol. 56, 1996, pp. 141-153.

Gusakov et al., "Kinetics of the Enzymatic Hydrolysis of Cellulose: 1. A Mathematical Model for a Batch Reactor Process", Enz. Microb. Technol., vol. 7, Jul. 1985, pp. 346-352.

Harmer et al., "Solid Acid Catalysis using Ion-Exchange Resins", Applied Catalysis A: General, vol. 221, 2001, pp. 45-62.

Hayes, Daniel J., "An Examination of Biorefining Processes, Catalysts and Challenges", Catalysis Today, vol. 145, 2009, pp. 138-151.

Binglin et al., "Studies on the Preparation and Hydrogenation Properties of Polymer Supported Colloidal Palladium Catalysts", Chemical Journal of Chinese Universities, vol. 11, No. 5, 1990, pp. 521-525. (English Abstract Submitted).

Hershberger et al., "Polymer-Supported Palladacycles: Efficient Reagents for Synthesis of Benzopyrans with Palladium Recovery. Relationship among Resin Loading, Pd:P Ratio, and Reactivity of Immobilized Palladacycles", The Journal of Organic Chemistry, vol. 71, No. 1, 2006, pp. 231-235.

(56) References Cited

OTHER PUBLICATIONS

He et al., "Preparation and Hydrogenation Properties of Polymer-Supported Colloidal Palladium Catalysts", Gaodeng Xuexiao Huaxue Xuebao, vol. 11, No. 5, 1990, pp. 521-525.
Mortlock, "The Evolution of Metabolic Function", Library of Congress Card No. 91-10575, 1992, pp. 1-6.
International Search Report and Written Opinion received for PCT Patent Application No. PCT/US2013/037862, mailed on Nov. 8, 2013, 29 pages.
Invitation to pay additional fees received for PCT Patent Application No. PCT/US2013/037862, mailed on Sep. 12, 2013, 2 pages.
Suganuma et al., "Hydrolysis of Cellulose by Amorphous Carbon Bearing SO3H, COOH, and OH Groups", Journal of the American Chemical Society, vol. 130, No. 38, 2008, pp. 12787-12793.
Sun et al., "An Extremely Active Solid Acid Catalyst, Nafion Resin/Silica Composite, for the Friedel-Crafts Benzylation of Benzene and p-Xylene with Benzyl Alcohol", Industrial & Engineering Chemistry Research, vol. 36, 1997, pp. 5541-5544.
Tanabe et al., "Industrial Application of Solid Acid-Base Catalysts", Applied Catalystsis, A: General, vol. 181, 1999, pp. 399-434.
Tang et al., "Heterogenization of Homogeneous Catalysts—The Immobilization of Transition Metal Complexes on Ion-Exchange Resins", Journal of Molecular Catalysis, vol. 9, 1980, pp. 313-321.
Templeton et al., "Determination of Acid-Insoluble Lignin in Biomass", NREL Laboratory Analytical Procedure, LAP-03, Jan. 30, 1995, 14 pages.
Toda et al., "Biodiesel made with Sugar Catalyst", Nature, vol. 438, Nov. 10, 2005, 1 page.
Valceanu et al., "Synthesis of a Triphenylphosphonium Salt Grafted on Gel-type Styrene-Divinylbenzene Copolymers", Revistade Chimie (Bucharest, Romania), vol. 45, No. 7, 1994, pp. 560-566.
Wang, Shaobin, "Application of Solid Ash Based Catalysts in Heterogeneous Catalysis", Environmental Science & Technology, vol. 42, 2008, pp. 7055-7063.
Wu et al., "Monobromination of Activated Aromatic Compounds with Polyvinylbenzyltriphenylphosphonium Supported Tribromide", Chinese Journal of Chemistry, vol. 19, No. 2, 2001, pp. 173-176.
Yamaguchi et al., "Hydrolysis of Cellulose by a Solid Acid Catalyst under Optimal Reaction Conditions", The Journal of Physical Chemistry C, vol. 113, 2009, pp. 3181-3188.
Il'Inskii et al., "Study of Kinetics of Phosphination of Chloromethylated Macroporous Copolymers of Styrene and Divinyl Benzene", Vysokomolekulyamye Soedineniya, Seriya A, vol. 26, No. 5, 1984, pp. 1033-1038. (English Abstract Submitted).
Zhang et al., "Determination of the Number-Average Degree of Polymerization of Cellodextrins and Cellulose with Application to Enzymatic Hydrolysis", Biomacromolecules, vol. 6, 2005, pp. 1510-1515.
Zhang et al., "Solid Acid and Microwave-Assisted Hydrolysis of Cellulose in Ionic Liquid", Carbohydrate Research, vol. 344, 2009, pp. 2069-2072.
Huang et al., "Template Imprinting Amphoteric Polymer for the Recognition of Proteins", Journal of Applied Polymer Science, vol. 95, 2005, pp. 358-361.
Zheng et al., "Study of Supported Liquid Phase Catalyst. I. Hydroformylation of Propylene to Butyl Aldehyde", Journal of Molecular Catalysis, vol. 1, No. 4, Dec. 1987, pp. 243-245. (English Abstract Submitted).
Stone et al., "Microwave-Assisted Solventless Single and Double Addition of HP (O)Ph2 to Alkynes", Journal of Molecular Catalysis A: Chemical, vol. 226, 2005, pp. 11-21.
Still et al., "Rapid Chromatographic Technique for Preparative Separations with Moderate Resolution", The Journal of Organic Chemistry, vol. 43, No. 14, 1978, pp. 2923-2925.
Stach et al., "Bewertung Von Ionen-Austauschen Unter Bes. Berücksichtigung Ihrer Austauschgeschwindigkeiten", Angewandte Chemie, vol. 63, No. 11, 1951, pp. 263-267.
Sheldon, Roger A., "Green Solvents for Sustainable Organic Synthesis: State of the Art", Green Chem, vol. 7, 2005, pp. 267-278.

Sheehan et al., "Enzymes, Energy, and the Environment: A Strategic Perspective on the U.S. Department of Energy's Research and Development Activities for Bioethanol", Biotechnology Progress, vol. 15, 1999, pp. 817-827.
Shaabani et al., "Cellulose Sulfuric Acid as a Bio-Supported and Recyclable Solid Acid Catalyst for the One-Pot Three-Component Synthesis of α-amino Nitriles", Applied Catalysis A: General, vol. 331, 2007, pp. 149-151.
Selke et al., "Asymmetric Hydrogenation by Heterogenized Cationic Rhodium Phosphinite Complexes", Journal of Molecular Catalysis, vol. 56, 1989, pp. 315-328.
Ryu et al., "Bioconversion of Waste Cellulose by Using an Attrition Bioreactor", Biotechnology and Bioengineering, vol. 25, 1983, pp. 53-65.
Ruiz et al., "Determination of Carbohydrates in Biomass by High Performance Liquid Chromatography", NREL Laboratory Analytical Procedure LAP-002, Aug. 12, 1996, 12 pages.
Ro et al., "Catalytic Properties of RhCl3 • 31-12O Immobilized on the Modified Poly(Styrene-Divinylbenzene) Copolymer in Aqueous Phase Hydroformylation of Propylene", Journal of Catalysis, vol. 145, Feb. 1994, pp. 327-334.
Ro et al., "Aqueous Phase Hydroformylation of Propene Catalyzed over Rhodium Complexes Immobilized on the Poly(Styrene-Divinylbenzene) Copolymer Containing—CH2P(C6H4SO3H)2 Groups", Applied Catalysis, vol. 69, No. 2, 1991, pp. 169-175.
Rinaldi et al., "Depolymerization of Cellulose Using Solid Catalysts in Ionic Liquids", Angewandte Chemie International Edition, vol. 47, 2008, pp. 8047-8050.
Rinaldi et al., "Acid Hydrolysis of Cellulose as the Entry Point into Biorefinery Schemes", ChemSusChem, vol. 2, 2009, pp. 1096-1107.
Renaud et al., "31P Spin Lattice Relaxation time Measurements of the Amphiphilic Ligands [Ph2P(CH2)nPMe3]+ in Solution and Tethered to a Solid Cationic Exchange Resin via the Tetra-Alkylphosphonium Groups", Journal of Molecular Catalysis, vol. 80, 1993, pp. 43-48.
Reddy et al., "Sulfated Zirconia as an Efficient Catalyst for Organic Synthesis and Transformation Reactions", Journal of Molecular Catalysis A: Chemical, vol. 237, 2005, pp. 93-100.
Reddy et al., "Polymer-Anchored Palladium Catalyst in Carbonylation of Organic Halides—The First Example of Triphase Catalysis", Indian Journal of Chemistry, vol. 28B, Feb., 1989, pp. 105-106.
Purdy et al., "Synthesis, Crystal Structure, and Reactivity of Alkali and Silver Salts of Sulfonated Imidazoles", Polyhedron, vol. 26, 2007, pp. 3930-3938.
Popa et al., "Study of Quaternary 'Onium' Salts Grafted on Polymers: Antibacterial Activity of Quaternary Phosphonium Salts Grafted on 'Gel-Type' Styrene-Divinylbenzene Copolymers", Reactive and Functional Polymers, vol. 55, 2003, pp. 151-158.
International Search Report and Written Opinion received for PCT Patent Application No. PCT/US2013/056389, mailed on Nov. 12, 2013, 13 pages.
International Search Report and Written Opinion received for PCT Patent Application No. PCT/US2012/026820, mailed on Jun. 19, 2012, 16 pages.
International Preliminary Report on Patentability received for PCT Patent Application No. PCT/US2012/026820, mailed on Sep. 12, 2013, 11 pages.
Onda et al., "Selective Hydrolysis of Cellulose into Glucose over Solid Acid Catalysts", Green Chemistry, vol. 10, 2008, pp. 1033-1037.
Onda et al., "Hydrolysis of Cellulose Selectively into Glucose Over Sulfonated Activated-Carbon Catalyst Under Hydrothermal Conditions", Top Catal, vol. 52, 2009, pp. 801-807.
Okuhara, Toshio, "Water-Tolerant Solid Acid Catalysts", Chemical Reviews, vol. 102, 2002, pp. 3641-3666.
Ngaosuwan et al., "Hydrolysis of Triglycerides Using Solid Acid Catalysts", Industrial & Engineering Chemistry Research, vol. 48, 2009, pp. 4757-4767.
Moreto et al., "Hydrogenation of Olefins using a Wilkinson Catalyst Bound to an Organic Polymer", Anales de Quimica, vol. 70, No. 7-8, 1974, pp. 638-641.

(56) References Cited

OTHER PUBLICATIONS

Mohandasa et al., "Introduction of Bifunctionality into the Phosphinic Acid Ion-Exchange Resin for Enhancing Metal ion Complexation", Desalination, vol. 232, 2008, pp. 3-10.
McCarty et al., "Ionic Electrets: Electrostatic Charging of Surfaces by Transferring Mobile Ions upon Contact", Journal of the American Chemical Society, vol. 129, No. 13, 2007, pp. 4075-4088.
Hojabri, Fereidun, "Effect of Phosphine Ligand on the Activity of Palladium / II-Catalysts", Polymer, vol. 17, Jan. 1976, pp. 58-60.
Lynd et al., "Microbial Cellulose Utilization: Fundamentals and Biotechnology", Microbiol Mol. Biol. Rev., vol. 66, No. 3, 2002, pp. 506-577.
Lotero et al., "Synthesis of Biodiesel via Acid Catalysis", Industrial & Engineering Chemistry Research, vol. 44, 2005, pp. 5353-5363.
Lavarack et al., "Measured Kinetics of the Acid-Catalysed Hydrolysis of Sugar Cane Bagasse to Produce Xylose", Catalysis Today, vol. 63, 2000, pp. 257-265.
Kuznetsov et al., "New Catalytic Processes for a Sustainable Chemistry of Cellulose Production from Wood Biomass", Catalysis Today, vol. 75, 2002, pp. 211-217.
Kalck et al., "Dinuclear Rhodium Complexes Immobilized on Functionalized Diphenylphosphino-(Styrene-Divinylbenzene) Resins Giving High Selectivities for Linear Aldehydes in Hydroformylation Reactions", Journal of Organometallic Chemistry, vol. 433, 1992, pp. C4-C8.
Jayaswal et al., "Effect of Chemical Modifications upon Exchange Capacity of Aminated Macroporous Styrene-Divinyl Benzene (PS-DVB) Copolymer Anion Exchange Resin", Journal of Applied Polymer Science, vol. 79, 2001, pp. 1735-1748.
Alizadeh et al., "Pretreatment of Switchgrass by Ammonia Fiber Explosion (AFEX)", Applied Biochemistry and Biotechnology, vol. 121-124, 2005, pp. 1133-1141.
Ballesteros et al., "Ethanol Production From Steam-Explosion Pretreated Wheat Straw", Applied Biochemistry and Biotechnology, vol. 129-132, 2006, pp. 496-508.
Chandra et al., "Substrate Pretreatment: The Key to Effective Enzymatic Hydrolysis of Lignocellulosics?", Advances in Biochemical Engineering/Biotechnology, vol. 108, 2007, pp. 67-93.
Chundawat et al., "Effect of Particle Size Based Separation of Milled Corn Stover on Afex Pretreatment and Enzymatic Digestibility", Biotechnology and Bioengineering, vol. 96, No. 2, Feb. 1, 2007, pp. 219-231.
Duff et al., "Bioconversion of Forest Products Industry Waste Cellulosics to Fuel Ethanol: A Review", Bioresource Technology, vol. 55, 1996, pp. 1-33.
Galbe et al., "A Review of the Production of Ethanol from Softwood", Applied Microbiology and Biotechnology, vol. 59, 2002, pp. 618-628.
Galbe et al., "Pretreatment of Lignocellulosic Materials for Efficient Bioethanol Production", Advances in Biochemical Engineering/Biotechnology, vol. 108, 2007, pp. 41-65.
Ghosh et al., "Physicochemical and Biological Treatments for Enzymatic/Microbial Conversion of Lignocellulosic Biomass", Advances in Applied Microbiology, vol. 39, 1993, pp. 295-333.
Gong et al., "Ethanol Production from Renewable Resources", Advances in Biochemical Engineering/Biotechnology vol. 65, 1999, pp. 207-241.
Gollapalli et al., "Predicting Digestibility of Ammonia Fiber Explosion (AFEX)-Treated Rice Straw", Applied Biochemistry and Biotechnology, vol. 98-100, 2002, pp. 23-35.
Hendriks et al., "Pretreatments to Enhance the Digestibility of Lignocellulosic Biomass", Bioresource Technology, vol. 100, 2009, pp. 10-18.
Kurabi et al., "Enzymatic Hydrolysis of Steam-Exploded and Ethanol Organosolv-Pretreated Douglas-Fir by Novel and Commercial Fungal Cellulases", Applied Biochemistry and Biotechnology, vol. 121-124, 2005, pp. 219-230.
Lee et al., "Dilute-Acid Hydrolysis of Lignocellulosic Biomass", Advances in Biochemical Engineering/Biotechnology, vol. 65, 1999, pp. 93-115.

Martin et al., "Investigation of Cellulose Convertibility and Ethanolic Fermentation of Sugarcane Bagasse Pretreated by Wet Oxidation and Steam Explosion", Journal of Chemical Technology and Biotechnology, vol. 81, Jul. 18, 2006, pp. 1669-1677.
McMillan, James D., "Pretreatment of Lignocellulosic Biomass", Chapter 15, Enzymatic Conversion of Biomass for Fuels Production, Himmel, M. E., et al., ACS Symposium Series, vol. 566, Oct. 7, 1994, pp. 292-324.
Mosier et al., "Features of Promising Technologies for Pretreatment of Lignocellulosic Biomass", Bioresource Technology, vol. 96, 2005, pp. 673-686.
Olsson et al., "Fermentation of Lignocellulosic Hydrolysates for Ethanol Production", Enzyme and Microbial Technology, vol. 18, Apr. 1996, pp. 312-331.
Palonen et al., "Evaluation of Wet Oxidation Pretreatment for Enzymatic Hydrolysis of Softwood", Applied Biochemistry and Biotechnology, vol. 117, 2004, pp. 1-17.
Pan et al., "Bioconversion of Hybrid Poplar to Ethanol and Co-Products Using an Organosolv Fractionation Process: Optimization of Process Yields", Biotechnology and Bioengineering, vol. 94, No. 5, Aug. 5, 2006, pp. 851-861.
Pan et al., "Biorefining of Softwoods using Ethanol Organosolv Pulping: Preliminary Evaluation of Process Streams for Manufacture of Fuel-Grade Ethanol and Co-Products", Biotechnology and Bioengineering, vol. 90, No. 4, May 20, 2005, pp. 473-481.
Sassner et al., "Bioethanol Production Based on Simultaneous Saccharification and Fermentation of Steam-Pretreated Salix at High Dry-Matter Content", Enzyme and Microbial Technology, vol. 39, 2006, pp. 756-762.
Schell et al., "A Bioethanol Process Development Unit: Initial Operating Experiences and Results with a Corn Fiber Feedstock", Bioresource Technology, vol. 91, 2004, pp. 179-188.
Schell et al., "Dilute—Sulfuric Acid Pretreatment of Corn Stover in Pilot-Scale Reactor", Applied Biochemistry and Biotechnology, vol. 105-108, 2003, pp. 69-85.
Schmidt et al., "Optimization of Wet Oxidation Pretreatment of Wheat Straw", Bioresource Technology, vol. 64, 1998, pp. 139-151.
Taherzadeh et al., "Pretreatment of Lignocellulosic Wastes to Improve Ethanol and Biogas Production: A Review", International Journal of Molecular Sciences, vol. 9, Sep. 1, 2008, pp. 1621-1651.
Teymouri et al., "Optimization of the Ammonia Fiber Explosion (AFEX) Treatment Parameters for Enzymatic Hydrolysis of Corn Stover", Bioresource Technology, vol. 96, Feb. 24, 2005, pp. 2014-2018.
Vallander et al., "Production of Ethanol from Lignocellulosic Materials: State of the Art", Advances in Biochemical Engineering/Biotechnology, vol. 42, 1990, pp. 63-95.
Varga et al., "High Solid Simultaneous Saccharification and Fermentation of Wet Oxidized Corn Stover to Ethanol", Biotechnology and Bioengineering, vol. 88, No. 5, Dec. 5, 2004, pp. 567-574.
Varga et al., "Optimization of Steam Pretreatment of Corn Stover to Enhance Enzymatic Digestibility", Applied Biochemistry and Biotechnology, vol. 113-116, 2004, pp. 509-523.
Wyman et al., "Coordinated Development of Leading Biomass Pretreatment Technologies", Bioresource Technology, vol. 96, Feb. 26, 2005, pp. 1959-1966.
Yang et al., "Pretreatment: The Key to Unlocking Low-Cost Cellulosic Ethanol", Biofuels, Bioproducts and Biorefining (Biofpr), vol. 2, 2008, pp. 26-40.
Non Final Office Action received for U.S. Appl. No. 13/406,517, mailed on Oct. 12, 2012, 10 pages.
Notice of Allowance received for U.S. Appl. No. 13/406,517, mailed on Feb. 19, 2013, 9 pages.
Notice of Allowance received for U.S. Appl. No. 13/657,724, mailed on Mar. 6, 2013, 13 pages.
Akelah et al., "Preparation of Poly(vinylbenzyltriphenylphosphonium perbromide) and its Application in the Bromination of Organic Compounds", Polymer Preprints (American Chemical Society, Division of Polymer Chemistry, vol. 24, No. 2, Aug. 1983, pp. 467-468.

(56) References Cited

OTHER PUBLICATIONS

Alexandratos et al., "Bifunctionality as a Means of Enhancing Complexation Kinetics in Selective Ion Exchange Resins", Industrial & Engineering Chemistry Research, vol. 34, No. 1, 1995, pp. 251-254.

Amarasekara et al., "Synthesis of a Sulfonic Acid Functionalized Acidic Ionic Liquid Modified Silica Catalyst and Applications in the Hydrolysis of Cellulose", Catalysis Communications, vol. 11, May 26, 2010, pp. 1072-1075.

Barbaro et al., "Ion Exchange Resins: Catalyst Recovery and Recycle", Chemical Reviews, vol. 109, 2009, pp. 515-529.

Butova et al., "Phosphazo Compounds Based on a Chloromethylated Copolymer of Styrene and Divinylbenzene", Zhurnal Obshchei Khimii, vol. 46, No. 4, 1976, pp. 923-924.

Davidescu et al., "Effect of Polymer-Supported Onium Salts on the Phase Transfer and Catalytic Activity of Hydrogen Peroxide in Triphase Catalysis", Chem. Bull. "POLITHENICA" Univ. (Timisoara), vol. 42, No. 56, 1997, pp. 130-138.

Davidescu et al., "Phosphonium Salts Grafted on Gel-Type Styrene-Divinylbenzene Copolymers. Aspects Concerning the Antibacterial Activity", Chem. Bull. "POLITEHNICA" Univ. (Timisoara), vol. 41, No. 55, 1996, pp. 50-58.

Davidescu et al., "Preparation of Polymeric Quaternary Phosphonium Salts by Reaction of Chloromethylated Polymers with Tertiary Phosphines", Revista de Chimie (Bucharest, Romania), vol. 52, No. 10, 2001, pp. 553-558.

Dias et al., "Modified Versions of Sulfated Zirconia as Catalysts for the of Xylose to Furfural", Catalysis Letters, vol. 114, Nos. 3-4, Apr. 2007, pp. 151-160.

Duboc et al., "Palladium Cross-Coupling Reactions on Solid Support using a New Silylated Linker", Journal of Organometallic Chemistry, vol. 643-644, 2002, pp. 512-515.

Dubois et al., "Colorimetric Method for Determination of Sugars and Related Substances", Division of Biochemistry, Analytical Chemistry, vol. 28, No. 3, Mar. 1956, pp. 350-356.

Ehrman, Tina, "Determination of Acid-Soluble Lignin in Biomass", NREL Laboratory Analytical Procedure, LAP-004, Sep. 25, 1996, 8 pages.

Ehrman, Tina, "Standard Method for Ash in Biomass", NREL Laboratory Analytical Procedure, Lap-005, Apr. 28, 1994, 7 pages.

Evans et al., "Molecular Weight Distribution of Cellulose as its Tricarbanilate by High Performance Size Exclusion Chromatography", Journal of Applied Polymer Science, vol. 37, 1989, pp. 3291-3303.

Feng et al., "Synthesis of P/Pd Resin and Study on its Catalytic Activity for Hydrogenation", Journal of Tianjin University, vol. 29, No. 4, Jul. 1996, pp. 521-526. (English Abstract Submitted).

Fernanda et al., "Optimal Control in Fed-Batch Reactor for the Cellobiose Hydrolysis", Acta Scientiarum. Technology, vol. 25, No. 1, 2003, pp. 33-38.

International Preliminary Report on Patentability received for PCT Patent Application No. PCT/US2013/037862, mailed on Nov. 6, 2014, 24 pages.

International Preliminary Report on Patentability received for PCT Patent Application No. PCT/US2013/056389, mailed on Mar. 5, 2015, 8 pages.

International Search Report & Written Opinion received for PCT Patent Application No. PCT/US2013/056462, mailed on Nov. 12, 2013, 10 pages.

International Preliminary Report on Patentability received for PCT Patent Application No. PCT/US2013/056462 mailed on Mar. 5, 2015, 8 pages.

Search Report and Written Opinion received for Singapore Patent Application No. 2013064654, mailed on Nov. 12, 2014, 14 pages.

Notice of Allowance received for U.S. Appl. No. 13/406,490, mailed on Dec. 8, 2014, 7 pages.

Non-Final Office Action received for U.S. Appl. No. 13/865,048, mailed on Mar. 6, 2015, 7 pages.

Gu et al., "Selectivity Enhancement of Silica-Supported Sulfonic Acid Catalysts in Water by Coating of Ionic Liquid", Organic Letters, vol. 9, No. 16, 2007, pp. 3145-3148.

Margelefsky et al., "Organized Surface Functional Groups: Cooperative Catalysis via Thiol/Sulfonic Acid Pairing", Journal of the American Chemical Society, vol. 129, No. 44, 2007, pp. 13691-13697.

Overberger et al., "Esterolytic Catalyses by Copolymers Containing Imidazole and Carboxyl Functions", Macromolecules, vol. 3, No. 3, Mar. 1970, pp. 214-220.

Zeidan et al., "Multifunctional Heterogeneous Catalysts: SBA-15-Containing Primary Amines and Sulfonic Acids", Angewandte Chemie International Edition, vol. 45, 2006, pp. 6332-6335.

Zhang et al., "A Silica Gel Supported Dual Acidic Ionic Liquid: An Efficient and Recyclable Heterogeneous Catalyst for the One-Pot Synthesis of Amidoalkyl Naphthols", Green Chemistry, vol. 12, 2010, pp. 2246-2254.

International Search Report and Written Opinion received for PCT Patent Application No. PCT/US2014/024177, mailed on Jul. 10, 2014, 8 pages.

Non-Final Office Action received for U.S. Appl. No. 13/406,490, mailed on Aug. 1, 2014, 16 pages.

Notice of Allowance received for U.S. Appl. No. 13/406,490, mailed on Apr. 13, 2015, 8 pages.

Notice of Allowance received for U.S. Appl. No. 13/865,048, mailed on Jul. 31, 2015, 8 pages.

\* cited by examiner

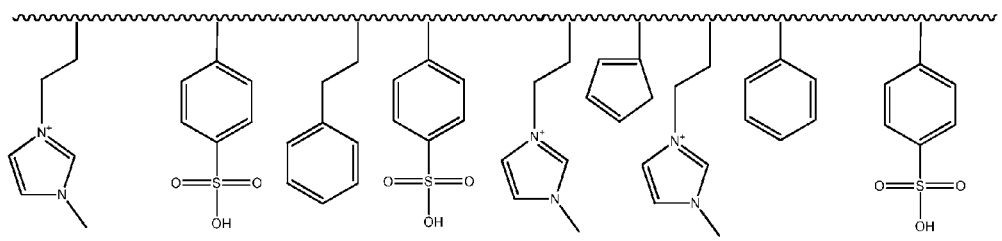
*FIG. 3A*
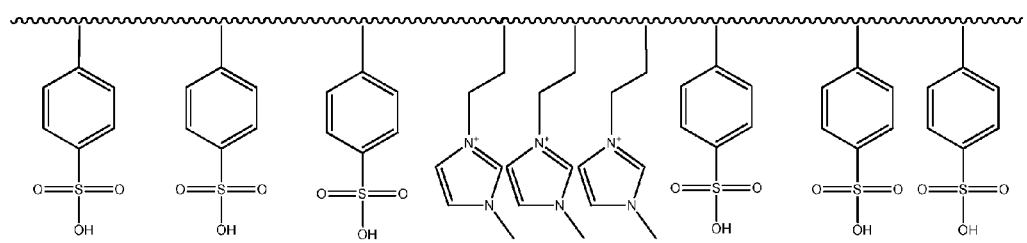
*FIG. 3B*
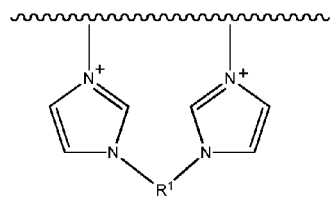 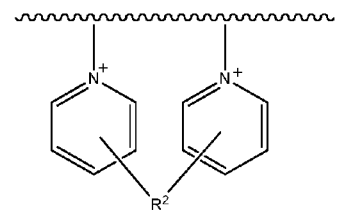
*FIG. 4A*     *FIG. 4B*

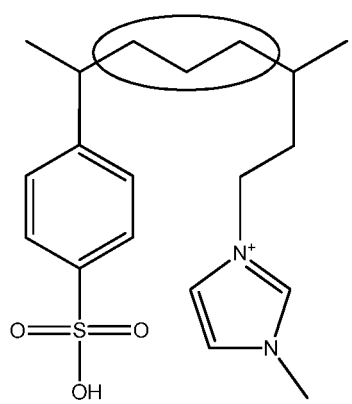 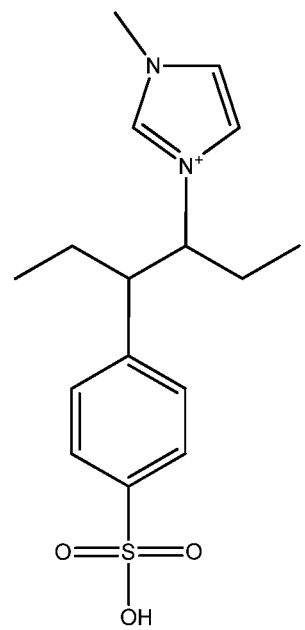
*FIG. 7A*  *FIG. 7B*

METHODS OF PRODUCING SUGARS FROM BIOMASS FEEDSTOCKS

CROSS-REFERENCE TO RELATED APPLICATIONS

This application claims the benefit of U.S. provisional patent application Ser. No. 61/693,210, filed Aug. 24, 2012, the disclosure of which is hereby incorporated by reference in its entirety.

FIELD

The present disclosure relates generally to methods of producing sugars from biomass, and more specifically to methods of producing sugars from various biomass feedstocks using catalysts, such as polymeric catalysts or solid-supported catalysts.

BACKGROUND

Saccharification of cellulosic materials, such as biomass waste products of agriculture, forestry and waste treatment are of great economic and environmental relevance. As part of biomass energy utilization, attempts have been made to obtain ethanol (bioethanol) by hydrolyzing cellulose or hemicellulose, which are major constituents of plants. The hydrolysis products, which include sugars and simple carbohydrates, can then be subjected to further biological and/or chemical conversion to produce fuels or other commodity chemicals. For example, ethanol is utilized as a fuel or mixed into a fuel such as gasoline. Major constituents of plants include, for example, cellulose (a polymer glucose, which is a six-carbon sugar), hemicellulose (a branched polymer of five- and six-carbon sugars), lignin, and starch. Current methods for liberating sugars from lignocellulosic materials, however, are inefficient on a commercial scale based on yields, as well as the water and energy used.

Work from the 1980's on the hydrolysis of β-glycosidic bonds using perfluorinated solid superacid microporous resins, such as Dupont Nafion®, attempted to develop catalytic methods for use in digesting cellulose. Batch reactors and continuous-flow fixed-bed tube reactors were used to demonstrate hydrolysis of cello-oligosaccharides to monomeric sugars; however, these processes were unable to achieve appreciable digestion of cellulose or hemicellulose, and notably, the crystalline domains of cellulose.

As such, there is an ongoing need for new methods using catalysts that can efficiently generate sugar and sugar-containing products from biomass on a commercially-viable scale.

SUMMARY

The present disclosure addresses this need by providing methods of producing one or more sugars from various biomass feedstocks using catalysts, including polymeric catalysts and solid-supported catalysts, to digest the hemicellulose and cellulose, including the crystalline domains of cellulose, in biomass. In some embodiments, the methods described herein using the catalysts can hydrolyze the cellulose and/or hemicellulose into monosaccharides and/or oligosaccharides.

In one aspect, provided is a method of producing one or more sugars from softwood, by:

a) providing softwood;
b) contacting the softwood with a catalyst to form a reaction mixture,
wherein the catalyst is a polymeric catalyst or a solid-supported catalyst,
wherein the polymeric catalyst includes acidic monomers and ionic monomers connected to form a polymeric backbone, wherein a plurality of acidic monomers independently includes at least one Bronsted-Lowry acid, and wherein a plurality of ionic monomers independently includes at least one nitrogen-containing cationic group, at least one phosphorous-containing cationic group, or a combination thereof,
wherein the solid-supported catalyst includes a solid support, acidic moieties attached to the solid support, and ionic moieties attached to the solid support, wherein a plurality of acidic moieties independently includes at least one Bronsted-Lowry acid, and wherein a plurality of ionic moieties independently includes at least one nitrogen-containing cationic group, at least one phosphorous-containing cationic group, or a combination thereof;
c) degrading the softwood in the reaction mixture to produce a liquid phase and a solid phase, wherein the liquid phase includes one or more sugars, and the solid phase includes residual softwood;
d) isolating at least a portion of the liquid phase from the solid phase; and
e) recovering the one or more sugars from the isolated liquid phase.

In some embodiments, the softwood is pine. In other embodiments, the softwood is in a form selected from chips, sawdust, bark, and any combination thereof.

In one aspect, provided is a method of producing one or more sugars from hardwood, by:

a) providing hardwood;
b) contacting the hardwood with a catalyst to form a reaction mixture,
wherein the catalyst is a polymeric catalyst or a solid-supported catalyst,
wherein the polymeric catalyst includes acidic monomers and ionic monomers connected to form a polymeric backbone, wherein a plurality of acidic monomers independently includes at least one Bronsted-Lowry acid, and wherein a plurality of ionic monomers independently includes at least one nitrogen-containing cationic group, at least one phosphorous-containing cationic group, or a combination thereof,
wherein the solid-supported catalyst includes a solid support, acidic moieties attached to the solid support, and ionic moieties attached to the solid support, wherein a plurality of acidic moieties independently includes at least one Bronsted-Lowry acid, and wherein a plurality of ionic moieties independently includes at least one nitrogen-containing cationic group, at least one phosphorous-containing cationic group, or a combination thereof;
c) degrading the hardwood in the reaction mixture to produce a liquid phase and a solid phase, wherein the liquid phase includes one or more sugars, and the solid phase includes residual hardwood;
d) isolating at least a portion of the liquid phase from the solid phase; and
e) recovering the one or more sugars from the isolated liquid phase.

In some embodiments, the hardwood is selected from birch, eucalyptus, aspen, maple, and any combination thereof. In other embodiments, the hardwood is in a form selected from chips, sawdust, bark, and any combination thereof.

In another aspect, provided is a method of producing one or more sugars from cassava, by:
a) providing cassava;
b) contacting the cassava with a catalyst to form a reaction mixture,
wherein the catalyst is a polymeric catalyst or a solid-supported catalyst,
wherein the polymeric catalyst includes acidic monomers and ionic monomers connected to form a polymeric backbone, wherein a plurality of acidic monomers independently includes at least one Bronsted-Lowry acid, and wherein a plurality of ionic monomers independently includes at least one nitrogen-containing cationic group, at least one phosphorous-containing cationic group, or a combination thereof,
wherein the solid-supported catalyst includes a solid support, acidic moieties attached to the solid support, and ionic moieties attached to the solid support, wherein a plurality of acidic moieties independently includes at least one Bronsted-Lowry acid, and wherein a plurality of ionic moieties independently includes at least one nitrogen-containing cationic group, at least one phosphorous-containing cationic group, or a combination thereof;
c) degrading the cassava in the reaction mixture to produce a liquid phase and a solid phases, wherein the liquid phase includes one or more sugars, and the solid phase includes residual cassava,
d) isolating at least a portion of the liquid phase from the solid phase; and
e) recovering the one or more sugars from the isolated liquid phase.

In one embodiment, the cassava is cassava stems.

In another aspect, provided is a method of producing one or more sugars from bagasse, by:
a) providing bagasse;
b) contacting the bagasse with a catalyst to form a reaction mixture,
wherein the catalyst is a polymeric catalyst or a solid-supported catalyst,
wherein the polymeric catalyst includes acidic monomers and ionic monomers connected to form a polymeric backbone, wherein a plurality of acidic monomers independently includes at least one Bronsted-Lowry acid, and wherein a plurality of ionic monomers independently includes at least one nitrogen-containing cationic group, at least one phosphorous-containing cationic group, or a combination thereof,
wherein the solid-supported catalyst includes a solid support, acidic moieties attached to the solid support, and ionic moieties attached to the solid support, wherein a plurality of acidic moieties independently includes at least one Bronsted-Lowry acid, and wherein a plurality of ionic moieties independently includes at least one nitrogen-containing cationic group, at least one phosphorous-containing cationic group, or a combination thereof;
c) degrading the bagasse in the reaction mixture to produce a liquid phase and a solid phase, wherein the liquid phase includes one or more sugars, and wherein the solid phase includes residual bagasse;
d) isolating at least a portion of the liquid phase from the solid phase; and
e) recovering the one or more sugars from the isolated liquid phase.

In one embodiment, the bagasse is sugarcane bagasse.

In another aspect, provided is a method of producing one or more sugars from oil palm, by:

a) providing oil palm;
b) contacting the oil palm with a catalyst to form a reaction mixture,
wherein the catalyst is a polymeric catalyst or a solid-supported catalyst,
wherein the polymeric catalyst includes acidic monomers and ionic monomers connected to form a polymeric backbone, wherein a plurality of acidic monomers independently includes at least one Bronsted-Lowry acid, and wherein a plurality of ionic monomers independently includes at least one nitrogen-containing cationic group, at least one phosphorous-containing cationic group, or a combination thereof,
wherein the solid-supported catalyst includes a solid support, acidic moieties attached to the solid support, and ionic moieties attached to the solid support, wherein a plurality of acidic moieties independently includes at least one Bronsted-Lowry acid, and wherein a plurality of ionic moieties independently includes at least one nitrogen-containing cationic group, at least one phosphorous-containing cationic group, or a combination thereof;
c) degrading the oil palm in the reaction mixture to produce a liquid phase and a solid phase, wherein the liquid phase includes one or more sugars, and wherein the solid phase includes residual oil palm;
d) isolating at least a portion of the liquid phase from the solid phase; and
e) recovering the one or more sugars from the isolated liquid phase.

In some embodiments, the oil palm is a palm oil waste material selected from empty fruit bunch, mesocarp fibre, and any combination thereof.

In yet another aspect, provided is a method of producing one or more sugars from corn stover, by:
a) providing corn stover;
b) contacting the corn stover with a catalyst to form a reaction mixture,
wherein the catalyst is a polymeric catalyst or a solid-supported catalyst,
wherein the polymeric catalyst includes acidic monomers and ionic monomers connected to form a polymeric backbone, wherein a plurality of acidic monomers independently includes at least one Bronsted-Lowry acid, and wherein a plurality of ionic monomer independently includes at least one nitrogen-containing cationic group, at least one phosphorous-containing cationic group, or a combination thereof,
wherein the solid-supported catalyst includes a solid support, acidic moieties attached to the solid support, and ionic moieties attached to the solid support, wherein a plurality of acidic moieties independently includes at least one Bronsted-Lowry acid, and wherein a plurality of ionic moieties independently includes at least one nitrogen-containing cationic group, at least one phosphorous-containing cationic group, or a combination thereof;
c) degrading the corn stover in the reaction mixture to produce a liquid phase and a solid phase, wherein the liquid phase includes one or more sugars, and wherein the solid phase includes residual corn stover;
d) isolating at least a portion of the liquid phase from the solid phase; and
e) recovering the one or more sugars from the isolated liquid phase.

In yet another aspect, provided is a method of producing one or more sugars from food waste, by:
a) providing food waste;
b) contacting the food waste with a catalyst to form a reaction mixture, wherein the catalyst is a polymeric catalyst or a solid-supported catalyst, wherein the polymeric catalyst includes acidic monomers and ionic monomers connected to form a polymeric backbone, wherein a plurality of acidic monomers independently includes at least one Bronsted-Lowry acid, and wherein a plurality of ionic monomers independently includes at least one nitrogen-containing cationic group, at least one phosphorous-containing cationic group, or a combination thereof, wherein the solid-supported catalyst includes a solid support, acidic moieties attached to the solid support, and ionic moieties attached to the solid support, wherein a plurality of acidic moieties independently includes at least one Bronsted-Lowry acid, and wherein a plurality of ionic moieties independently includes at least one nitrogen-containing cationic group, at least one phosphorous-containing cationic group, or a combination thereof;

c) degrading the food waste in the reaction mixture to produce a liquid phase and a solid phase, wherein the liquid phase includes one or more sugars, and wherein the solid phase includes residual food waste;

d) isolating at least a portion of the liquid phase from the solid phase; and e) recovering the one or more sugars from the isolated liquid phase.

In yet another aspect, provided is a method of producing one or more sugars from enzymatic digestion residuals, by:

a) providing enzymatic digestion residuals;

b) contacting the enzymatic digestion residuals with a catalyst to form a reaction mixture, wherein the catalyst is a polymeric catalyst or a solid-supported catalyst, wherein the polymeric catalyst includes acidic monomers and ionic monomers connected to form a polymeric backbone, wherein a plurality of acidic monomers independently includes at least one Bronsted-Lowry acid, and wherein a plurality of ionic monomers independently includes at least one nitrogen-containing cationic group, at least one phosphorous-containing cationic group, or a combination thereof, wherein the solid-supported catalyst includes a solid support, acidic moieties attached to the solid support, and ionic moieties attached to the solid support, wherein a plurality of acidic moieties independently includes at least one Bronsted-Lowry acid, and wherein a plurality of ionic moieties independently includes at least one nitrogen-containing cationic group, at least one phosphorous-containing cationic group, or a combination thereof;

c) degrading the enzymatic digestion residuals in the reaction mixture to produce a liquid phase and a solid phase, wherein the liquid phase includes one or more sugars, and the solid phase includes residual enzymatic digestion residuals;

d) isolating at least a portion of the liquid phase from the solid phase; and e) recovering the one or more sugars from the isolated liquid phase.

In yet another aspect, provided is a method of producing one or more sugars from beer bottoms, by:

a) providing beer bottoms;

b) contacting the beer bottoms with a catalyst to form a reaction mixture, wherein the catalyst is a polymeric catalyst or a solid-supported catalyst, wherein the polymeric catalyst includes acidic monomers and ionic monomers connected to form a polymeric backbone, wherein a plurality of acidic monomers independently includes at least one Bronsted-Lowry acid, and wherein a plurality of ionic monomers independently includes at least one nitrogen-containing cationic group, at least one phosphorous-containing cationic group, or a combination thereof, wherein the solid-supported catalyst includes a solid support, acidic moieties attached to the solid support, and ionic moieties attached to the solid support, wherein a plurality of acidic moieties independently includes at least one Bronsted-Lowry acid, and wherein a plurality of ionic moieties independently includes at least one nitrogen-containing cationic group, at least one phosphorous-containing cationic group, or a combination thereof;

c) degrading the beer bottoms in the reaction mixture to produce a liquid phase and a solid phase, wherein the liquid phase includes one or more sugars, and the solid phase includes residual beer bottoms;

d) isolating at least a portion of the liquid phase from the solid phase; and e) recovering the one or more sugars from the isolated liquid phase.

In some embodiments of any of the methods described above, the method further includes pretreating the feedstock (e.g., softwood, hardwood, cassava, bagasse, sugarbeet pulp, straw, paper sludge, oil palm, corn stover, food waste, enzymatic digestion residuals, beer bottoms, and any combination thereof) before contacting the feedstock with the catalyst to form the reaction mixture. In certain embodiments, the pretreatment of the feedstock is selected from washing, solvent-extraction, solvent-swelling, comminution, milling, steam pretreatment, explosive steam pretreatment, dilute acid pretreatment, hot water pretreatment, alkaline pretreatment, lime pretreatment, wet oxidation, wet explosion, ammonia fiber explosion, organosolvent pretreatment, biological pretreatment, ammonia percolation, ultrasound, electroporation, microwave, supercritical $CO_2$, supercritical $H_2O$, ozone, and gamma irradiation, or any combination thereof.

In some embodiments of any of the methods described above, the isolating of at least a portion of the liquid phase from the solid phase in step (d) produces a residual feedstock mixture, and the method further includes:

i) providing additional feedstock (e.g., softwood, hardwood, cassava, bagasse, sugarbeet pulp, straw, paper sludge, oil palm, corn stover, food waste, enzymatic digestion residuals, beer bottoms, and any combination thereof);

ii) contacting the additional feedstock with the residual feedstock mixture;

iii) degrading the additional feedstock and the residual feedstock mixture to produce a second liquid phase and a second solid phase, wherein the second liquid phase includes one or more additional sugars, and wherein the second solid phase includes additional residual feedstock mixture;

iv) isolating at least a portion of the second liquid phase from the second solid phase; and v) recovering the one or more additional sugars from the isolated second liquid phase.

In some embodiments, the additional feedstock (e.g., softwood, hardwood, cassava, bagasse, sugarbeet pulp, straw, paper sludge, oil palm, corn stover, food waste, enzymatic digestion residuals, beer bottoms, and any combination thereof) in step (i) is the same type or a different type as the feedstock in step (a). In other embodiments, the one or more additional sugars produced in step (iii) is the same or a different type as the one or more sugars produced in step (c).

In certain embodiments, the method further includes contacting the additional feedstock and the residual feedstock mixture in step (iii) with additional catalyst, in which the additional catalyst can be any of the catalysts described herein (e.g., a polymeric catalyst, a solid-supported catalyst, or a combination thereof). In certain embodiments, the additional catalyst is the same or different as the catalyst in step (b).

In other embodiments, the method further includes contacting the additional feedstock and the residual feedstock mixture with additional solvent. In certain embodiments, the additional solvent is the same or different as the solvent in step (b). In one embodiment, the additional solvent includes water.

In some embodiments, the method further includes recovering the catalyst after isolating at least a portion of the second liquid phase.

In some embodiments of any of the methods described above, the catalyst described herein has one or more catalytic properties selected from:
 a) disruption of a hydrogen bond in cellulosic materials;
 b) intercalation of the catalyst into crystalline domains of cellulosic materials; and
 c) cleavage of a glycosidic bond in cellulosic materials.

In some embodiments of any of the methods described above, the catalyst has a greater specificity for cleavage of a glycosidic bond than dehydration of a monosaccharide in cellulosic materials.

DESCRIPTION OF THE FIGURES

FIG. 3A illustrates a portion of an exemplary polymeric catalyst, in which the monomers are randomly arranged in an alternating sequence.

FIG. 3B illustrates a portion of an exemplary polymeric catalyst, in which the monomers are arranged in blocks of monomers, and the block of acidic monomers alternates with the block of ionic monomers.

FIGS. 4A and 4B illustrate a portion of exemplary polymeric catalysts with cross-linking within a given polymeric chain.

FIG. 7A illustrates two side chains in an exemplary polymeric catalyst, in which there are three carbon atoms between the side chain with the Bronsted-Lowry acid and the side chain with the cationic group.

FIG. 7B illustrates two side chains in another exemplary polymeric catalyst, in which there are zero carbons between the side chain with the Bronsted-Lowry acid and the side chain with the cationic group.

DETAILED DESCRIPTION

Figure 1:
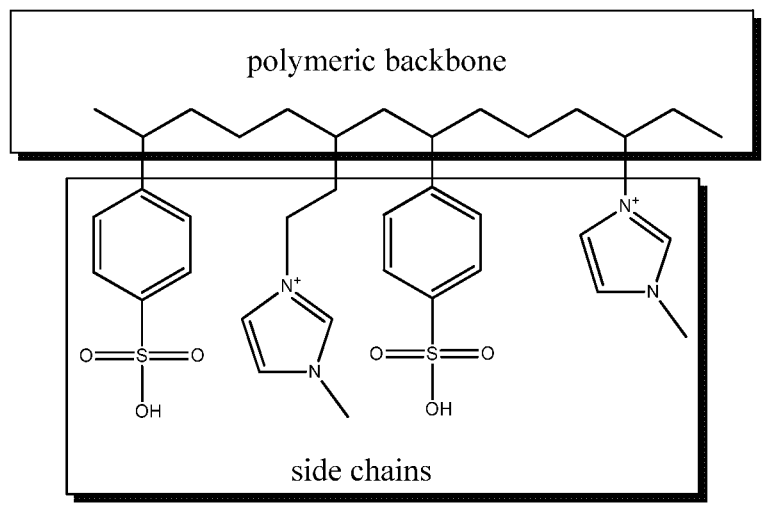
FIG. 1 illustrates a portion of an exemplary catalyst that has a polymeric backbone and side chains.
Figure 2:
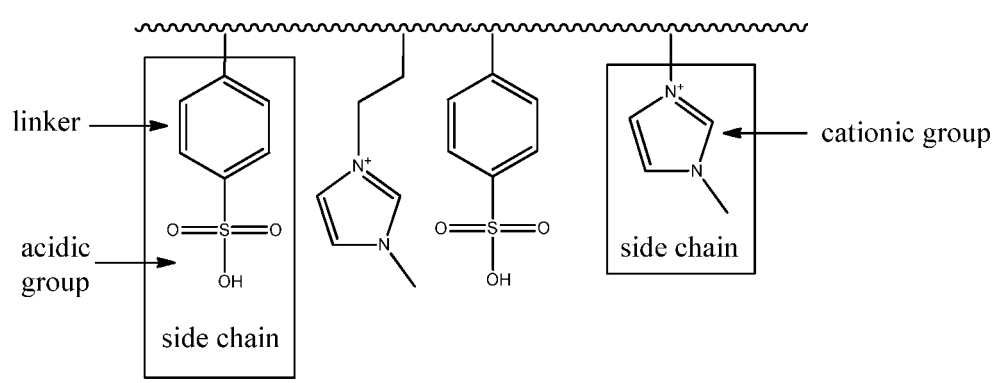
FIG. 2 illustrates a portion of an exemplary catalyst, in which a side chain with the acidic group is connected to the polymeric backbone by a linker and in which a side chain with the cationic group is connected directly to the polymeric backbone.

The following description sets forth exemplary methods, parameters and the like. It should be recognized, however, that such description is not intended as a limitation on the scope of the present disclosure but is instead provided as a description of exemplary embodiments.

While specific embodiments of the present disclosure have been discussed, the specification is illustrative and not restrictive. Many variations of this disclosure will become apparent to those skilled in the art upon review of this specification. The full scope of the disclosure should be determined by reference to the claims, along with their full scope of equivalents, and the specification, along with such variations.

When ranges are used herein for physical properties, such as molecular weight, or chemical properties, such as chemical formulae, all combinations and subcombinations of ranges and specific embodiments therein are intended to be included. Unless otherwise indicated, all numbers expressing quantities of ingredients, reaction conditions, and so forth used in the specification and claims are to be understood as being modified in all instances by the term "about." The term "about" when referring to a number or a numerical range means that the number or numerical range referred to is an approximation within experimental variability (or within statistical experimental error), and thus the number or numerical range can vary from, for example, but not limited to, between 0.1% and 15% of the stated number or numerical range. Accordingly, unless indicated to the contrary, the numerical parameters set forth in this specification and attached claims are approximations that can vary depending upon the desired properties sought to be obtained by the present disclosure.

Unless defined otherwise, all technical and scientific terms used herein have the same meaning as is commonly understood by one of skill in the art to which this specification pertains.

As used in the specification and claims, the singular form "a", "an" and "the" includes plural references unless the context clearly dictates otherwise.

"Bronsted-Lowry acid" refers to a molecule, or substituent thereof, in neutral or ionic form that is capable of donating a proton (hydrogen cation, $H^+$).

"Homopolymer" refers to a polymer having at least two monomer units, and where all the units contained within the polymer are derived from the same monomer in the same manner. A non-limiting example is polyethylene, where ethylene monomers are linked to form a uniform repeating chain ($-CH_2-CH_2-CH_2-$). Another non-limiting example is polyvinyl chloride, having a structure ($-CH_2-CHCl-CH_2-CHCl-$) where the $-CH_2-CHCl-$ repeating unit is derived from the $H_2C=CHCl$ monomer.

"Heteropolymer" refers to a polymer having at least two monomer units, and where at least one monomeric unit differs from the other monomeric units in the polymer. Heteropolymer also refers to polymers having difunctionalized, or trifunctionalized, monomer units that can be incorporated in the polymer in different ways. The different monomer units in the polymer can be in a random order, in an alternating sequence of any length of a given monomer, or in blocks of monomers. A non-limiting example is polyethyleneimidazolium, where if in an alternating sequence, would be the polymer depicted in FIG. 6C. Another non-limiting example is polystyrene-co-divinylbenzene, where if in an alternating sequence, could be ($-CH_2-CH(phenyl)-CH_2-CH(4-ethylenephenyl)-CH_2-CH(phenyl)-CH_2-CH(4-ethylenephenyl)-$). Here, the ethenyl functionality could be at the 2, 3, or 4 position on the phenyl ring.

As used herein, ∿∿∿∿ denotes a generic polymeric backbone to which one or more substituents or side chains can be attached, as denoted by a straight perpendicular line descending from the ∿∿∿∿ mark.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a straight or branched hydrocarbon chain group consisting solely of carbon and hydrogen atoms, containing no unsaturation, having from one to ten carbon atoms (e.g., $C_1$-$C_{10}$ alkyl, 1-10C, C1-C10 or C1-10). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_6$ alkyl group. In some embodiments, alkyl groups have 1 to 10, 1 to 6, or 1 to 3 carbon atoms. Representative saturated straight chain alkyls include -methyl, -ethyl, -n-propyl, -n-butyl, -n-pentyl, and -n-hexyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. When an alkyl residue having a specific number of carbons is named, all geometric isomers having that number of carbons are intended to be encompassed and described; thus, for example, "butyl" is meant to include n-butyl, sec-butyl, iso-butyl, and tert-butyl; "propyl" includes n-propyl, and iso-propyl. As used herein, "alkylene" refers to the same residues as alkyl, but having bivalency. Examples of alkylene include methylene (—$CH_2$—), ethylene (—$CH_2CH_2$—), propylene (—$CH_2CH_2CH_2$—), butylene (—$CH_2CH_2CH_2CH_2$—). Unless stated otherwise in the specification, an alkyl group is optionally substituted by one or more of substituents which independently include: alkyl, alkoxy, alkylaryl, cycloalkyl, aralkyl, aryl, aryloxy, amino, amido, carbamate, carbonyl, heteroalkyl, heteroaryl, heterocycloalkyl, cyano, halo, haloalkoxy, haloalkyl, ether, thio, alkylthio, arylthio, —$OR_a$, —$SR_a$, —$N(R_a)_2$, —$C(O)R_a$, —$C(O)N(R_a)_2$, —$N(R_a)C(O)R_a$, —$N(R_a)S(O)tR_a$ (where t is 1 or 2), and —$S(O)tN(R_a)_2$ (where t is 1 or 2), where each $R_a$ is independently hydrogen, alkyl, haloalkyl, cycloalkyl, aryl, aralkyl, heterocycloalkyl, or heteroaryl and each of these moieties can be optionally substituted as defined herein.

"Perhaloalkyl" refers to an alkyl group in which all of the hydrogen atoms have been replaced with a halogen selected from fluoro, chloro, bromo, and iodo. In some embodiments, all of the hydrogen atoms are each replaced with fluoro. In some embodiments, all of the hydrogen atoms are each replaced with chloro. Examples of perhaloalkyl groups include —$CF_3$, —$CF_2CF_3$, —$CF_2CF_2CF_3$, —$CCl_3$, —$CFCl_2$, —$CF_2Cl$ and the like.

"Alkylaryl" refers to an -(alkyl)aryl group where aryl and alkyl are as disclosed herein and which are optionally substituted by one or more of the substituents described as suitable substituents for aryl and alkyl respectively. The "alkylaryl" is bonded to the parent molecular structure through the alkyl group.

The term "alkoxy" refers to the group —O-alkyl, including from 1 to 10 carbon atoms of a straight, branched, cyclic configuration and combinations thereof, attached to the parent molecular structure through an oxygen atom. Examples include methoxy, ethoxy, propoxy, isopropoxy, cyclopropyloxy, cyclohexyloxy and the like. "Lower alkoxy" refers to alkoxy groups containing one to six carbons. In some embodiments, $C_1$-$C_4$ alkoxy is an alkoxy group which encompasses both straight and branched chain alkyls of from 1 to 4 carbon atoms. Unless stated otherwise in the specification, an alkoxy group is optionally substituted by one or more substituents which independently include: alkyl, alkoxy, alkylaryl, cycloalkyl, aralkyl, aryl, aryloxy, amino, amido, carbamate, carbonyl, heteroalkyl, heteroaryl, heterocycloalkyl, cyano, halo, haloalkoxy, haloalkyl, ether, thio, alkylthio, arylthio, —$OR_a$, —$SR_a$, —$N(R_a)_2$, —$C(O)R_a$, —$C(O)N(R_a)_2$, —$N(R_a)C(O)R_a$, —$N(R_a)S(O)tR_a$ (where t is 1 or 2), and —$S(O)tN(R_a)_2$ (where t is 1 or 2), where each $R_a$ is independently hydrogen, alkyl, haloalkyl, cycloalkyl, aryl, aralkyl, heterocycloalkyl, or heteroaryl and each of these moieties can be optionally substituted as defined herein.

"Alkenyl" refers to a straight or branched hydrocarbon chain group consisting solely of carbon and hydrogen atoms, containing at least one double bond, and having from two to ten carbon atoms (i.e., C2-C10 alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., C2-C5 alkenyl). When an alkenyl residue having a specific number of carbons is named, all geometric isomers having that number of carbons are intended to be encompassed and described; thus, for example, "butenyl" is meant to include n-butenyl, sec-butenyl, and iso-butenyl. Examples of alkenyl can include —$CH=CH_2$, —$CH_2$—$CH=CH_2$ and —$CH_2$—$CH=CH$—$CH=CH_2$. The alkenyl is attached to the parent molecular structure by a single bond, for example, ethenyl (i.e., vinyl), prop 1 enyl (i.e., allyl), but 1 enyl, pent 1 enyl, penta 1,4 dienyl, and the like. The one or more carbon-carbon double bonds can be internal (such as in 2-butenyl) or terminal (such as in 1-butenyl). Examples of $C_{2-4}$ alkenyl groups include ethenyl (C2), 1-propenyl (C3), 2-propenyl (C3), 1-butenyl (C4), 2-butenyl (C4), butadienyl (C4) and the like. Examples of C2-6 alkenyl groups include the aforementioned C2-4 alkenyl groups as well as pentenyl (C5), pentadienyl (C5), hexenyl (C6) and the like. Additional examples of alkenyl include heptenyl (C7), octenyl (C8), octatrienyl (C8) and the like. As used herein, "alkenylene" refers to the same residues as alkenyl, but having bivalency. Examples of alkenylene include ethylene (—$CH=CH$—), propylene (—$CH_2$—$CH=CH$—) and butylene (—$CH_2$—$CH=CH$—$CH_2$—). Alkenyl contains only C and H when unsubstituted. Unless stated otherwise in the specification, an alkenyl group is optionally substituted by one or more substituents which independently include: alkyl, alkoxy, alkylaryl, cycloalkyl, aralkyl, aryl, aryloxy, amino, amido, carbamate, carbonyl, heteroalkyl, heteroaryl, heterocycloalkyl, cyano, halo, haloalkoxy, haloalkyl, ether, thio, alkylthio, arylthio, —$OR_a$, —$SR_a$, —$N(R_a)_2$, —$C(O)R_a$, —$C(O)N(R_a)_2$, —$N(R_a)C(O)R_a$, —$N(R_a)S(O)tR_a$ (where t is 1 or 2), and —$S(O)tN(R_a)_2$ (where t is 1 or 2), where each $R_a$ is independently hydrogen, alkyl, haloalkyl, cycloalkyl, aryl, aralkyl, heterocycloalkyl, or heteroaryl and each of these moieties can be optionally substituted as defined herein.

"Amino" or "amine" refers to a —$N(R^b)_2$, —$N(R^b)R^b$—, or —$R_bN(R_b)R_b$— group, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. When a —N($R^b$)$_2$ group has two $R^b$ other than hydrogen, they can be combined with the nitrogen atom to form a 3-, 4-, 5-, 6-, or 7-membered ring. For example, —N($R^b$)$_2$ is meant to include, but not be limited to, 1-pyrrolidinyl and 4-morpholinyl. Unless stated otherwise in the specification, an amino group is optionally substituted by one or more substituents which independently include: alkyl, alkoxy, alkylaryl, cycloalkyl, aralkyl, aryl, aryloxy, amino, amido, carbamate, carbonyl, heteroalkyl, heteroaryl, heterocycloalkyl, cyano, halo, haloalkoxy, haloalkyl, ether, thio, alkylthio, arylthio, —O$R_a$, —S$R_a$, —N($R_a$)$_2$, —C(O)$R_a$, —C(O)N($R_a$)$_2$, —N($R_a$)C(O) $R_a$, —N($R_a$)S(O)t$R_a$ (where t is 1 or 2), and —S(O)tN($R_a$)$_2$ (where t is 1 or 2), where each $R_a$ is independently hydrogen, alkyl, haloalkyl, cycloalkyl, aryl, aralkyl, heterocycloalkyl, or heteroaryl and each of these moieties can be optionally substituted as defined herein.

The term "amino" also refers to N-oxides of the groups —N$^+$(H)($R^a$)O$^-$, and —N$^+$($R^a$)($R^a$)O$^-$, $R^a$ as described above, where the N-oxide is bonded to the parent molecular structure through the N atom. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N($R^b$)$_2$ or —N$R^b$C(O)$R^b$, where $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. In some embodiments, this group is a $C_1$-$C_4$ amido or amide group, which includes the amide carbonyl in the total number of carbons in the group. When a —C(O)N($R^b$)$_2$ has two $R^b$ other than hydrogen, they can be combined with the nitrogen atom to form a 3-, 4-, 5-, 6-, or 7-membered ring. For example, N($R^b$)$_2$ portion of a —C(O)N($R^b$)$_2$ group is meant to include, but not be limited to, 1-pyrrolidinyl and 4-morpholinyl. Unless stated otherwise in the specification, an amido $R^b$ group is optionally substituted by one or more substituents which independently include: alkyl, alkoxy, alkylaryl, cycloalkyl, aralkyl, aryl, aryloxy, amino, amido, carbamate, carbonyl, heteroalkyl, heteroaryl, heterocycloalkyl, cyano, halo, haloalkoxy, haloalkyl, ether, thio, alkylthio, arylthio, —O$R_a$, —S$R_a$, —N($R_a$)$_2$, —C(O)$R_a$, —C(O)N($R_a$)$_2$, —N($R_a$)C(O)$R_a$, —N($R_a$)S(O)t$R_a$ (where t is 1 or 2), and —S(O)tN($R_a$)$_2$ (where t is 1 or 2), where each $R_a$ is independently hydrogen, alkyl, haloalkyl, cycloalkyl, aryl, aralkyl, heterocycloalkyl, or heteroaryl and each of these moieties can be optionally substituted as defined herein.

"Aromatic" or "aryl" refers to a group with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). The aromatic carbocyclic group can have a single ring (e.g., phenyl) or multiple condensed rings (e.g., naphthyl or anthryl), which condensed rings may or may not be aromatic. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. An aryl group having more than one ring where at least one ring is non-aromatic can be connected to the parent structure at either an aromatic ring position or at a non-aromatic ring position. Whenever it appears herein, a numerical range such as "6 to 10 aryl" refers to each integer in the given range; e.g., "6 to 10 ring atoms" means that the aryl group can consist of 6 ring atoms, 7 ring atoms, etc., up to and including 10 ring atoms. The term includes monocyclic or fused-ring polycyclic (i.e., rings which share adjacent pairs of ring atoms) groups. Examples of aryl can include phenyl, phenol, and benzyl. Unless stated otherwise in the specification, an aryl moiety can be optionally substituted by one or more substituents which independently include: alkyl, alkoxy, alkylaryl, cycloalkyl, aralkyl, aryl, aryloxy, amino, amido, carbamate, carbonyl, heteroalkyl, heteroaryl, heterocycloalkyl, cyano, halo, haloalkoxy, haloalkyl, ether, thio, alkylthio, arylthio, —O$R_a$, —S$R_a$, —N($R_a$)$_2$, —C(O)$R_a$, —C(O)N($R_a$)$_2$, —N($R_a$)C(O) $R_a$, —N($R_a$)S(O)t$R_a$ (where t is 1 or 2), and —S(O)tN($R_a$)$_2$ (where t is 1 or 2), where each $R_a$ is independently hydrogen, alkyl, haloalkyl, cycloalkyl, aryl, aralkyl, heterocycloalkyl, or heteroaryl and each of these moieties can be optionally substituted as defined herein.

"Aralkyl" or "arylalkyl" refers to an (aryl)alkyl-group where aryl and alkyl are as disclosed herein and which are optionally substituted by one or more of the substituents described as suitable substituents for aryl and alkyl respectively. The "aralkyl/arylalkyl" is bonded to the parent molecular structure through the alkyl group. The terms "aralkenyl/arylalkenyl" and "aralkynyl/arylalkynyl" mirror the above description of "aralkyl/arylalkyl" wherein the "alkyl" is replaced with "alkenyl" or "alkynyl" respectively, and the "alkenyl" or "alkynyl" terms are as described herein.

"Azide" refers to a —$N_3$ radical.

"Carbamate" refers to any of the following groups: —O—(C=O)—N$R^b$—, —O—(C=O)—N($R^b$)$_2$, —N($R^b$)—(C=O)—O—, and —N($R^b$)—(C=O)—O$R^b$, wherein each $R^b$ is independently selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Cyano" refers to a —CN group.

"Cycloalkyl" refers to a monocyclic or polycyclic group that contains only carbon and hydrogen, and can be saturated, or partially unsaturated. Partially unsaturated cycloalkyl groups can be termed "cycloalkenyl" if the carbocycle contains at least one double bond, or "cycloalkynyl" if the carbocycle contains at least one triple bond. The cycloalkyl can consist of one ring, such as cyclohexyl, or multiple rings, such as adamantyl. A cycloalkyl with more than one ring can be fused, spiro or bridged, or combinations thereof. Cycloalkyl groups include groups having from 3 to 10 ring atoms (i.e., $C_3$-$C_{10}$ cycloalkyl). Whenever it appears herein, a numerical range such as "3 to 10" refers to each integer in the given range; e.g., "3 to 10 carbon atoms" means that the cycloalkyl group can consist of 3 carbon atoms, 4 carbon atoms, 5 carbon atoms, etc., up to and including 10 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. In some embodiments, it is a $C_3$-$C_8$ cycloalkyl group. In some embodiments, it is a $C_3$-$C_5$ cycloalkyl group. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-8}$ carbocyclyl groups include the aforementioned $C_{3-6}$ carbocyclyl groups as well as cycloheptyl ($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-10}$ carbocyclyl groups include the aforementioned $C_{3-8}$ carbocyclyl groups as well as octahydro-1H-indenyl, decahydronaphthalenyl, spiro[4.5]decanyl and the like. As used herein, "cycloalkylene" refers to the same residues as cycloalkyl, but having bivalency. Unless stated otherwise in the specification, a cycloalkyl group is optionally substituted by one or more substituents which independently include: alkyl, alkoxy, alkylaryl, cycloalkyl, aralkyl, aryl, aryloxy, amino, amido, carbamate, carbonyl, heteroalkyl, heteroaryl, heterocycloalkyl, cyano, halo, haloalkoxy, haloalkyl, ether, thio, alkylthio, arylthio, —$OR_a$, —$SR_a$, —$N(R_a)_2$, —$C(O)R_a$, —$C(O)N(R_a)_2$, —$N(R_a)C(O)R_a$, —$N(R_a)S(O)tR_a$ (where t is 1 or 2), and —$S(O)tN(R_a)_2$ (where t is 1 or 2), where each $R_a$ is independently hydrogen, alkyl, haloalkyl, cycloalkyl, aryl, aralkyl, heterocycloalkyl, or heteroaryl and each of these moieties can be optionally substituted as defined herein.

"Ether" refers to a —$R^b$—O—$R^b$— group where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, and the like. Each of the alkyl, alkenyl, alkynyl and alkoxy groups can be optionally substituted as defined herein.

"Heteroalkyl" includes optionally substituted alkyl, alkenyl and alkynyl groups, respectively, and which have one or more skeletal chain atoms selected from an atom other than carbon, e.g., oxygen, nitrogen, sulfur, phosphorus or combinations thereof. A numerical range can be given, e.g., $C_1$-$C_4$ heteroalkyl which refers to the chain length in total, which in this example is 4 atoms long. For example, a —$CH_2OCH_2CH_3$ group is referred to as a "$C_4$" heteroalkyl, which includes the heteroatom center in the atom chain length description. Connection to the rest of the parent molecular structure can be through either a heteroatom or a carbon in the heteroalkyl chain. Exemplary heteroalkyl groups include, without limitation, ethers such as methoxyethanyl (—$CH_2CH_2OCH_3$), ethoxymethanyl (—$CH_2OCH_2CH_3$), (methoxymethoxy)ethanyl (—$CH_2CH_2OCH_2OCH_3$), (methoxymethoxy)methanyl (—$CH_2OCH_2OCH_3$) and (methoxyethoxy)methanyl (—$CH_2OCH_2$ $CH_2OCH_3$) and the like; amines such as —$CH_2CH_2NHCH_3$, —$CH_2CH_2N$ ($CH_3$)$_2$, —$CH_2NHCH_2CH_3$, —$CH_2N(CH_2CH_3)(CH_3)$ and the like. A heteroalkyl group can be optionally substituted by one or more substituents which independently include: alkyl, alkoxy, alkylaryl, cycloalkyl, aralkyl, aryl, aryloxy, amino, amido, carbamate, carbonyl, heteroalkyl, heteroaryl, heterocycloalkyl, cyano, halo, haloalkoxy, haloalkyl, ether, thio, alkylthio, arylthio, —$OR_a$, —$SR_a$, —$N(R_a)_2$, —$C(O)R_a$, —$C(O)N(R_a)_2$, —$N(R_a)C(O)R_a$, —$N(R_a)S(O)tR_a$ (where t is 1 or 2), and —$S(O)tN(R_a)_2$ (where t is 1 or 2), where each $R_a$ is independently hydrogen, alkyl, haloalkyl, cycloalkyl, aryl, aralkyl, heterocycloalkyl, or heteroaryl and each of these moieties can be optionally substituted as defined herein.

"Heteroaryl" or, alternatively, "heteroaromatic" refers to a refers to a group of a 5-18 membered monocyclic or polycyclic (e.g., bicyclic or tricyclic) aromatic ring system (e.g., having 6, 10 or 14 electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). A heteroaryl group may have a single ring (e.g., pyridyl, pyridinyl, imidazolyl) or multiple condensed rings (e.g., indolizinyl, benzothienyl) which condensed rings may or may not be aromatic. A heteroaryl group having more than one ring where at least one ring is non-aromatic can be connected to the parent structure at either an aromatic ring position or at a non-aromatic ring position. In one variation, a heteroaryl group having more than one ring where at least one ring is non-aromatic is connected to the parent structure at an aromatic ring position. Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. For example, bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene.

For example, an N-containing "heteroaromatic" or "heteroaryl" moiety refers to an aromatic group in which at least one of the skeletal atoms of the ring is a nitrogen atom. One or more heteroatom(s) in the heteroaryl group can be optionally oxidized. One or more nitrogen atoms, if present, are optionally quaternized. "Heteroaryl" also includes ring systems substituted with one or more oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment is either on the aryl or on the heteroaryl ring, or wherein the heteroaryl ring, as defined above, is fused with one or more carbocycyl or heterocycyl groups wherein the point of attachment is on the heteroaryl ring. For polycyclic heteroaryl groups wherein one ring does not contain a heteroatom (e.g., indolyl, quinolinyl, carbazolyl and the like) the point of attachment can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinykisothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, -2-pyridine-co-divinylbenzene) (5 g) was stated otherwise in the specification, a heteroaryl moiety optionally substituted by one or more substituents which independently include: alkyl, alkoxy, alkylaryl, cycloalkyl, aralkyl, aryl, aryloxy, amino, amido, carbamate, carbonyl, heteroalkyl, heteroaryl, heterocycloalkyl, cyano, halo, haloalkoxy, haloalkyl, ether, thio, alkylthio, arylthio, —OR$_a$, —SR$_a$, —N(R$_a$)$_2$, —C(O)R$_a$, —C(O)N(R$_a$)$_2$, —N(R$_a$)C(O)R$_a$, —N(R$_a$)S(O)tR$_a$ (where t is 1 or 2), and —S(O)tN(R$_a$)$_2$ (where t is 1 or 2), where each R$_a$ is independently hydrogen, alkyl, haloalkyl, cycloalkyl, aryl, aralkyl, heterocycloalkyl, or heteroaryl and each of these moieties can be optionally substituted as defined herein.

"Heterocyclyl", "heterocycloalkyl" or "heterocarbocyclyl" refer to any 3- to 18-membered non-aromatic monocyclic or polycyclic moiety comprising at least one heteroatom selected from nitrogen, oxygen, phosphorous and sulfur. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or both rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "3 to 18" refers to each integer in the given range; e.g., "5 to 18 ring atoms" means that the heterocyclyl group can consist of 5 ring atoms, 6 ring atoms, etc., up to and including 18 ring atoms. For example, bivalent radicals derived from univalent heterocyclyl radicals whose names end in "-yl" by removal of one hydrogen atom from the atom with the free valence are named by adding "-idene" to the name of the corresponding univalent radical, e.g., a piperidine group with two points of attachment is a piperidylidene.

An N-containing heterocyclyl moiety refers to an non-aromatic group in which at least one of the skeletal atoms of the ring is a nitrogen atom. The heteroatom(s) in the heterocyclyl group is optionally oxidized. One or more nitrogen atoms, if present, are optionally quaternized. "Heterocyclyl" also includes ring systems substituted with one or more oxide (—O—) substituents, such as piperidinyl N-oxides. The heterocyclyl is attached to the parent molecular structure through any atom of the ring(s).

"Heterocyclyl" also includes ring systems wherein the heterocycyl ring, as defined above, is fused with one or more carbocycyl groups wherein the point of attachment is either on the carbocycyl or heterocyclyl ring, or ring systems wherein the heterocyclyl ring, as defined above, is fused with one or more aryl or heteroaryl groups, wherein the point of attachment is on the heterocyclyl ring. In some embodiments, a heterocyclyl group is a 5-10 membered non-aromatic ring system having ring carbon atoms and 1-4 ring heteroatoms, wherein each heteroatom is independently selected from nitrogen, oxygen and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen and sulfur ("5-6 membered heterocyclyl"). In some embodiments, the 5-6 membered heterocyclyl has 1-3 ring heteroatoms selected from nitrogen, oxygen and sulfur. In some embodiments, the 5-6 membered heterocyclyl has 1-2 ring heteroatoms selected from nitrogen, oxygen and sulfur. In some embodiments, the 5-6 membered heterocyclyl has 1 ring heteroatom selected from nitrogen, oxygen and sulfur.

Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

Unless stated otherwise, heterocyclyl moieties are optionally substituted by one or more substituents which independently include: alkyl, alkoxy, alkylaryl, cycloalkyl, aralkyl, aryl, aryloxy, amino, amido, carbamate, carbonyl, heteroalkyl, heteroaryl, heterocycloalkyl, cyano, halo, haloalkoxy, haloalkyl, ether, thio, alkylthio, arylthio, —$OR_a$, —$SR_a$, —$S(O)tR_a$, —$N(R_a)_2$, —$C(O)R_a$, —$C(O)N(R_a)_2$, —$N(R_a)C(O)R_a$, —$N(R_a)S(O)tR_a$ (where t is 1 or 2), and —$S(O)tN(R_a)_2$ (where t is 1 or 2), where each $R_a$ is independently hydrogen, alkyl, haloalkyl, cycloalkyl, aryl, aralkyl, heterocycloalkyl, or heteroaryl and each of these moieties can be optionally substituted as defined herein.

"Imino" refers to the "—(C=N)—$R^b$" group where $R^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Moiety" refers to a specific segment or functional group of a molecule. Chemical moieties are often recognized chemical entities embedded in or appended to a molecule.

"Nitro" refers to the —$NO_2$ group.

As used herein, the term "unsubstituted" means that for carbon atoms, only hydrogen atoms are present besides those valencies linking the atom to the parent molecular group. A non-limiting example is propyl (—$CH_2$—$CH_2$—$CH_3$). For nitrogen atoms, valencies not linking the atom to the parent molecular group are either hydrogen or an electron pair. For sulfur atoms, valencies not linking the atom to the parent molecular group are either hydrogen, oxygen or electron pair(s).

As used herein, the term "substituted" or "substitution" means that at least one hydrogen present on a group (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents include one or more group(s) individually and independently selected from alkyl, alkoxy, alkylaryl, cycloalkyl, aralkyl, aryl, aryloxy, amino, amido, carbamate, carbonyl, heteroalkyl, heteroaryl, heterocycloalkyl, cyano, halo, haloalkoxy, haloalkyl, ether, thio, alkylthio, arylthio, —$OR_a$, —$SR_a$, —$N(R_a)_2$, —$C(O)R_a$, —$C(O)N(R_a)_2$, —$N(R_a)C(O)R_a$, —$N(R_a)S(O)tR_a$ (where t is 1 or 2), and —$S(O)tN(R_a)_2$ (where t is 1 or 2), where each $R_a$ is independently hydrogen, alkyl, haloalkyl, cycloalkyl, aryl, aralkyl, heterocycloalkyl, or heteroaryl and each of these moieties can be optionally substituted as defined herein.

"Sulfanyl", "sulfide", and "thio" each refer to the groups: —S—$R^b$, wherein $R^b$ is selected from alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. For instance, an "alkylthio" refers to the "alkyl-S-" group, and "arylthio" refers to the "aryl-S-" group, each of which are bound to the parent molecular group through the S atom. The terms "thiol", "mercapto", and "mercaptan" each refer to the group —$R^cSH$.

"Sulfinyl" refers to the —S(O)—$R^b$ group, wherein $R^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfonyl" refers to the —$S(O_2)$—$R^b$ group, wherein $R^b$ is selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein.

"Sulfonamidyl" or "sulfonamido" refers to a —$S(=O)_2$—$NR^bR^b$ or —$N(R^b)$—$S(=O)_2$-group, where each $R^b$ is independently selected from hydrogen, alkyl, alkenyl, alkynyl, haloalkyl, heteroalkyl (bonded through a chain carbon), cycloalkyl, cycloalkylalkyl, aryl, aralkyl, heterocycloalkyl (bonded through a ring carbon), heterocycloalkylalkyl, heteroaryl (bonded through a ring carbon) or heteroarylalkyl, unless stated otherwise in the specification, each of which moiety can itself be optionally substituted as described herein. The $R^b$ groups in —$NR^bR^b$ of the —$S(=O)_2$—$NR^bR^b$ group can be taken together with the nitrogen to which they are attached to form a 4-, 5-, 6-, or 7-membered ring. In some embodiments, the term designates a $C_1$-$C_4$ sulfonamido, wherein each R in sulfonamido contains 1 carbon, 2 carbons, 3 carbons, or 4 carbons total.

"Sulfoxyl" refers to a —$S(=O)_2OH$ group.

Where substituent groups are specified by their conventional chemical formulae, written from left to right, they equally encompass the chemically identical substituents that would result from writing the structure from right to left, e.g., —$CH_2O$— is equivalent to —$OCH_2$—.

Described herein are methods to produce sugars from biomass feedstocks using catalysts, including polymeric catalysts and/or solid-supported catalysts. In some embodiments, the catalysts provided herein can disrupt the hydrogen bond superstructure typically found in natural cellulosic materials, allowing the acidic pendant groups of the catalyst to come into chemical contact with the interior glycosidic bonds in the crystalline domains of cellulose.

Unlike traditional catalysts known in the art used to hydrolyze cellulosic materials (e.g., enzymes, concentrated acids or dilute aqueous acids), the catalysts described herein provide effective cellulose digestion, as well as ease of recycle and reuse. The ability to recycle and reuse the catalyst presents several advantages, including reducing the cost of converting lignocellulose into industrially important chemicals, such as sugars, oligosaccharides, organic acids, alcohols and aldehydes. Unlike enzymes and dilute aqueous acids, the catalysts described herein can penetrate deeply into the crystalline structure of cellulose, resulting in higher yields and faster kinetics for hydrolyzing cellulosic materials to produce monosaccharides and/or oligosaccharides. Unlike concentrated acids, which require costly, energy-intensive solvent extraction and/or distillation processes to recover the catalyst following lignocellulose digestion, the catalysts described herein are less corrosive, more easily handled, and can be easily recovered because they naturally phase separate from aqueous products. Further, the use of the catalysts provided herein does not require solubilization of the cellulosic material in a solvent such as molten metal halides, ionic liquids, or acid/organic solvent mixtures.

Saccharification Using Disclosed Catalysts

In one aspect, provided are methods for saccharification of a feedstock containing cellulosic materials (e.g., biomass) using the catalysts described herein. Saccharification refers to the hydrolysis of cellulosic materials (e.g., biomass) into one or more sugars, by breaking down the complex carbohydrates of cellulose (and hemicellulose, where present) in the biomass. The one or more sugars can be monosaccharides and/or oligosaccharides. As used herein, "oligosaccharide" refers to a compound containing two or more monosaccharide units linked by glycosidic bonds. In certain embodiments, the one or more sugars are selected from glucose, cellobiose, xylose, xylulose, arabinose, mannose and galactose.

It should be understood that the cellulosic material can be subjected to a one-step or a multi-step hydrolysis process. For example, in some embodiments, the cellulosic material is first contacted with the catalyst, and then the resulting product is contacted with one or more catalysts in a second hydrolysis reaction (e.g., using enzymes).

The one or more sugars obtained from hydrolysis of cellulosic material can be used in a subsequent fermentation process to produce biofuels (e.g., ethanol) and other bio-based chemicals. For example, in some embodiments, the one or more sugars obtained by the methods described herein can undergo subsequent bacterial or yeast fermentation to produce biofuels and other bio-based chemicals.

Further, it should be understood that any method known in the art that includes pretreatment, enzymatic hydrolysis (saccharification), fermentation, or a combination thereof, can be used with the catalysts in the methods described herein. The catalysts can be used before or after pretreatment methods to make the cellulose (and hemicellulose, where present) in the biomass more accessible to hydrolysis.

The feedstocks provided for the methods described herein may be obtained from any source (including any commercially available sources), and are described in further detail below.

a) Feedstocks

In some embodiments, the feedstock used in the methods described herein can be selected from softwood, hardwood, cassava, bagasse, sugarbeet pulp, straw, paper sludge, oil palm, corn stover, food waste, enzymatic digestion residuals, and beer bottoms. A combination of feedstocks can also be used in the methods described herein. For example, the methods can use a combination of one or more softwoods and one or more hardwoods.

Softwoods (also known as conifers) can include, for example, Araucaria (e.g., Hoop Pine, Parana Pine, Chile Pine), Cedar (e.g., red cedar, white cedar, yellow cedar), Celery Top Pine, Cypress (e.g., Arizona Cypress, Bald Cypress, Hinoki Cypress, Lawson's Cypress, Mediterranean Cypress), Rocky Mountain Douglas-Fir, European Yew, Fir (e.g., Balsam Fir, Silver Fir, Noble Fir), Hemlock (e.g., Eastern Hemlock, Mountain Hemlock, Western Hemlock), Huan Pine, Kauri, Kaya, Larch (e.g., European Larch, Japanese Larch, Tamarack Larch, Western Larch), Pine (e.g., Corsican Pine, Jack Pine, Lodgepole Pine, Monterey Pine, Ponderosa Pine, Red Pine, Scots Pine, White Pine (e.g., Eastern White Pine, Western White Pine, Sugar Pine), Southern Yellow Pine (e.g., Loblolly Pine, Longleaf Pine, Pitch Pine, Shortleaf Pine), Redcedar (e.g., Eastern Redcedar, Western Redcedar), Redwood, Rimu, Spruce (e.g., Norway Spruce, Black Spruce, Red Spruce, Sitka Spruce, White Spruce), Sugi, Whitecedar (e.g., Northern Whitecedar, Southern Whitecedar), and Yellowcedar. In one embodiment, the softwood is pine.

Hardwoods (also known as angiosperms) can include, for example, African Zebrawood, Afzelia, Agba, Alder (e.g., Black Alder, Red Alder), Applewood, Ash (e.g., Black Ash, Blue Ash, Common Ash, Green Ash, Oregon Ash, Pumpkin Ash, White Ash), Aspen (e.g., Bigtooth Aspen, European Aspen, Quaking Aspen), Australian Red Cedar, Ayan, Balsa, Basswood (e.g., American Basswoord, White Basswood), Beech (e.g., European Beech, American Beech), Birch (e.g., Gray Birch, River Birch, Paper Birch, Sweet Birch, Yellow Birch, Silver Birch, White Birch), Blackbean, Blackgum, Blackwood (e.g., Australian Blackwood, African Blackwood), Bloodwood, Bocote, Boxelder, Brazilwood, Bubinga, Buckeye (e.g., Common Horse-Chestnut, Ohio Buckeye, Yellow Buckeye), Butternut, Camphor Laurel, Carapa, Catalpa, Chemy (e.g., Black Chemy, Red Chemy, Whild Chemy), Chestnut (e.g., Cape Chestnut), Coachwood, Cocobolo, Corkwood, Cottonwood (e.g., Balsam Poplar, Eastern Cottonwood, Plains Cottonwood, Swamp Cottonwood), Cucumbertree, Dogwood (e.g., Flowering Dogwood, Pacific Dogwood), Ebony (e.g., Andaman Marble-Wood, Ebène Marbre, Gabon Ebony), Elm (e.g., American Elm, English Elm, Rock Elm, Red Elm, Wych Elm), Eucalyptus (e.g., White Mahogany, Souther Mahogany, River Red Gum, Karri, Blue Gum, Flooded Gum, West Australian Eucalyptus, Tallowwood, Grey Ironbark, Blackbutt, Tasmanian Oak, Red Mahogany, Swamp Mahogany, Blue Gum, Ironbark), Goncalo Alves, Greenheart, Grenadilla, Gum, Hackberry, Hickory (e.g., Mockernut Hickory, Pecan, Pignut Hickory, Shagbark Hickory, Shellbark Hickory), Hornbeam, Hophornbeam, Ipe, Iroko, Brazilian rosewood, Jatobá, Kingwood, Lacewood, Laurel, Limba, Lignum vitae, Locust (e.g., Black Locust, Yellow Locust, Honey Locust), Maple (e.g., Sugar Maple, Black Maple, Manitoba Maple, Red Maple, Silver Maple, Sycamore Maple), Oak (e.g., Bur Oak, White Oak, Post Oak, Swamp White Oak, Southern Live Oak, Swamp Chestnut Oak, Chestnut Oak, Chinkapin Oak, Canyon Live Oak, Overcup Oak, English Oak, Red Oak, Black Oak, Laurel Oak, Southern Red Oak, Water Oak, Willow Oak, Nuttall's Oak), Obeche, Okoume, Olive, Oregan Myrtle, California Bay Laurel, Padauk Palisander, Pear, Pink Ivory, Poplar (e.g., Balsam Poplar, Black Poplar, Hybrid Poplar, Yellow Poplar), Purple Heart, Ramin, Redheart, Teak, Walnut (e.g., Black Walnut, Persian Walnut, Brazilian Walnut), Wenge, and Willow (e.g., Black Willow, Cricket-Bat Willow, White Willow). In certain embodiments, the hardwood is selected from birch, eucalyptus, aspen, maple, and any combination thereof.

The softwood or hardwood used in the methods described herein can be in any suitable form including, for example, chips, sawdust, bark, and any combination thereof.

Cassava (*Manihot esculenta*) is a woody shrub of the Euphorbiaceae (spurge family). Cassava stems can be used in the methods described herein.

Bagasse is the fibrous material (stalks and stems) that remains after sugarcane or sorghum stalks are crushed from juice extraction. Bagasse straw refers to the leaves of the sugarcane plant. Sugarbeet pulp is the byproduct that remains after processing the sugarbeets to extract sugar-containing juices.

Oil palm can include, for example, African Oil Palm, American Oil Palm, and Malaysian Oil Palm. The oil palm used in the methods described herein can be a palm oil waste material selected from empty fruit bunches, mesocarp fibre, palm kernel shell, and nut. In one embodiment, the oil palm is empty fruit bunch or mesocarp fibre.

Corn stover includes the leaves and stalks of maize (*Zea mays*).

Kenaf fibers include those found in the bark and core of the kenaf plant. Other fibers include wheat straw, rice straw, switch grass and miscanthus.

Food waste can include any food substance, in solid and/or liquid form, that is raw or cooked that is discarded or intends to be discarded. Food waste includes organic residues generated by the handling, storage, sale, preparation, cooking and serving of foods.

Enzymatic digestion residuals can include any residual biomass materials, in solid and/or liquid form, that results from the enzymatic hydrolysis of biomass. Enzymatic digestion residuals can include residual amounts of cellulose, hemicellulose, and/or lignin.

Beer bottoms can include any residual materials that results from the fermentation in a beer brewing process.

Paper sludge includes solid residue recovered from the wastewater stream from paper and pulp mills The feedstocks used in the methods described herein include cellulosic materials, which can include any material containing cellulose and/or hemicellulose. In certain embodiments, cellulosic materials can be lignocellulosic materials that contain lignin in addition to cellulose and/or hemicellulose. Cellulose is a polysaccharide that includes a linear chain of beta-(1-4)-D-glucose units. Hemicellulose is also a polysaccharide; however, unlike cellulose, hemicellulose is a branched polymer that typically includes shorter chains of sugar units. Hemicellulose can include a diverse number of sugar monomers including, for example, xylans, xyloglucans, arabinoxylans, and mannans.

Cellulosic materials can typically be found in biomass. In some embodiments, the methods described herein use a feedstock containing a substantial proportion of cellulosic material, such as about 5%, about 10%, about 15%, about 20%, about 25%, about 50%, about 75%, about 90% or greater than about 90% cellulose. In certain embodiments, cellulosic materials can include herbaceous materials, agricultural residues, forestry residues, municipal solid waste, waste paper, and pulp and paper mill residues. In certain embodiments, the cellulosic material is corn stover, corn fiber, or corn cob. In other embodiments, the cellulosic material is bagasse, rice straw, wheat straw, switch grass or miscanthus. In yet other embodiments, cellulosic material can also include chemical cellulose (e.g., Avicel®), industrial cellulose (e.g., paper or paper pulp), bacterial cellulose, or algal cellulose. As described herein and known in the art, the cellulosic materials can be used as obtained from the source, or can be subjected to one or pretreatments. For example, pretreated corn stover ("PCS") is a cellulosic material derived from corn stover by treatment with heat and/or dilute sulfuric acid, and is suitable for use with the catalysts described herein.

Several different crystalline structures of cellulose are known in the art. For example, crystalline cellulose are forms of cellulose where the linear beta-(1-4)-glucan chains can be packed into a three-dimensional superstructure. The aggregated beta-(1-4)-glucan chains are typically held together via inter- and intra-molecular hydrogen bonds. Steric hindrance resulting from the structure of crystalline cellulose can impede access of the reactive species, such as enzymes or chemical catalysts, to the beta-glycosidic bonds in the glucan chains. In contrast, non-crystalline cellulose and amorphous cellulose are forms of cellulose in which individual beta-(1-4)-glucan chains are not appreciably packed into a hydrogen-bonded super-structure, where access of reactive species to the beta-glycosidic bonds in the cellulose is hindered.

One of skill in the art would recognize that natural sources of cellulose can include a mixture of crystalline and non-crystalline domains. The regions of a beta-(1-4)-glucan chain where the sugar units are present in their crystalline form are referred to herein as the "crystalline domains" of the cellulosic material. Generally, the beta-(1-4)-glucan chains present in natural cellulose exhibit a number average degree of polymerization between about 1,000 and about 4,000 anhydroglucose ("AHG") units (i.e., about 1,000-4,000 glucose molecules linked via beta-glycosidic bonds), while the number average degree of polymerization for the crystalline domains is typically between about 200 and about 300 AHG units. See e.g., R. Rinaldi, R. Palkovits, and F. Schüth, *Angew. Chem. Int. Ed.*, 47, 8047-8050 (2008); Y.-H. P. Zhang and L. R. Lynd, *Biomacromolecules*, 6, 1501-1515 (2005).

Typically, cellulose has multiple crystalline domains that are connected by non-crystalline linkers that can include a small number of anhydroglucose units. One of skill in the art would recognize that traditional methods to digest biomass, such as dilute acidic conditions, can digest the non-crystalline domains of natural cellulose, but not the crystalline domains. Dilute acid treatment does not appreciably disrupt the packing of individual beta-(1-4)-glucan chains into a hydrogen-bonded super-structure, nor does it hydrolyze an appreciable number of glycosidic bonds in the packed beta-(1-4)-glucan chains. Consequently, treatment of natural cellulosic materials with dilute acid reduces the number average degree of polymerization of the input cellulose to approximately 200-300 anhydroglucose units, but does not further reduce the degree of polymerization of the cellulose to below about 150-200 anhydroglucose units (which is the typical size of the crystalline domains).

In certain embodiments, the catalysts described herein can be used to digest natural cellulosic materials. The catalysts can be used to digest crystalline cellulose by a chemical transformation in which the average degree of polymerization of cellulose is reduced to a value less than the average degree of polymerization of the crystalline domains. Digestion of crystalline cellulose can be detected by observing reduction of the average degree of polymerization of cellulose. In certain embodiments, the catalysts can reduce the average degree of polymerization of cellulose from at least about 300 AGH units to less than about 200 AHG units.

It should be understood that the catalysts described herein can be used to digest crystalline cellulose, as well as microcrystalline cellulose. One of skill in the art would recognize that crystalline cellulose typically has a mixture of crystalline and amorphous or non-crystalline domains, whereas microcrystalline cellulose typically refers to a form of cellulose where the amorphous or non-crystalline domains have been removed by chemical processing such that the residual cellulose substantially has only crystalline domains.

b) Pretreatment of the Feedstock

In some embodiments, the catalysts described herein can be used with feedstock that has been pretreated. In other embodiments, the catalysts described herein can be used with feedstock before pretreatment.

Any pretreatment process known in the art can be used to disrupt plant cell wall components of cellulosic material, including, for example, chemical or physical pretreatment processes. See, e.g., Chandra et al., Substrate pretreatment: The key to effective enzymatic hydrolysis of lignocellulosics?, *Adv. Biochem. Engin./Biotechnol.*, 108: 67-93 (2007); Galbe and Zacchi, Pretreatment of lignocellulosic materials for efficient bioethanol production, *Adv. Biochem. Engin./Biotechnol.*, 108: 41-65 (2007); Hendriks and Zeeman, Pretreatments to enhance the digestibility of lignocellulosic biomass, *Bioresource Technol.*, 100: 10-18 (2009); Mosier et al., Features of promising technologies for pretreatment of lignocellulosic biomass, *Bioresource Technol.*, 96: 673-686 (2005); Taherzadeh and Karimi, Pretreatment of lignocellulosic wastes to improve ethanol and biogas production: A review, *Int. J. of Mol. Sci.*, 9: 1621-1651 (2008); Yang and Wyman, Pretreatment: the key to unlocking low-cost cellulosic ethanol, *Biofuels Bioproducts and Biorefining (Biofpr)*, 2: 26-40 (2008). Examples of suitable pretreatment methods are described by Schell et al. (*Appl. Biochem. and Biotechnol.*, 105-108: 69-85 (2003) and Mosier et al. (*Bioresource Technol.*, 96: 673-686 (2005), and in U.S. Patent Application No. 2002/0164730.

Suitable pretreatments can include, for example, washing, solvent-extraction, solvent-swelling, comminution, milling, steam pretreatment, explosive steam pretreatment, dilute acid pretreatment, hot water pretreatment, alkaline pretreatment, lime pretreatment, wet oxidation, wet explosion, ammonia fiber explosion, organosolvent pretreatment, biological pretreatment, ammonia percolation, ultrasound, electroporation, microwave, supercritical CO2, supercritical H2O, ozone, and gamma irradiation, or a combination thereof. One of skill in the art would recognize the conditions suitable to pretreat biomass. See e.g., U.S. Patent Application No. 2002/0164730; Schell et al., Appl. Biochem. Biotechnol., 105-108: 69-85 (2003); Mosier et al., Bioresource Technol., 96: 673-686 (2005); Duff and Murray, Bioresource Technol., 855: 1-33 (1996); Galbe and Zacchi, Appl. Microbiol. Biotechnol., 59: 618-628 (2002); Ballesteros et al., Appl. Biochem. Biotechnol., 129-132: 496-508 (2006); Varga et al., Appl. Biochem. Biotechnol., 113-116: 509-523 (2004); Sassner et al., Enzyme Microb. Technol., 39: 756-762 (2006); Schell et al., Bioresource Technol., 91: 179-188 (2004); Lee et al., Adv. Biochem. Eng. Biotechnol., 65: 93-115 (1999); Wyman et al., Bioresource Technol., 96: 1959-1966 (2005); Mosier et al., Bioresource Technol., 96: 673-686 (2005); Schmidt and Thomsen, Bioresource Technol., 64: 139-151 (1998); Palonen et al., Appl. Biochem. Biotechnol., 117: 1-17 (2004); Varga et al., Biotechnol. Bioeng., 88: 567-574 (2004); Martin et al., J. Chem. Technol. Biotechnol., 81: 1669-1677 (2006); WO 2006/032282; Gollapalli et al., Appl. Biochem. Biotechnol., 98: 23-35 (2002); Chundawat et al., Biotechnol. Bioeng., 96: 219-231 (2007); Alizadeh et al., Appl. Biochem. Biotechnol., 121: 1133-1141 (2005); Teymouri et al., Bioresource Technol., 96: 2014-2018 (2005); Pan et al., Biotechnol. Bioeng., 90: 473-481 (2005); Pan et al., Biotechnol. Bioeng., 94: 851-861 (2006); Kurabi et al., Appl. Biochem. Biotechnol., 121: 219-230 (2005); Hsu, T.-A., Pretreatment of Biomass, in Handbook on Bioethanol: Production and Utilization, Wyman, C. E., ed., Taylor & Francis, Washington, D.C., 179-212 (1996); Ghosh and Singh, Physicochemical and biological treatments for enzymatic/microbial conversion of cellulosic biomass, Adv. Appl. Microbiol., 39: 295-333 (1993); McMillan, J. D., Pretreating lignocellulosic biomass: a review, in Enzymatic Conversion of Biomass for Fuels Production, Himmel, M. E., Baker, J. O., and Overend, R. P., eds., ACS Symposium Series 566, American Chemical Society, Washington, D.C., Chapter 15 (1994); Gong, C. S., Cao, N. J., Du, J., and Tsao, G. T., Ethanol production from renewable resources, in Advances in Biochemical Engineering/Biotechnology, Scheper, T., ed., Springer-Verlag Berlin Heidelberg, Germany, 65: 207-241 (1999); Olsson and Hahn-Hagerdal, Fermentation of lignocellulosic hydrolysates for ethanol production, Enz. Microb. Tech., 18: 312-331 (1996); and Vallander and Eriksson, Production of ethanol from lignocellulosic materials: State of the art, Adv. Biochem. Eng./Biotechnol., 42: 63-95 (1990).

In other embodiments, the catalysts described herein can be used with feedstock that has not been pretreated. Further, the feedstock can also be subjected to other processes instead of or in addition to pretreatment including, for example, particle size reduction, pre-soaking, wetting, washing, or conditioning.

Moreover, the use of the term "pretreatment" does not imply or require any specific timing of the steps of the methods described herein. For example, the feedstock can be pretreated before hydrolysis. Alternatively, the pretreatment can be carried out simultaneously with hydrolysis. In some embodiments, the pretreatment step itself results in some conversion of biomass to sugars (for example, even in the absence of the catalysts described herein).

Disclosed herein is a method for pretreating feedstock before hydrolysis of the biomass to produce one or more sugars, comprising:

a) providing feedstock;

b) combining the feedstock with a disclosed catalyst for a period of time sufficient to partially degrade the feedstock; and c) pretreating the partially degraded feedstock before hydrolysis to produce one or more sugars.

Step b) can further include combining the feedstock and the catalyst with a solvent, such as water. The feedstock of step a) can include cellulose, hemicellulose, or a combination thereof. In some embodiments, pretreating the partially degraded feedstock can include washing, solvent-extraction, solvent-swelling, comminution, milling, steam pretreatment, explosive steam pretreatment, dilute acid pretreatment, hot water pretreatment, alkaline pretreatment, lime pretreatment, wet oxidation, wet explosion, ammonia fiber explosion, organosolvent pretreatment, biological pretreatment, ammonia percolation, ultrasound, electroporation, microwave, supercritical $CO_2$, supercritical $H_2O$, ozone, and gamma irradiation, or a combination thereof.

Further, the pretreated partially degraded biomass can be hydrolyzed to produce one or more sugars. Either chemical or enzymatic hydrolysis methods can be used. In some embodiments, the one or more sugars can include glucose, galactose, fructose, xylose, and arabinose.

Provided herein are methods of hydrolyzing pretreated feedstock to produce one or more sugars, comprising:

a) providing pretreated feedstock; and b) hydrolyzing the pretreated feedstock to produce one or more sugars.

The pretreated feedstock can be hydrolyzed using catalysts as described herein, or other methods such as, but not limited to, chemical and enzymatic hydrolysis. In some embodiments, the sugars obtained are selected from glucose, galactose, fructose, xylose, and arabinose.

Several common methods that can be used to pretreat cellulose materials for use with the catalysts are described below.

Steam Pretreatment

Feedstock containing cellulosic materials is heated to disrupt the plant cell wall components (e.g., lignin, hemicellulose, cellulose) to make the cellulose and/or hemicellulose more accessible to enzymes. The feedstock is typically passed to or through a reaction vessel, where steam is injected to increase the temperature to the required temperature and pressure is retained therein for the desired reaction time.

In certain embodiments where steam pretreatment is employed to pretreat the cellulosic materials, the pretreatment can be performed at a temperature between about 140° C. and about 230° C., between about 160° C. and about 200° C., or between about 170° C. and about 190° C. It should be understood, however, that the optimal temperature range for steam pretreatment can vary depending on the polymeric catalyst used.

In certain embodiments, the residence time for the steam pretreatment is about 1 to about 15 minutes, about 3 to about 12 minutes, or about 4 to about 10 minutes. It should be understood, however, that the optimal residence time for steam pretreatment can vary depending on the temperature range and the polymeric catalyst used.

In some embodiments, steam pretreatment can be combined with an explosive discharge of the material after the pretreatment, which is known as steam explosion—a rapid flashing to atmospheric pressure and turbulent flow of the material to increase the accessible surface area by fragmentation. See Duff and Murray, *Bioresource Technol.*, 855: 1-33 (1996); Galbe and Zacchi, *Appl. Microbiol. Biotechnol.*, 59: 618-628 (2002); U.S. Patent Application No. 2002/0164730.

During steam pretreatment, acetyl groups in hemicellulose can be cleaved, and the resulting acid can autocatalyze the partial hydrolysis of the hemicellulose to monosaccharides and/or oligosaccharides. One of skill in the art would recognize, however, that lignin (when present in the feedstock) is removed to only a limited extent. Thus, in certain embodiments, a catalyst such as sulfuric acid (typically 0.3% to 3% w/w) can be added prior to steam pretreatment, to decrease the time and temperature, increase the recovery, and improve enzymatic hydrolysis. See Ballesteros et al., *Appl. Biochem. Biotechnol.*, 129-132: 496-508 (2006); Varga et al., *Appl. Biochem. Biotechnol.*, 113-116: 509-523 (2004); Sassner et al., *Enzyme Microb. Technol.*, 39: 756-762 (2006).

Chemical Pretreatment

Chemical pretreatment of feedstock can promote the separation and/or release of cellulose, hemicellulose, and/or lignin by chemical processes. Examples of suitable chemical pretreatment processes include, for example, dilute acid pretreatment, lime pretreatment, wet oxidation, ammonia fiber/freeze explosion (AFEX), ammonia percolation (APR), and organosolvent pretreatments.

In one embodiment, dilute or mild acid pretreatment can be employed. Cellulosic material can be mixed with a dilute acid and water to form a slurry, heated by steam to a certain temperature, and after a residence time flashed to atmospheric pressure. Suitable acids for this pretreatment method can include, for example, sulfuric acid, acetic acid, citric acid, nitric acid, phosphoric acid, tartaric acid, succinic acid, hydrogen chloride, or mixtures thereof. In one variation, sulfuric acid is used. The dilute acid treatment can be conducted in a pH range of about 1-5, a pH range of about 1-4, or a pH range of about 1-3. The acid concentration can be in the range from about 0.01 to about 20 wt % acid, about 0.05 to about 10 wt % acid, about 0.1 to about 5 wt % acid, or about 0.2 to about 2.0 wt % acid. The acid is contacted with cellulosic material, and can be held at a temperature in the range of about 160-220° C., or about 165-195° C., for a period of time ranging from seconds to minutes (e.g., about 1 second to about 60 minutes). The dilute acid pretreatment can be performed with a number of reactor designs, including for example plug-flow reactors, counter-current reactors, and continuous counter-current shrinking bed reactors. See Duff and Murray (1996), supra; Schell et al., *Bioresource Technol.*, 91: 179-188 (2004); Lee et al., *Adv. Biochem. Eng. Biotechnol.*, 65: 93-115 (1999).

In another embodiment, an alkaline pretreatment can be employed. Examples of suitable alkaline pretreatments include, for example, lime pretreatment, wet oxidation, ammonia percolation (APR), and ammonia fiber/freeze explosion (AFEX). Lime pretreatment can be performed with calcium carbonate, sodium hydroxide, or ammonia at temperatures of about 85° C. to about 150° C., and at residence times from about 1 hour to several days. See Wyman et al., *Bioresource Technol.*, 96: 1959-1966 (2005); Mosier et al., *Bioresource Technol.*, 96: 673-686 (2005).

In yet another embodiment, wet oxidation can be employed. Wet oxidation is a thermal pretreatment that can be performed, for example, at 180° C. to 200° C. for 5-15 minutes with addition of an oxidative agent such as hydrogen peroxide or over-pressure of oxygen. See Schmidt and Thomsen, *Bioresource Technol.*, 64: 139-151 (1998); Palonen et al., *Appl. Biochem. Biotechnol.*, 117: 1-17 (2004); Varga et al., *Biotechnol. Bioeng.*, 88: 567-574 (2004); Martin et al., *J. Chem. Technol. Biotechnol.*, 81: 1669-1677 (2006). Wet oxidation can be performed, for example, at about 1-40% dry matter, about 2-30% dry matter, or about 5-20% dry matter, and the initial pH can also be increased by the addition of alkali (e.g., sodium carbonate). A modification of the wet oxidation pretreatment method, known as wet explosion—a combination of wet oxidation and steam explosion, can handle dry matter up to about 30%. In wet explosion, the oxidizing agent can be introduced during pretreatment after a certain residence time, and the pretreatment can end by flashing to atmospheric pressure. See WO 2006/032282.

In yet another embodiment, pretreatment methods using ammonia can be employed. See e.g., WO 2006/110891; WO 2006/11899; WO 2006/11900; and WO 2006/110901. For example, ammonia fiber explosion (AFEX) involves treating the feedstock with liquid or gaseous ammonia at moderate temperatures (e.g., about 90-100° C.) and at high pressure (e.g., about 17-20 bar) for a given duration (e.g., about 5-10 minutes), where the dry matter content can be in some instances as high as about 60%. See Gollapalli et al., *Appl. Biochem. Biotechnol.*, 98: 23-35 (2002); Chundawat et al., *Biotechnol. Bioeng.*, 96: 219-231 (2007); Alizadeh et al., *Appl. Biochem. Biotechnol.*, 121: 1133-1141 (2005); Teymouri et al., *Bioresource Technol.*, 96: 2014-2018 (2005). AFEX pretreatment can depolymerize cellulose, partial hydrolyze hemicellulose, and, in some instances, cleave some lignin-carbohydrate complexes.

Organosolvent Pretreatment

An organosolvent solution can be used to delignify cellulosic material. In one embodiment, an organosolvent pretreatment involves extraction using aqueous ethanol (e.g., about 40-60% ethanol) at an elevated temperature (e.g., about 160-200° C.) for a period of time (e.g., about 30-60 minutes). See Pan et al., Biotechnol. Bioeng., 90: 473-481 (2005); Pan et al., Biotechnol. Bioeng., 94: 851-861 (2006); Kurabi et al., Appl. Biochem. Biotechnol., 121: 219-230 (2005). In one variation, sulfuric acid is added to the organosolvent solution as a catalyst to delignify the cellulosic material. One of skill in the art would recognize that an organosolvent pretreatment can typically breakdown the majority of hemicellulose.

Physical Pretreatment

Physical pretreatment of feedstock can promote the separation and/or release of cellulose, hemicellulose, and/or lignin by physical processes. Examples of suitable physical pretreatment processes can involve irradiation (e.g., microwave irradiation), steaming/steam explosion, hydrothermolysis, and combinations thereof.

Physical pretreatment can involve high pressure and/or high temperature. In one embodiment, the physical pretreatment is steam explosion. In some variations, high pressure refers to a pressure in the range of about 300-600 psi, about 350-550 psi, or about 400-500 psi, or about 450 psi. In some variations, high temperature refers to temperatures in the range of about 100-300° C., or about 140-235° C.

In another embodiment, the physical pretreatment is a mechanical pretreatment. Suitable examples of mechanical pretreatment can include various types of grinding or milling (e.g., dry milling, wet milling, or vibratory ball milling). In some variations, mechanical pretreatment is performed in a batch-process, such as in a steam gun hydrolyzer system that uses high pressure and high temperature (e.g., a Sunds Hydrolyzer available from Sunds Defibrator AB, Sweden).

Combined Physical and Chemical Pretreatment

In some embodiments, the feedstock can be pretreated both physically and chemically. For instance, in one variation, the pretreatment step can involve dilute or mild acid treatment and high temperature and/or pressure treatment. It should be understood that the physical and chemical pretreatments can be carried out sequentially or simultaneously. In other variation, the pretreatment can also include a mechanical pretreatment, in addition to chemical pretreatment.

Biological Pretreatment

Biological pretreatment techniques can involve applying lignin-solubilizing microorganisms. See, e.g., Hsu, T.-A., Pretreatment of Biomass, in Handbook on Bioethanol: Production and Utilization, Wyman, C. E., ed., Taylor & Francis, Washington, D.C., 179-212 (1996); Ghosh and Singh, Physicochemical and biological treatments for enzymatic/microbial conversion of cellulosic biomass, *Adv. Appl. Microbiol.*, 39: 295-333 (1993); McMillan, J. D., Pretreating lignocellulosic biomass: a review, in Enzymatic Conversion of Biomass for Fuels Production, Himmel, M. E., Baker, J. O., and Overend, R. P., eds., ACS Symposium Series 566, American Chemical Society, Washington, D.C., chapter 15 (1994); Gong, C. S., Cao, N. J., Du, J., and Tsao, G. T., Ethanol production from renewable resources, in Advances in Biochemical Engineering/Biotechnology, Scheper, T., ed., Springer-Verlag Berlin Heidelberg, Germany, 65: 207-241 (1999); Olsson and Hahn-Hagerdal, Fermentation of lignocellulosic hydrolysates for ethanol production, *Enz. Microb. Tech.*, 18: 312-331 (1996); and Vallander and Eriksson, Production of ethanol from lignocellulosic materials: State of the art, *Adv. Biochem. Eng./Biotechnol.*, 42: 63-95 (1990). In some embodiments, pretreatment can be performed in an aqueous slurry. In other embodiments, the feedstock is present during pretreatment in amounts between about 10-80 wt %, between about 20-70 wt %, or between about 30-60 wt %, or about 50 wt %. Furthermore, after pretreatment, the pretreated feedstock can be unwashed or washed using any method known in the art (e.g., washed with water) before hydrolysis to produce one or more sugars or use with the catalyst.

c) Saccharification

In some embodiments of any of the methods described above, the catalyst is capable of degrading the feedstock (e.g., softwood, hardwood, cassava, bagasse, sugarbeet pulp, straw, paper sludge, oil palm, corn stover, food waste, enzymatic digestion residuals, beer bottoms, and any combination thereof) into one or more sugars at a first-order rate constant of at least about 0.001 per hour. In other embodiments, the catalyst is capable of degrading the feedstock (e.g., softwood, hardwood, cassava, bagasse, sugarbeet pulp, straw, paper sludge, oil palm, corn stover, food waste, enzymatic digestion residuals, beer bottoms, and any combination thereof) to produce the sugars at a first-order rate constant of at least about 0.1, at least about 0.15, at least about 0.2, at least about 0.25, at least about 0.3 or at least about 0.5 per hour.

In some embodiments of any of the methods described above, the catalyst is capable of converting the feedstock (e.g., softwood, hardwood, cassava, bagasse, sugarbeet pulp, straw, paper sludge, oil palm, corn stover, food waste, enzymatic digestion residuals, beer bottoms, and any combination thereof) into one or more sugars and residual biomass, wherein the residual feedstock has a degree of polymerization of less than about 300. In other embodiments, the catalyst is capable of converting the feedstock (e.g., softwood, hardwood, cassava, bagasse, sugarbeet pulp, straw, paper sludge, oil palm, corn stover, food waste, enzymatic digestion residuals, beer bottoms, and any combination thereof) into one or more sugars and residual feedstock, wherein the residual feedstock has a degree of polymerization of less than about 100, less than about 90, less than about 80, less than about 70, less than about 60, or less than about 50.

Saccharification is typically performed in stirred-tank reactors or vessels under controlled pH, temperature, and mixing conditions. One skilled in the art would recognize that suitable processing time, temperature and pH conditions can vary depending on the type of feedstock (including the type and amount of cellulosic material in the feedstock), catalyst, and solvent used. These factors are described in further detail below.

In one aspect, provided is a method of producing one or more sugars from feedstock, by:

a) providing a first composition comprising feedstock selected from softwood, hardwood, cassava, bagasse, sugarbeet pulp, straw, paper sludge, oil palm, corn stover, food waste, enzymatic digestion residuals, beer bottoms, and any combination thereof;

b) providing an effective amount of a catalyst to form a reaction mixture, wherein the catalyst is a polymeric catalyst or a solid-supported catalyst, wherein the polymeric catalyst includes acidic monomers and ionic monomers connected to form a polymeric backbone, wherein a plurality of acidic monomers independently includes at least one Bronsted-Lowry acid, and wherein a plurality of ionic monomers independently includes at least one nitrogen-containing cationic group, at least one phosphorous-containing cationic group, or a combination thereof, wherein the solid-supported catalyst includes a solid support, acidic moieties attached to the solid support, and ionic moieties attached to the solid support, wherein a plurality of acidic moieties independently includes at least one Bronsted-Lowry acid, and wherein a plurality of ionic moieties independently includes at least one nitrogen-containing cationic group, at least one phosphorous-containing cationic group, or a combination thereof;

c) degrading the feedstock in the reaction mixture to produce a liquid phase and a solid phase, wherein the liquid phase includes one or more sugars, and the solid phase includes residual feedstock;

d) isolating at least a portion of the liquid phase from the solid phase; and e) recovering the one or more sugars from the isolated liquid phase.

Also disclosed herein is a method of producing one or more sugars from feedstock, by:

a) providing a first composition comprising feedstock selected from softwood, hardwood, cassava, bagasse, sugarbeet pulp, straw, paper sludge, oil palm, corn stover, food waste, enzymatic digestion residuals, beer bottoms, and any combination thereof; and b) providing an effective amount of a catalyst composition to form a reaction mixture, wherein the catalyst is a polymeric catalyst or a solid-supported catalyst, wherein the polymeric catalyst includes acidic monomers and ionic monomers connected to form a polymeric backbone, wherein a plurality of acidic monomers independently includes at least one Bronsted-Lowry acid, and wherein a plurality of ionic monomers independently includes at least one nitrogen-containing cationic group, at least one phosphorous-containing cationic group, or a combination thereof, wherein the solid-supported catalyst includes a solid support, acidic moieties attached to the solid support, and ionic moieties attached to the solid support, wherein a plurality of acidic moieties independently includes at least one Bronsted-Lowry acid, and wherein a plurality of ionic moieties independently includes at least one nitrogen-containing cationic group, at least one phosphorous-containing cationic group, or a combination thereof.

The method can further include c) degrading the feedstock in the reaction mixture to produce a liquid phase and a solid phase, wherein the liquid phase includes one or more sugars, and the solid phase includes residual feedstock.

In some embodiments, the method can further include d) isolating at least a portion of the liquid phase from the solid phase; and e) recovering the one or more sugars from the isolated liquid phase.

In some embodiments, the residual feedstock has at least a portion of the catalyst composition. The catalyst composition can be isolated from the solid phase, either before or after isolation step d). In some embodiments, isolating a portion of the composition from the solid phase occurs substantially contemporaneously with step d). "Substantially contemporaneously" as used herein refers to two or more steps occurring during time periods that overlap at least about 5%, at least about 10%, at least about 20%, at least about 30%, at least about 40% or at least about 50% of the time.

In some embodiments, the first composition can be contacted with a solvent, such as water.

In some embodiments, the isolating at least a portion of the liquid phase from the solid phase in step (d) produces a residual feedstock mixture, and the method further includes:

i) providing additional feedstock (e.g., softwood, hardwood, cassava, bagasse, sugarbeet pulp, straw, paper sludge, sugarbeet pulp, straw, paper sludge, oil palm, corn stover, food waste, enzymatic digestion residuals, beer bottoms, and any combination thereof);

ii) contacting the additional feedstock with the residual feedstock mixture;

iii) degrading the additional feedstock and the residual feedstock mixture to produce a second liquid phase and a second solid phase, wherein the second liquid phase includes one or more additional sugars, and wherein the second solid phase includes additional residual feedstock;

iv) isolating at least a portion of the second liquid phase from the second solid phase; and v) recovering the one or more additional sugars from the isolated second liquid phase.

In some embodiments, the additional feedstock (e.g., softwood, hardwood, cassava, bagasse, sugarbeet pulp, straw, paper sludge, oil palm, corn stover, food waste, enzymatic digestion residuals, beer bottoms, and any combination thereof) in step (i) is the same type or a different type as the feedstock in step (a). In other embodiments, the one or more additional sugars produced in step (iii) is the same or a different type as the one or more sugars produced in step (c).

In certain embodiments, the method further includes contacting the additional feedstock and the residual feedstock mixture in step (iii) with additional catalyst, in which the additional catalyst can be any of the catalysts described herein (e.g., a polymeric catalyst, a solid-supported catalyst, or a combination thereof). In certain embodiments, the additional catalyst is the same or different as the catalyst in step (b). In some embodiments, the additional feedstock mixture is combined with at least a portion of the catalyst composition.

In other embodiments, the method further includes contacting the additional feedstock and the residual feedstock mixture with additional solvent. In certain embodiments, the additional solvent is the same or different as the solvent in step (b). In one embodiment, the additional solvent includes water.

In some embodiments, the second feedstock comprises cellulose, hemicellulose, or a combination thereof. In other embodiments, the residual feedstock mixture comprises at least a portion of the composition that has an effective amount of the polymeric catalyst.

In some embodiments, the method further includes recovering the catalyst after isolating at least a portion of the second liquid phase.

The feedstock can be selected from softwood, hardwood, cassava, bagasse, sugarbeet pulp, straw, paper sludge, oil palm, corn stover, food waste, enzymatic digestion residuals, and beer bottoms, or any combination thereof. In one embodiment, the feedstock is softwood. In one embodiment, the feedstock is hardwood. In one embodiment, the feedstock is cassava. In one embodiment, the feedstock is bagasse. In one embodiment, the feedstock is sugarbeet pulp. In one embodiment, the feedstock is straw. In one embodiment, the feedstock is paper sludge. In one embodiment, the feedstock is oil palm. In one embodiment, the feedstock is corn stover. In one embodiment, the feedstock is food waste. In one embodiment, the feedstock is enzymatic digestion residuals. In one embodiment, the feedstock is beer bottoms.

In some embodiments of any of the methods described above, the catalyst described herein has one or more catalytic properties selected from:

a) disruption of a hydrogen bond in cellulosic materials;

b) intercalation of the catalyst into crystalline domains of cellulosic materials; and c) cleavage of a glycosidic bond in cellulosic materials.

In some embodiments of any of the methods described above, the catalyst has a greater specificity for cleavage of a glycosidic bond than dehydration of a monosaccharide in cellulosic materials.

In some embodiments, the feedstock includes cellulose and hemicellulose, and during the above method, the feedstock is combined with the catalyst at a temperature and at a pressure suitable to a) hydrolyze the cellulose to a greater extent than the hemicellulose, or b) hydrolyze the hemicellulose to a greater extent than the cellulose.

In some embodiments, the additional feedstock and the residual feedstock mixture are combined with a second catalyst as disclosed herein. In some embodiments, the additional feedstock and the residual feedstock mixture are combined with a second solvent, such as water. In some embodiments, the second feedstock has at least a portion of the composition that has an effective amount of the catalyst. This composition, or a portion thereof, can be isolated from the additional residual feedstock. The portion can be isolated from the second solid phase, either before or after step iv). In some embodiments, isolating a portion of the composition from the second solid phase occurs substantially contemporaneously with step iv).

The one or more sugars produced in these methods can be selected from one or more monosaccharides, one or more oligosaccharides, or a combination thereof. The one or more monosaccharides can include one or more C4-C6 monosaccharides. In some embodiments, the monosaccharides can be selected from glucose, galactose, fructose, xylose, and arabinose.

Processing Time, Temperature and pH Conditions

In some embodiments, saccharification can last up to about 200 hours. In other embodiments, the feedstock can be in contact with the catalyst from about 1 to about 96 hours, from about 12 to about 72 hours, or from about 12 to about 48 hours.

In some embodiments, the feedstock can be in contact with the polymer at temperature in the range of about 25° C. to about 150° C. In other embodiments, the feedstock can be in contact with the polymer in the range of about 30° C. to about 125° C., about 30° C. to about 140° C., about 80° C. to about 120° C., about 80° C. to about 130° C., about 100° C. to 110° C., or about 100° C. to about 130° C.

The pH for saccharification is generally affected by the intrinsic properties of the catalyst used. In some embodiments, the acidic moiety of the catalyst can affect the pH of saccharification. For example, the use of sulfuric acid moiety in a catalyst results in saccharification at a pH of about 3. In other embodiments, saccharification is performed at a pH between about 0 and about 6. The reacted effluent typically has a pH of at least about 4, or a pH that is compatible with other processes such as enzymatic treatment. It should be understood, however, that the pH can be modified and controlled by the addition of acids, bases or buffers.

Moreover, the pH can vary within the reactor. For example, high acidity at or near the surface of the catalyst can be observed, whereas regions distal to the catalyst surface can have a substantially neutral pH. Thus, one of skill would recognize that determination of the solution pH should account for such spatial variation.

It should also be understood that, in certain embodiments, the saccharification methods described herein can further include monitoring the pH of the saccharification reaction, and optionally adjusting the pH within the reactor. In some instances, as a low pH in solution can indicate an unstable catalyst, in which the catalyst can be losing at least a portion of its acidic groups to the surrounding environment through leaching. In some embodiments, the pH near the surface of the catalyst is below about 7, below about 6, or below about 5.

Amount of Feedstock Used

The amount of the feedstock used in the methods described herein relative to the amount solvent used can affect the rate of reaction and yield. The amount of the cellulosic material used can be characterized by the dry solids content. In certain embodiments, dry solids content refers to the total solids of a slurry as a percentage on a dry weight basis. In some embodiments, the dry solids content of the cellulosic materials is between about 5 wt % to about 95 wt %, between about 10 wt % to about 80 wt %, between about 15 wt % to about 75 wt %, or between about 15 wt % to about 50 wt %.

Amount of Catalyst Used

The amount of the polymeric catalysts used in the saccharification methods described herein can depend on several factors including, for example, the type of cellulosic material, the concentration of the cellulosic material, the type and number of pretreatment(s) applied to the cellulosic material, and the reaction conditions (e.g., temperature, time, and pH). In one embodiment, the weight ratio of the catalyst to the cellulose material is about 0.1 g/g to about 50 g/g, about 0.1 g/g to about 25 g/g, about 0.1 g/g to about 10 g/g, about 0.1 g/g to about 5 g/g, about 0.1 g/g to about 2 g/g, about 0.1 g/g to about 1 g/g, or about 0.1 to about 1.0 g/g. An effective amount of the polymeric catalysts disclosed herein refers to an amount sufficient to degrade biomass to, for instance, attain one or more desired factor levels listed above. A non-limiting example would be that the effective amount is the amount of catalyst that would degrade more than about 5%, more than about 10%, more than about 20%, more than about 30%, more than about 40%, or more than about 50%. In some embodiments, the effective amount can be any of the weight ratio ranges listed above.

Solvent

In certain embodiments, hydrolysis using the catalyst is carried out in an aqueous environment. One suitable aqueous solvent is water, which can be obtained from various sources. Generally, water sources with lower concentrations of ionic species are useful, as such ionic species can reduce effectiveness of the catalyst. In some embodiments where the aqueous solvent is water, the water has less than about 10% of ionic species (e.g., salts of sodium, phosphorous, ammonium, magnesium, or other species found naturally in lignocellulosic biomass).

Moreover, as the cellulosic material in the feedstock is hydrolyzed, water is consumed on a mole-for-mole basis with the sugars produced. In certain embodiments, the saccharification methods described herein can further include monitoring the amount of water present in the saccharification reaction and/or the ratio of water to biomass over a period of time. In other embodiments, the saccharification methods described herein can further include supplying water directly to the reaction, for example, in the form of steam or steam condensate. For example, in some embodiments, the hydration conditions in the reactor are such that the water-to-cellulosic material ratio is about 5:1, about 4:1, about 3:1, about 2:1, about 1:1, about 1:2, about 1:3, about 1:4, about 1:5, or less than about 1:5. It should be understood, however, that the ratio of water to cellulosic material can be adjusted based on the specific catalyst used.

Batch Versus Continuous Processing

Generally, the catalyst and the feedstock are introduced into an interior chamber of a reactor, either concurrently or sequentially. Saccharification can be performed in a batch process or a continuous process. For example, in one embodiment, saccharification is performed in a batch process, where the contents of the reactor are continuously mixed or blended, and all or a substantial amount of the products of the reaction are removed. In one variation, saccharification is performed in a batch process, where the contents of the reactor are initially intermingled or mixed but no further physical mixing is performed. In another variation, saccharification is performed in a batch process, wherein once further mixing of the contents, or periodic mixing of the contents of the reactor, is performed (e.g., at one or more times per hour), all or a substantial amount of the products of the reaction are removed after a certain period of time.

In other embodiments, saccharification is performed in a continuous process, where the contents flow through the reactor with an average continuous flow rate but with no explicit mixing. After introduction of the catalyst and the feedstock into the reactor, the contents of the reactor are continuously or periodically mixed or blended, and after a period of time, less than all of the products of the reaction are removed. In one variation, saccharification is performed in a continuous process, where the mixture containing the catalyst and feedstock is not actively mixed. Additionally, mixing of catalyst and feedstock can occur as a result of the redistribution of catalysts settling by gravity, or the non-active mixing that occurs as the material flows through a continuous reactor.

Reactors

The reactors used for the saccharification methods described herein can be open or closed reactors suitable for use in containing the chemical reactions described herein. Suitable reactors can include, for example, a fed-batch stirred reactor, a batch stirred reactor, a continuous flow stirred reactor with ultrafiltration, a continuous plug-flow column reactor, an attrition reactor, or a reactor with intensive stirring induced by an electromagnetic field. See e.g., Fernanda de Castilhos Corazza, Flavio Faria de Moraes, Gisella Maria Zanin and Ivo Neitzel, Optimal control in fed-batch reactor for the cellobiose hydrolysis, *Acta Scientiarum. Technology*, 25: 33-38 (2003); Gusakov, A. V., and Sinitsyn, A. P., Kinetics of the enzymatic hydrolysis of cellulose: 1. A mathematical model for a batch reactor process, *Enz. Microb. Technol.*, 7: 346-352 (1985); Ryu, S. K., and Lee, J. M., Bioconversion of waste cellulose by using an attrition bioreactor, Biotechnol. Bioeng. 25: 53-65 (1983); Gusakov, A. V., Sinitsyn, A. P., Davydkin, I. Y., Davydkin, V. Y., Protas, O. V., Enhancement of enzymatic cellulose hydrolysis using a novel type of bioreactor with intensive stirring induced by electromagnetic field, *Appl. Biochem. Biotechnol.*, 56: 141-153 (1996). Other suitable reactor types can include, for example, fluidized bed, upflow blanket, immobilized, and extruder type reactors for hydrolysis and/or fermentation.

In certain embodiments where saccharification is performed as a continuous process, the reactor can include a continuous mixer, such as a screw mixer. The reactors can be generally fabricated from materials that are capable of withstanding the physical and chemical forces exerted during the processes described herein. In some embodiments, such materials used for the reactor are capable of tolerating high concentrations of strong liquid acids; however, in other embodiments, such materials can not be resistant to strong acids.

At the start of the hydrolysis on larger scale, the reactor can be filled with cellulosic material by a top-load feeder containing a hopper capable of holding cellulosic material. Further, the reactor typically contains an outlet means for removal of contents (e.g., a sugar-containing solution) from the reactor. Optionally, such outlet means is connected to a device capable of processing the contents removed from the reactor. Alternatively, the removed contents are stored. In some embodiments, the outlet means of the reactor is linked to a continuous incubator into which the reacted contents are introduced. Further, the outlet means provides for removal of residual cellulosic material by, e.g., a screw feeder, by gravity, or a low shear screw.

It should also be understood that additional feedstock and/or catalyst can be added to the reactor, either at the same time or one after the other.

Rate and Yield of Saccharification

The use of the catalysts described herein can increase the rate and/or yield of saccharification. The ability of the catalyst to hydrolyze the cellulose and hemicellulose components of biomass to soluble sugars can be measured by determining the effective first-order rate constant, $$k_1(\text{species } i) = -\frac{\ln(1 - X_i)}{\Delta t},$$

where $\Delta t$ is the duration of the reaction and $X_i$ is the extent of reaction for species i (e.g., glucan, xylan, arabinan). In some embodiments, the catalysts described herein are capable of degrading biomass into one or more sugars at a first-order rate constant of at least about 0.001 per hour, at least about 0.01 per hour, at least about 0.1 per hour, at least about 0.2 per hour, at least about 0.3 per hour, at least about 0.4 per hour, at least about 0.5 per hour, or at least about 0.6 per hour.

The hydrolysis yield of the cellulose and hemicellulose components of feedstock to soluble sugars by the catalyst can be measured by determining the degree of polymerization of the residual biomass. The lower the degree of polymerization of the residual biomass, the greater the hydrolysis yield. In some embodiments, the catalysts described herein are capable of converting feedstock into one or more sugars and residual biomass, wherein the residual biomass has a degree of polymerization of less than about 300, less than about 250, less than about 200, less than about 150, less than about 100, less than about 90, less than about 80, less than about 70, less than about 60, or less than about 50.

d) Separation and Purification of the Sugars

In some embodiments, the methods for producing one or more sugars from the feedstock using the catalysts described herein further include recovering the sugars that are produced from the hydrolysis of the feedstock. In another embodiment, the method for producing one or more sugars from the feedstock using the catalyst described herein further includes recovering the degraded or converted feedstock.

The sugars, which are typically soluble, can be separated from the insoluble residual feedstock using technology well known in the art such as, for example, centrifugation, filtration, and gravity settling.

Separation of the sugars can be performed in the hydrolysis reactor or in a separator vessel. In an exemplary embodiment, the method for producing one or more sugars from the feedstock is performed in a system with a hydrolysis reactor and a separator vessel. Reactor effluent containing the monosaccharides and/or oligosaccharides is transferred into a separator vessel and is washed with a solvent (e.g., water), by adding the solvent into the separator vessel and then separating the solvent in a continuous centrifuge. Alternatively, in another exemplary embodiment, a reactor effluent containing residual solids (e.g., residual feedstock) is removed from the reactor vessel and washed, for example, by conveying the solids on a porous base (e.g., a mesh belt) through a solvent (e.g., water)

wash stream. Following contact of the stream with the reacted solids, a liquid phase containing the monosaccharides and/or oligosaccharides is generated. Optionally, residual solids can be separated by a cyclone. Suitable types of cyclones used for the separation can include, for example, tangential cyclones, spark and rotary separators, and axial and multi-cyclone units.

In another embodiment, separation of the sugars is performed by batch or continuous differential sedimentation. Reactor effluent is transferred to a separation vessel, optionally combined with water and/or enzymes for further treatment of the effluent. Over a period of time, solid biomaterials (e.g., residual treated biomass), the catalyst, and the sugar-containing aqueous material can be separated by differential sedimentation into a plurality of phases (or layers). Generally, the catalyst layer can sediment to the bottom, and depending on the density of the residual biomass, the biomass phase can be on top of, or below, the aqueous phase. When the phase separation is performed in a batch mode, the phases are sequentially removed, either from the top of the vessel or an outlet at the bottom of the vessel. When the phase separation is performed in a continuous mode, the separation vessel contains one or more than one outlet means (e.g., two, three, four, or more than four), generally located at different vertical planes on a lateral wall of the separation vessel, such that one, two, or three phases are removed from the vessel. The removed phases are transferred to subsequent vessels or other storage means. By these processes, one of skill in the art would be able to capture (1) the catalyst layer and the aqueous layer or biomass layer separately, or (2) the catalyst, aqueous, and biomass layers separately, allowing efficient catalyst recycling, retreatment of biomass, and separation of sugars. Moreover, controlling rate of phase removal and other parameters allows for increased efficiency of catalyst recovery. Subsequent to removal of each of the separated phases, the catalyst and/or biomass can be separately washed by the aqueous layer to remove adhered sugar molecules.

In some embodiments, the sugars isolated from the vessel can be subjected to further processing steps (e.g., as in drying, fermentation) to produce biofuels and other bio-products. In some embodiments, the monosaccharides that are isolated can be at least about 1% pure, at least about 5% pure, at least about 10% pure, at least about 20% pure, at least about 40% pure, at least about 60% pure, at least about 80% pure, at least about 90% pure, at least about 95% pure, at least about 99% pure, or greater than about 99% pure, as determined by analytical procedures known in the art, such as, but not limited to, determination by high performance liquid chromatography (HPLC), functionalization and analysis by gas chromatography, mass spectrometry, spectrophotometric procedures based on chromophore complexation and/or carbohydrate oxidation-reduction chemistry.

The residual biomass isolated from the vessels can be useful as a combustion fuel or as a feed source of non-human animals such as livestock.

e) Recovery of the Catalysts

The catalysts used for saccharification of biomass can be recovered and reused. Sedimentation of the catalyst is used to recover the catalyst following use. In some embodiments, the catalyst can sink, while other residuals solids can remain suspended in the saccharification reaction mixture. Residual feedstock and residual feedstock mixtures can include, but are not limited to, remaining feedstock after a digestion process, unreactive material in the feedstock, catalyst or catalyst composition, digestion byproducts (e.g., lignin), one or more sugars, one or more sugar degradation products, and water or other solvents.

The sedimentation rate can be measured by the sedimentation coefficient, $$s = \frac{mv}{F}$$

where m is the mass of the particle, v is its sinking velocity (terminal velocity of the sinking particle in the selected solvent), and F is the force applied to cause the sinking. For gravity sedimentation, F=mg, and $$s = \frac{v}{g}$$

where g is the acceleration due to gravity.

For simple gravimetric sedimentation in water, the sedimentation rate of the catalyst can, in some embodiments, be about $10^{-6}$-$10^{-2}$, about $10^{-5}$-$10^{-3}$, or about $10^{-4}$-$10^{-3}$.

The density of the catalyst can also have an impact on its ease of recovery from saccharification. In some embodiments, the gravimetric density of the catalyst is about 0.5-3.0 kg/L, about 1.0-3.0 kg/L, or about 1.1-3.0 kg/L. One of skill in the art would recognize that various methods and techniques suitable for measuring the density of a catalyst as described herein.

Disclosed Catalyst Embodiments and Properties

The catalysts described herein can be polymeric catalysts, which are polymers made up of acidic monomers and ionic monomers (which are also known as "ionomers) connected to form a polymeric backbone, or the catalysts can be solid-supported catalysts having pendant acidic and ionic moieties. These moieties perform the same functions as the acidic and ionic monomers of polymeric catalysts, and their chemical identity and properties thereof, can be similar if not substantially the same. Thus, the description of polymeric monomers herein applies equally to the acidic and ionic moieties of solid-supported catalysts.

Each acidic monomer or moiety includes at least one Bronsted-Lowry acid, and each ionic monomer or moiety includes at least one nitrogen-containing cationic group or phosphorous-containing cationic group. Some of the acidic and ionic monomers or moieties can also include a linker that connects the Bronsted-Lowry acid and cationic group, respectively, to the polymeric backbone or solid support. For the acidic monomers or moieties, the Bronsted-Lowry acid and the linker together form a side chain. Similarly, for the ionic monomers or moieties, the cationic group and the linker together form a side chain. With reference to the portion of the exemplary polymeric catalyst depicted in FIG. 1, the side chains are pendant from the polymeric backbone.

a) Acidic and Ionic Monomers and Moieties

In some embodiments of the methods described above, the catalyst is a polymeric catalyst. In other embodiments of the methods described above, the catalyst is a solid-supported catalyst. In certain embodiments, a plurality of acidic monomers or moieties has one Bronsted-Lowry acid. In certain embodiments, a plurality of acidic monomers or moieties has two Bronsted-Lowry acids. In other embodiments, some of the acidic monomers or moieties have one Bronsted-Lowry acid, while others have two Bronsted-Lowry acids. In some embodiments, a plurality of ionic monomers or moieties has one nitrogen-containing cationic group or one phosphorous-containing cationic group. In some embodiments, a plurality of ionic monomers or moieties has two nitrogen-containing cationic groups, two phosphorous-containing cationic group, or one nitrogen-containing cationic group and one phosphorous-containing cationic group. In other embodiments, some of the ionic monomers or moieties have one nitrogen-containing cationic group or phosphorous-containing cationic group, while others have two nitrogen-containing cationic groups or phosphorous-containing cationic groups.

In some embodiments, a plurality of Bronsted-Lowry acids is independently selected from sulfonic acid, phosphonic acid, acetic acid, isophthalic acid, and boronic acid. In certain embodiments, a plurality of Bronsted-Lowry acids is independently sulfonic acid or phosphonic acid. In one embodiment, each Bronsted-Lowry acid is sulfonic acid.

In some embodiments, one or more of the acidic monomers or moieties are directly connected to the polymeric backbone or solid support. In other embodiments, one or more of the acidic monomers or moieties each further include a linker connecting the Bronsted-Lowry acid to the polymeric backbone or solid support. In certain embodiments, some of the Bronsted-Lowry acids are directly connected to the polymeric backbone, while other the Bronsted-Lowry acids are connected to the polymeric backbone by a linker. In certain embodiments, some of the Bronsted-Lowry acids are directly connected to the solid support, while other the Bronsted-Lowry acids are connected to the solid support by a linker.

In those embodiments where the Bronsted-Lowry acid is connected to the polymeric backbone or solid support by a linker, each linker is independently selected from unsubstituted or substituted alkylene, unsubstituted or substituted cycloalkylene, unsubstituted or substituted alkenylene, unsubstituted or substituted arylene, and unsubstituted or substituted heteroarylene, where the terms unsubstituted and substituted have the meanings as disclosed herein. In certain embodiments, the linker is unsubstituted or substituted arylene, or unsubstituted or substituted heteroarylene. In certain embodiments, the linker is unsubstituted or substituted arylene. In one embodiment, the linker is phenylene. In another embodiment, the linker is hydroxyl-substituted phenylene.

Disclosed herein are polymeric catalysts that include acidic monomers and ionic monomers connected to form a polymeric backbone. Also disclosed herein are solid-supported catalysts bearing acidic moieties and ionic moieties.

Disclosed herein is a polymer comprising two or more monomers or a solid support comprising two or more moieties, wherein a plurality of acidic monomers or moieties independently comprises at least one Bronsted-Lowry acid, wherein at least one of the acidic monomers or moieties comprises a linker connecting the Bronsted-Lowry acid to the polymeric backbone or solid support, wherein each ionic monomer or moiety independently comprises at least one nitrogen-containing cationic group or phosphorous-containing cationic group, and wherein at least one of the ionic monomers or moieties comprises a linker connecting the nitrogen-containing cationic group or the phosphorous-containing cationic group to the polymeric backbone or solid support.

In some embodiments, the acidic monomers and acidic moieties can be selected from Formulas IA-VIA:

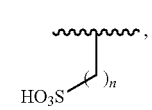
IA

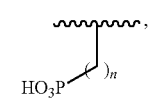
IB

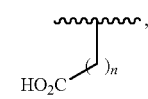
IC

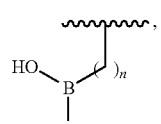
ID

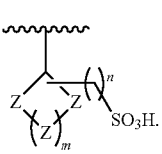
IIA

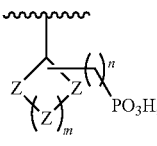
IIB

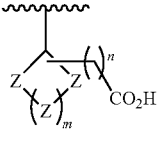
IIC

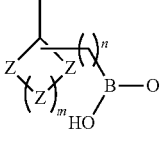
IID

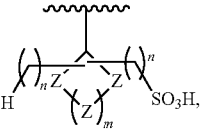
IIIA

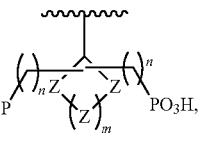
IIIB

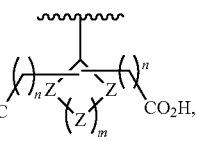
IIIC

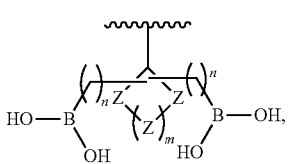
IIID

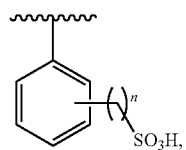

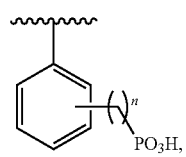

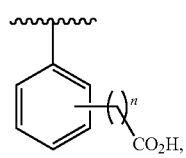

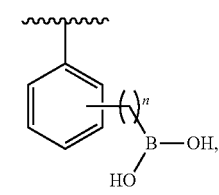

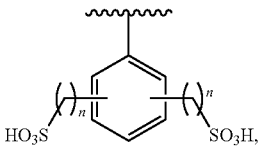

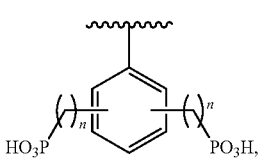

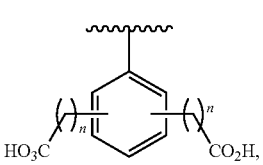

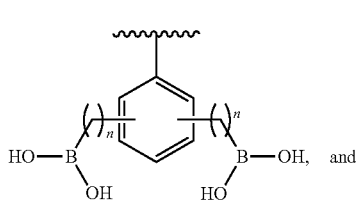
and

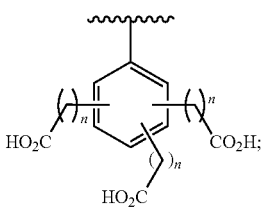
VIA wherein each Z is independently selected from $C(R^2)(R^3)$, $N(R^4)$, S, $S(R^5)(R^6)$, $S(O)(R^5)(R^6)$, $SO_2$, and O, where any two adjacent Z can be joined by a double bond;

each m is independently selected from 0, 1, 2, and 3;

each n is independently selected from 0, 1, 2, and 3;

each $R^2$, $R^3$, and $R^4$ is independently selected from hydrogen, alkyl, heteroalkyl, cycloalkyl, heterocyclyl, aryl, and heteroaryl;

each $R^5$ and $R^6$ is independently selected from alkyl, heteroalkyl, cycloalkyl, heterocyclyl, aryl, and heteroaryl; and where any two adjacent Z can be taken together to form a group selected from cycloalkyl, heterocycloalkyl, aryl and heteroaryl.

In some embodiments, the acidic monomer or moiety can be selected from Formulas IA, IB, IVA, and IVB. In other embodiments, the acidic monomer or moiety can be selected from Formulas IIA, IIB, IIC, IVA, IVB, and IVC. In other embodiments, the acidic monomer or moiety can be selected from IIIA, IIIB, and IIIC. In some embodiments, the acidic monomer or moiety can be selected from VA, VB, and VC. In some embodiments, the acidic monomer or moiety can be selected from IA. In other embodiments, the acidic monomer or moiety can be selected from IB.

In some embodiments, Z can be chosen from $C(R_2)(R_3)$, $N(R_4)$, $SO_2$, and O. In some embodiments, any two adjacent Z can be taken together to form a group selected from a heterocycloalkyl, aryl, and heteroaryl. In other embodiments, any two adjacent Z can be joined by a double bond. Any combination of these embodiments is also contemplated.

In some embodiments, m is selected from 2 or 3, such as 3. In other embodiments, n is selected from 1, 2, and 3, such as 2 or 3. In some embodiments, $R^1$ can be selected from hydrogen, alkyl and heteroalkyl. In some embodiments, $R^1$ can be selected from hydrogen, methyl, or ethyl. In some embodiments, each $R^2$, $R^3$, and $R^4$ can be independently selected from hydrogen, alkyl, heterocyclyl, aryl, and heteroaryl. In other embodiments, each $R^2$, $R^3$ and $R^4$ can be independently selected from heteroalkyl, cycloalkyl, heterocyclyl, and heteroaryl. In some embodiments, each $R^5$ and $R^6$ can be independently selected from alkyl, heterocyclyl, aryl, and heteroaryl. In another embodiment, any two adjacent Z can be taken together to form a group selected from cycloalkyl, heterocycloalkyl, aryl and heteroaryl.

In some embodiments, the polymeric catalysts and solid-supported catalysts described herein contain monomers or moieties that have at least one Bronsted-Lowry acid and at least one cationic group. The Bronsted-Lowry acid and the cationic group can be on different monomers/moieties or on the same monomer/moiety.

In certain embodiments, the acidic monomers or moieties can have a side chain with a Bronsted-Lowry acid that is connected to the polymeric backbone or solid support by a linker. Side chains with one or more Bronsted-Lowry acids connected by a linker can include, for example,

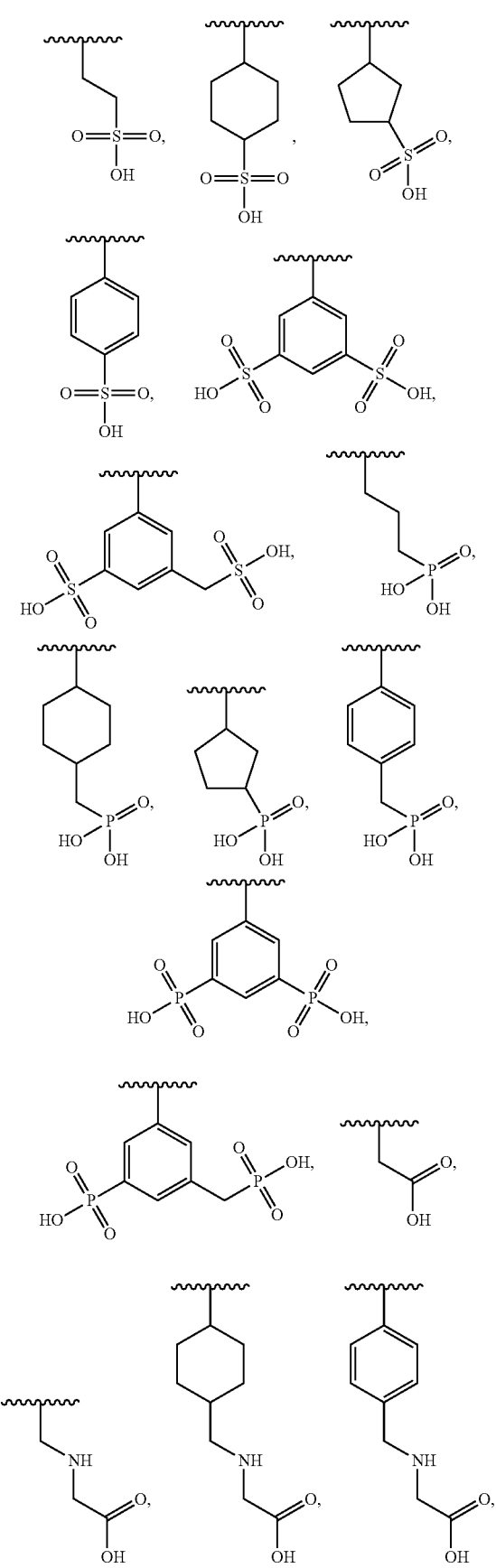
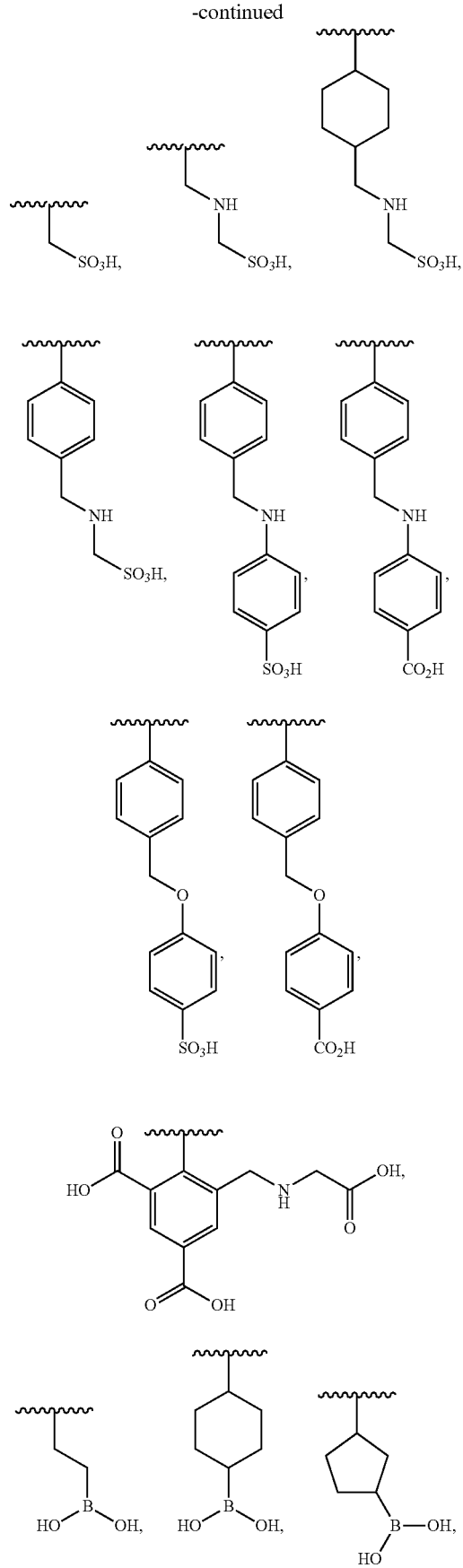

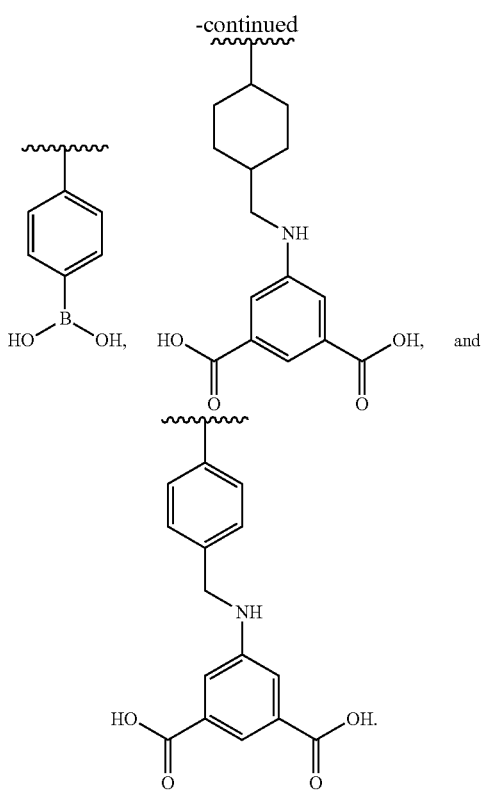

In some embodiments, the acidic side chain can be selected from

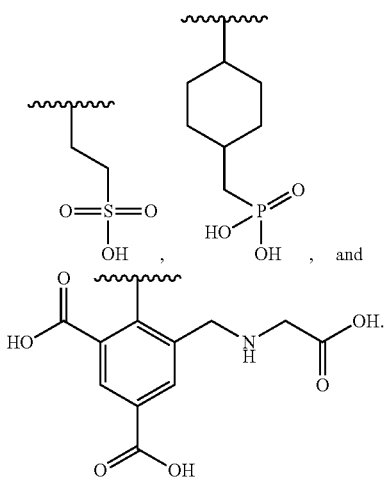

In some embodiments, the acidic side chain can be selected from

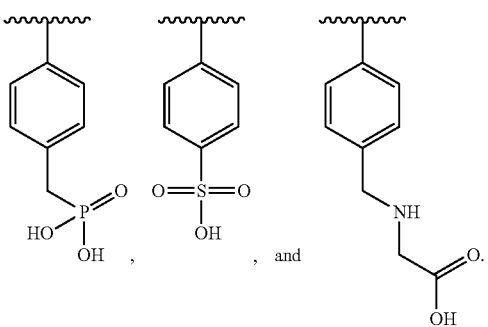

In some embodiments, the acidic side chain can be selected from

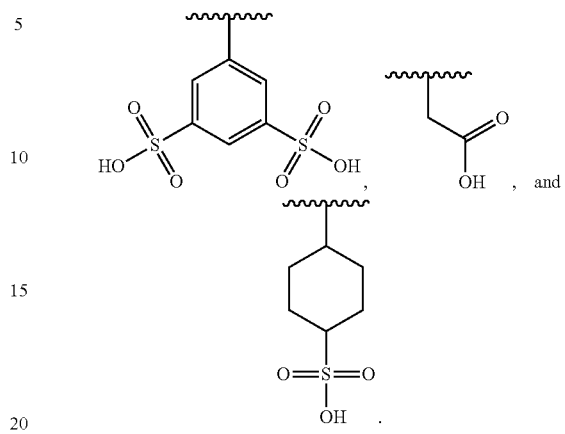

In other embodiments, the acidic monomers or moieties can have a side chain with a Bronsted-Lowry acid that is directly connected to the polymeric backbone or solid support. Side chains with a Bronsted-Lowry acid directly connected to the polymeric backbone or solid support can include, for example,

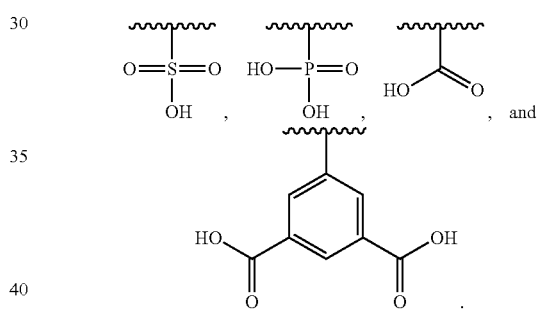

In some embodiments, the ionic monomers or moieties can have one cationic group. In other embodiments, the ionic monomers or moieties can have two or more cationic groups, as is chemically feasible. When the ionic monomers or moieties have two or more cationic groups, the cationic groups can be the same or different.

In some embodiments, each cationic group in the polymeric catalyst or solid-supported catalyst is a nitrogen-containing cationic group. In other embodiments, each cationic group in the polymeric catalyst or solid-supported catalyst is a phosphorous-containing cationic group. In yet other embodiments, the cationic group in some monomers or moieties of the polymeric catalyst or solid-supported catalyst is a nitrogen-containing cationic group, whereas the cationic group in other monomers or moieties of the polymeric catalyst or solid-supported catalyst is a phosphorous-containing cationic group. In an exemplary embodiment, each cationic group in the polymeric catalyst or solid-supported catalyst is imidazolium. In another exemplary embodiment, the cationic group in some monomers or moieties of the polymeric catalyst or solid-supported catalyst is imidazolium, while the cationic group in other monomers or moieties of the polymeric catalyst or solid-supported catalyst is pyridinium. In yet another exemplary embodiment, each cationic group in the polymeric catalyst or solid-supported catalyst is a substituted phosphonium. In yet another exemplary embodiment, the cationic group in some monomers or moieties of the polymeric catalyst or solid-supported catalyst is triphenyl phosphonium, while the cationic group in other monomers or moieties of the polymeric catalyst or solid-supported catalyst is imidazolium.

In some embodiments, the nitrogen-containing cationic group at each occurrence can be independently selected from pyrrolium, imidazolium, pyrazolium, oxazolium, thiazolium, pyridinium, pyrimidinium, pyrazinium, pyradizimium, thiazinium, morpholinium, piperidinium, piperizinium, and pyrollizinium. In other embodiments, the nitrogen-containing cationic group at each occurrence can be independently selected from imidazolium, pyridinium, pyrimidinium, morpholinium, piperidinium, and piperizinium. In some embodiments, the nitrogen-containing cationic group can be imidazolium.

In some embodiments, the phosphorous-containing cationic group at each occurrence can be independently selected from triphenyl phosphonium, trimethyl phosphonium, triethyl phosphonium, tripropyl phosphonium, tributyl phosphonium, trichloro phosphonium, and trifluoro phosphonium. In other embodiments, the phosphorous-containing cationic group at each occurrence can be independently selected from triphenyl phosphonium, trimethyl phosphonium, and triethyl phosphonium. In other embodiments, the phosphorous-containing cationic group can be triphenyl phosphonium.

In some embodiments, each ionic monomer or moiety is independently selected from Formulas VIIA-XIB:

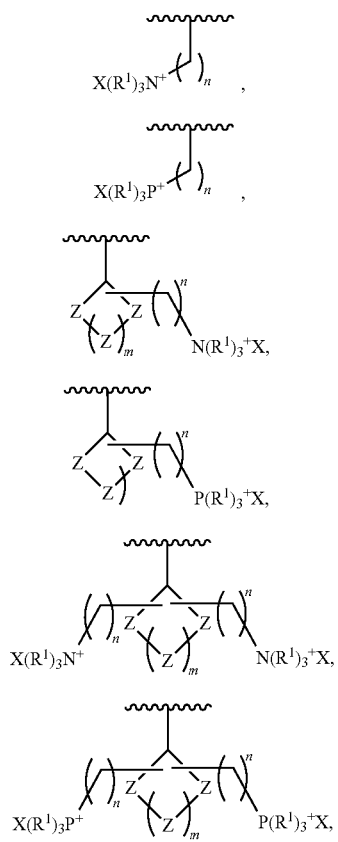

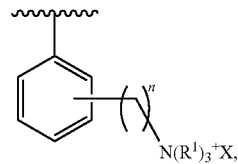

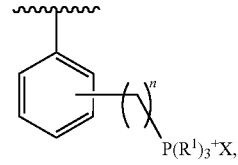

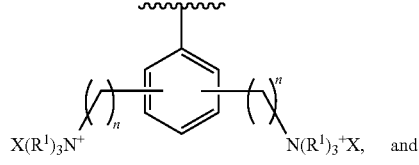

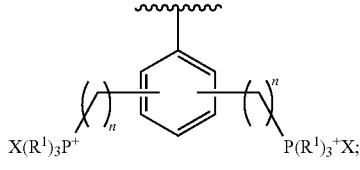

wherein each Z is independently selected from $C(R^2)(R^3)$, $N(R^4)$, S, $S(R^5)(R^6)$, $S(O)(R^5)(R^6)$, $SO_2$, and O, where any two adjacent Z may be joined by a double bond;

each X is independently selected from $F^-$, $Cl^-$, $Br^-$, $I^-$, $NO_2^-$, $NO_3^-$, $SO_4^{2-}$, $R^7SO_4^-$, $R^7CO_2^-$, $PO_4^{2-}$, $R^7PO_3^-$, and $R^7PO_2^-$, where $SO_4^{2-}$ and $PO_4^{2-}$ are each independently associated with at least two cationic groups at any X position on any ionic monomer, and each m is independently selected from 0, 1, 2, and 3;

each n is independently selected from 0, 1, 2, and 3;

each $R^1$, $R^2$, $R^3$ and $R^4$ is independently selected from hydrogen, alkyl, heteroalkyl, cycloalkyl, heterocyclyl, aryl, and heteroaryl;

each $R^5$ and $R^6$ is independently selected from alkyl, heteroalkyl, cycloalkyl, heterocyclyl, aryl, and heteroaryl;

where any two adjacent Z can be taken together to form a group selected from cycloalkyl, heterocycloalkyl, aryl and heteroaryl; and each $R^7$ is independently selected from hydrogen, $C_{1-4}$alkyl, and $C_{1-4}$ heteroalkyl.

In some embodiments, Z can be chosen from $C(R^2)(R^3)$, $N(R^4)$, $SO_2$, and O. In some embodiments, any two adjacent Z can be taken together to form a group selected from a heterocycloalkyl, aryl and heteroaryl. In other embodiments, any two adjacent Z can be joined by a double bond. In some embodiments, each X can be selected from $Cl^-$, $NO_3^-$, $SO_4^{2-}$, $R^7SO_4^-$, and $R^7CO_2^-$, where $R^7$ can be selected from hydrogen and $C_{1-4}$alkyl. In another embodiment, each X can be selected from $Cl^-$, $Br^-$, $I^-$, $HSO_4^-$, $HCO_2^-$, $CH_3CO_2^-$, and $NO_3^-$. In other embodiments, X is acetate. In other embodiments, X is bisulfate. In other embodiments, X is chloride. In other embodiments, X is nitrate.

In some embodiments, m is selected from 2 or 3, such as 3. In other embodiments, n is selected from 1, 2, and 3, such as 2 or 3. In some embodiments, $R^1$ can be selected from hydrogen, alkyl, and heteroalkyl. In some embodiments, $R^1$ can be selected from hydrogen, methyl, or ethyl. In some embodiments, each $R^2$, $R^3$, and $R^4$ can be independently selected from hydrogen, alkyl, heterocyclyl, aryl, and heteroaryl. In other embodiments, each $R^2$, $R^3$ and $R^4$ can be independently selected from heteroalkyl, cycloalkyl, heterocyclyl, and heteroaryl. In some embodiments, each $R^5$ and $R^6$ can be independently selected from alkyl, heterocyclyl, aryl, and heteroaryl. In another embodiment, any two adjacent Z can be taken together to form a group selected from cycloalkyl, heterocycloalkyl, aryl and heteroaryl.

In certain embodiments, the ionic monomers or moieties can have a side chain with a cationic group that is connected to the polymeric backbone or solid support by a linker. Side chains with one or more cationic groups connected by a linker can include, for example,

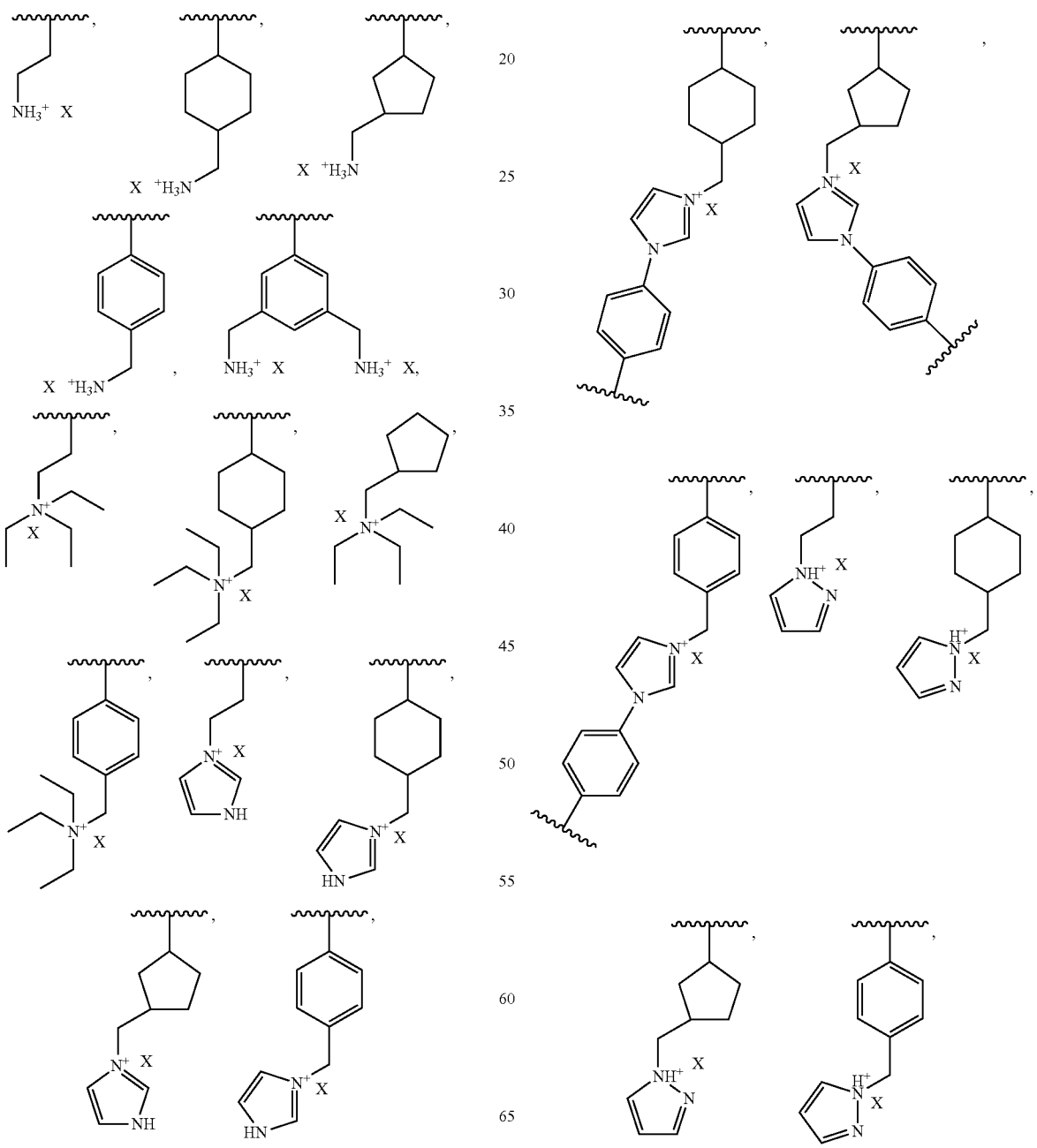

-continued

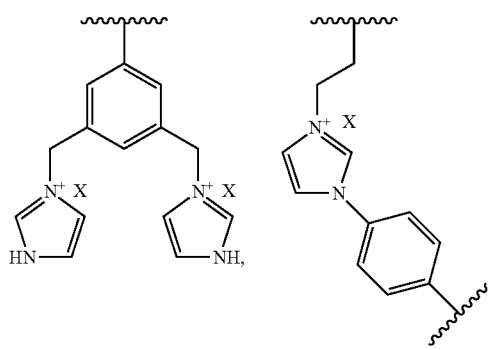

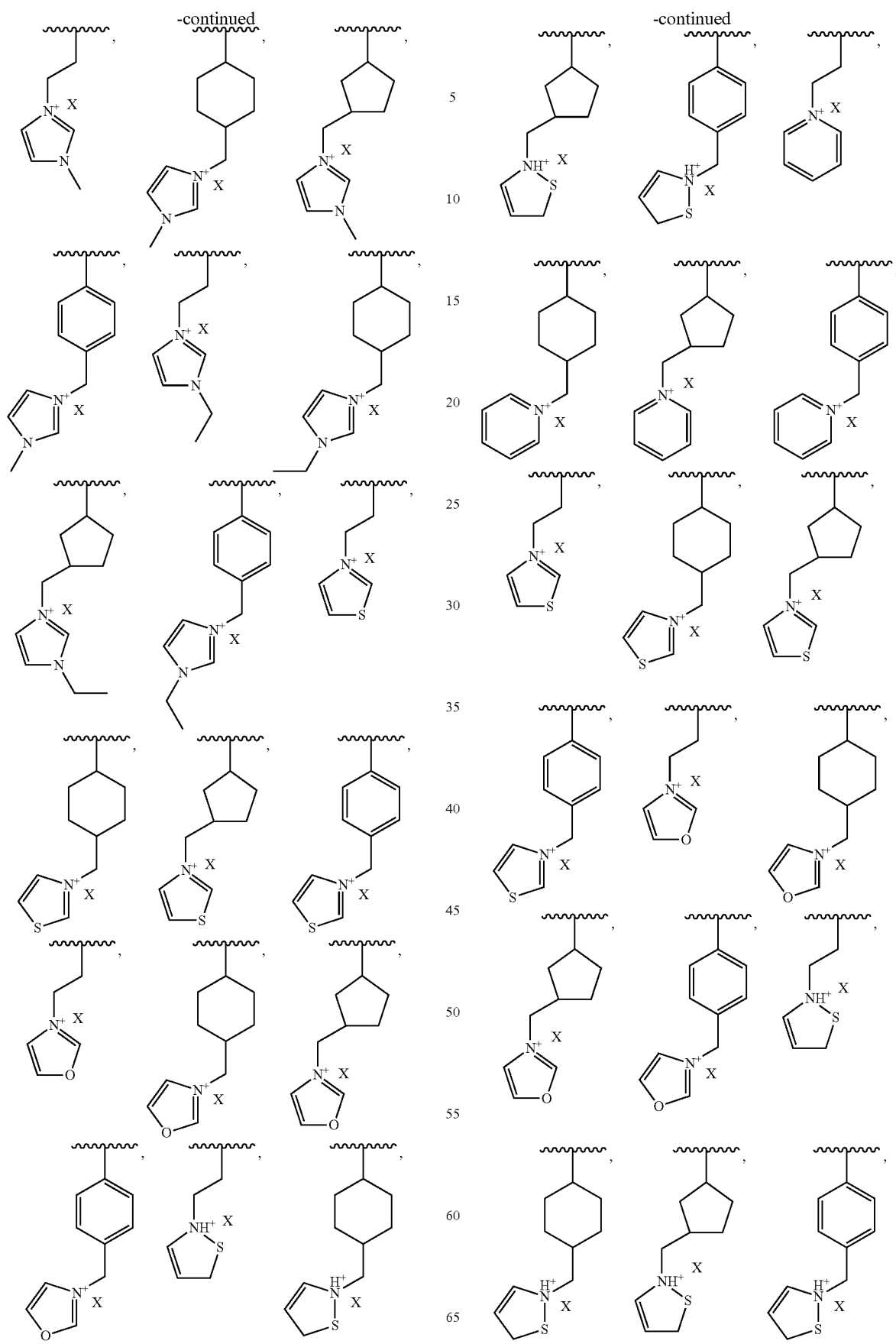

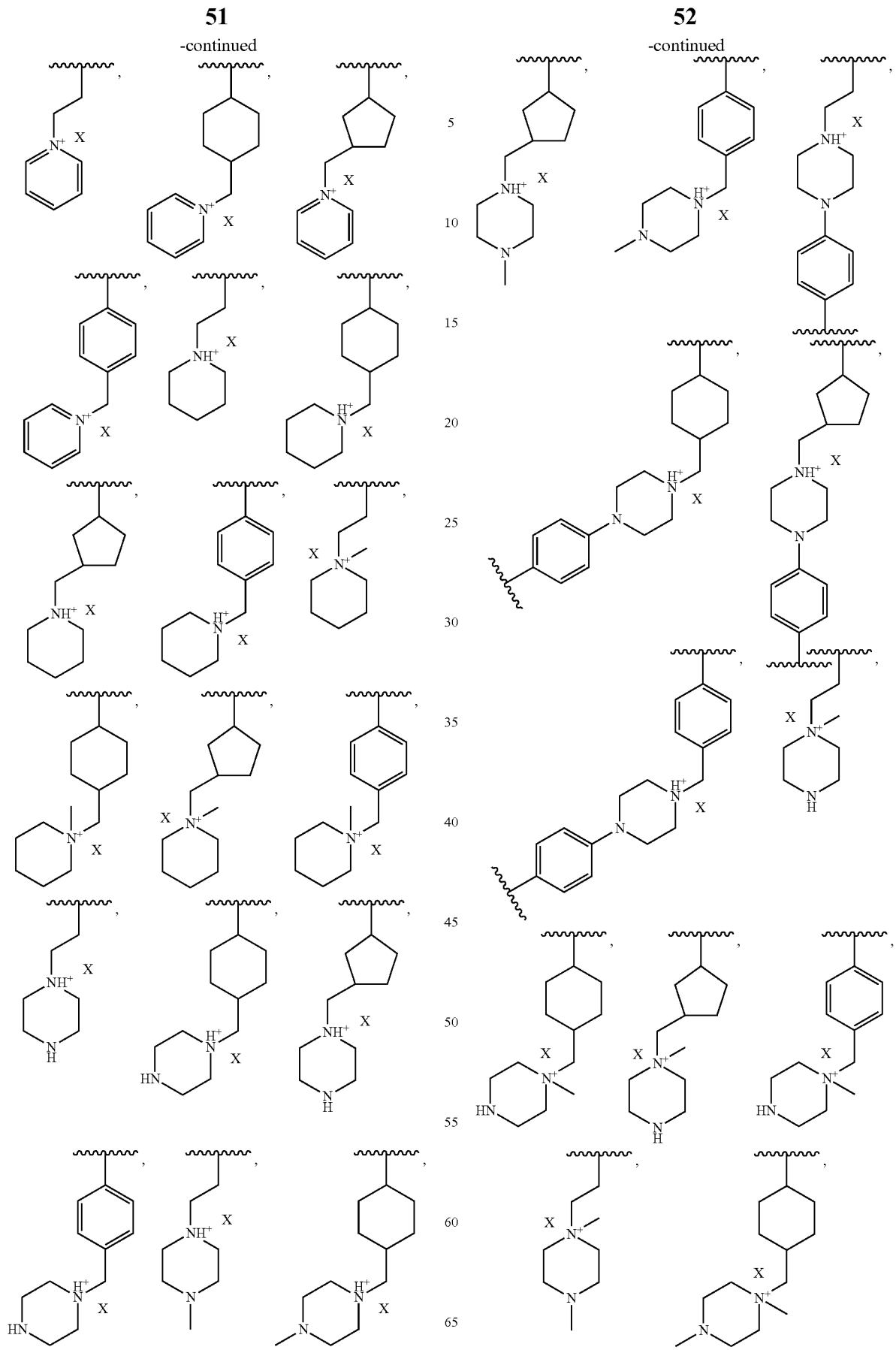

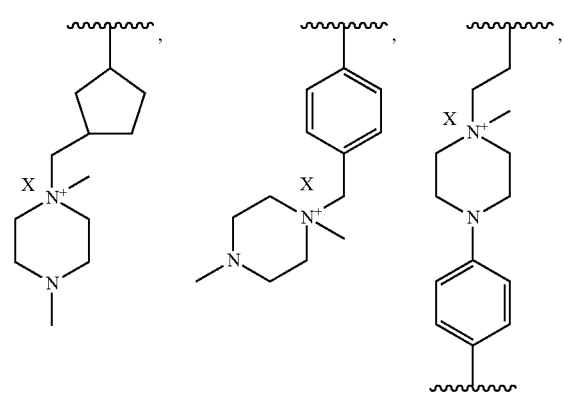
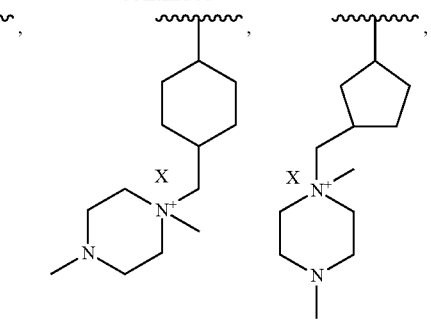
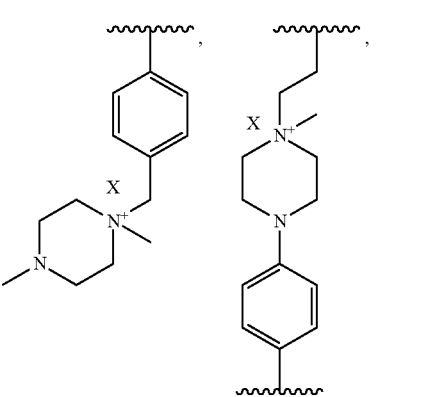
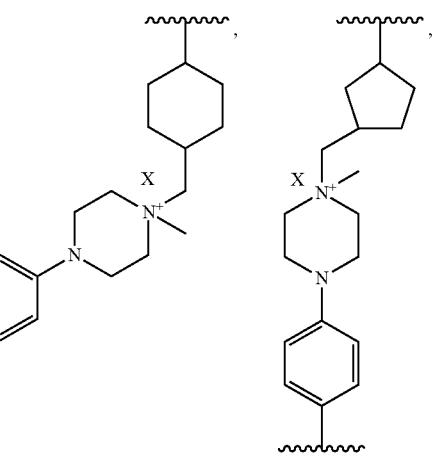
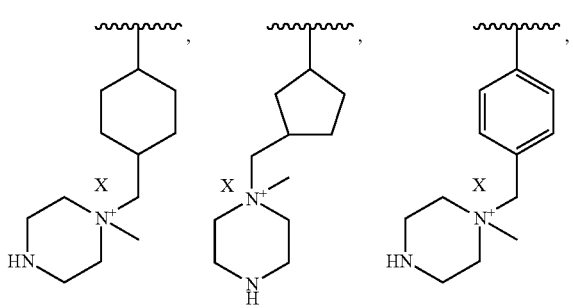
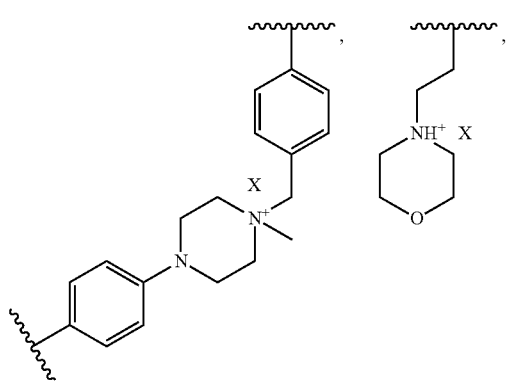

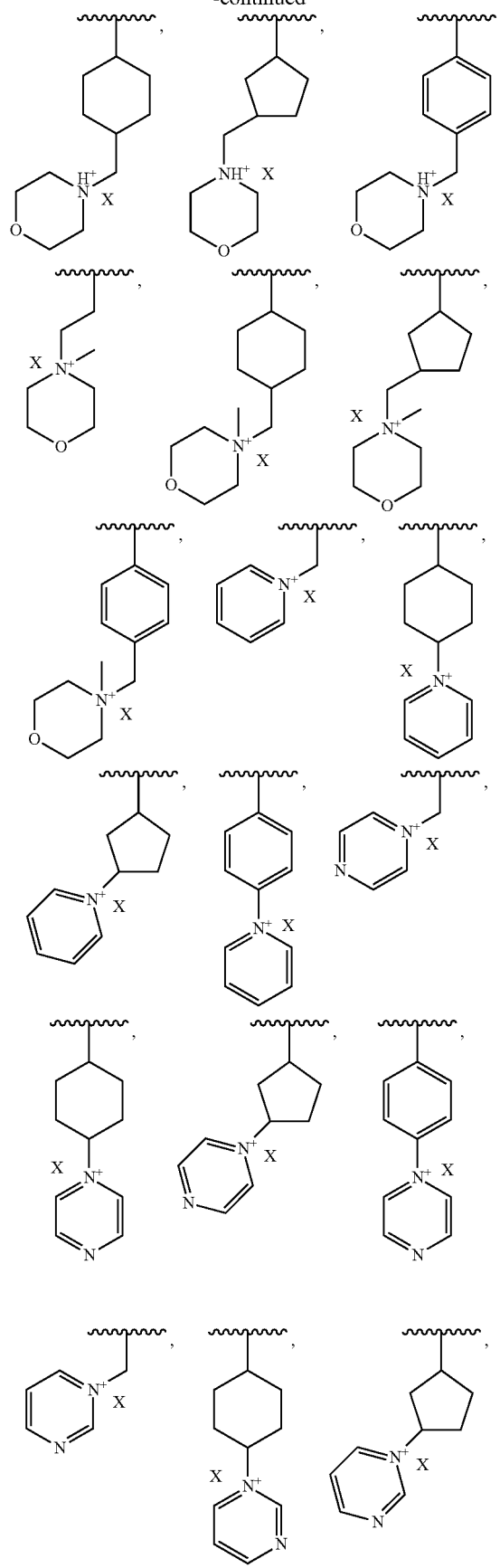
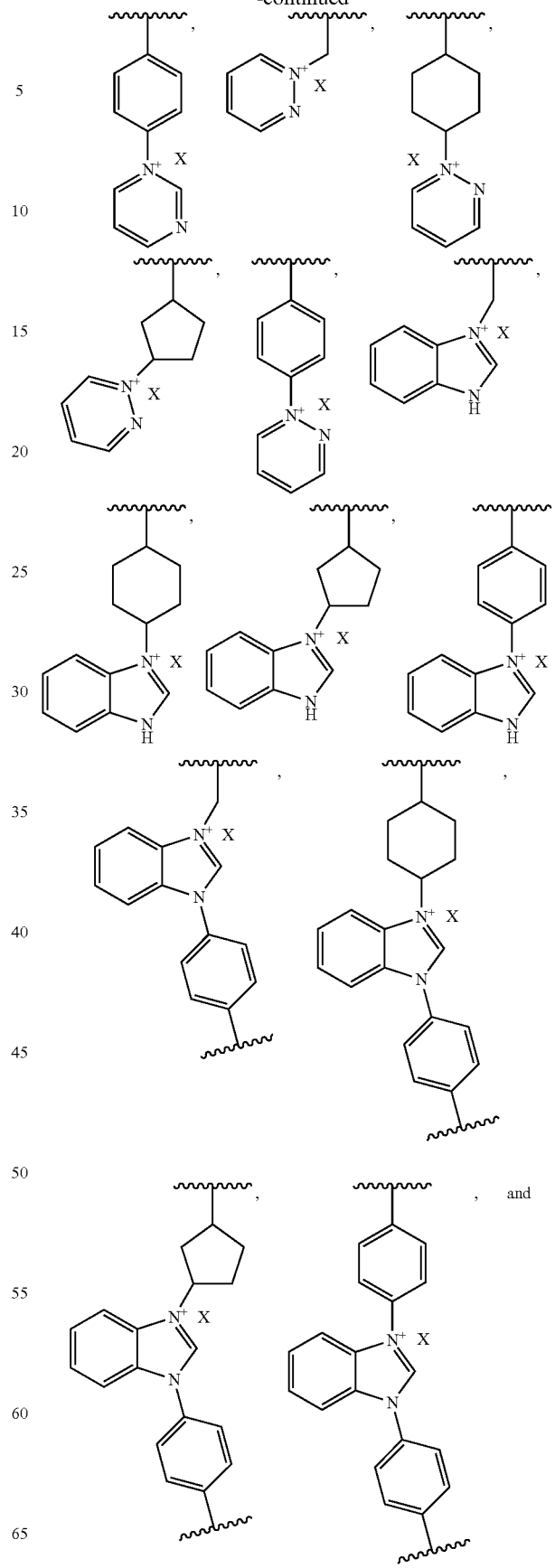

-continued

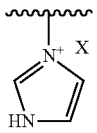

In some embodiments, the nitrogen-containing side chain is independently selected from

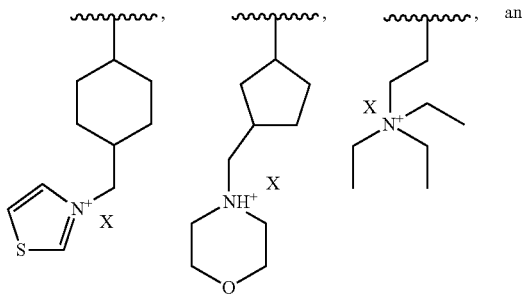

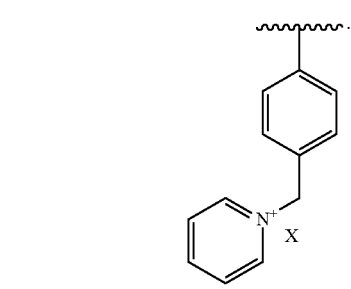

In some embodiments, the nitrogen-containing side chain is independently selected from

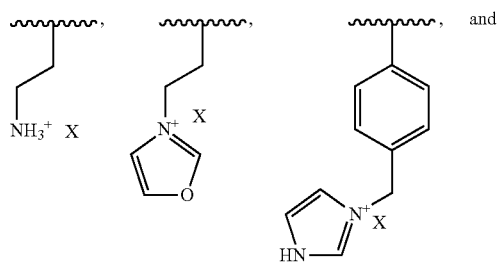

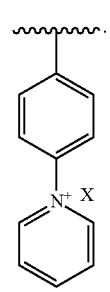

In some embodiments, the nitrogen-containing side chain is independently selected from

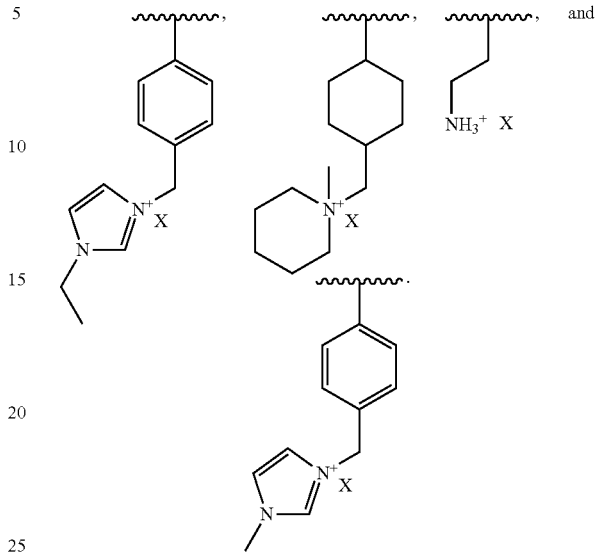

In some embodiments, the nitrogen-containing side chain is independently selected from

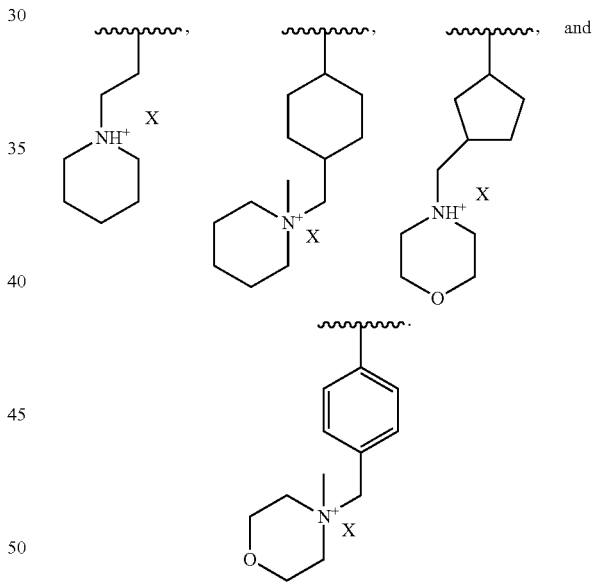

In some embodiments, the nitrogen-containing side chain is independently selected from

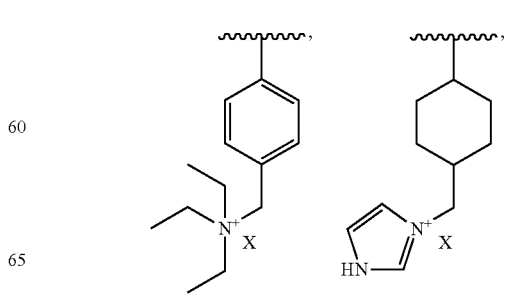

-continued

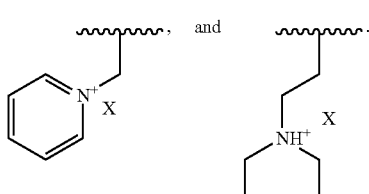

In some embodiments, the nitrogen-containing side chain is independently selected from

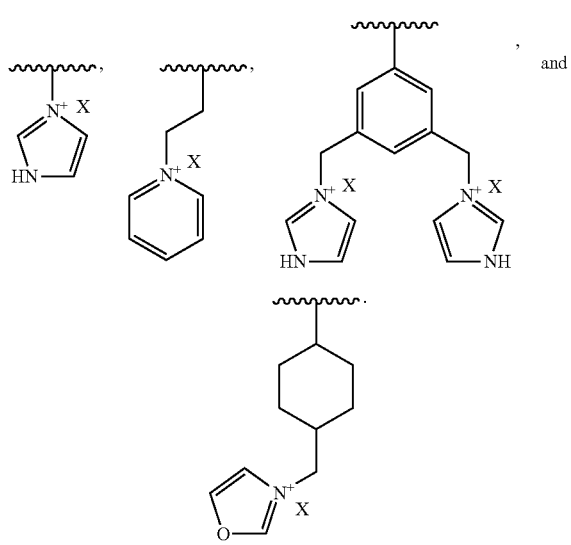

In other embodiments, the ionic monomers or moieties can have a side chain with a cationic group that is directly connected to the polymeric backbone or solid support. Side chains with a nitrogen-containing cationic group directly connected to the polymeric backbone or solid support can include, for example,

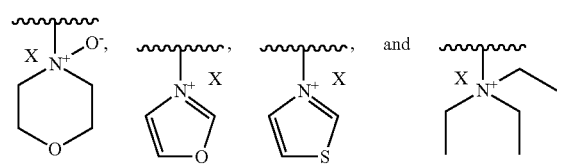

In another embodiment, such nitrogen-containing side chains can include

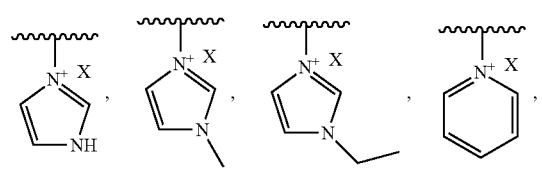

-continued

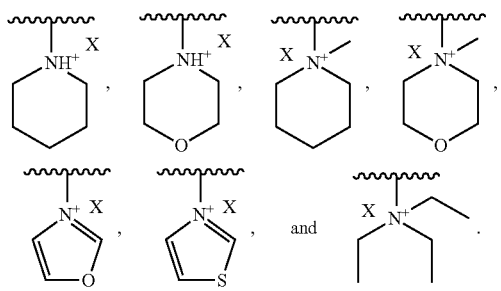

In some embodiments, the nitrogen-containing cationic group can be an N-oxide, where the negatively charged oxide (O—) is not readily dissociable from the nitrogen cation. Non-limiting examples of such groups include, for example,

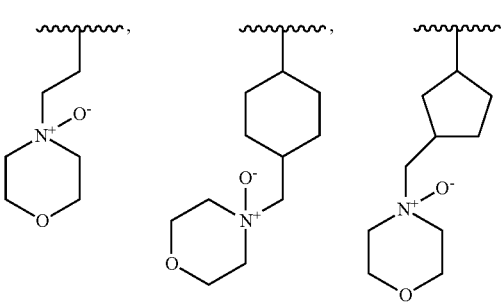

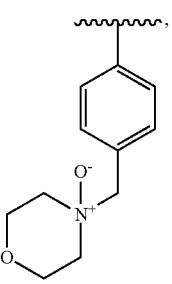

Side chains with a phosphorous-containing cationic group directly connected to the polymeric backbone can include, for example,

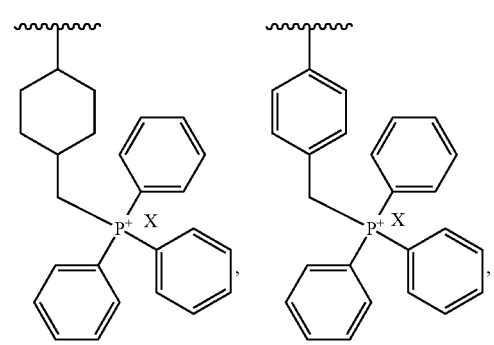

-continued

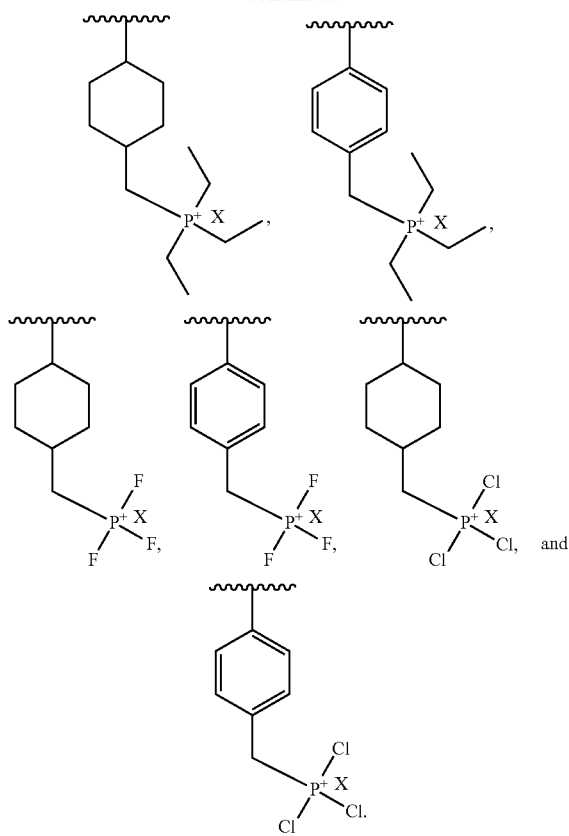

In some embodiments, the phosphorous-containing side chain is independently selected from

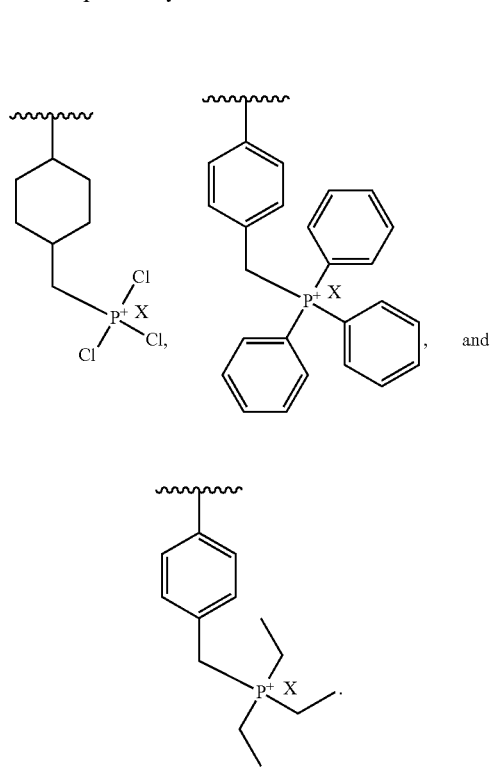

In some embodiments, the phosphorous-containing side chain is independently selected from

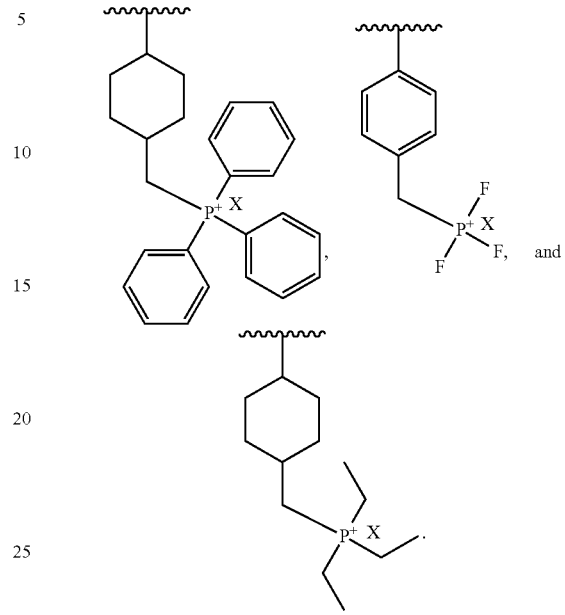

In other embodiments, the ionic monomers or moieties can have a side chain with a cationic group that is directly connected to the polymeric backbone or solid support. Side chains with a phosphorous-containing cationic group directly connected to the polymeric backbone or solid support can include, for example,

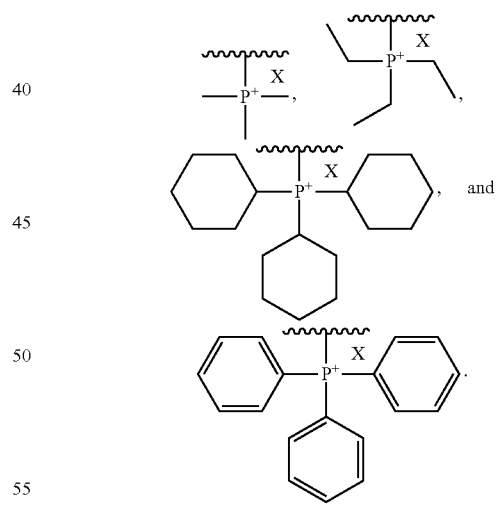

The ionic monomers or moieties can either all have the same cationic group, or can have different cationic groups. In some embodiments, each cationic group in the polymeric catalyst or solid-supported catalyst is a nitrogen-containing cationic group. In other embodiments, each cationic group in the polymeric catalyst or solid-supported catalyst is a phosphorous-containing cationic group. In yet other embodiments, the cationic group in some monomers or moieties of the polymeric catalyst or solid-supported catalyst is a nitrogen-containing cationic group, whereas the cationic group in other monomers or moieties of the polymeric catalyst or solid-supported catalyst is a phosphorous-containing cationic group. In an exemplary embodiment, each cationic group in the polymeric catalyst or solid-supported catalyst is imidazolium. In another exemplary embodiment, the cationic group in some monomers or moieties of the polymeric catalyst or solid-supported catalyst is imidazolium, while the cationic group in other monomers or moieties of the polymeric catalyst or solid-supported catalyst is pyridinium. In yet another exemplary embodiment, each cationic group in the polymeric catalyst or solid-supported catalyst is a substituted phosphonium. In yet another exemplary embodiment, the cationic group in some monomers or moieties of the polymeric catalyst or solid-supported catalyst is triphenyl phosphonium, while the cationic group in other monomers or moieties of the polymeric catalyst or solid-supported catalyst is imidazolium.

In other embodiments, the monomers or moieties can have a side chain containing both a Bronsted-Lowry acid and a cationic group, where either the Bronsted-Lowry acid is connected to the polymeric backbone or solid support by a linker or the cationic group is connected to the polymeric backbone or solid support by a linker. In certain embodiments, the Bronsted-Lowry acid at each occurrence in the acidic-ionic monomer or moiety is independently selected from sulfonic acid, phosphonic acid, acetic acid, isophthalic acid, and boronic acid. In certain embodiments, the Bronsted-Lowry acid at each occurrence is independently sulfonic acid or phosphonic acid. In one embodiment, the Bronsted-Lowry acid at each occurrence is sulfonic acid. In exemplary embodiments, a side chain of an acidic-ionic monomer can contain imidazolium and acetic acid, or pyridinium and boronic acid.

In some embodiments, the nitrogen-containing cationic group at each occurrence in the acidic-ionic monomer is independently selected from pyrrolium, imidazolium, pyrazolium, oxazolium, thiazolium, pyridinium, pyrimidinium, pyrazinium, pyradizimium, thiazinium, morpholinium, piperidinium, piperizinium, and pyrollizinium. In one embodiment, the nitrogen-containing cationic group is imidazolium.

In some embodiments, the phosphorous-containing cationic group at each occurrence in the acidic-ionic monomer is independently selected from triphenyl phosphonium, trimethyl phosphonium, triethyl phosphonium, tripropyl phosphonium, tributyl phosphonium, trichloro phosphonium, and trifluoro phosphonium. In one embodiment, the phosphorous-containing cationic group is triphenyl phosphonium.

In some embodiments, the polymeric catalyst or solid-supported catalyst can include at least one acidic-ionic monomer or moiety connected to the polymeric backbone or solid support, wherein at least one acidic-ionic monomer or moiety comprises at least one Bronsted-Lowry acid, and at least one cationic group, and wherein at least one of the acidic-ionic monomers or moieties comprises a linker connecting the acidic-ionic monomer to the polymeric backbone or solid support. The cationic group can be a nitrogen-containing cationic group or a phosphorous-containing cationic group as described herein. The linker can be selected from unsubstituted or substituted alkylene, unsubstituted or substituted cycloalkylene, unsubstituted or substituted alkenylene, unsubstituted or substituted arylene, and unsubstituted or substituted heteroarylene, where the terms unsubstituted and substituted have the meanings as disclosed herein.

In other embodiments, the monomers or moieties can have a side chain containing both a Bronsted-Lowry acid and a cationic group, where the Bronsted-Lowry acid is directly connected to the polymeric backbone or solid support, the cationic group is directly connected to the polymeric backbone or solid support, or both the Bronsted-Lowry acid and the cationic group are directly connected to the polymeric backbone or solid support.

In certain embodiments, the linker is unsubstituted or substituted arylene, or unsubstituted or substituted heteroarylene. In certain embodiments, the linker is unsubstituted or substituted arylene. In one embodiment, the linker is phenylene. In another embodiment, the linker is hydroxyl-substituted phenylene.

Ionomers that have side chains containing both a Bronsted-Lowry acid and a cationic group can also be called "acidic ionomers". Such side chains in acidic-ionic monomers that are connected by a linker can include, for example,

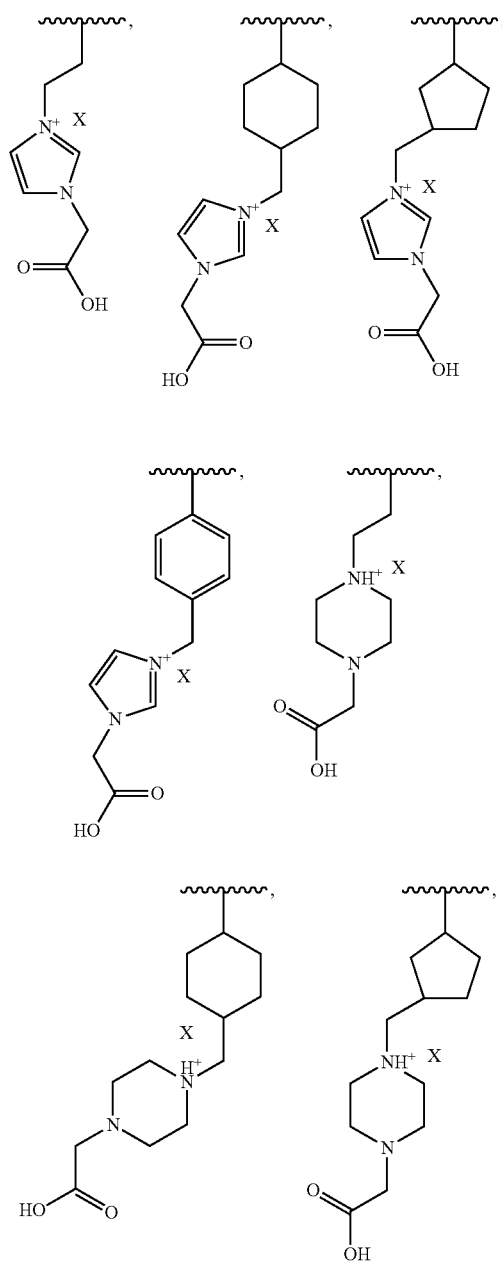

65
-continued
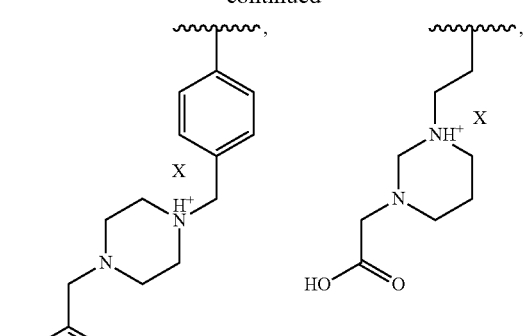
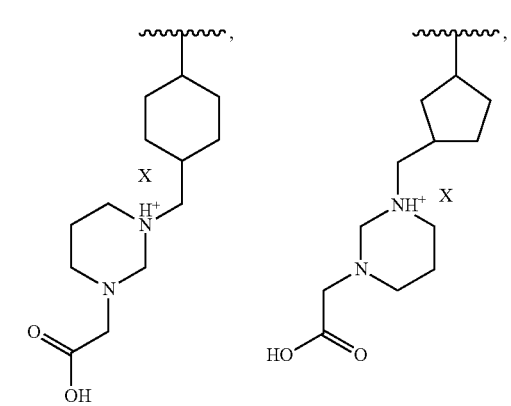
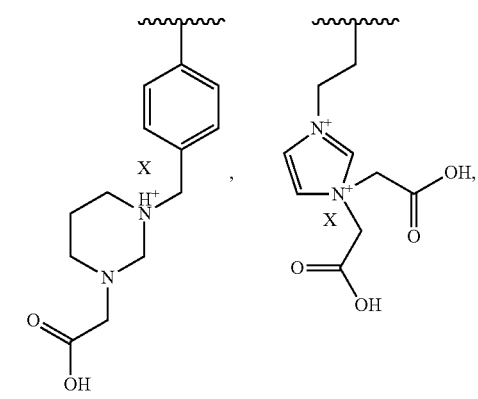
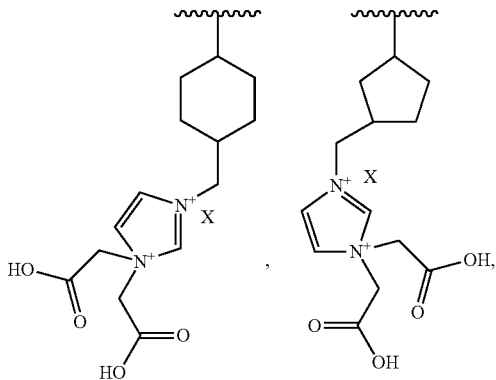
66
-continued
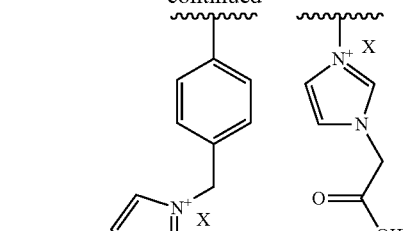
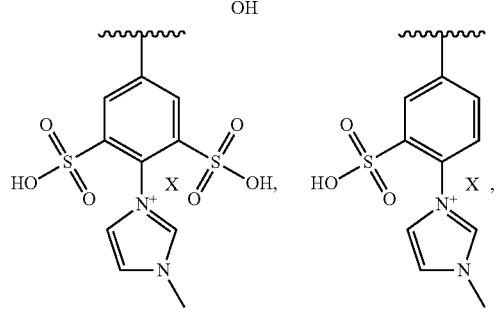
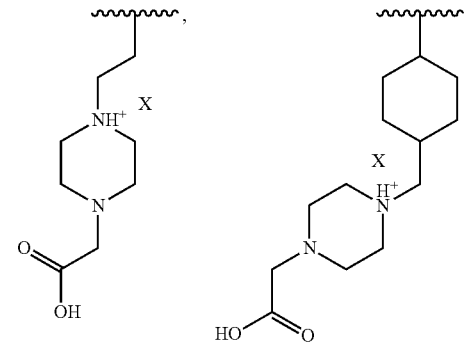
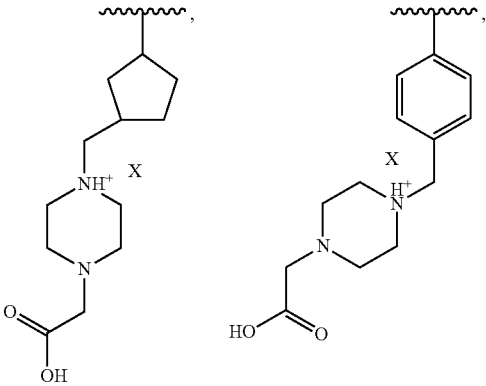

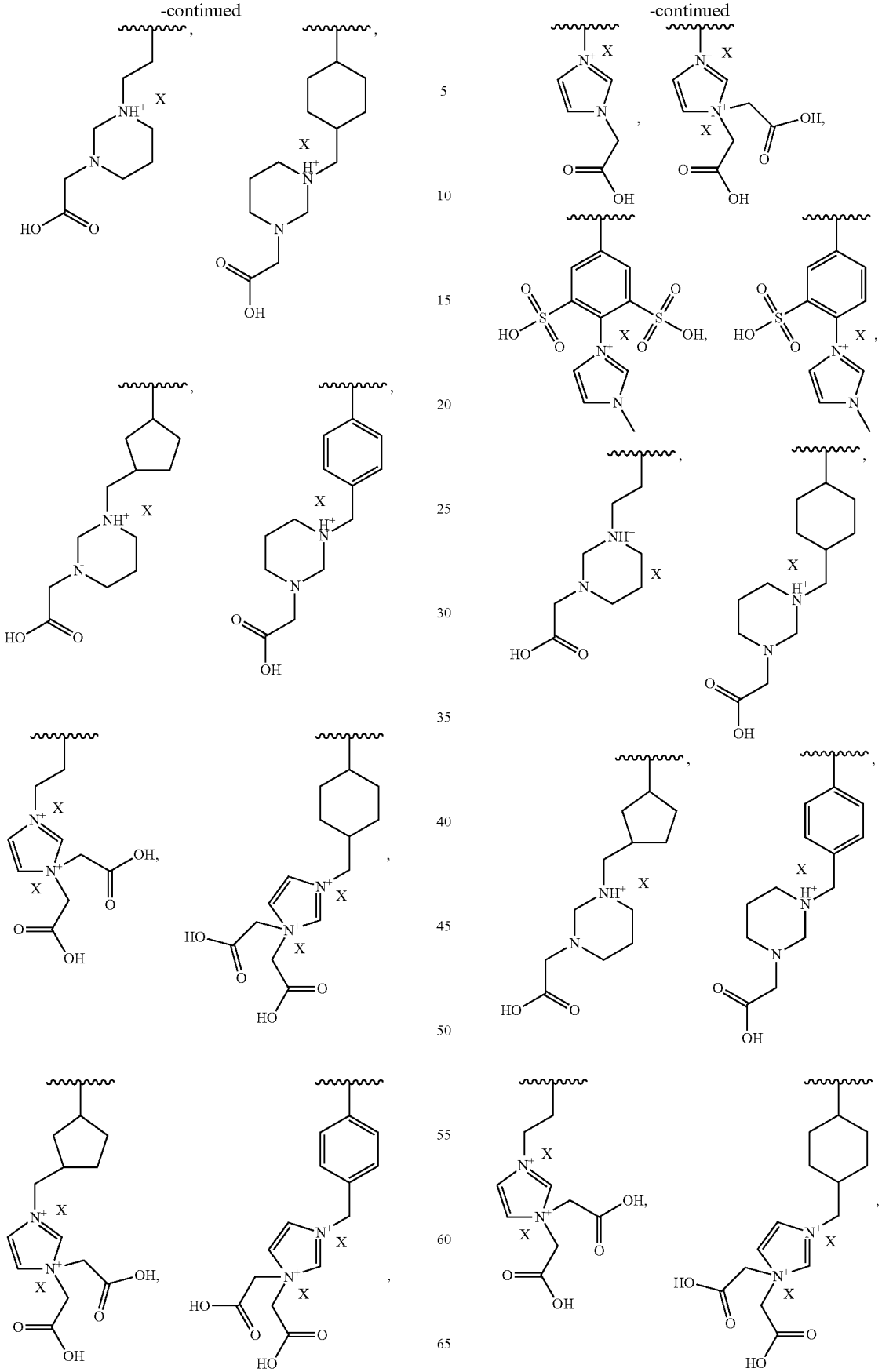

-continued

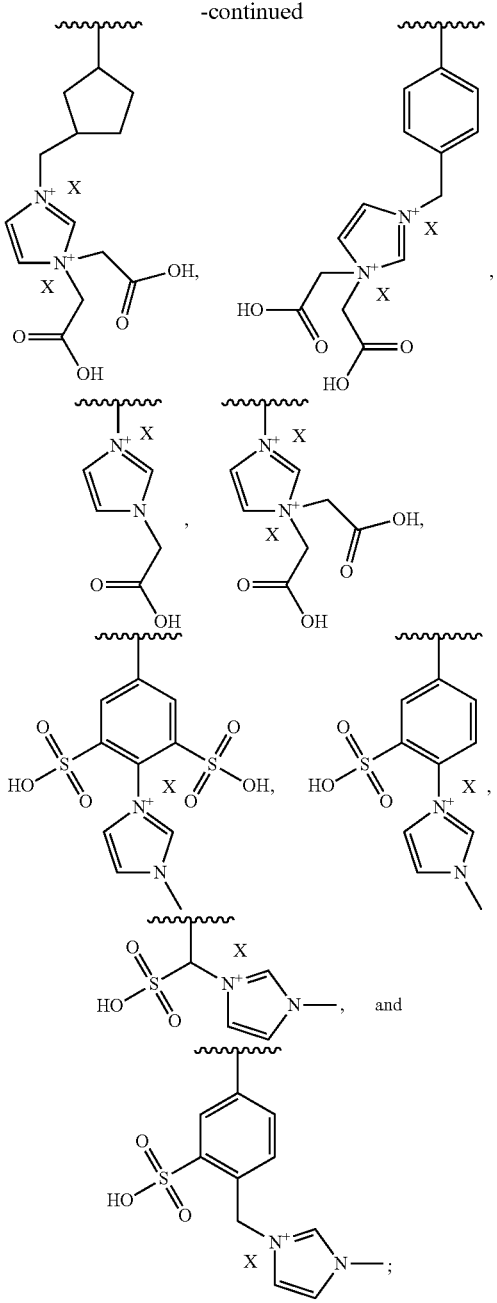

wherein each X is independently selected from F⁻, Cl⁻, Br⁻, I⁻, $NO_2^-$, $NO_3^-$, $SO_4^{2-}$, $R^7SO_4^-$, $R^7CO_2^-$, $PO_4^{2-}$, $R^7PO_3^-$, and $R^7PO_2^-$, where $SO_4^{2-}$ and $PO_4^{2-}$ are each independently associated with at least two Bronsted-Lowry acids at any X position on any side chain, and each $R^7$ is independently selected from hydrogen, $C_{1-4}$alkyl, and $C_{1-4}$ heteroalkyl.

In some embodiments, $R^1$ can be selected from hydrogen, alkyl, and heteroalkyl. In some embodiments, $R^1$ can be selected from hydrogen, methyl, or ethyl. In some embodiments, each X can be selected from Cl⁻, $NO_3^-$, $SO_4^{2-}$, $R^7SO_4^{2-}$, and $R^7CO_2^-$, where $R^7$ can be selected from hydrogen and $C_{1-4}$alkyl. In another embodiment, each X can be selected from Cl⁻, Br⁻, I⁻, $HSO_4^-$, $HCO_2^-$, $CH_3CO_2^-$, and $NO_3^-$. In other embodiments, X is acetate. In other embodiments, X is bisulfate. In other embodiments, X is chloride. In other embodiments, X is nitrate.

In some embodiments, the acidic-ionic side chain is independently selected from

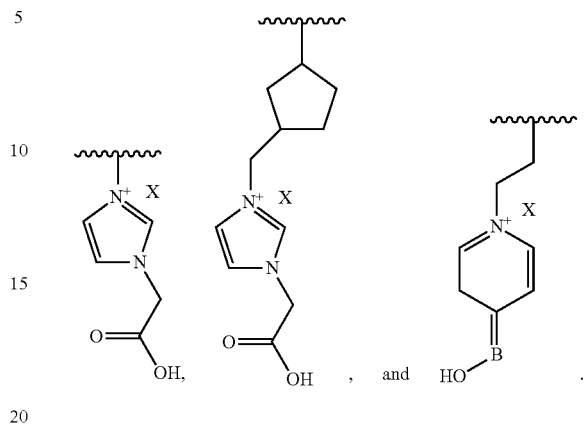

In some embodiments, the acidic-ionic side chain is independently selected from

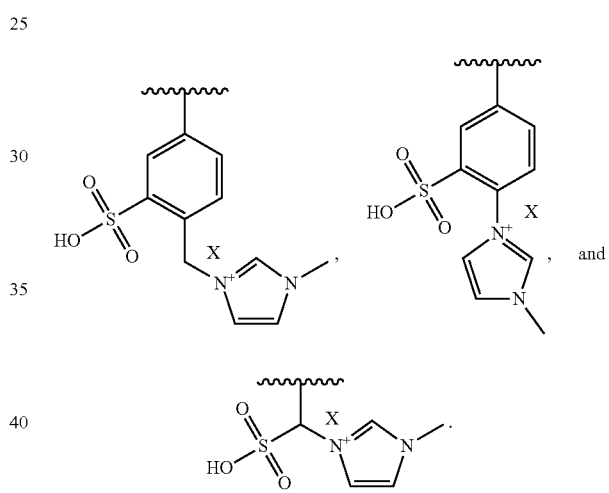

In other embodiments, the monomers or moieties can have a side chain containing both a Bronsted-Lowry acid and a cationic group, where the Bronsted-Lowry acid is directly connected to the polymeric backbone or solid support, the cationic group is directly connected to the polymeric backbone or solid support, or both the Bronsted-Lowry acid and the cationic group are directly connected to the polymeric backbone or solid support. Such side chains in acidic-ionic monomers or moieties can include, for example,

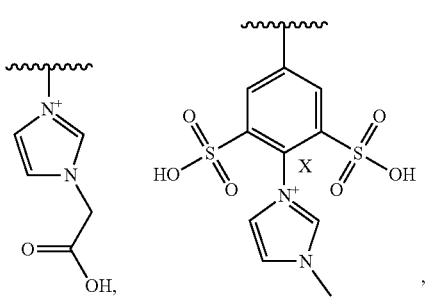

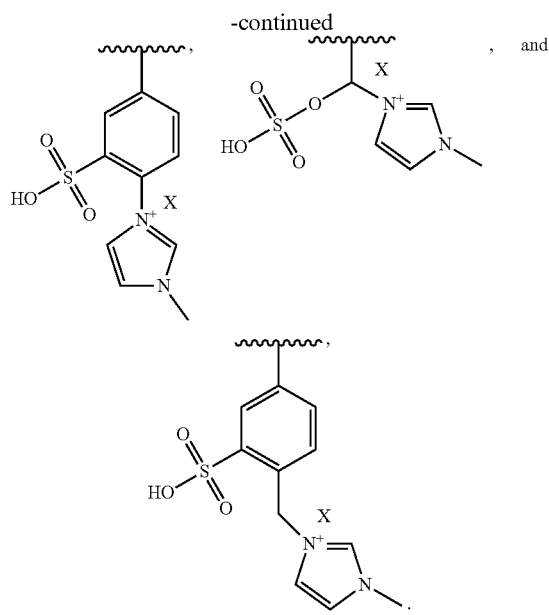

In some embodiments, the acidic and ionic monomers make up a substantial portion of the polymeric catalyst or solid-supported catalyst. In certain embodiments, the acidic and ionic monomers or moieties make up at least about 30%, at least about 40%, at least about 50%, at least about 60%, at least about 70%, at least about 80%, at least about 90%, at least about 95%, or at least about 99% of the monomers or moieties of the polymer or solid support, based on the ratio of the number of acidic and ionic monomers/moieties to the total number of monomers/moieties present in the polymeric catalyst or solid support.

In some embodiments of the polymeric catalyst and solid-supported catalyst, the polymer or solid support further includes hydrophobic monomers or moieties connected to form the polymeric backbone or solid support, in which each hydrophobic monomer or moiety has at least one hydrophobic group. In certain embodiments of the polymeric catalyst or solid-supported catalyst, each hydrophobic monomer or moiety has one hydrophobic group. In certain embodiments of the polymeric catalyst or solid-supported catalyst, each hydrophobic monomer or moiety has two hydrophobic groups. In other embodiments of the polymeric catalyst or solid-supported catalyst, some of the hydrophobic monomers or moieties have one hydrophobic group, while others have two hydrophobic groups.

In some embodiments of the polymeric catalyst or solid-supported catalyst, each hydrophobic group is independently selected from an unsubstituted or substituted alkyl, an unsubstituted or substituted cycloalkyl, an unsubstituted or substituted aryl, and an unsubstituted or substituted heteroaryl, where the terms unsubstituted and substituted have the meanings as disclosed herein. In certain embodiments of the polymeric catalyst or solid-supported catalyst, each hydrophobic group is an unsubstituted or substituted aryl, or an unsubstituted or substituted heteroaryl. In one embodiment, each hydrophobic group is phenyl.

In some embodiments of the polymeric catalyst or solid-supported catalyst, the hydrophobic group is directly connected to form the polymeric backbone.

In some embodiments, the polymeric catalyst or solid-supported catalyst has a total amount of Bronsted-Lowry acid of between about 0.1 and about 20 mmol, between about 0.1 and about 15 mmol, between about 0.01 and about 12 mmol, between about 0.05 and about 10 mmol, between about 1 and about 8 mmol, between about 2 and about 7 mmol, between about 3 and about 6 mmol, between about 1 and about 5, or between about 3 and about 5 mmol per gram of the polymeric catalyst or solid-supported catalyst.

In some embodiments of the polymeric catalyst or solid-supported catalyst, at least a portion of the acidic monomers have sulfonic acid. In those embodiments of the polymeric catalyst or solid-supported catalyst where at least a portion of the acidic monomers or moieties have sulfonic acid, the total amount of sulfonic acid in the polymeric catalyst or solid-supported catalyst is between about 0.05 and about 10 mmol, between about 1 and about 8 mmol, or between about 2 and about 6 mmol per gram of the polymeric catalyst or solid-supported catalyst.

In some embodiments of the polymeric catalyst or solid-supported catalyst, at least a portion of the acidic monomers or moieties have phosphonic acid. In those embodiments of the polymeric catalyst or solid-supported catalyst where at least a portion of the acidic monomers or moieties have phosphonic acid in the polymer, the total amount of phosphonic acid in the polymeric catalyst or solid-supported catalyst is between about 0.01 and about 12 mmol, between about 0.05 and about 10 mmol, between about 1 and about 8 mmol, or between about 2 and about 6 mmol per gram of the polymeric catalyst or solid-supported catalyst.

In some embodiments of the polymeric catalyst or solid-supported catalyst, at least a portion of the acidic monomers or moieties have acetic acid. In those embodiments of the polymeric catalyst or solid-supported catalyst where at least a portion of the acidic monomers or moieties have acetic acid, the total amount of acetic acid in the polymeric catalyst or solid-supported catalyst is between about 0.01 and about 12 mmol, between about 0.05 and about 10 mmol, between about 1 and about 8 mmol, or between about 2 and about 6 mmol per gram of the polymeric catalyst or solid-supported catalyst.

In some embodiments of the polymeric catalyst or solid-supported catalyst, at least a portion of the acidic monomers or moieties have isophthalic acid. In those embodiments of the polymeric catalyst or solid-supported catalyst where at least a portion of the acidic monomers or moieties have isophthalic acid, the total amount of isophthalic acid in the polymeric catalyst or solid-supported catalyst is between about 0.01 and about 5 mmol, between about 0.05 and about 5 mmol, between about 1 and about 4 mmol, or between about 2 and about 3 mmol per gram of the polymeric catalyst or solid-supported catalyst.

In some embodiments of the polymeric catalyst or solid-supported catalyst, at least a portion of the acidic monomers or moieties have boronic acid. In those embodiments of the polymeric catalyst or solid-supported catalyst where at least a portion of the acidic monomers or moieites have boronic acid, the total amount of boronic acid in the polymeric catalyst or solid-supported catalyst is between about 0.01 and about 20 mmol, between about 0.05 and about 10 mmol, between about 1 and about 8 mmol, or between about 2 and about 6 mmol per gram of the polymeric catalyst or solid-supported catalyst.

In some embodiments of the polymeric catalyst or solid-supported catalyst, each ionic monomer further includes a counterion for each nitrogen-containing cationic group or phosphorous-containing cationic group. In certain embodiments of the polymeric catalyst or solid-supported catalyst, each counterion is independently selected from halide, nitrate, sulfate, formate, acetate, or organosulfonate. In some embodiments of the polymeric catalyst or solid-supported catalyst, the counterion is fluoride, chloride, bromide, or iodide. In one embodiment of the polymeric catalyst or solid-supported catalyst, the counterion is chloride. In another embodiment of the polymeric catalyst or solid-supported catalyst, the counterion is sulfate. In yet another embodiment of the polymeric catalyst or solid-supported catalyst, the counterion is acetate.

In some embodiments, the polymeric catalyst or solid-supported catalyst has a total amount of nitrogen-containing cationic groups and counterions or a total amount of phosphorous-containing cationic groups and counterions of between about 0.01 and about 10 mmol, between about 0.05 and about 10 mmol, between about 1 and about 8 mmol, between about 2 and about 6 mmol, or between about 3 and about 5 mmol per gram of the polymeric catalyst or solid-supported catalyst.

In some embodiments, the polymeric catalyst or solid-supported catalyst has at least a portion of the ionic monomers have imidazolium. In those embodiments of the polymeric catalyst or solid-supported catalyst where at least a portion of the ionic monomers or moieties have imidazolium, the total amount of imidazolium and counterions in the polymeric catalyst or solid-supported catalyst is between about 0.01 and about 8 mmol, between about 0.05 and about 8 mmol, between about 1 and about 6 mmol, or between about 2 and about 5 mmol per gram of the polymeric catalyst.

In some embodiments of the polymeric catalyst or solid-supported catalyst, at least a portion of the ionic monomers have pyridinium. In those embodiments of the polymeric catalyst or solid-supported catalyst where at least a portion of the ionic monomers or moieties have pyridinium, the total amount of pyridinium and counterions in the polymeric catalyst or solid-supported catalyst is between about 0.01 and about 8 mmol, between about 0.05 and about 8 mmol, between about 1 and about 6 mmol, or between about 2 and about 5 mmol per gram of the polymeric catalyst or solid-supported catalyst.

In some embodiments of the polymeric catalyst or solid-supported catalyst, at least a portion of the ionic monomers or moieties have triphenyl phosphonium. In those embodiments of the polymeric catalyst or solid-supported catalyst where at least a portion of the ionic monomers or moieties have triphenyl phosphonium, the total amount of triphenyl phosphonium and counterions in the polymeric catalyst or solid-supported catalyst is between about 0.01 and about 5 mmol, between about 0.05 and about 5 mmol, between about 1 and about 4 mmol, or between about 2 and about 3 mmol per gram of the polymeric catalyst or solid-supported catalyst.

In some embodiments, the acidic and ionic monomers make up a substantial portion of the polymeric catalyst or solid-supported catalyst. In certain embodiments, the acidic and ionic monomers or moieties make up at least about 30%, at least about 40%, at least about 50%, at least about 60%, at least about 70%, at least about 80%, at least about 90%, at least about 95%, or at least about 99% of the monomers of the polymeric catalyst or solid-supported catalyst, based on the ratio of the number of acidic and ionic monomers or moieties to the total number of monomers or moieties present in the polymeric catalyst or solid-supported catalyst.

The ratio of the total number of acidic monomers or moieties to the total number of ionic monomers or moieties can be varied to tune the strength of the catalyst. In some embodiments, the total number of acidic monomers or moieties exceeds the total number of ionic monomers or moieties in the polymer or solid support. In other embodiments, the total number of acidic monomers or moieties is at least about 2, at least about 3, at least about 4, at least about 5, at least about 6, at least about 7, at least about 8, at least about 9 or at least about 10 times the total number of ionic monomers or moieties in the polymeric catalyst or solid-supported catalyst. In certain embodiments, the ratio of the total number of acidic monomers or moieties to the total number of ionic monomers or moieties is about 1:1, about 2:1, about 3:1, about 4:1, about 5:1, about 6:1, about 7:1, about 8:1, about 9:1 or about 10:1.

In some embodiments, the total number of ionic monomers or moieties exceeds the total number of acidic monomers or moieties in the catalyst. In other embodiments, the total number of ionic monomers or moieties is at least about 2, at least about 3, at least about 4, at least about 5, at least about 6, at least about 7, at least about 8, at least about 9 or at least about 10 times the total number of acidic monomers or moieties in the polymeric catalyst or solid-supported catalyst. In certain embodiments, the ratio of the total number of ionic monomers or moieties to the total number of acidic monomers or moieties is about 1:1, about 2:1, about 3:1, about 4:1, about 5:1, about 6:1, about 7:1, about 8:1, about 9:1 or about 10:1.

The polymeric catalysts or solid-supported catalysts described herein can be characterized by the chemical functionalization of the polymeric catalyst or solid-supported catalyst. In some embodiments, the polymeric catalyst or solid-supported catalyst can have between about 0.1 and about 20 mmol, between about 0.1 and about 15 mmol, between about 0.01 and about 12 mmol, between about 0.01 and about 10 mmol, between about 1 and about 8 mmol, between about 2 and about 7 mmol, between about 3 and about 6 mmol, between about 1 and about 5, or between about 3 and about 5 mmol of the Bronsted-Lowry acid per gram of the polymeric catalyst or solid-supported catalyst. In some embodiments where the polymeric catalyst or solid-supported catalyst has at least some monomers or moieties with side chains having sulfonic acid as the Bronsted-Lowry acid, the polymeric catalyst or solid-supported catalyst can have between about 0.05 to about 10 mmol of the sulfonic acid per gram of the polymeric catalyst or solid-supported catalyst. In other embodiments where the polymeric catalyst or solid-supported catalyst has at least some monomers or moieties with side chains having phosphonic acid as the Bronsted-Lowry acid, the polymeric catalyst or solid-supported catalyst can have between about 0.01 and about 12 mmol of the phosphonic acid per gram of the polymeric catalyst or solid-supported catalyst.

In other embodiments where the polymeric catalyst or solid-supported catalyst has at least some monomers or moieties with side chains having acetic acid as the Bronsted-Lowry acid, the polymeric catalyst or solid-supported catalyst can have between about 0.01 and about 12 mmol of the carboxylic acid per gram of the polymeric catalyst or solid-supported catalyst. In other embodiments where the polymeric catalyst or solid-supported catalyst has at least some monomers or moieties with side chains having isophthalic acid as the Bronsted-Lowry acid, the polymeric catalyst or solid-supported catalyst can have between about 0.01 and about 5 mmol of the isophthalic acid per gram of the polymeric catalyst or solid-supported catalyst. In other embodiments where the polymeric catalyst or solid-supported catalyst has at least some monomers or moieties with side chains having boronic acid as the Bronsted-Lowry acid, the polymeric catalyst or solid-supported catalyst can have between about 0.01 and about 20 mmol of the boronic acid per gram of the polymeric catalyst or solid-supported catalyst. In other embodiments where the polymeric catalyst or solid-supported catalyst has at least some monomers or moieties with side chains having a perfluorinated acid, such as trifluoroacetic acid, as the Bronsted-Lowry acid, the polymeric catalyst or solid-supported catalyst can have between about 0.01 and about 5 mmol of the perfluorinated acid per gram of the polymeric catalyst or solid-supported catalyst In some embodiments, the polymeric catalyst or solid-supported catalyst can have between about 0.01 and about 10 mmol, between about 0.01 and about 8.0 mmol, between about 0.01 and about 4 mmol, between about 1 and about 10 mmol, between about 2 and about 8 mmol, or between about 3 and about 6 mmol of the ionic group. In such embodiments, the ionic group includes the cationic group listed, as well as any suitable counterion described herein (e.g., halide, nitrate, sulfate, formate, acetate, or organosulfonate).

In some embodiments where the polymeric catalyst or solid-supported catalyst has at least some monomers or moieties with side chains having imidazolium as part of the ionic group, the polymeric catalyst or solid-supported catalyst can have between about 0.01 and about 8 mmol of the ionic group per gram of the polymeric catalyst or solid-supported catalyst. In other embodiments where the polymeric catalyst or solid-supported catalyst has at least some monomers or moieties with side chains having pyridinium as part of the ionic group, the polymeric catalyst or solid-supported catalyst can have between about 0.01 and about 8 mmol of the ionic group per gram of the polymeric catalyst or solid-supported catalyst.

In other embodiments where the polymeric catalyst or solid-supported catalyst has at least some monomers or moieties with side chains having triphenyl phosphonium as part of the ionic group, the polymeric catalyst or solid-supported catalyst can have between about 0.01 and about 4 mmol of the ionic group per gram of the polymeric catalyst or solid-supported catalyst.

In some embodiments, the counterion is derived from acids selected from hydrofluoric acid, hydrochloric acid, hydrobromic acid, hydroioidic acid, nitric acid, nitrous acid, sulfuric acid, carbonic acid, phosphoric acid, phosphorous acid, acetic acid, formic acid, citric acid, methanesulfonic acid, ethanesulfonic acid, benzenesulfonic acid, dodecylsulfonic acid, and benzene phosphonic acid.

Polymeric Catalysts a) Arrangement of Monomers

In some embodiments, the acidic monomers, the ionic monomers, the acidic-ionic monomers and the hydrophobic monomers, where present, can be arranged in alternating sequence or in a random order as blocks of monomers. In some embodiments, each block has not more than twenty, fifteen, ten, six, or three monomers.

In some embodiments, the monomers of the polymeric catalyst are randomly arranged in an alternating sequence. With reference to the portion of the exemplary polymeric catalyst depicted in FIG. 3A, the monomers are randomly arranged in an alternating sequence.

In other embodiments, the monomers of the polymeric catalyst are randomly arranged as blocks of monomers. With reference to the portion of the exemplary polymeric catalyst depicted in FIG. 3B, the monomers are arranged in blocks of monomers. In certain embodiments where the acidic monomers and the ionic monomers are arranged in blocks of monomers, each block has no more than 20, 19, 18, 17, 16, 15, 14, 13, 12, 11, 10, 9, 8, 7, 6, 5, 4, or 3 monomers.

The polymeric catalysts described herein can also be cross-linked. Such cross-linked polymeric catalysts can be prepared by introducing cross-linking groups. In some embodiments, cross-linking can occur within a given polymeric chain, with reference to the portion of the exemplary polymeric catalysts depicted in FIGS. 4A and 4B. In other embodiments, cross-linking can occur between two or more polymeric chains, with reference to the portion of the exemplary polymeric catalysts in FIGS. 5A, 5B, 5C and 5D.

Figure 5A:
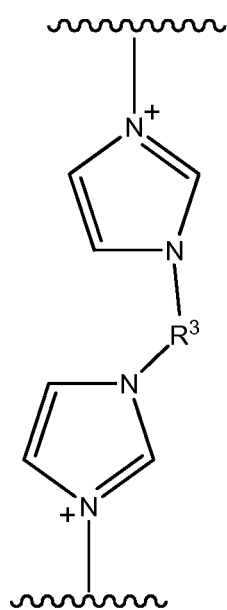
FIGS. 5A, 5B, 5C and 5D illustrate a portion of exemplary polymeric catalysts with cross-linking between two polymeric chains.
Figure 5B:
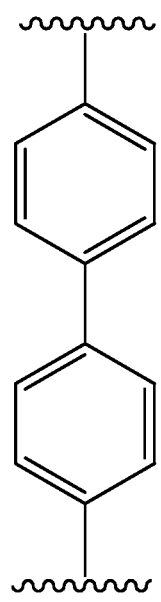
Figure 5C:
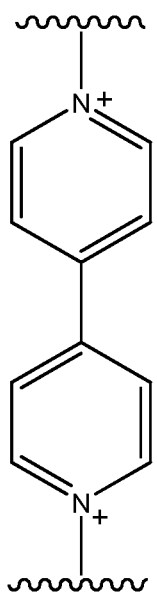
Figure 5D:
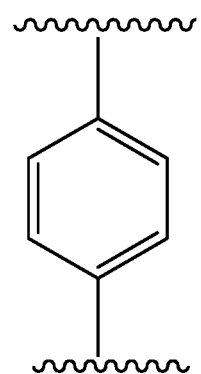

With reference to FIGS. 4A, 4B and 5A, it should be understood that $R^1$, $R^2$ and $R^3$, respectively, are exemplary cross linking groups. Suitable cross-linking groups that can be used to form a cross-linked polymeric catalyst with the polymers described herein include, for example, substituted or unsubstituted divinyl alkanes, substituted or unsubstituted divinyl cycloalkanes, substituted or unsubstituted divinyl aryls, substituted or unsubstituted heteroaryls, dihaloalkanes, dihaloalkenes, and dihaloalkynes, where the substituents are those as defined herein. For example, cross-linking groups can include divinylbenzene, diallylbenzene, dichlorobenzene, divinylmethane, dichloromethane, divinylethane, dichloroethane, divinylpropane, dichloropropane, divinylbutane, dichlorobutane, ethylene glycol, and resorcinol. In one embodiment, the crosslinking group is divinyl benzene.

In some embodiments, the polymer is cross-linked. In certain embodiments, at least about 1%, at least about 2%, at least about 3%, at least about 4%, at least about 5%, at least about 6%, at least about 7%, at least about 8%, at least about 9%, at least about 10%, at least about 15%, at least about 20%, at least about 30%, at least about 40%, at least about 50%, at least about 60%, at least about 70%, at least about 80%, at least about 90% or at least about 99% of the polymer is cross-linked.

In some embodiments, the polymers described herein are not substantially cross-linked, such as less than about 0.9% cross-linked, less than about 0.5% cross-linked, less than about 0.1% cross-linked, less than about 0.01% cross-linked, or less than 0.001% cross-linked.

d) Polymeric Backbone

The polymeric backbone described herein can include, for example, polyalkylenes, polyalkenyl alcohols, polycarbonate, polyarylenes, polyaryletherketones, and polyamide-imides. In certain embodiments, the polymeric backbone can be selected from polyethylene, polypropylene, polyvinyl alcohol, polystyrene, polyurethane, polyvinyl chloride, polyphenol-aldehyde, polytetrafluoroethylene, polybutylene terephthalate, polycaprolactam, and poly(acrylonitrile butadiene styrene). In certain embodiments of the polymeric catalyst, the polymeric backbone is polyethyelene or polypropylene. In one embodiment of the polymeric catalyst, the polymeric backbone is polyethylene. In another embodiment of the polymeric catalyst, the polymeric backbone is polyvinyl alcohol. In yet another embodiment of the polymeric catalyst, the polymeric backbone is polystyrene.

Figure 6A:
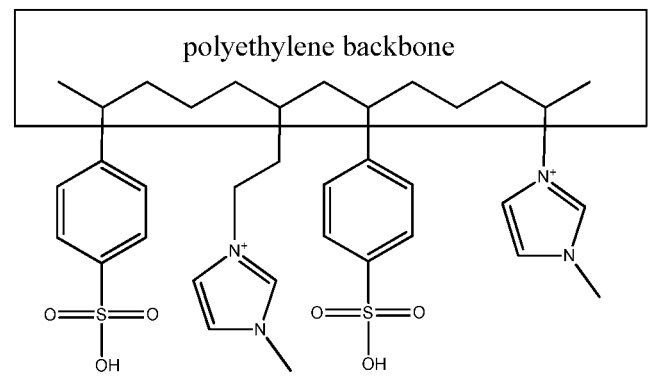
FIG. 6A illustrates a portion of an exemplary polymeric catalyst with a polyethylene backbone.
Figure 6B:
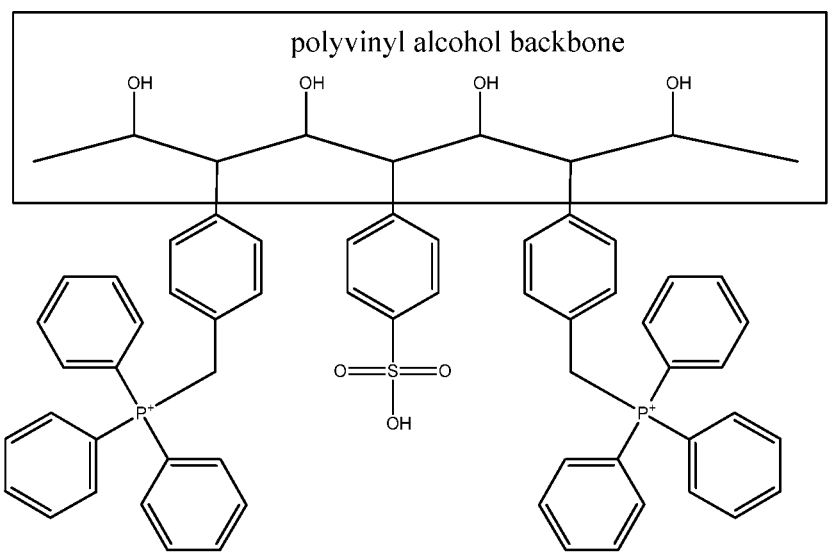
FIG. 6B illustrates a portion of an exemplary polymeric catalyst with a polyvinylalcohol backbone.

With reference to FIG. 6A, in one exemplary embodiment, the polymeric backbone is polyethylene. With reference to FIG. 6B, in another exemplary embodiment, the polymeric backbone is polyvinyl alcohol.

The polymeric backbone described herein can also include an ionic group integrated as part of the polymeric backbone. Such polymeric backbones can also be called "ionomeric backbones". In certain embodiments, the polymeric backbone can be selected from: polyalkyleneammonium, polyalkylenediammonium, polyalkylenepyrrolium, polyalkyleneimidazolium, polyalkylenepyrazolium, polyalkyleneoxazolium, polyalkylenethiazolium, polyalkylenepyridinium, polyalkylenepyrimidinium, polyalkylenepyrazinium, polyalkylenepyradizimium, polyalkylenethiazinium, polyalkylenemorpholinium, polyalkylenepiperidinium, polyalkylenepiperizinium, polyalkylenepyrollizinium, polyalkylenetriphenylphosphonium, polyalkylenetrimethylphosphonium, polyalkylenetriethylphosphonium, polyalkylenetripropylphosphonium, polyalkylenetributylphosphonium, polyalkylenetrichlorophosphonium, polyalkylenetrifluorophosphonium, and polyalkylenediazolium, polyarylalkyleneammonium, polyarylalkylenediammonium, polyarylalkylenepyrrolium, polyarylalkyleneimidazolium, polyarylalkylenepyrazolium, polyarylalkyleneoxazolium, polyarylalkylenethiazolium, polyarylalkylenepyridinium, polyarylalkylenepyrimidinium, polyarylalkylenepyrazinium, polyarylalkylenepyradizimium, polyarylalkylenethiazinium, polyarylalkylenemorpholinium, polyarylalkylenepiperidinium, polyarylalkylenepiperizinium, polyarylalkylenepyrollizinium, polyarylalkylenetriphenylphosphonium, polyarylalkylenetrimethylphosphonium, polyarylalkylenetriethylphosphonium, polyarylalkylenetripropylphosphonium, polyarylalkylenetributylphosphonium, polyarylalkylenetrichlorophosphonium, polyarylalkylenetrifluorophosphonium, and polyarylalkylenediazolium.

Cationic polymeric backbones can be associated with one or more anions, including but not limited to, $F^-$, $Cl^-$, $Br^-$, $I^-$, $NO_2^-$, $NO_3^-$, $SO_4^{2-}$, $R^7SO_4^-$, $R^7CO_2^-$, $PO_4^{2-}$, $R^7PO_3^-$, and $R^7PO_2^-$, where $R^7$ is selected from hydrogen, $C_{1-4}$alkyl, and $C_{1-4}$ heteroalkyl. In one embodiment, each X can be selected from $Cl^-$, $Br^-$, $I^-$, $HSO_4^-$, $HCO_2^-$, $CH_3CO_2^-$, and $NO_3^-$. In other embodiments, X is acetate. In other embodiments, X is bisulfate. In other embodiments, X is chloride. In other embodiments, X is nitrate.

In other embodiments, the polymeric backbone is alkyleneimidazolium, which refers to an alkylene moiety, in which one or more of the methylene units of the alkylene moiety has been replaced with imidazolium. In one embodiment, the polymeric backbone is selected from polyethyleneimidazolium, polyprolyeneimidazolium, and polybutyleneimidazolium. It should further be understood that, in other embodiments of the polymeric backbone, when a nitrogen-containing cationic group or a phosphorous-containing cationic group follows the term "alkylene", one or more of the methylene units of the alkylene moiety is substituted with that nitrogen-containing cationic group or phosphorous-containing cationic group.

Further, the number of atoms between side chains in the polymeric backbone can vary. In some embodiments, there are between zero and twenty atoms, zero and ten atoms, zero and six atoms, or zero and three atoms between side chains attached to the polymeric backbone.

In some embodiments, the polymer can be a homopolymer having at least two monomer units, and where all the units contained within the polymer are derived from the same monomer in the same manner. In other embodiments, the polymer can be a heteropolymer having at least two monomer units, and where at least one monomeric unit contained within the polymer that differs from the other monomeric units in the polymer. The different monomer units in the polymer can be in a random order, in an alternating sequence of any length of a given monomer, or in blocks of monomers.

Other exemplary polymers include, but are not limited to, polyalkylene backbones that are substituted with one or more groups selected from hydroxyl, carboxylic acid, unsubstituted and substituted phenyl, halides, unsubstituted and substituted amines, unsubstituted and substituted ammonias, unsubstituted and substituted pyrroles, unsubstituted and substituted imidazoles, unsubstituted and substituted pyrazoles, unsubstituted and substituted oxazoles, unsubstituted and substituted thiazoles, unsubstituted and substituted pyridines, unsubstituted and substituted pyrimidines, unsubstituted and substituted pyrazines, unsubstituted and substituted pyradazines, unsubstituted and substituted thiazines, unsubstituted and substituted morpholines, unsubstituted and substituted piperidines, unsubstituted and substituted piperizines, unsubstituted and substituted pyrollizines, unsubstituted and substituted triphenylphosphonates, unsubstituted and substituted trimethylphosphonates, unsubstituted and substituted triethylphosphonates, unsubstituted and substituted tripropylphosphonates, unsubstituted and substituted tributylphosphonates, unsubstituted and substituted trichlorophosphonates, unsubstituted and substituted trifluorophosphonates, and unsubstituted and substituted diazoles, where the terms unsubstituted and substituted have the meanings as disclosed herein.

For the polymers as described herein, multiple naming conventions are well recognized in the art. For instance, a polyethylene backbone with a direct bond to an unsubstituted phenyl group (—$CH_2$—CH(phenyl)-$CH_2$—CH(phenyl)-) is also known as polystyrene. Should that phenyl group be substituted with an ethenyl group, the polymer can be named a polydivinylbenzene (—$CH_2$—CH(4-vinylphenyl)-$CH_2$—CH(4-vinylphenyl)-). Further non-limiting examples of heteropolymers include those that are functionalized after polymerization.

A non-limiting example would be polystyrene-co-divinylbenzene: (—$CH_2$—CH(phenyl)-$CH_2$—CH(4-ethylenephenyl)-$CH_2$—CH(phenyl)-$CH_2$—CH(4-ethylenephenyl)-).
Here, the ethenyl functionality could be at the 2, 3, or 4 position on the phenyl ring.

Figure 6C:
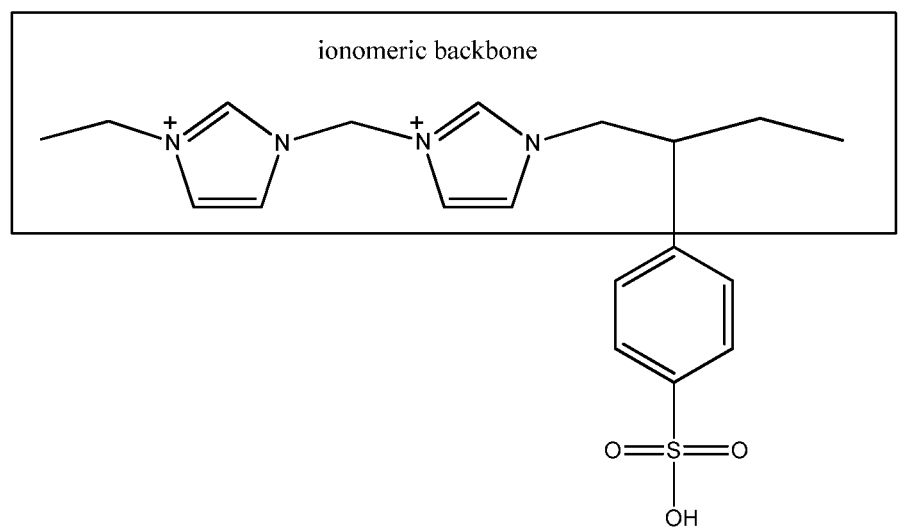
FIG. 6C illustrates a portion of an exemplary polymeric catalyst with an ionomeric backbone.

With reference to FIG. 6C, in yet another exemplary embodiment, the polymeric backbone is a polyalkyleneimidazolium.

Further, the number of atoms between side chains in the polymeric backbone can vary. In some embodiments, there are between zero and twenty atoms, zero and ten atoms, or zero and six atoms, or zero and three atoms between side chains attached to the polymeric backbone. With reference to FIG. 7A, in one exemplary embodiment, there are three carbon atoms between the side chain with the Bronsted-Lowry acid and the side chain with the cationic group. In another example, with reference to FIG. 7B, there are zero atoms between the side chain with the acidic moiety and the side chain with the ionic moiety.

Exemplary Polymers

It should be understood that the polymeric catalysts can include any of the Bronsted-Lowry acids, cationic groups, counterions, linkers, hydrophobic groups, cross-linking groups, and polymeric backbones described herein, as if each and every combination were listed separately. For example, in one embodiment, the polymeric catalyst can include benzenesulfonic acid (i.e., a sulfonic acid with a phenyl linker) connected to a polystyrene backbone, and an imidazolium chloride connected directly to the polystyrene backbone. In another embodiment, the polymeric catalyst can include boronyl-benzyl-pyridinium chloride (i.e., a boronic acid and pyridinium chloride in the same monomer unit with a phenyl linker) connected to a polystyrene backbone. In yet another embodiment, the polymeric catalyst can include benzenesulfonic acid and an imidazolium sulfate moiety each individually connected to a polyvinyl alcohol backbone.

In some embodiments, the polymeric catalyst is selected from:
poly[styrene-co-4-vinylbenzenesulfonic acid-co-3-methyl-1-(4-vinylbenzyl)-3H-imidazol-1-ium chloride-co-divinylbenzene];
poly[styrene-co-4-vinylbenzenesulfonic acid-co-3-methyl-1-(4-vinylbenzyl)-3H-imidazol-1-ium bisulfate-co-divinylbenzene];

poly[styrene-co-4-vinylbenzenesulfonic acid-co-3-methyl-1-(4-vinylbenzyl)-3H-imidazol-1-ium acetate-co-divinylbenzene];
poly[styrene-co-4-vinylbenzenesulfonic acid-co-3-methyl-1-(4-vinylbenzyl)-3H-imidazol-1-ium nitrate-co-divinylbenzene];
poly[styrene-co-4-vinylbenzenesulfonic acid-co-3-ethyl-1-(4-vinylbenzyl)-3H-imidazol-1-ium chloride-co-divinylbenzene];
poly[styrene-co-4-vinylbenzenesulfonic acid-co-3-ethyl-1-(4-vinylbenzyl)-3H-imidazol-1-ium bisulfate-co-divinylbenzene];
poly[styrene-co-4-vinylbenzenesulfonic acid-co-3-ethyl-1-(4-vinylbenzyl)-3H-imidazol-1-ium acetate-co-divinylbenzene];
poly[styrene-co-4-vinylbenzenesulfonic acid-co-3-ethyl-1-(4-vinylbenzyl)-3H-imidazol-1-ium nitrate-co-divinylbenzene];
poly[styrene-co-4-vinylbenzenesulfonic acid-co-1-(4-vinylbenzyl)-3H-imidazol-1-ium chloride-co-divinylbenzene];
poly[styrene-co-4-vinylbenzenesulfonic acid-co-1-(4-vinylbenzyl)-3H-imidazol-1-ium iodide-co-divinylbenzene];
poly[styrene-co-4-vinylbenzenesulfonic acid-co-1-(4-vinylbenzyl)-3H-imidazol-1-ium bromide-co-divinylbenzene];
poly[styrene-co-4-vinylbenzenesulfonic acid-co-1-(4-vinylbenzyl)-3H-imidazol-1-ium bisulfate-co-divinylbenzene];
poly[styrene-co-4-vinylbenzenesulfonic acid-co-1-(4-vinylbenzyl)-3H-imidazol-1-ium acetate-co-divinylbenzene];
poly[styrene-co-4-vinylbenzenesulfonic acid-co-3-methyl-1-(4-vinylbenzyl)-3H-benzoimidazol-1-ium chloride-co-divinylbenzene];
poly[styrene-co-4-vinylbenzenesulfonic acid-co-3-methyl-1-(4-vinylbenzyl)-3H-benzoimidazol-1-ium bisulfate-co-divinylbenzene];
poly[styrene-co-4-vinylbenzenesulfonic acid-co-3-methyl-1-(4-vinylbenzyl)-3H-benzoimidazol-1-ium acetate-co-divinylbenzene];
poly[styrene-co-4-vinylbenzenesulfonic acid-co-3-methyl-1-(4-vinylbenzyl)-3H-benzoimidazol-1-ium formate-co-divinylbenzene];
poly[styrene-co-4-vinylbenzenesulfonic acid-co-1-(4-vinylbenzyl)-pyridinium-chloride-co-divinylbenzene];
poly[styrene-co-4-vinylbenzenesulfonic acid-co-1-(4-vinylbenzyl)-pyridinium-bisulfate-co-divinylbenzene];
poly[styrene-co-4-vinylbenzenesulfonic acid-co-1-(4-vinylbenzyl)-pyridinium-acetate-co-divinylbenzene];
poly[styrene-co-4-vinylbenzenesulfonic acid-co-1-(4-vinylbenzyl)-pyridinium-nitrate-co-divinylbenzene];
poly[styrene-co-4-vinylbenzenesulfonic acid-co-1-(4-vinylbenzyl)-pyridinium-chloride-co-3-methyl-1-(4-vinylbenzyl)-3H-imidazol-1-ium bisulfate-co-divinylbenzene];
poly[styrene-co-4-vinylbenzenesulfonic acid-co-1-(4-vinylbenzyl)-pyridinium-bromide-co-3-methyl-1-(4-vinylbenzyl)-3H-imidazol-1-ium bisulfate-co-divinylbenzene];
poly[styrene-co-4-vinylbenzenesulfonic acid-co-1-(4-vinylbenzyl)-pyridinium-iodide-co-3-methyl-1-(4-vinylbenzyl)-3H-imidazol-1-ium bisulfate-co-divinylbenzene];
poly[styrene-co-4-vinylbenzenesulfonic acid-co-1-(4-vinylbenzyl)-pyridinium-bisulfate-co-3-methyl-1-(4-vinylbenzyl)-3H-imidazol-1-ium bisulfate-co-divinylbenzene];
poly[styrene-co-4-vinylbenzenesulfonic acid-co-1-(4-vinylbenzyl)-pyridinium-acetate-co-3-methyl-1-(4-vinylbenzyl)-3H-imidazol-1-ium bisulfate-co-divinylbenzene];
poly[styrene-co-4-vinylbenzenesulfonic acid-co-4-methyl-4-(4-vinylbenzyl)-morpholin-4-ium chloride-co-divinylbenzene];
poly[styrene-co-4-vinylbenzenesulfonic acid-co-4-methyl-4-(4-vinylbenzyl)-morpholin-4-ium bisulfate-co-divinylbenzene];
poly[styrene-co-4-vinylbenzenesulfonic acid-co-4-methyl-4-(4-vinylbenzyl)-morpholin-4-ium acetate-co-divinylbenzene];
poly[styrene-co-4-vinylbenzenesulfonic acid-co-4-methyl-4-(4-vinylbenzyl)-morpholin-4-ium formate-co-divinylbenzene];
poly[styrene-co-4-vinylbenzenesulfonic acid-co-triphenyl-(4-vinylbenzyl)-phosphonium chloride-co-divinylbenzene];
poly[styrene-co-4-vinylbenzenesulfonic acid-co-triphenyl-(4-vinylbenzyl)-phosphonium bisulfate-co-divinylbenzene];
poly[styrene-co-4-vinylbenzenesulfonic acid-co-triphenyl-(4-vinylbenzyl)-phosphonium acetate-co-divinylbenzene];
poly[styrene-co-4-vinylbenzenesulfonic acid-co-1-methyl-1-(4-vinylbenzyl)-piperidin-1-ium chloride-co-divinylbenzene];
poly[styrene-co-4-vinylbenzenesulfonic acid-co-1-methyl-1-(4-vinylbenzyl)-piperidin-1-ium bisulfate-co-divinylbenzene];
poly[styrene-co-4-vinylbenzenesulfonic acid-co-1-methyl-1-(4-vinylbenzyl)-piperidin-1-ium acetate-co-divinylbenzene];
poly[styrene-co-4-vinylbenzenesulfonic acid-co-4-(4-vinylbenzyl)-morpholine-4-oxide-co-divinylbenzene];
poly[styrene-co-4-vinylbenzenesulfonic acid-co-triethyl-(4-vinylbenzyl)-ammonium chloride-co-divinylbenzene];
poly[styrene-co-4-vinylbenzenesulfonic acid-co-triethyl-(4-vinylbenzyl)-ammonium bisulfate-co-divinylbenzene];
poly[styrene-co-4-vinylbenzenesulfonic acid-co-triethyl-(4-vinylbenzyl)-ammonium acetate-co-divinylbenzene];
poly[styrene-co-3-methyl-1-(4-vinylbenzyl)-3H-imidazol-1-ium chloride-co-4-boronyl-1-(4-vinylbenzyl)-pyridinium chloride-co-divinylbenzene];
poly[styrene-co-3-methyl-1-(4-vinylbenzyl)-3H-imidazol-1-ium chloride-co-1-(4-vinylphenyl)methylphosphonic acid-co-divinylbenzene];
poly[styrene-co-3-methyl-1-(4-vinylbenzyl)-3H-imidazol-1-ium bisulfate-co-1-(4-vinylphenyl)methylphosphonic acid-co-divinylbenzene];
poly[styrene-co-3-methyl-1-(4-vinylbenzyl)-3H-imidazol-1-ium acetate-co-1-(4-vinylphenyl)methylphosphonic acid-co-divinylbenzene];
poly[styrene-co-3-methyl-1-(4-vinylbenzyl)-3H-imidazol-1-ium nitrate-co-1-(4-vinylphenyl)methylphosphonic acid-co-divinylbenzene];
poly[styrene-co-4-vinylbenzenesulfonic acid-co-vinylbenzylchloride-co-1-methyl-2-vinyl-pyridinium chloride-co-divinylbenzene];
poly[styrene-co-4-vinylbenzenesulfonic acid-co-vinylbenzylchloride-co-1-methyl-2-vinyl-pyridinium bisulfate-co-divinylbenzene];
poly[styrene-co-4-vinylbenzenesulfonic acid-co-vinylbenzylchloride-co-1-methyl-2-vinyl-pyridinium acetate-co-divinylbenzene];
poly[styrene-co-4-vinylbenzenesulfonic acid-co-4-(4-vinylbenzyl)-morpholine-4-oxide-co-divinylbenzene];
poly[styrene-co-4-vinylphenylphosphonic acid-co-3-methyl-1-(4-vinylbenzyl)-3H-imidazol-1-ium chloride-co-divinylbenzene];
poly[styrene-co-4-vinylphenylphosphonic acid-co-3-methyl-1-(4-vinylbenzyl)-3H-imidazol-1-ium bisulfate-co-divinylbenzene];

poly[styrene-co-4-vinylphenylphosphonic acid-co-3-methyl-1-(4-vinylbenzyl)-3H-imidazol-1-ium acetate-co-divinylbenzene];
poly[styrene-co-3-carboxymethyl-1-(4-vinylbenzyl)-3H-imidazol-1-ium chloride-co-divinylbenzene];
poly[styrene-co-3-carboxymethyl-1-(4-vinylbenzyl)-3H-imidazol-1-ium bisulfate-co-divinylbenzene];
poly[styrene-co-3-carboxymethyl-1-(4-vinylbenzyl)-3H-imidazol-1-ium acetate-co-divinylbenzene];
poly[styrene-co-5-(4-vinylbenzylamino)-isophthalic acid-co-3-methyl-1-(4-vinylbenzyl)-3H-imidazol-1-ium chloride-co-divinylbenzene];
poly[styrene-co-5-(4-vinylbenzylamino)-isophthalic acid-co-3-methyl-1-(4-vinylbenzyl)-3H-imidazol-1-ium bisulfate-co-divinylbenzene];
poly[styrene-co-5-(4-vinylbenzylamino)-isophthalic acid-co-3-methyl-1-(4-vinylbenzyl)-3H-imidazol-1-ium acetate-co-divinylbenzene];
poly[styrene-co-(4-vinylbenzylamino)-acetic acid-co-3-methyl-1-(4-vinylbenzyl)-3H-imidazol-1-ium chloride-co-divinylbenzene];
poly[styrene-co-(4-vinylbenzylamino)-acetic acid-co-3-methyl-1-(4-vinylbenzyl)-3H-imidazol-1-ium bisulfate-co-divinylbenzene];
poly[styrene-co-(4-vinylbenzylamino)-acetic acid-co-3-methyl-1-(4-vinylbenzyl)-3H-imidazol-1-ium acetate-co-divinylbenzene];
poly(styrene-co-4-vinylbenzenesulfonic acid-co-vinylbenzylmethylimidazolium chloride-co-vinylbenzylmethylmorpholinium chloride-co-vinylbenzyltriphenyl phosphonium chloride-co-divinylbenzene);
poly(styrene-co-4-vinylbenzenephosphonic acid-co-vinylbenzylmethylimidazolium chloride-co-vinylbenzylmethylmorpholinium chloride-co-vinylbenzyltriphenyl phosphonium chloride-co-divinylbenzene);
poly(styrene-co-4-vinylbenzenesulfonic acid-co-vinylbenzylmethylimidazolium bisulfate-co-vinylbenzylmethylmorpholinium bisulfate-co-vinylbenzyltriphenyl phosphonium bisulfate-co-divinylbenzene);
poly(styrene-co-4-vinylbenzenephosphonic acid-co-vinylbenzylmethylimidazolium bisulfate-co-vinylbenzylmethylmorpholinium bisulfate-co-vinylbenzyltriphenyl phosphonium bisulfate-co-divinylbenzene);
poly(styrene-co-4-vinylbenzenesulfonic acid-co-vinylbenzylmethylimidazolium acetate-co-vinylbenzylmethylmorpholinium acetate-co-vinylbenzyltriphenyl phosphonium acetate-co-divinylbenzene);
poly(styrene-co-4-vinylbenzenephosphonic acid-co-vinylbenzylmethylimidazolium acetate-co-vinylbenzylmethylmorpholinium acetate-co-vinylbenzyltriphenyl phosphonium acetate-co-divinylbenzene);
poly(styrene-co-4-vinylbenzenesulfonic acid-co-vinylbenzylmethylmorpholinium chloride-co-vinylbenzyltriphenylphosphonium chloride-co-divinylbenzene);
poly(styrene-co-4-vinylbenzenephosphonic acid-co-vinylbenzylmethylmorpholinium chloride-co-vinylbenzyltriphenylphosphonium chloride-co-divinylbenzene);
poly(styrene-co-4-vinylbenzenesulfonic acid-co-vinylbenzylmethylmorpholinium bisulfate-co-vinylbenzyltriphenylphosphonium bisulfate-co-divinylbenzene);
poly(styrene-co-4-vinylbenzenephosphonic acid-co-vinylbenzylmethylmorpholinium bisulfate-co-vinylbenzyltriphenylphosphonium bisulfate-co-divinylbenzene);
poly(styrene-co-4-vinylbenzenesulfonic acid-co-vinylbenzylmethylmorpholinium acetate-co-vinylbenzyltriphenylphosphonium bisulfate-co-divinylbenzene);
poly(styrene-co-4-vinylbenzenephosphonic acid-co-vinylbenzylmethylmorpholinium acetate-co-vinylbenzyltriphenylphosphonium bisulfate-co-divinylbenzene)
poly(styrene-co-4-vinylbenzenesulfonic acid-co-vinylmethylimidazolium chloride-co-divinylbenzene);
poly(styrene-co-4-vinylbenzenesulfonic acid-co-vinylmethylimidazolium bisulfate-co-divinylbenzene);
poly(styrene-co-4-vinylbenzenesulfonic acid-co-vinylmethylimidazolium acetate-co-divinylbenzene);
poly(styrene-co-4-vinylbenzenesulfonic acid-co-vinylmethylimidazolium nitrate-co-divinylbenzene);
poly(styrene-co-4-vinylbenzenephosphonic acid-co-vinylmethylimidazolium chloride-co-divinylbenzene);
poly(styrene-co-4-vinylbenzenephosphonic acid-co-vinylmethylimidazolium bisulfate-co-divinylbenzene);
poly(styrene-co-4-vinylbenzenephosphonic acid-co-vinylmethylimidazolium acetate-co-divinylbenzene);
poly(styrene-co-4-vinylbenzenesulfonic acid-co-vinylbenzyltriphenylphosphonium chloride-co-divinylbenzene);
poly(styrene-co-4-vinylbenzenesulfonic acid-co-vinylbenzyltriphenylphosphonium bisulfate-co-divinylbenzene);
poly(styrene-co-4-vinylbenzenesulfonic acid-co-vinylbenzyltriphenylphosphonium acetate-co-divinylbenzene);
poly(styrene-co-4-vinylbenzenephosphonic acid-co-vinylbenzyltriphenylphosphonium chloride-co-divinylbenzene);
poly(styrene-co-4-vinylbenzenephosphonic acid-co-vinylbenzyltriphenylphosphonium bisulfate-co-divinylbenzene);
poly(styrene-co-4-vinylbenzenephosphonic acid-co-vinylbenzyltriphenylphosphonium acetate-co-divinylbenzene);
poly(styrene-co-4-vinylbenzenesulfonic acid-co-vinylbenzylmethylimidazolium chloride-co-divinylbenzene);
poly(styrene-co-4-vinylbenzenesulfonic acid-co-vinylbenzylmethylimidazolium bisulfate-co-divinylbenzene);
poly(styrene-co-4-vinylbenzenesulfonic acid-co-vinylbenzylmethylimidazolium acetate-co-divinylbenzene);
poly(styrene-co-4-vinylbenzenephosphonic acid-co-vinylbenzylmethylimidazolium chloride-co-divinylbenzene);
poly(styrene-co-4-vinylbenzenephosphonic acid-co-vinylbenzylmethylimidazolium bisulfate-co-divinylbenzene);
poly(styrene-co-4-vinylbenzenephosphonic acid-co-vinylbenzylmethylimidazolium acetate-co-divinylbenzene);
poly(styrene-co-4-vinylbenzenesulfonic acid-co-vinylbenzyltriphenylphosphonium chloride-co-divinylbenzene);
poly(styrene-co-4-vinylbenzenesulfonic acid-co-vinylbenzyltriphenylphosphonium bisulfate-co-divinylbenzene);
poly(styrene-co-4-vinylbenzenesulfonic acid-co-vinylbenzyltriphenylphosphonium acetate-co-divinylbenzene);
poly(styrene-co-4-vinylbenzenephosphonic acid-co-vinylbenzyltriphenylphosphonium chloride-co-divinylbenzene);
poly(styrene-co-4-vinylbenzenephosphonic acid-co-vinylbenzyltriphenylphosphonium bisulfate-co-divinylbenzene);
poly(styrene-co-4-vinylbenzenephosphonic acid-co-vinylbenzyltriphenylphosphonium acetate-co-divinylbenzene);
poly(butyl-vinylimidazolium chloride-co-butylimidazolium bisulfate-co-4-vinylbenzenesulfonic acid);
poly(butyl-vinylimidazolium bisulfate-co-butylimidazolium bisulfate-co-4-vinylbenzenesulfonic acid);
poly(benzyl alcohol-co-4-vinylbenzylalcohol sulfonic acid-co-vinylbenzyltriphenylphosphonium chloride-co-divinylbenzyl alcohol); and
poly(benzyl alcohol-co-4-vinylbenzylalcohol sulfonic acid-co-vinylbenzyltriphenylphosphonium bisulfate-co-divinylbenzyl alcohol).

In some embodiments, exemplary polymers can include
poly[styrene-co-4-vinylbenzene sulfonic acid-co-3-methyl-1-(4-vinylbenzyl)-3H-imidazol-1-ium nitrate-co-divinylbenzene];
poly[styrene-co-4-vinylbenzene sulfonic acid-co-1-(4-vinylbenzyl)-3H-imidazol-1-ium iodide-co-divinylbenzene];
poly[styrene-co-4-vinylbenzene sulfonic acid-co-3-methyl-1-(4-vinylbenzyl)-3H-benzoimidazol-1-ium chloride-co-divinylbenzene];
poly[styrene-co-4-vinylbenzene sulfonic acid-co-3-methyl-1-(4-vinylbenzyl)-3H-imidazol-1-ium bisulfate-co-divinylbenzene];
poly[styrene-co-4-vinylbenzene sulfonic acid-co-1-(4-vinylbenzyl)-pyridinium-bisulfate-co-divinylbenzene];
poly[styrene-co-4-vinylbenzene sulfonic acid-co-1-(4-vinylbenzyl)-pyridinium-chloride-co-3-methyl-1-(4-vinylbenzyl)-3H-imidazol-1-ium bisulfate-co-divinylbenzene];
poly[styrene-co-4-vinylbenzene sulfonic acid-co-4-methyl-4-(4-vinylbenzyl)-morpholin-4-ium chloride-co-divinylbenzene];
poly[styrene-co-4-vinylbenzene sulfonic acid-co-1-(4-vinylbenzyl)-3H-imidazol-1-ium bisulfate-co-divinylbenzene];
poly[styrene-co-4-vinylbenzene sulfonic acid-co-4-(4-vinylbenzyl)-morpholine-4-oxide-co-divinylbenzene];
poly[styrene-co-3-methyl-1-(4-vinylbenzyl)-3H-imidazol-1-ium bisulfate-co-1-(4-vinylphenyl)methyl phosphoninc acid-co-divinylbenzene];
poly[styrene-co-4-vinylbenzene sulfonic acid-co-vinylbenzylchloride-co-1-methyl-2-vinyl-pyridinium bisulfate-co-divinylbenzene];
poly[styrene-co-4-vinylbenzene sulfonic acid-co-4-(4-vinylbenzyl)-morpholine-4-oxide-co-divinylbenzene];
poly[styrene-co-4-vinylbenzene sulfonic acid-co-triphenyl-(4-vinylbenzyl)-phosphonium bisulfate-co-divinylbenzene];
poly[styrene-co-5-(4-vinylbenzylamino)-isophthalic acid-co-3-methyl-1-(4-vinylbenzyl)-3H-imidazol-1-ium chloride-co-divinylbenzene];
poly(styrene-co-4-vinylbenzene sulfonic acid-co-vinylbenzylmethylimidazolium chloride-co-vinylbenzylmethylmorpholinium chloride-co-vinylbenzyltriphenyl phosphonium chloride-co-divinylbenzene);
poly(styrene-co-4-vinylbenzene sulfonic acid-co-vinylmethylimidazolium acetate-co-divinylbenzene);
poly(styrene-co-4-vinylbenzene sulfonic acid-co-vinylbenzyltriphenylphosphonium chloride-co-divinylbenzene);
poly(styrene-co-4-vinylbenzene phosphonic acid-co-vinylbenzyltriphenylphosphonium chloride-co-divinylbenzene);
poly(styrene-co-4-vinylbenzene phosphonic acid-co-vinylbenzyltriphenylphosphonium bisulfate-co-divinylbenzene); and
poly(styrene-co-4-vinylbenzene sulfonic acid-co-vinylbenzyltriphenylphosphonium chloride-co-divinylbenzene).

In some embodiments, exemplary polymers can include
poly[styrene-co-4-vinylbenzene sulfonic acid-co-1-(4-vinylbenzyl)-pyridinium-chloride-co-3-methyl-1-(4-vinylbenzyl)-3H-imidazol-1-ium bisulfate-co-divinylbenzene];
poly[styrene-co-4-vinylbenzene sulfonic acid-co-vinylbenzylchloride-co-1-methyl-2-vinyl-pyridinium bisulfate-co-divinylbenzene];
poly(styrene-co-4-vinylbenzene phosphonic acid-co-vinylbenzyltriphenylphosphonium chloride-co-divinylbenzene);
poly[styrene-co-4-vinylbenzene sulfonic acid-co-1-(4-vinylbenzyl)-3H-imidazol-1-ium bisulfate-co-divinylbenzene]; and
poly(styrene-co-4-vinylbenzene sulfonic acid-co-vinylmethylimidazolium acetate-co-divinylbenzene).

In some embodiments, exemplary polymers can include
poly[styrene-co-4-vinylbenzene sulfonic acid-co-3-methyl-1-(4-vinylbenzyl)-3H-benzoimidazol-1-ium chloride-co-divinylbenzene];
poly[styrene-co-4-vinylbenzene sulfonic acid-co-3-methyl-1-(4-vinylbenzyl)-3H-imidazol-1-ium bisulfate-co-divinylbenzene];
poly[styrene-co-4-vinylbenzene sulfonic acid-co-1-(4-vinylbenzyl)-pyridinium-bisulfate-co-divinylbenzene];
poly(styrene-co-4-vinylbenzene sulfonic acid-co-vinylbenzylmethylimidazolium chloride-co-vinylbenzylmethylmorpholinium chloride-co-vinylbenzyltriphenyl phosphonium chloride-co-divinylbenzene); and
poly[styrene-co-4-vinylbenzene sulfonic acid-co-4-(4-vinylbenzyl)-morpholine-4-oxide-co-divinylbenzene].

In some embodiments, exemplary polymers can include
poly[styrene-co-4-vinylbenzene sulfonic acid-co-4-(4-vinylbenzyl)-morpholine-4-oxide-co-divinylbenzene];
poly(styrene-co-4-vinylbenzene sulfonic acid-co-vinylbenzyltriphenylphosphonium chloride-co-divinylbenzene);
poly[styrene-co-4-vinylbenzene sulfonic acid-1-(4-vinylbenzyl)-3H-imidazol-1-ium iodide-co-divinylbenzene];
poly[styrene-co-4-vinylbenzene sulfonic acid-co-triphenyl-(4-vinylbenzyl)-phosphonium bisulfate-co-divinylbenzene]; and
poly[styrene-co-3-methyl-1-(4-vinylbenzyl)-3H-imidazol-1-ium bisulfate-co-1-(4-vinylphenyl)methyl phosphonic acid-co-divinylbenzene].

In some embodiments, the polymeric backbone is formed from one or more substituted or unsubstituted monomers. Polymerization processes using a wide variety of monomers are well known in the art (see, e.g., International Union of Pure and Applied Chemistry, et al., IUPAC Gold Book, *Polymerization*. (2000)). One such process involves monomer(s) with unsaturated substitution, such as vinyl, propenyl, butenyl, or other such substitutent(s). These types of monomers can undergo radical initiation and chain polymerization.

In other embodiments, monomers having heteroatoms can be combined with one or more difunctionalized compounds, such as, but not limited to, dihaloalkanes, di(alkylsulfonyloxy)alkanes, and di(arylsulfonyloxy)alkanes to form polymers. The monomers have at least two heteroatoms to link with the difunctionalized alkane to create the polymeric chain. These difunctionalized compounds can be further substituted as described herein. In some embodiments, the difunctionalized compound(s) can be selected from 1,2-dichloroethane, 1,2-dichloropropane, 1,3-dichloropropane, 1,2-dichlorobutane, 1,3-dichlorobutane, 1,4-dichlorobutane, 1,2-dichloropentane, 1,3-dichloropentane, 1,4-dichloropentane, 1,5-dichloropentane, 1,2-dibromoethane, 1,2-dibromopropane, 1,3-dibromopropane, 1,2-dibromobutane, 1,3-dibromobutane, 1,4-dibromobutane, 1,2-dibromopentane, 1,3-dibromopentane, 1,4-dibromopentane, 1,5-dibromopentane, 1,2-diiodoethane, 1,2-diiodopropane, 1,3-diiodopropane, 1,2-diiodobutane, 1,3-diiodobutane, 1,4-diiodobutane, 1,2-diiodopentane, 1,3-diiodopentane, 1,4-diiodopentane, 1,5-diiodopentane, 1,2-dimethanesulfoxyethane, 1,2-dimethanesulfoxypropane, 1,3-dimethanesulfoxypropane, 1,2-dimethanesulfoxybutane, 1,3-dimethanesulfoxybutane, 1,4-dimethanesulfoxybutane, 1,2-dimethanesulfoxypentane, 1,3-dimethanesulfoxypentane, 1,4-dimethanesulfoxypentane, 1,5-dimethanesulfoxypentane, 1,2-diethanesulfoxyethane, 1,2-diethanesulfoxypropane, 1,3-diethanesulfoxypropane, 1,2-diethanesulfoxybutane, 1,3-diethanesulfoxybutane, 1,4-diethanesulfoxybutane, 1,2- diethanesulfoxypentane, 1,3-diethanesulfoxypentane, 1,4-diethanesulfoxypentane, 1,5-diethanesulfoxypentane, 1,2-dibenzenesulfoxyethane, 1,2-dibenzenesulfoxypropane, 1,3-dibenzenesulfoxypropane, 1,2-dibenzenesulfoxybutane, 1,3-dibenzenesulfoxybutane, 1,4-dibenzenesulfoxybutane, 1,2-dibenzenesulfoxypentane, 1,3-dibenzenesulfoxypentane, 1,4-dibenzenesulfoxypentane, 1,5-dibenzenesulfoxypentane, 1,2-di-p-toluenesulfoxyethane, 1,2-di-p-toluenesulfoxypropane, 1,3-di-p-toluenesulfoxypropane, 1,2-di-p-toluenesulfoxybutane, 1,3-di-p-toluenesulfoxybutane, 1,4-di-p-toluenesulfoxybutane, 1,2-di-p-toluenesulfoxypentane, 1,3-di-p-toluene sulfoxypentane, 1,4-di-p-toluene sulfoxypentane, and 1,5-di-p-toluene sulfoxypentane.

In some embodiments, the polymeric backbone is formed from one or more substituted or unsubstituted monomers selected from ethylene, propylene, hydroxyethylene, acetaldehyde, styrene, divinyl benzene, isocyanates, vinyl chloride, vinyl phenols, tetrafluoroethylene, butylene, terephthalic acid, caprolactam, acrylonitrile, butadiene, ammonias, diammonias, pyrrole, imidazole, pyrazole, oxazole, thiazole, pyridine, pyrimidine, pyrazine, pyradizimine, thiazine, morpholine, piperidine, piperizines, pyrollizine, triphenylphosphonate, trimethylphosphonate, triethylphosphonate, tripropylphosphonate, tributylphosphonate, trichlorophosphonate, trifluorophosphonate, and diazole, where the terms unsubstituted and substituted have the meanings as disclosed herein.

The polymeric catalysts described herein can form solid particles. One of skill in the art would recognize the various known techniques and methods to make solid particles from the polymers described herein. For example, a solid particle can be formed through the procedures of emulsion or dispersion polymerization, which are known to one of skill in the art. In other embodiments, the solid particles can be formed by grinding or breaking the polymer into particles, which are also techniques and methods that are known to one of skill in the art. Methods known in the art to prepare solid particles include coating the polymers described herein on the surface of a solid core. Suitable materials for the solid core can include an inert material (e.g., aluminum oxide, corn cob, crushed glass, chipped plastic, pumice, silicon carbide, or walnut shell) or a magnetic material. Polymeric coated core particles can be made by dispersion polymerization to grow a cross-linked polymer shell around the core material, or by spray coating or melting.

Other methods known in the art to prepare solid particles include coating the polymers described herein on the surface of a solid core. The solid core can be a non-catalytic support. Suitable materials for the solid core can include an inert material (e.g., aluminum oxide, corn cob, crushed glass, chipped plastic, pumice, silicon carbide, or walnut shell) or a magnetic material. In one embodiment of the polymeric catalyst, the solid core is made up of iron. Polymeric coated core particles can be made by techniques and methods that are known to one of skill in the art, for example, by dispersion polymerization to grow a cross-linked polymer shell around the core material, or by spray coating or melting.

The solid supported polymer catalyst particle can have a solid core where the polymer is coated on the surface of the solid core. In some embodiments, at least about 5%, at least about 10%, at least about 20%, at least about 30%, at least about 40%, or at least about 50% of the catalytic activity of the solid particle can be present on or near the exterior surface of the solid particle. In some embodiments, the solid core can have an inert material or a magnetic material. In one embodiment, the solid core is made up of iron.

The solid particles coated with the polymer described herein have one or more catalytic properties. In some embodiments, at least about 50%, at least about 60%, at least about 70%, at least about 80% or at least about 90% of the catalytic activity of the solid particle is present on or near the exterior surface of the solid particle.

In some embodiments, the solid particle is substantially free of pores, for example, having no more than about 50%, no more than about 40%, no more than about 30%, no more than about 20%, no more than about 15%, no more than about 10%, no more than about 5%, or no more than about 1% of pores. Porosity can be measured by methods well known in the art, such as determining the Brunauer-Emmett-Teller (BET) surface area using the absorption of nitrogen gas on the internal and external surfaces of a material (Brunauer, S. et al., J. Am. Chem. Soc. 1938, 60:309). Other methods include measuring solvent retention by exposing the material to a suitable solvent (such as water), then removing it thermally to measure the volume of interior pores. Other solvents suitable for porosity measurement of the polymeric catalysts include, but are not limited to, polar solvents such as DMF, DMSO, acetone, and alcohols.

In other embodiments, the solid particles include a microporous gel resin. In yet other embodiments, the solid particles include a macroporous gel resin.

In other embodiments, the solid particle having the polymer coating has at least one catalytic property selected from:
a) disruption of at least one hydrogen bond in cellulosic materials;
b) intercalation of the polymer into crystalline domains of cellulosic materials; and
c) cleavage of at least one glycosidic bond in cellulosic materials.

Solid-Supported Catalysts

In some embodiments, the polymer can include a support and a plurality of acidic moieties and cationic moieties attached to the support. In certain embodiments, the support is selected from biochar, carbon, amorphous carbon, activated carbon, silica, silica gel, alumina, magnesia, titania, zirconia, clays (e.g., kaolinite), magnesium silicate, silicon carbide, zeolites (e.g., mordenite), ceramics, and any combinations thereof. In one embodiment, the material is carbon. The material for carbon support can be biochar, amorphous carbon, or activated carbon. In one embodiment, the material is activated carbon.

In certain embodiments, the acidic groups on the acidic moiety are selected from sulfonic acid, phosphonic acid, acetic acid, isophthalic acid, and boronic acid. In certain embodiments, the ionic groups on the ionic moiety are selected from pyrrolium, imidazolium, pyrazolium, oxazolium, thiazolium, pyridinium, pyrimidinium, pyrazinium, pyradizimium, thiazinium, morpholinium, piperidinium, piperizinium, and pyrollizinium, phosphonium, trimethyl phosphonium, triethyl phosphonium, tripropyl phosphonium, tributyl phosphonium, trichloro phosphonium, triphenyl phosphonium and trifluoro phosphonium.

In some embodiments of the solid-supported catalyst where the Bronsted-Lowry acid is attached to the solid support by a linker, each linker is independently selected from unsubstituted or substituted alkylene, unsubstituted or substituted cycloalkylene, unsubstituted or substituted alkenylene, unsubstituted or substituted arylene, or unsubstituted or substituted heteroarylene, where the substituents are those as defined herein. In certain embodiments of the solid-supported catalyst, the linker is unsubstituted or substituted arylene, unsubstituted or substituted heteroarylene. In certain embodiments of the solid-supported catalyst, the linker is unsubstituted or substituted arylene. In one embodiment of the solid-supported catalyst, the linker is phenylene. In another embodiment of the solid-supported catalyst, the linker is hydroxyl-substituted phenylene.

In some embodiments of the solid-supported catalyst, each Bronsted-Lowry acid is directly attached to the solid support. In other embodiments of the solid-supported catalyst, the acidic moieties each further include a linker attaching the Bronsted-Lowry acid to the solid support. In certain embodiments of the solid-supported catalyst, some of the Bronsted-Lowry acids are directly connected to the solid support, while other Bronsted-Lowry acids are attached to the solid support by a linker.

The carbon support can have a surface area from 0.01 to 50 $m^2/g$ of dry material. The carbon support can have a density from 0.5 to 2.5 kg/L. The support can be characterized using any suitable instrumental analysis methods or techniques known in the art, including for example scanning electron microscopy (SEM), powder X-ray diffraction (XRD), Raman spectroscopy, and Fourier Transform infrared spectroscopy (FTIR). The carbon support can be prepared from carbonaceous materials, including for example, shrimp shell, chitin, coconut shell, wood pulp, paper pulp, cotton, cellulose, hard wood, soft wood, wheat straw, sugarcane bagasse, cassava stem, corn stover, oil palm residue, bitumen, asphaltum, tar, coal, pitch, and any combinations thereof. One of skill in the art would recognize suitable methods to prepare the carbon supports used herein. See e.g., M. Inagaki, L. R. Radovic, *Carbon*, vol. 40, p. 2263 (2002), or A. G. Pandolfo and A. F. Hollenkamp, "Review: Carbon Properties and their role in supercapacitors," *Journal of Power Sources*, vol. 157, pp. 11-27 (2006).

In other embodiments, the material is silica, silica gel, alumina, or silica-alumina. One of skill in the art would recognize suitable methods to prepare these silica- or alumina-based solid supports used herein. See e.g., Catalyst supports and supported catalysts, by A. B. Stiles, Butterworth Publishers, Stoneham Mass., 1987.

In yet other embodiments, the material is a combination of a carbon support, with one or more other supports selected from silica, silica gel, alumina, magnesia, titania, zirconia, clays (e.g., kaolinite), magnesium silicate, silicon carbide, zeolites (e.g., mordenite), and ceramics.

In some embodiments, the solid-supported catalyst is selected from:

amorphous carbon-supported pyrrolium chloride sulfonic acid;
amorphous carbon-supported imidazolium chloride sulfonic acid;
amorphous carbon-supported pyrazolium chloride sulfonic acid;
amorphous carbon-supported oxazolium chloride sulfonic acid;
amorphous carbon-supported thiazolium chloride sulfonic acid;
amorphous carbon-supported pyridinium chloride sulfonic acid;
amorphous carbon-supported pyrimidinium chloride sulfonic acid;
amorphous carbon-supported pyrazinium chloride sulfonic acid;
amorphous carbon-supported pyradizimium chloride sulfonic acid;
amorphous carbon-supported thiazinium chloride sulfonic acid;
amorphous carbon-supported morpholinium chloride sulfonic acid;
amorphous carbon-supported piperidinium chloride sulfonic acid;
amorphous carbon-supported piperizinium chloride sulfonic acid;
amorphous carbon-supported pyrollizinium chloride sulfonic acid;
amorphous carbon-supported triphenyl phosphonium chloride sulfonic acid;
amorphous carbon-supported trimethyl phosphonium chloride sulfonic acid;
amorphous carbon-supported triethyl phosphonium chloride sulfonic acid;
amorphous carbon-supported tripropyl phosphonium chloride sulfonic acid;
amorphous carbon-supported tributyl phosphonium chloride sulfonic acid;
amorphous carbon-supported trifluoro phosphonium chloride sulfonic acid;
amorphous carbon-supported pyrrolium bromide sulfonic acid;
amorphous carbon-supported imidazolium bromide sulfonic acid;
amorphous carbon-supported pyrazolium bromide sulfonic acid;
amorphous carbon-supported oxazolium bromide sulfonic acid;
amorphous carbon-supported thiazolium bromide sulfonic acid;
amorphous carbon-supported pyridinium bromide sulfonic acid;
amorphous carbon-supported pyrimidinium bromide sulfonic acid;
amorphous carbon-supported pyrazinium bromide sulfonic acid;
amorphous carbon-supported pyradizimium bromide sulfonic acid;
amorphous carbon-supported thiazinium bromide sulfonic acid;
amorphous carbon-supported morpholinium bromide sulfonic acid;
amorphous carbon-supported piperidinium bromide sulfonic acid;
amorphous carbon-supported piperizinium bromide sulfonic acid;
amorphous carbon-supported pyrollizinium bromide sulfonic acid;
amorphous carbon-supported triphenyl phosphonium bromide sulfonic acid;
amorphous carbon-supported trimethyl phosphonium bromide sulfonic acid;
amorphous carbon-supported triethyl phosphonium bromide sulfonic acid;
amorphous carbon-supported tripropyl phosphonium bromide sulfonic acid;
amorphous carbon-supported tributyl phosphonium bromide sulfonic acid;
amorphous carbon-supported trifluoro phosphonium bromide sulfonic acid;
amorphous carbon-supported pyrrolium bisulfate sulfonic acid;
amorphous carbon-supported imidazolium bisulfate sulfonic acid;
amorphous carbon-supported pyrazolium bisulfate sulfonic acid;
amorphous carbon-supported oxazolium bisulfate sulfonic acid;

amorphous carbon-supported thiazolium bisulfate sulfonic acid;
amorphous carbon-supported pyridinium bisulfate sulfonic acid;
amorphous carbon-supported pyrimidinium bisulfate sulfonic acid;
amorphous carbon-supported pyrazinium bisulfate sulfonic acid;
amorphous carbon-supported pyradizimium bisulfate sulfonic acid;
amorphous carbon-supported thiazinium bisulfate sulfonic acid;
amorphous carbon-supported morpholinium bisulfate sulfonic acid;
amorphous carbon-supported piperidinium bisulfate sulfonic acid;
amorphous carbon-supported piperizinium bisulfate sulfonic acid;
amorphous carbon-supported pyrollizinium bisulfate sulfonic acid;
amorphous carbon-supported triphenyl phosphonium bisulfate sulfonic acid;
amorphous carbon-supported trimethyl phosphonium bisulfate sulfonic acid;
amorphous carbon-supported triethyl phosphonium bisulfate sulfonic acid;
amorphous carbon-supported tripropyl phosphonium bisulfate sulfonic acid;
amorphous carbon-supported tributyl phosphonium bisulfate sulfonic acid;
amorphous carbon-supported trifluoro phosphonium bisulfate sulfonic acid;
amorphous carbon-supported pyrrolium formate sulfonic acid;
amorphous carbon-supported imidazolium formate sulfonic acid;
amorphous carbon-supported pyrazolium formate sulfonic acid;
amorphous carbon-supported oxazolium formate sulfonic acid;
amorphous carbon-supported thiazolium formate sulfonic acid;
amorphous carbon-supported pyridinium formate sulfonic acid;
amorphous carbon-supported pyrimidinium formate sulfonic acid;
amorphous carbon-supported pyrazinium formate sulfonic acid;
amorphous carbon-supported pyradizimium formate sulfonic acid;
amorphous carbon-supported thiazinium formate sulfonic acid;
amorphous carbon supported morpholinium formate sulfonic acid;
amorphous carbon-supported piperidinium formate sulfonic acid;
amorphous carbon-supported piperizinium formate sulfonic acid;
amorphous carbon-supported pyrollizinium formate sulfonic acid;
amorphous carbon-supported triphenyl phosphonium formate sulfonic acid;
amorphous carbon-supported trimethyl phosphonium formate sulfonic acid;
amorphous carbon-supported triethyl phosphonium formate sulfonic acid;
amorphous carbon-supported tripropyl phosphonium formate sulfonic acid;
amorphous carbon-supported tributyl phosphonium formate sulfonic acid;
amorphous carbon-supported trifluoro phosphonium formate sulfonic acid;
amorphous carbon-supported pyrrolium acetate sulfonic acid;
amorphous carbon-supported imidazolium acetate sulfonic acid;
amorphous carbon-supported pyrazolium acetate sulfonic acid;
amorphous carbon-supported oxazolium acetate sulfonic acid;
amorphous carbon-supported thiazolium acetate sulfonic acid;
amorphous carbon-supported pyridinium acetate sulfonic acid;
amorphous carbon-supported pyrimidinium acetate sulfonic acid;
amorphous carbon-supported pyrazinium acetate sulfonic acid;
amorphous carbon-supported pyradizimium acetate sulfonic acid;
amorphous carbon-supported thiazinium acetate sulfonic acid;
amorphous carbon-supported morpholinium acetate sulfonic acid;
amorphous carbon-supported piperidinium acetate sulfonic acid;
amorphous carbon-supported piperizinium acetate sulfonic acid;
amorphous carbon-supported pyrollizinium acetate sulfonic acid;
amorphous carbon-supported triphenyl phosphonium acetate sulfonic acid;
amorphous carbon-supported trimethyl phosphonium acetate sulfonic acid;
amorphous carbon-supported triethyl phosphonium acetate sulfonic acid;
amorphous carbon-supported tripropyl phosphonium acetate sulfonic acid;
amorphous carbon-supported tributyl phosphonium acetate sulfonic acid;
amorphous carbon-supported trifluoro phosphonium acetate sulfonic acid;
amorphous carbon-supported pyrrolium chloride phosphonic acid;
amorphous carbon-supported imidazolium chloride phosphonic acid;
amorphous carbon-supported pyrazolium chloride phosphonic acid;
amorphous carbon-supported oxazolium chloride phosphonic acid;
amorphous carbon-supported thiazolium chloride phosphonic acid;
amorphous carbon-supported pyridinium chloride phosphonic acid;
amorphous carbon-supported pyrimidinium chloride phosphonic acid;
amorphous carbon-supported pyrazinium chloride phosphonic acid;
amorphous carbon-supported pyradizimium chloride phosphonic acid;
amorphous carbon-supported thiazinium chloride phosphonic acid;

amorphous carbon-supported morpholinium chloride phosphonic acid;

amorphous carbon-supported piperidinium chloride phosphonic acid;

amorphous carbon-supported piperizinium chloride phosphonic acid;

amorphous carbon-supported pyrollizinium chloride phosphonic acid;

amorphous carbon-supported triphenyl phosphonium chloride phosphonic acid;

amorphous carbon-supported trimethyl phosphonium chloride phosphonic acid;

amorphous carbon-supported triethyl phosphonium chloride phosphonic acid;

amorphous carbon-supported tripropyl phosphonium chloride phosphonic acid;

amorphous carbon-supported tributyl phosphonium chloride phosphonic acid;

amorphous carbon-supported trifluoro phosphonium chloride phosphonic acid;

amorphous carbon-supported pyrrolium bromide phosphonic acid;

amorphous carbon-supported imidazolium bromide phosphonic acid;

amorphous carbon-supported pyrazolium bromide phosphonic acid;

amorphous carbon-supported oxazolium bromide phosphonic acid;

amorphous carbon-supported thiazolium bromide phosphonic acid;

amorphous carbon-supported pyridinium bromide phosphonic acid;

amorphous carbon-supported pyrimidinium bromide phosphonic acid;

amorphous carbon-supported pyrazinium bromide phosphonic acid;

amorphous carbon-supported pyradizimium bromide phosphonic acid;

amorphous carbon-supported thiazinium bromide phosphonic acid;

amorphous carbon-supported morpholinium bromide phosphonic acid;

amorphous carbon-supported piperidinium bromide phosphonic acid;

amorphous carbon-supported piperizinium bromide phosphonic acid;

amorphous carbon-supported pyrollizinium bromide phosphonic acid;

amorphous carbon-supported triphenyl phosphonium bromide phosphonic acid;

amorphous carbon-supported trimethyl phosphonium bromide phosphonic acid;

amorphous carbon-supported triethyl phosphonium bromide phosphonic acid;

amorphous carbon-supported tripropyl phosphonium bromide phosphonic acid;

amorphous carbon-supported tributyl phosphonium bromide phosphonic acid;

amorphous carbon-supported trifluoro phosphonium bromide phosphonic acid;

amorphous carbon-supported pyrrolium bisulfate phosphonic acid;

amorphous carbon-supported imidazolium bisulfate phosphonic acid;

amorphous carbon-supported pyrazolium bisulfate phosphonic acid;

amorphous carbon-supported oxazolium bisulfate phosphonic acid;

amorphous carbon-supported thiazolium bisulfate phosphonic acid;

amorphous carbon-supported pyridinium bisulfate phosphonic acid;

amorphous carbon-supported pyrimidinium bisulfate phosphonic acid;

amorphous carbon-supported pyrazinium bisulfate phosphonic acid;

amorphous carbon-supported pyradizimium bisulfate phosphonic acid;

amorphous carbon-supported thiazinium bisulfate phosphonic acid;

amorphous carbon-supported morpholinium bisulfate phosphonic acid;

amorphous carbon-supported piperidinium bisulfate phosphonic acid;

amorphous carbon-supported piperizinium bisulfate phosphonic acid;

amorphous carbon-supported pyrollizinium bisulfate phosphonic acid;

amorphous carbon-supported triphenyl phosphonium bisulfate phosphonic acid;

amorphous carbon-supported trimethyl phosphonium bisulfate phosphonic acid;

amorphous carbon-supported triethyl phosphonium bisulfate phosphonic acid;

amorphous carbon-supported tripropyl phosphonium bisulfate phosphonic acid;

amorphous carbon-supported tributyl phosphonium bisulfate phosphonic acid;

amorphous carbon-supported trifluoro phosphonium bisulfate phosphonic acid;

amorphous carbon-supported pyrrolium formate phosphonic acid;

amorphous carbon-supported imidazolium formate phosphonic acid;

amorphous carbon-supported pyrazolium formate phosphonic acid;

amorphous carbon-supported oxazolium formate phosphonic acid;

amorphous carbon-supported thiazolium formate phosphonic acid;

amorphous carbon-supported pyridinium formate phosphonic acid;

amorphous carbon-supported pyrimidinium formate phosphonic acid;

amorphous carbon-supported pyrazinium formate phosphonic acid;

amorphous carbon-supported pyradizimium formate phosphonic acid;

amorphous carbon-supported thiazinium formate phosphonic acid;

amorphous carbon-supported morpholinium formate phosphonic acid;

amorphous carbon-supported piperidinium formate phosphonic acid;

amorphous carbon-supported piperizinium formate phosphonic acid;

amorphous carbon-supported pyrollizinium formate phosphonic acid;

amorphous carbon-supported triphenyl phosphonium formate phosphonic acid;

amorphous carbon-supported trimethyl phosphonium formate phosphonic acid;

amorphous carbon-supported triethyl phosphonium formate phosphonic acid;
amorphous carbon-supported tripropyl phosphonium formate phosphonic acid;
amorphous carbon-supported tributyl phosphonium formate phosphonic acid;
amorphous carbon-supported trifluoro phosphonium formate phosphonic acid;
amorphous carbon-supported pyrrolium acetate phosphonic acid;
amorphous carbon-supported imidazolium acetate phosphonic acid;
amorphous carbon-supported pyrazolium acetate phosphonic acid;
amorphous carbon-supported oxazolium acetate phosphonic acid;
amorphous carbon-supported thiazolium acetate phosphonic acid;
amorphous carbon-supported pyridinium acetate phosphonic acid;
amorphous carbon-supported pyrimidinium acetate phosphonic acid;
amorphous carbon-supported pyrazinium acetate phosphonic acid;
amorphous carbon-supported pyradizimium acetate phosphonic acid;
amorphous carbon-supported thiazinium acetate phosphonic acid;
amorphous carbon-supported morpholinium acetate phosphonic acid;
amorphous carbon-supported piperidinium acetate phosphonic acid;
amorphous carbon-supported piperizinium acetate phosphonic acid;
amorphous carbon-supported pyrollizinium acetate phosphonic acid;
amorphous carbon-supported triphenyl phosphonium acetate phosphonic acid;
amorphous carbon-supported trimethyl phosphonium acetate phosphonic acid;
amorphous carbon-supported triethyl phosphonium acetate phosphonic acid;
amorphous carbon-supported tripropyl phosphonium acetate phosphonic acid;
amorphous carbon-supported tributyl phosphonium acetate phosphonic acid; and
amorphous carbon-supported trifluoro phosphonium acetate phosphonic acid.
In other embodiments, the solid-supported catalyst is selected from:
activated carbon-supported pyrrolium chloride sulfonic acid;
activated carbon-supported imidazolium chloride sulfonic acid;
activated carbon-supported pyrazolium chloride sulfonic acid;
activated carbon-supported oxazolium chloride sulfonic acid;
activated carbon-supported thiazolium chloride sulfonic acid;
activated carbon-supported pyridinium chloride sulfonic acid;
activated carbon-supported pyrimidinium chloride sulfonic acid;
activated carbon-supported pyrazinium chloride sulfonic acid;
activated carbon-supported pyradizimium chloride sulfonic acid;
activated carbon-supported thiazinium chloride sulfonic acid;
activated carbon-supported morpholinium chloride sulfonic acid;
activated carbon-supported piperidinium chloride sulfonic acid;
activated carbon-supported piperizinium chloride sulfonic acid;
activated carbon-supported pyrollizinium chloride sulfonic acid;
activated carbon-supported triphenyl phosphonium chloride sulfonic acid;
activated carbon-supported trimethyl phosphonium chloride sulfonic acid;
activated carbon-supported triethyl phosphonium chloride sulfonic acid;
activated carbon-supported tripropyl phosphonium chloride sulfonic acid;
activated carbon-supported tributyl phosphonium chloride sulfonic acid;
activated carbon-supported trifluoro phosphonium chloride sulfonic acid;
activated carbon-supported pyrrolium bromide sulfonic acid;
activated carbon-supported imidazolium bromide sulfonic acid;
activated carbon-supported pyrazolium bromide sulfonic acid;
activated carbon-supported oxazolium bromide sulfonic acid;
activated carbon-supported thiazolium bromide sulfonic acid;
activated carbon-supported pyridinium bromide sulfonic acid;
activated carbon-supported pyrimidinium bromide sulfonic acid;
activated carbon-supported pyrazinium bromide sulfonic acid;
activated carbon-supported pyradizimium bromide sulfonic acid;
activated carbon-supported thiazinium bromide sulfonic acid;
activated carbon-supported morpholinium bromide sulfonic acid;
activated carbon-supported piperidinium bromide sulfonic acid;
activated carbon-supported piperizinium bromide sulfonic acid;
activated carbon-supported pyrollizinium bromide sulfonic acid;
activated carbon-supported triphenyl phosphonium bromide sulfonic acid;
activated carbon-supported trimethyl phosphonium bromide sulfonic acid;
activated carbon-supported triethyl phosphonium bromide sulfonic acid;
activated carbon-supported tripropyl phosphonium bromide sulfonic acid;
activated carbon-supported tributyl phosphonium bromide sulfonic acid;
activated carbon-supported trifluoro phosphonium bromide sulfonic acid;
activated carbon-supported pyrrolium bisulfate sulfonic acid;

activated carbon-supported imidazolium bisulfate sulfonic acid;
activated carbon-supported pyrazolium bisulfate sulfonic acid;
activated carbon-supported oxazolium bisulfate sulfonic acid;
activated carbon-supported thiazolium bisulfate sulfonic acid;
activated carbon-supported pyridinium bisulfate sulfonic acid;
activated carbon-supported pyrimidinium bisulfate sulfonic acid;
activated carbon-supported pyrazinium bisulfate sulfonic acid;
activated carbon-supported pyradizimium bisulfate sulfonic acid;
activated carbon-supported thiazinium bisulfate sulfonic acid;
activated carbon-supported morpholinium bisulfate sulfonic acid;
activated carbon-supported piperidinium bisulfate sulfonic acid;
activated carbon-supported piperizinium bisulfate sulfonic acid;
activated carbon-supported pyrollizinium bisulfate sulfonic acid;
activated carbon-supported triphenyl phosphonium bisulfate sulfonic acid;
activated carbon-supported trimethyl phosphonium bisulfate sulfonic acid;
activated carbon-supported triethyl phosphonium bisulfate sulfonic acid;
activated carbon-supported tripropyl phosphonium bisulfate sulfonic acid;
activated carbon-supported tributyl phosphonium bisulfate sulfonic acid;
activated carbon-supported trifluoro phosphonium bisulfate sulfonic acid;
activated carbon-supported pyrrolium formate sulfonic acid;
activated carbon-supported imidazolium formate sulfonic acid;
activated carbon-supported pyrazolium formate sulfonic acid;
activated carbon-supported oxazolium formate sulfonic acid;
activated carbon-supported thiazolium formate sulfonic acid;
activated carbon-supported pyridinium formate sulfonic acid;
activated carbon-supported pyrimidinium formate sulfonic acid;
activated carbon-supported pyrazinium formate sulfonic acid;
activated carbon-supported pyradizimium formate sulfonic acid;
activated carbon-supported thiazinium formate sulfonic acid;
activated carbon supported morpholinium formate sulfonic acid;
activated carbon-supported piperidinium formate sulfonic acid;
activated carbon-supported piperizinium formate sulfonic acid;
activated carbon-supported pyrollizinium formate sulfonic acid;
activated carbon-supported triphenyl phosphonium formate sulfonic acid;
activated carbon-supported trimethyl phosphonium formate sulfonic acid;
activated carbon-supported triethyl phosphonium formate sulfonic acid;
activated carbon-supported tripropyl phosphonium formate sulfonic acid;
activated carbon-supported tributyl phosphonium formate sulfonic acid;
activated carbon-supported trifluoro phosphonium formate sulfonic acid;
activated carbon-supported pyrrolium acetate sulfonic acid;
activated carbon-supported imidazolium acetate sulfonic acid;
activated carbon-supported pyrazolium acetate sulfonic acid;
activated carbon-supported oxazolium acetate sulfonic acid;
activated carbon-supported thiazolium acetate sulfonic acid;
activated carbon-supported pyridinium acetate sulfonic acid;
activated carbon-supported pyrimidinium acetate sulfonic acid;
activated carbon-supported pyrazinium acetate sulfonic acid;
activated carbon-supported pyradizimium acetate sulfonic acid;
activated carbon-supported thiazinium acetate sulfonic acid;
activated carbon-supported morpholinium acetate sulfonic acid;
activated carbon-supported piperidinium acetate sulfonic acid;
activated carbon-supported piperizinium acetate sulfonic acid;
activated carbon-supported pyrollizinium acetate sulfonic acid;
activated carbon-supported triphenyl phosphonium acetate sulfonic acid;
activated carbon-supported trimethyl phosphonium acetate sulfonic acid;
activated carbon-supported triethyl phosphonium acetate sulfonic acid;
activated carbon-supported tripropyl phosphonium acetate sulfonic acid;
activated carbon-supported tributyl phosphonium acetate sulfonic acid;
activated carbon-supported trifluoro phosphonium acetate sulfonic acid;
activated carbon-supported pyrrolium chloride phosphonic acid;
activated carbon-supported imidazolium chloride phosphonic acid;
activated carbon-supported pyrazolium chloride phosphonic acid;
activated carbon-supported oxazolium chloride phosphonic acid;
activated carbon-supported thiazolium chloride phosphonic acid;
activated carbon-supported pyridinium chloride phosphonic acid;
activated carbon-supported pyrimidinium chloride phosphonic acid;

activated carbon-supported pyrazinium chloride phosphonic acid;
activated carbon-supported pyradizimium chloride phosphonic acid;
activated carbon-supported thiazinium chloride phosphonic acid;
activated carbon-supported morpholinium chloride phosphonic acid;
activated carbon-supported piperidinium chloride phosphonic acid;
activated carbon-supported piperizinium chloride phosphonic acid;
activated carbon-supported pyrollizinium chloride phosphonic acid;
activated carbon-supported triphenyl phosphonium chloride phosphonic acid;
activated carbon-supported trimethyl phosphonium chloride phosphonic acid;
activated carbon-supported triethyl phosphonium chloride phosphonic acid;
activated carbon-supported tripropyl phosphonium chloride phosphonic acid;
activated carbon-supported tributyl phosphonium chloride phosphonic acid;
activated carbon-supported trifluoro phosphonium chloride phosphonic acid;
activated carbon-supported pyrrolium bromide phosphonic acid;
activated carbon-supported imidazolium bromide phosphonic acid;
activated carbon-supported pyrazolium bromide phosphonic acid;
activated carbon-supported oxazolium bromide phosphonic acid;
activated carbon-supported thiazolium bromide phosphonic acid;
activated carbon-supported pyridinium bromide phosphonic acid;
activated carbon-supported pyrimidinium bromide phosphonic acid;
activated carbon-supported pyrazinium bromide phosphonic acid;
activated carbon-supported pyradizimium bromide phosphonic acid;
activated carbon-supported thiazinium bromide phosphonic acid;
activated carbon-supported morpholinium bromide phosphonic acid;
activated carbon-supported piperidinium bromide phosphonic acid;
activated carbon-supported piperizinium bromide phosphonic acid;
activated carbon-supported pyrollizinium bromide phosphonic acid;
activated carbon-supported triphenyl phosphonium bromide phosphonic acid;
activated carbon-supported trimethyl phosphonium bromide phosphonic acid;
activated carbon-supported triethyl phosphonium bromide phosphonic acid;
activated carbon-supported tripropyl phosphonium bromide phosphonic acid;
activated carbon-supported tributyl phosphonium bromide phosphonic acid;
activated carbon-supported trifluoro phosphonium bromide phosphonic acid;
activated carbon-supported pyrrolium bisulfate phosphonic acid;
activated carbon-supported imidazolium bisulfate phosphonic acid;
activated carbon-supported pyrazolium bisulfate phosphonic acid;
activated carbon-supported oxazolium bisulfate phosphonic acid;
activated carbon-supported thiazolium bisulfate phosphonic acid;
activated carbon-supported pyridinium bisulfate phosphonic acid;
activated carbon-supported pyrimidinium bisulfate phosphonic acid;
activated carbon-supported pyrazinium bisulfate phosphonic acid;
activated carbon-supported pyradizimium bisulfate phosphonic acid;
activated carbon-supported thiazinium bisulfate phosphonic acid;
activated carbon-supported morpholinium bisulfate phosphonic acid;
activated carbon-supported piperidinium bisulfate phosphonic acid;
activated carbon-supported piperizinium bisulfate phosphonic acid;
activated carbon-supported pyrollizinium bisulfate phosphonic acid;
activated carbon-supported triphenyl phosphonium bisulfate phosphonic acid;
activated carbon-supported trimethyl phosphonium bisulfate phosphonic acid;
activated carbon-supported triethyl phosphonium bisulfate phosphonic acid;
activated carbon-supported tripropyl phosphonium bisulfate phosphonic acid;
activated carbon-supported tributyl phosphonium bisulfate phosphonic acid;
activated carbon-supported trifluoro phosphonium bisulfate phosphonic acid;
activated carbon-supported pyrrolium formate phosphonic acid;
activated carbon-supported imidazolium formate phosphonic acid;
activated carbon-supported pyrazolium formate phosphonic acid;
activated carbon-supported oxazolium formate phosphonic acid;
activated carbon-supported thiazolium formate phosphonic acid;
activated carbon-supported pyridinium formate phosphonic acid;
activated carbon-supported pyrimidinium formate phosphonic acid;
activated carbon-supported pyrazinium formate phosphonic acid;
activated carbon-supported pyradizimium formate phosphonic acid;
activated carbon-supported thiazinium formate phosphonic acid;
activated carbon-supported morpholinium formate phosphonic acid;
activated carbon-supported piperidinium formate phosphonic acid;
activated carbon-supported piperizinium formate phosphonic acid;

activated carbon-supported pyrollizinium formate phosphonic acid;
activated carbon-supported triphenyl phosphonium formate phosphonic acid;
activated carbon-supported trimethyl phosphonium formate phosphonic acid;
activated carbon-supported triethyl phosphonium formate phosphonic acid;
activated carbon-supported tripropyl phosphonium formate phosphonic acid;
activated carbon-supported tributyl phosphonium formate phosphonic acid;
activated carbon-supported trifluoro phosphonium formate phosphonic acid;
activated carbon-supported pyrrolium acetate phosphonic acid;
activated carbon-supported imidazolium acetate phosphonic acid;
activated carbon-supported pyrazolium acetate phosphonic acid;
activated carbon-supported oxazolium acetate phosphonic acid;
activated carbon-supported thiazolium acetate phosphonic acid;
activated carbon-supported pyridinium acetate phosphonic acid;
activated carbon-supported pyrimidinium acetate phosphonic acid;
activated carbon-supported pyrazinium acetate phosphonic acid;
activated carbon-supported pyradizimium acetate phosphonic acid;
activated carbon-supported thiazinium acetate phosphonic acid;
activated carbon-supported morpholinium acetate phosphonic acid;
activated carbon-supported piperidinium acetate phosphonic acid;
activated carbon-supported piperizinium acetate phosphonic acid;
activated carbon-supported pyrollizinium acetate phosphonic acid;
activated carbon-supported triphenyl phosphonium acetate phosphonic acid;
activated carbon-supported trimethyl phosphonium acetate phosphonic acid;
activated carbon-supported triethyl phosphonium acetate phosphonic acid;
activated carbon-supported tripropyl phosphonium acetate phosphonic acid;
activated carbon-supported tributyl phosphonium acetate phosphonic acid; and
activated carbon-supported trifluoro phosphonium acetate phosphonic acid.

Properties of the Disclosed Catalysts

The catalysts described herein have one or more catalytic properties. As used herein, a "catalytic property" of a material is a physical and/or chemical property that increases the rate and/or extent of a reaction involving the material. The catalytic properties can include at least one of the following properties: a) disruption of a hydrogen bond in cellulosic materials; b) intercalation of the catalyst into crystalline domains of cellulosic materials; and c) cleavage of a glycosidic bond in cellulosic materials. In other embodiments, the catalysts that have two or more of the catalytic properties described above, or all three of the catalytic properties described above.

In certain embodiments, the catalysts described herein have the ability to catalyze a chemical reaction by donation of a proton, and can be regenerated during the reaction process. In other embodiments, the catalysts described herein have a greater specificity for cleavage of a glycosidic bond than dehydration of a monosaccharide.

Catalyst-Containing Compositions

Provided herein are also compositions involving the catalysts that can be used in a variety of methods described herein, including the break-down of cellulosic material. As used herein, the term "catalyst composition" refers to any composition that contains one or more catalysts selected from polymeric catalysts as disclosed herein or solid-supported catalysts as disclosed herein.

Provided are also compositions that include feedstock and the catalysts described herein. In some embodiments, the composition can include feedstock and an effective amount of a catalyst as described herein. In some embodiments, the composition further includes a solvent (e.g., water). In some embodiments, the feedstock includes cellulose, hemicellulose, or a combination thereof.

In yet another aspect, provided are compositions that include the catalysts described herein, one or more sugars, and residual feedstock. In some embodiments, the one or more sugars are one or more monosaccharides, one or more oligosaccharides, or a mixture thereof. In certain embodiments, the one or more sugars are two or more sugars including at least one C4-C6 monosaccharide and at least one oligosaccharide. In one embodiment, the one or more sugars are selected from glucose, galactose, fructose, xylose, and arabinose.

Provided is also a composition that includes feedstock (e.g., softwood, hardwood, cassava, bagasse, sugarbeet pulp, straw, paper sludge, oil palm, corn stover, food waste, enzymatic digestion residuals, beer bottoms, and any combination thereof) and any of the catalysts described herein. In some embodiments, the composition further includes a solvent. In one embodiment, the composition further includes water. In some embodiments, the feedstock has cellulose, hemicellulose, or a combination thereof. In yet other embodiments, the feedstock also has lignin.

Provided is also a chemically-hydrolyzed feedstock composition that includes any of the catalysts described herein, one or more sugars, and residual feedstock. In some embodiments, the one or more sugars are one or more monosaccharides, one or more oligosaccharides, or a mixture thereof. In other embodiments, the one or more sugars are two or more sugars that include at least one C4-C6 monosaccharide and at least one oligosaccharide. In yet other embodiments, the one or more sugars are selected from glucose, galactose, fructose, xylose, and arabinose.

Provided is also a saccharification intermediate that includes any of the catalysts described herein hydrogen-bonded to the feedstock (e.g., softwood, hardwood, cassava, bagasse, sugarbeet pulp, straw, paper sludge, oil palm, corn stover, food waste, enzymatic digestion residuals, beer bottoms, and any combination thereof). In certain embodiments of the saccharification intermediate, the ionic monomer or moiety of the catalyst is hydrogen-bonded to the carbohydrate alcohol groups present in cellulose, hemicellulose, and other oxygen-containing components of feedstock. In certain embodiments of the saccharification intermediate, the acidic monomer or moiety of the catalyst is hydrogen-bonded to the carbohydrate alcohol groups present in cellulose, hemicellulose, and other oxygen-containing components of lignocellulose present in the feedstock, including the glycosidic linkages between sugar monomers. In some embodiments, the feedstock has cellulose, hemicellulose or a combination thereof.

Downstream Products a) Fermentation of Isolated Sugars

The sugars obtained from hydrolysis of cellulosic material can be used in downstream processes to produce biofuels and other bio-based chemicals. In another aspect, the one or more sugars obtained from hydrolysis of cellulosic material using the catalyst described herein can be fermented to produce one or more downstream products (e.g., ethanol and other biofuels, vitamins, lipids, proteins).

The saccharide composition can undergo fermentation to produce one or more difunctional compounds. Such difunctional compounds can have an n-carbon chain, with a first functional group and a second functional group. In some embodiments, the first and second functional groups can be independently selected from —OH, —NH$_2$, —COH, and —COOH.

The difunctional compounds can include, but are not limited to, alcohols, carboxylic acids, hydroxyacids, or amines. Exemplary difunctional alcohols can include ethylene glycol, 1,3-propanediol, and 1,4-butanediol. Exemplary difunctional carboxylic acids can include succinic acid, adipic acid, and pimelic acid. Exemplary difunctional hydroxyacids can include glycolic acid and 3-hydroxypropanoic acid. Exemplary difunctional amines can include 1,4-diaminobutane, 1,5-diaminopentane, and 1,6-diaminohexane.

In some embodiments, the methods described herein include contacting the saccharide composition with a fermentation host to produce a fermentation product mixture that can include ethylene glycol, succinic acid, adipic acid, or butanediol, or a combination thereof.

In some embodiments, the difunctional compounds can be isolated from the fermentation product mixture, and/or further purified. Any suitable isolation and purification techniques known in the art can be used.

b) Fermentation Host

The fermentation host can be bacteria or yeast. In one embodiment, the fermentation host is bacteria. In some embodiments, the bacteria are classified in the family of Enterobacteriaceae. Examples of genera in the family include *Aranicola, Arsenophonus, Averyella, Biostraticola, Brenneria, Buchnera, Budvicia, Buttiauxella, Candidatus, Curculioniphilus, Cuticobacterium, Candidatus Ishikawaella, Macropleicola, Phlomobacter, Candidatus Riesia, Candidatus Stammerula, Cedecea, Citrobacter, Cronobacter, Dickeya, Edwardsiella, Enterobacter, Erwinia, Escherichia, Ewingella, Grimontella, Hafnia, Klebsiella, Kluyvera, Leclercia, Leminorella, Margalefia, Moellerella, Morganella, Obesumbacterium, Pantoea, Pectobacterium, Photorhabdus, Phytobacter, Plesiomonas, Pragia, Proteus, Providencia, Rahnella, Raoultella, Salmonella, Samsonia, Serratia, Shigella, Sodalis, Tatumella, Thorasellia, Tiedjeia, Trabulsiella, Wigglesworthia, Xenorhabdus, Yersinia*, and *Yokenella*. In one embodiment, the bacteria are *Escherichia coli (E. coli)*.

In some embodiments, the fermentation host is genetically modified. In one embodiment, the fermentation host is genetically modified *E. coli*. For example, the fermentation host can be genetically modified to enhance the efficiency of specific pathways encoded by certain genes. In one embodiment, the fermentation host can be modified to enhance expression of endogenous genes that can positively regulate specific pathways. In another embodiment, the fermentation host can be further modified to suppress expression of certain endogenous genes.

c) Fermentation Conditions

Any suitable fermentation conditions in the art can be employed to ferment the saccharide composition described herein to produce bio-based products, and components thereof.

In some embodiments, saccharification can be combined with fermentation in a separate or a simultaneous process. The fermentation can use the aqueous sugar phase or, if the sugars are not substantially purified from the reacted biomass, the fermentation can be performed on an impure mixture of sugars and reacted biomass. Such methods include, for example, separate hydrolysis and fermentation (SHF), simultaneous saccharification and fermentation (SSF), simultaneous saccharification and cofermentation (SSCF), hybrid hydrolysis and fermentation (HHF), separate hydrolysis and co-fermentation (SHCF), hybrid hydrolysis and co-fermentation (HHCF), and direct microbial conversion (DMC).

For example, SHF uses separate process steps to first enzymatically hydrolyze cellulosic material to fermentable sugars (e.g., glucose, cellobiose, cellotriose, and pentose sugars), and then ferment the sugars to ethanol.

In SSF, the enzymatic hydrolysis of cellulosic material and the fermentation of sugars to ethanol are combined in one step. See Philippidis, G. P., Cellulose bioconversion technology, in Handbook on Bioethanol: Production and Utilization, Wyman, C. E., ed., Taylor & Francis, Washington, D.C., 179-212 (1996).

SSCF involves the cofermentation of multiple sugars. See Sheehan, J., and Himmel, M., Enzymes, energy and the environment: A strategic perspective on the U.S. Department of Energy's research and development activities for bioethanol, *Biotechnol. Prog.*, 15: 817-827 (1999).

HHF involves a separate hydrolysis step, and in addition a simultaneous saccharification and hydrolysis step, which can be carried out in the same reactor. The steps in an HHF process can be carried out at different temperatures; for example, high temperature enzymatic saccharification followed by SSF at a lower temperature that the fermentation strain can tolerate.

DMC combines all three processes (enzyme production, hydrolysis, and fermentation) in one or more steps where the same organism is used to produce the enzymes for conversion of the cellulosic material to fermentable sugars and to convert the fermentable sugars into a final product. See Lynd, L. R., Weimer, P. J., van Zyl, W. H., and Pretorius, I. S., Microbial cellulose utilization: Fundamentals and biotechnology, *Microbiol. Mol. Biol. Reviews*, 66: 506-577 (2002).

General Methods of Preparing the Catalysts a) Methods of Preparing the Polymeric Catalysts The polymeric catalysts described herein can be made using polymerization techniques known in the art, including for example techniques to initiate polymerization of a plurality of monomer units.

In some embodiments, the polymeric catalysts described herein can be formed by first forming an intermediate polymer functionalized with the ionic group, but is free or substantially free of the acidic group. The intermediate polymer can then be functionalized with the acidic group.

In other embodiments, the polymeric catalysts described herein can be formed by first forming an intermediate polymer functionalized with the acidic group, but is free or substantially free of the ionic group. The intermediate polymer can then be functionalized with the ionic group.

In yet other embodiments, the polymeric catalysts described herein can be formed by polymerizing monomers with both acidic and ionic groups.

Provided is also a method of preparing any of the polymers described herein, by:
a) providing a starting polymer;
b) combining the starting polymer with a nitrogen-containing compound or phosphorous-containing compound to produce an ionic polymer having at least one cationic group;
c) combining the ionic polymer with an effective acidifying reagent to produce an intermediate polymer; and
d) combining the intermediate polymer with an effective amount of one or more ionic salts to produce the polymer;
wherein the steps a), b), c), and d) are performed in the order a), b), c), and d); or in the order a), c), d), and b); or in the order a), c), b), and d).

In some embodiments, the starting polymer is selected from polyethylene, polypropylene, polyvinyl alcohol, polycarbonate, polystyrene, polyurethane, or a combination thereof. In certain embodiments, the starting polymer is a polystyrene. In certain embodiments, the starting polymer is poly(styrene-co-vinylbenzylhalide-co-divinylbenzene). In another embodiment, the starting polymer is poly(styrene-co-vinylbenzylchloride-co-divinylbenzene).

In some embodiments of the method to prepare any of the polymers described herein, the nitrogen-containing compound is selected from a pyrrolium compound, an imidazolium compound, a pyrazolium compound, an oxazolium compound, a thiazolium compound, a pyridinium compound, a pyrimidinium compound, a pyrazinium compound, a pyradizimium compound, a thiazinium compound, a morpholinium compound, a piperidinium compound, a piperizinium compound, and a pyrollizinium compound. In certain embodiments, the nitrogen-containing compound is an imidazolium compound.

In some embodiments of the method to prepare any of the polymers described herein, the phosphorus-containing compound is selected from a triphenyl phosphonium compound, a trimethyl phosphonium compound, a triethyl phosphonium compound, a tripropyl phosphonium compound, a tributyl phosphonium compound, a trichloro phosphonium compound, and a trifluoro phosphonium compound.

In some embodiments of the method to prepare any of the polymers described herein, the acid is selected from sulfuric acid, phosphoric acid, hydrochloric acid, acetic acid and boronic acid. In one embodiment, the acid is sulfuric acid.

In some embodiments, the ionic salt is selected from lithium chloride, lithium bromide, lithium nitrate, lithium sulfate, lithium phosphate, sodium chloride, sodium bromide, sodium sulfate, sodium hydroxide, sodium phosphate, potassium chloride, potassium bromide, potassium nitrate, potassium sulfate, potassium phosphate, ammonium chloride, ammonium bromide, ammonium phosphate, ammonium sulfate, tetramethylammonium chloride, tetramethylammonium bromide, tetraethylammonium chloride, di-methylimidazolium chloride, methylbutylimidazoliumchloride, di-methylmorpholinium chloride, zinc (II) chloride, zinc (II) bromide, magnesium (II) chloride, and calcium (II) chloride.

Also provided is a method of preparing any of the polymers described herein having a polystyrene backbone, by: a) providing a polystyrene; b) reacting the polystyrene with a nitrogen-containing compound to produce an ionic polymer; and c) reacting the ionic polymer with an acid to produce a third polymer. In certain embodiments, the polystyrene is poly(styrene-co-vinylbenzylhalide-co-divinylbenzene). In one embodiment, the polystyrene is poly(styrene-co-vinylbenzylchloride-co-divinylbenzene).

In some embodiments, the polymer has one or more catalytic properties selected from:
a) disruption of at least one hydrogen bond in cellulosic materials;
b) intercalation of the polymer into crystalline domains of cellulosic materials; and
c) cleavage of at least one glycosidic bond in cellulosic materials.

Provided herein are also such intermediate polymers, including those obtained at different points within a synthetic pathway for producing the fully functionalized polymers described herein. In some embodiments, the polymers described herein can be made, for example, on a scale of at least about 100 g, at least about 1 kg, at least about 20 kg, at least about 100 kg, at least about 500 kg, or at least about 1 ton in a batch or continuous process.

b) Methods of Preparing the Solid-Supported Catalysts

The solid-supported catalysts described herein with carbon supports can be prepared by subjecting a carbonaceous material to: (1) support preparation, (2) support activation, and (3) support functionalization. An exemplary preparation sequence is provided in Table 1. One of skill in the art would recognize that two or more of the support preparation, support activation, and catalyst functionalization steps can be combined into a single step.

TABLE 1

Exemplary steps for preparing a dual-functionalized solid carbon supported catalyst

| Step | Reactant | Reaction | Product |
| --- | --- | --- | --- |
| 1. Support Preparation | Carbonaceous material | Partial carbonization | Carbon Support |
| 2. Support Activation | Carbon Support | Haloalkylation, haloacylation, or diazonium displacement | Activated Support |
| 3. First Functionalization | Activated Support | Quaternization | First Functionalized Support |
| 4. Second Functionalization | First Functionalized Support | Acidification | Dual-Functionalized Solid Carbon Supported Catalyst |

Support Preparation

Support preparation can be accomplished by any methods known in the art. For example, pyrolysis can be used to convert a carbonaceous material into a carbon support. Incomplete carbonization can also be employed to obtain a carbon support. In some embodiments, a carbonaceous material can be subjected to an oxygen-deficient atmosphere at a controlled temperature to produce a carbon support. In yet other embodiments, commercially-available carbon supports can be used.

The carbonaceous material can be naturally-occurring. Suitable carbonaceous materials can include, for example, shrimp shell, chitin, coconut shell, wood pulp, paper pulp, cotton, cellulose, hard wood, soft wood, wheat straw, sugarcane bagasse, cassava stem, corn stover, oil palm residue, bitumen, asphaltum, tar, coal, pitch, or any combinations thereof.

In some embodiments, the carbon content of the carbonaceous material is greater than about 20% g carbon/g dry material, greater than about 30% g carbon/g dry material, or greater than about 40% g carbon/g dry material. In addition to carbon, the carbonaceous material can also contain oxygen, nitrogen, or a combination thereof. For example, with reference to FIG. 8A, carbon support 802 can have one or more functional groups, including for example hydroxyl, amino and carboxyl groups. In some embodiments, the oxygen content of the carbonaceous material is between about 10% to about 60% g oxygen/g dry material, between about 20% to about 40% g oxygen/g dry material, or between about 20% to about 30% g oxygen/g dry material. In other embodiments, the nitrogen content of the carbonaceous material is greater than about 1% g nitrogen/g dry material, greater than about 5% g nitrogen/g dry material, or greater than about 10% g nitrogen/g dry material.

One of skill in the art would recognize that the conditions under which the carbonaceous material is carbonized can vary depending on the carbonaceous material used. In some embodiments, the carbonaceous material is carbonized in an atmosphere containing less than about 20% oxygen, less than about 10% oxygen, less than about 1% oxygen, less than about 1 part per thousand of oxygen, less than about 100 parts per million of oxygen, or less than about 10 parts per million of oxygen. In some embodiments, the carbonaceous material is carbonized in an atmosphere containing nitrogen. In other embodiments, the carbonaceous material is carbonized in an atmosphere containing purified nitrogen.

In some embodiments, the carbonaceous material is carbonized at a temperature between about 200° C. and about 500° C., between about 250° C. and about 400° C., or between about 275° C. and about 350° C. The temperature can be controlled to within plus or minus about 50° C., within plus or minus about 10° C., within plus or minus about 5° C., or to within plus or minus about 2° C. In some embodiments, the carbonaceous material is carbonized within about 2 to about 10 hours, within about 2 to about 5 hours, within about 3 to about 5 hours, or within about 3 to about 4 hours.

The carbonaceous material can undergo incomplete carbonization based on the carbonization conditions described above. Incomplete carbonization transforms the carbonaceous material into a poly-aromatic heterocyclic superstructure. The superstructure can include, for example, poly-condensed fused ring sub-structures that are attached to one another with random orientation to form the overall superstructure.

Heteroatoms, such as oxygen and nitrogen present in the carbonaceous starting material, become incorporated into the superstructure. Some of the heteroatoms can be incorporated into the carbon support, as saturated, unsaturated, and aromatic heterocycles, many of which can be fused rings. For example, the carbon support (and hence the final solid-supported catalyst) can have furanic rings with 4-7 oxygen atoms and/or 4-7 nitrogen atoms. Some of the heteroatoms in the solid-supported catalyst can also be from the moieties attached to the carbon support. For example, oxygen can be from alcohol moieties (e.g., phenol, alcohols) and carboxylic acid moieties (e.g., formic, formyl, acetic, acetyl) covalently bonded to the edge of the heterocyclic sub-structures. Nitrogen can be from amino moieties (e.g., aniline, alkylamino).

The heteroatom content of the carbon support can affect the reactivity in functionalizing the support with acidic and/or ionic moieties. For example, the heteroatoms incorporated into the superstructure can affect the electronic nature of the carbon support, and hence its reactivity with the functional moieties.

The carbonaceous materials that can be used to prepare the carbon support can, in some embodiments, contain: about 30%-about 70% g carbon/g starting material; about 2%-about 8% g hydrogen/g starting material; about 0%-about 60% g oxygen/g starting material; and about 0%-about 60% g oxygen/g starting material. Following incomplete carbonization, the heteroatom content of the carbon support, can in some embodiments, contain: about 0-40%, about 5-30%, about 10-30%, or about 15-30% g oxygen/g backbone; and about 0-15%, about 2-10%, or about 5-10% g nitrogen/g backbone.

The overall heteroatom content of the solid-supported catalyst can vary depending in part on the functional moieties attached to the solid support. For example, haloacylation or haloalkylation can introduce the oxygen and/or halogen content. Quaternization (alkylation) can introduce the phosphorous and/or nitrogen content. Sulfonation can increase the sulfur and oxygen content.

In some embodiments, the solid-supported catalyst can contain: about 10-50%, about 15-40%, about 10-30% g oxygen/g catalyst; about 0-15%, about 2-10%, about 5-10% g nitrogen/g catalyst; about 5-20%, about 5-15%, or about 10-15% g sulfur/g catalyst; and about 5-20%, about 5-15%, about 8-15% g phosphorous/g catalyst.

The carbon supports prepared according to the methods described above can be used in combination with other solid supports, including for example silica, silica gel, alumina, magnesia, titania, zirconia, clays, magnesium silicate, silicon carbide, zeolites, and ceramics.

Support Activation

Support activation step involves subjecting the carbon support to a chemical functionalization reaction to attach reactive linkers to the carbon support. Suitable reactive linkers can include, for example, haloalkanes, haloacyl compounds, amines, and diazo compounds. Such reactive linkers activate the carbon support, making the support more susceptible to further functionalization to attach acidic, ionic, acidic-ionic and/or hydrophobic moieties.

Figure 8A:
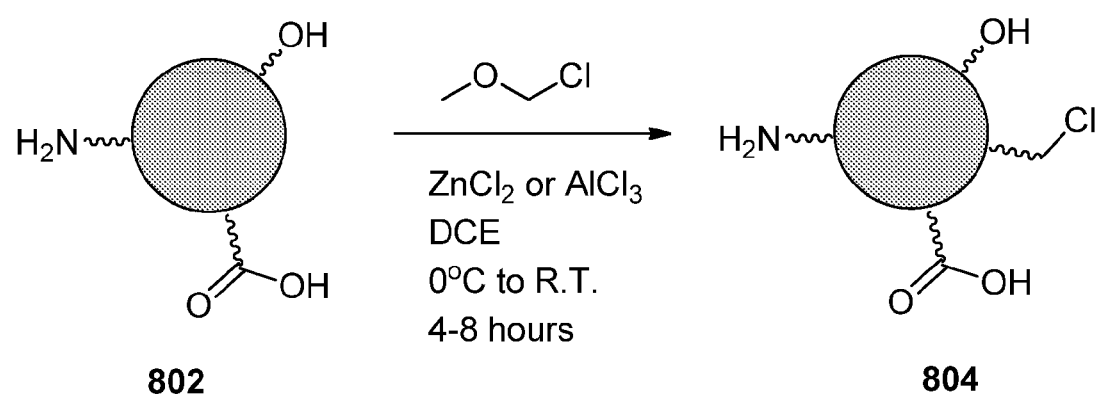
FIG. 8A depicts an exemplary reaction to activate a carbon support by introducing a reactive linker by a Friedel-Crafts reaction.

In some embodiments, the reactive linker can be introduced to the carbon support by a halomethylating agent. In certain embodiments, the reactive linker can be introduced to the carbon support by a chloromethylating agent. With reference to FIG. 8A, the chloromethylating agent is chloromethyl methyl ether.

In other embodiments, the reactive linker can be introduced to the carbon support by a haloacylating agent. In certain embodiments, the reactive linker can be introduced to the carbon support by a chloroacylating agent. A suitable example of a chloroacylating agent is chloroacetyl chloride.

The chloromethylating agent or the chloroacylating agent can be enacted using a Lewis acid catalyst. In certain embodiments, the Lewis acid catalyst is selected from zinc (II) chloride, aluminum (III) chloride, and iron (III) chloride. With reference to FIG. 8A, the Lewis acid can be zinc chloride ($ZnCl_2$) or aluminum chloride ($AlCl_3$).

The reactive linker can be introduced to the carbon support via a Friedel-Crafts alkylation or a Friedel-Crafts acylation reaction. An exemplary reaction to introduce such a reactive linker to the carbon support is depicted in FIG. 8A. In some embodiments, the chloromethylating or chloroacylating reaction can be performed in an inert solvent. Suitable inert solvents can include any solvent that is suitable for a Friedel-Crafts reaction. For example, suitable inert solvents can include, for example, dichloromethane (DCM), dichloroethane (DCE), diethyl ether, tetrahydrofuran (THF), or ionic liquids.

The chloromethylation or chloroacylation reaction can be performed at a temperature below about 25° C., below about 10° C., below about 5° C., or at or below about 0° C.

With reference again to FIG. 8A, activated carbon support 804 has a chloromethane moiety as the reactive linker. In other exemplary embodiments, other halo moieties can be added as a reactive linker, and a plurality of reactive linkers can be attached to the activated carbon support.

Support Functionalization

Figure 8B:
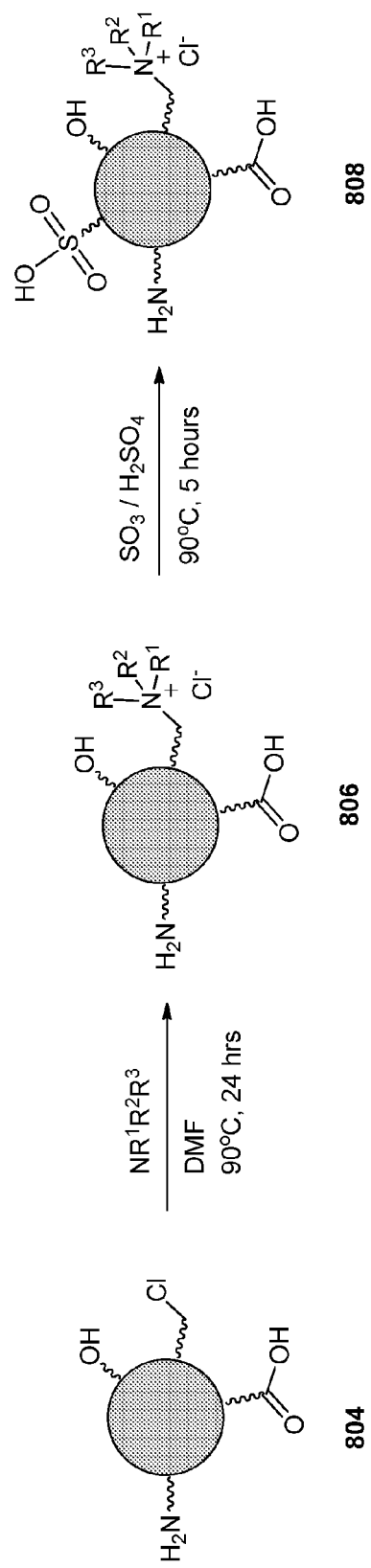
FIG. 8B depicts an exemplary reaction scheme to prepare a dual-functionalized catalyst from an activated carbon support, in which the catalyst has both acidic and ionic moieties.

The activated solid supports can undergo one or more reactions to attach acidic and/or ionic moieties to the solid support. With reference to FIG. 8B, activated carbon support 804 is first quaternized to attach a nitrogen-containing cationic group to the solid support. The exemplary nitrogen-containing cationic group in FIG. 8B has a formula $NR^1R^2R^3$, wherein each $R^1$, $R^2$ and $R^3$ is independently hydrogen or alkyl, or $R^1$ is taken together with $R^2$ and the nitrogen atom to which they are attached to form a heterocycloalkyl, or $R^1$, $R^2$ and $R^3$ are taken together with the nitrogen atom to which they are attached to form a heteroaryl.

Quaternized solid support 806 undergoes acid-treatment to produce dual-functionalized solid supported catalyst 808. While only one cationic group and one acidic group is depicted in catalyst 808 of FIG. 8B, it should be understood that a plurality of cationic groups and a plurality of acidic groups can be attached to the solid support using the methods described herein.

In other embodiments, the activated solid support can be acidified before quaternization to produce a dual-functionalized solid-supported catalyst. In yet other embodiments, the activated support can be functionalized with an acidic-ionic group. In yet other embodiments, one or more other functional groups can be attached to the solid-supported catalysts, including hydrophobic groups.

The entire disclosure of each of the patent documents and non-patent literature referred to herein is incorporated by reference in its entirety for all purposes. This application incorporates by reference in its entirety U.S. application Ser. No. 13/406,490, U.S. application Ser. No. 13/406,517, and U.S. application Ser. No. 13/657,724.

EXAMPLES

Except where otherwise indicated, commercial reagents were obtained from Sigma-Aldrich, St. Louis, Mo., USA, and were purified prior to use following the guidelines of Perrin and Armarego. See Perrin, D. D. & Armarego, W. L. F., *Purification of Laboratory Chemicals*, 3rd ed.; Pergamon Press, Oxford, 1988. Nitrogen gas for use in chemical reactions was of ultra-pure grade, and was dried by passing it through a drying tube containing phosphorous pentoxide. Unless indicated otherwise, all non-aqueous reagents were transferred under an inert atmosphere via syringe or Schlenk flask. Organic solutions were concentrated under reduced pressure on a Buchi rotary evaporator. Where necessary, chromatographic purification of reactants or products was accomplished using forced-flow chromatography on 60 mesh silica gel according to the method described of Still et al., See Still et al., *J. Org. Chem.*, 43: 2923 (1978). Thin-layer chromatography (TLC) was performed using silica-coated glass plates. Visualization of the developed chromatogram was performed using either Cerium Molybdate (i.e., Hanessian) stain or $KMnO_4$ stain, with gentle heating, as required. Fourier-Transform Infrared (FTIR) spectroscopic analysis of solid samples was performed on a Perkin-Elmer 1600 instrument equipped with a horizontal attenuated total reflectance (ATR) attachment using a Zinc Selenide (ZnSe) crystal.

Preparation of Polymeric Catalysts

Example A1

Preparation of poly[styrene-co-vinylbenzylchloride-co-divinylbenzene]

To a 500 mL round bottom flask (RBF) containing a stirred solution of 1.08 g of poly(vinylalcohol) in 250.0 mL of deionized $H_2O$ at 0° C., was gradually added a solution containing 50.04 g (327.9 mmol) of vinylbenzyl chloride (mixture of 3- and 4-isomers), 10.13 g (97.3 mmol) of styrene, 1.08 g (8.306 mmol) of divinylbenzene (DVB, mixture of 3- and 4-isomers) and 1.507 g (9.2 mmol) of azobisisobutyronitrile (AIBN) in 150 mL of a 1:1 (by volume) mixture of benzene/tetrahydrofuran (THF) at 0° C. After 2 hours of stirring at 0° C. to homogenize the mixture, the reaction flask was transferred to an oil bath to increase the reaction temperature to 75° C., and the mixture was stirred vigorously for 28 hours. The resulting polymer beads were vacuum filtered using a fritted-glass funnel to collect the polymer product. The beads were washed repeatedly with 20% (by volume) methanol in water, THF, and MeOH, and dried overnight at 50° C. under reduced pressure to yield 59.84 g of polymer. The polymer beads were separated by size using sieves with mesh sizes 100, 200, and 400.

Example A2

Preparation of poly[styrene-co-3-methyl-1-(4-vinylbenzyl)-3H-imidazol-1-ium chloride-co-divinylbenzene]

Poly(styrene-co-vinylbenzylchloride-co-divinylbenzene) ($Cl^-$ density=~4.0 mmol/g, 50 g, 200 mmol) was charged into a 500 mL three neck flask (TNF) equipped with a mechanical stirrer, a dry nitrogen line, and purge valve. Dry dimethylformamide (185 ml) was added into the flask (via cannula under $N_2$) and stirred to form a viscous slurry of polymer resin. 1-Methylimidazole (36.5 g, 445 mmol) was then added and stirred at 95° C. for 8 h. After cooling, the reaction mixture was filtered using a fritted glass funnel under vacuum, washed sequentially with de-ionized water and ethanol, and finally air dried.

The chemical functionalization of the polymer material, expressed in millimoles of functional groups per gram of dry polymer resin (mmol/g) was determined by ion exchange titrimetry. For the determination of cation-exchangable acidic protons, a known dry mass of polymer resin was added to a saturated aqueous solution of sodium chloride and titrated against a standard sodium hydroxide solution to the phenolphthalein end point. For the determination of anion-exchangeable ionic chloride content, a known dry mass of polymer resin was added to an aqueous solution of sodium nitrate and neutralized with sodium carbonate. The resulting mixture was titrated against a standardized solution of silver nitrate to the potassium chromate endpoint. For polymeric materials in which the exchangeable anion was not chloride, the polymer was first treated by stirring the material in aqueous hydrochloric acid, followed by washing repeatedly with water until the effluent was neutral (as determined by pH paper). The chemical functionalization of the polymer resin with methylimidazolium chloride groups was determined to be 2.60 mmol/g via gravimetry and 2.61 mmol/g via titrimetry.

Example A3

Preparation of poly[styrene-co-4-vinylbenzene-sulfonic acid-co-3-methyl-1-(4-vinylbenzyl)-3H-imidazol-1-ium bisulfate-co-divinylbenzene]

Poly[styrene-co-3-methyl-1-(4-vinylbenzyl)-3H-imidazol-1-ium chloride-co-divinylbenzene] (63 g) was charged into a 500 mL flask equipped with a magnetic stir bar and condenser. Cold concentrated sulfuric acid (>98% w/w, $H_2SO_4$, 300 mL) was gradually added into the flask under stirring which resulted in formation of dark-red colored slurry of resin. The slurry was stirred at 85° C. for 4 h. After cooling to room temperature, the reaction mixture was filtered using fritted glass funnel under vacuum and then washed repeatedly with de-ionized water until the effluent was neutral, as determined by pH paper. The sulfonated resin beads were finally washed with ethanol and air dried. The chemical functionalization of the polymer resin with sulfonic acid groups was determined to be 1.60 mmol/g, as determined by titrimetry following the procedure of Example A2.

Example A4

Preparation of poly[styrene-co-4-vinylbenzene-sulfonic acid-co-3-methyl-1-(4-vinylbenzyl)-3H-imidazol-1-ium chloride-co-divinylbenzene]

Poly[styrene-co-4-vinylbenzenesulfonic acid-co-3-methyl-1-(4-vinylbenzyl)-3H-imidazol-1-ium bisulfate-co-divinylbenzene](sample of Example A3), contained in fritted glass funnel, was washed repeatedly with 0.1 M HCl solution to ensure complete exchange of $HSO_4^-$ with $Cl^-$. The resin was then washed with de-ionized water until the effluent was neutral, as determined by pH paper. The resin was finally air-dried.

Example A5

Preparation of poly[styrene-co-4-vinylbenzene-sulfonic acid-co-3-methyl-1-(4-vinylbenzyl)-3H-imidazol-1-ium acetate-co-divinylbenzene]

The suspension of poly[styrene-co-4-vinylbenzene-sulfonic acid-co-3-methyl-1-(4-vinylbenzyl)-3H-imidazol-1-ium bisulfate-co-divinylbenzene](sample of Example A3) in 10% aqueous acetic acid solution was stirred for 2 h at 60° C. to ensure complete exchange of $HSO_4^-$ with $AcO^-$. The resin was filtered using fritted glass funnel and then washed multiple times with de-ionized water until the effluent was neutral. The resin was finally air-dried.

Example A6

Preparation of poly[styrene-co-3-ethyl-1-(4-vinyl-benzyl)-3H-imidazol-1-ium chloride-co-divinylbenzene]

Poly(styrene-co-vinylbenzylchloride-co-divinylbenzene) ($Cl^-$ density=~4.0 mmol/g, 10 g, 40 mmol) was charged into a 250 three neck flask (TNF) equipped with a mechanical stirrer, a dry nitrogen line, and purge valve. Dry dimethylformamide (80 ml) was added into the flask (via cannula under $N_2$) and stirred to give viscous resin slurry. 1-Ethylimidazole (4.3 g, 44.8 mmol) was then added to the resin slurry and stirred at 95° C. under 8 h. After cooling, the reaction mixture was filtered using fritted glass funnel under vacuum, washed sequentially with de-ionized water and ethanol, and finally air dried. The chemical functionalization of the polymer resin with ethylimidazolium chloride groups was determined to be 1.80 mmol/g, as determined by titrimetry following the procedure of Example A1.

Example A7

Preparation of poly[styrene-co-4-vinylbenzene-sulfonic acid-co-3-ethyl-1-(4-vinylbenzyl)-3H-imidazol-1-ium bisulfate-co-divinylbenzene]

Poly[styrene-co-3-ethyl-1-(4-vinylbenzyl)-3H-imidazol-1-ium chloride-co-divinylbenzene] (5 g) was charged into a 100 mL flask equipped with a magnetic stir bar and condenser. Cold concentrated sulfuric acid (>98% w/w, $H_2SO_4$, 45 mL) was gradually added into the flask under stirring which resulted in the formation of dark-red colored uniform slurry of resin. The slurry was stirred at 95-100° C. for 6 h. After cooling, the reaction mixture was filtered using fritted glass funnel under vacuum and then washed repeatedly with de-ionized water until the effluent was neutral, as determined by pH paper. The sulfonated beads were finally washed with ethanol and air dried. The chemical functionalization of the polymer with sulfonic acid groups was determined to be 1.97 mmol/g, as determined by titrimetry following the procedure of Example A2.

Example A8

Preparation of poly[styrene-co-4-vinylbenzene-sulfonic acid-co-3-ethyl-1-(4-vinylbenzyl)-3H-imidazol-1-ium chloride-co-divinylbenzene]

Poly[styrene-co-4-vinylbenzenesulfonic acid-co-3-ethyl-1-(4-vinylbenzyl)-3H-imidazol-1-ium bisulfate-co-divinyl-benzene]resin beads (sample of Example A7) contained in fritted glass funnel was washed multiple times with 0.1 M HCl solution to ensure complete exchange of $HSO_4^-$ with $Cl^-$. The resin was then washed with de-ionized water until the effluent was neutral, as determined by pH paper. The resin was finally washed with ethanol and air dried.

Example A9

Preparation of poly[styrene-co-1-(4-vinylbenzyl)-3H-imidazol-1-ium chloride-co-divinylbenzene]

Poly(styrene-co-vinylbenzylchloride-co-divinylbenzene) ($Cl^-$ density=~4.0 mmol/g, 10 g, 40 mmol) was charged into a 100 mL flask equipped with a magnetic stir bar and condenser. Chloroform (50 ml) was added into the flask and stirred to form slurry of resin. Imidazole (2.8 g, 41.13 mmol) was then added to the resin slurry and stirred at 40° C. for 18 h. After completion of reaction, the reaction mixture was filtered using fritted glass funnel under vacuum, washed sequentially with de-ionized water and ethanol, and finally air dried. The chemical functionalization of the polymer resin with imidazolium chloride groups was determined to be 2.7 mmol/g, as determined by titrimetry following the procedure of Example A2.

Example A10

Preparation of poly[styrene-co-4-vinylbenzene-sulfonic acid-co-1-(4-vinylbenzyl)-3H-imidazol-1-ium bisulfate-co-divinylbenzene]

Poly[styrene-co-1-(4-vinylbenzyl)-3H-imidazol-1-ium chloride-co-divinylbenzene] (5 g) was charged into a 100 mL flask equipped with a magnetic stir bar and condenser. Cold concentrated sulfuric acid (>98% w/w, $H_2SO_4$, 80 mL) was gradually added into the flask and stirred to form dark-red colored slurry of resin. The slurry was stirred at 95° C. for 8 h. After cooling, the reaction mixture was filtered using fritted glass funnel under vacuum and then washed repeatedly with de-ionized water until the effluent was neutral, as determined by pH paper. The sulfonated beads were finally washed with ethanol and air dried. The chemical functionalization of the polymer resin with sulfonic acid groups was determined to be 1.26 mmol/g, as determined by titrimetry following the procedure of Example A2.

Example A11

Preparation of poly[styrene-co-3-methyl-1-(4-vinylbenzyl)-3H-benzoimidazol-1-ium chloride-co-divinylbenzene]

Poly(styrene-co-vinylbenzylchloride-co-divinylbenzene) ($Cl^-$ density=~4.0 mmol/g, 4 g, 16 mmol) was charged into a 100 mL flask equipped with a magnetic stir bar and condenser. Dry dimethylformamide (50 ml) was added into the flask (via cannula under $N_2$) and stirred to form viscous slurry of polymer resin. 1-Methylbenzimidazole (3.2 g, 24.2 mmol) was then added to the resin slurry and the resulting reaction mixture was stirred at 95° C. for 18 h. After cooling, the reaction mixture was filtered using fritted glass funnel under vacuum, washed sequentially with de-ionized water and ethanol, and finally air dried. The chemical functionalization of the polymer with methylbenzimidazolium chloride groups was determined to be 1.63 mmol/g, as determined by titrimetry following the procedure of Example A2.

Example A12

Preparation of poly[styrene-co-4-vinylbenzene-sulfonic acid-co-3-methyl-1-(4-vinylbenzyl)-3H-benzoimidazol-1-ium bisulfate-co-divinylbenzene]

Poly[styrene-co-3-methyl-1-(4-vinylbenzyl)-3H-benzoimidazol-1-ium chloride-co-divinylbenzene] (5.5 g) was charged into a 100 mL flask equipped with a magnetic stir bar and condenser. Cold concentrated sulfuric acid (>98% w/w, $H_2SO_4$, 42 mL) and fuming sulfuric acid (20% free $SO_3$, 8 mL) was gradually added into the flask and stirred to form dark-red colored slurry of resin. The slurry was stirred at 85° C. for 4 h. After cooling, the reaction mixture was filtered using fritted glass funnel under vacuum and then washed repeatedly with de-ionized water until the effluent was neutral, as determined by pH paper. The sulfonated beads were finally washed with ethanol and air dried. The chemical functionalization of the polymer with sulfonic acid groups was determined to be 1.53 mmol/g, as determined by titrimetry following the procedure of Example A2.

Example A13

Preparation of poly[styrene-co-1-(4-vinylbenzyl)-pyridinium chloride-co-divinylbenzene]

Poly(styrene-co-vinylbenzylchloride-co-divinylbenzene) ($Cl^-$ density=~4.0 mmol/g, 5 g, 20 mmol) was charged into a 100 mL flask equipped with a magnetic stir bar and condenser. Dry dimethylformamide (45 ml) was added into the flask (via cannula under $N_2$) while stirring and consequently, the uniform viscous slurry of polymer resin was obtained. Pyridine (3 mL, 37.17 mmol) was then added to the resin slurry and stirred at 85-90° C. for 18 h. After cooling, the reaction mixture was filtered using fritted glass funnel under vacuum, washed sequentially with de-ionized water and ethanol, and finally air dried. The chemical functionalization of the polymer resin with pyridinium chloride groups was determined to be 3.79 mmol/g, as determined by titrimetry following the procedure of Example A2.

Example A14

Preparation of poly[styrene-co-4-vinylbenzene-sulfonic acid-co-1-(4-vinylbenzyl)-pyridinium-bisulfate-co-divinylbenzene]

Poly[styrene-co-1-(4-vinylbenzyl)-pyridinium chloride-co-divinylbenzene] (4 g) resin beads were charged into a 100 mL flask equipped with a magnetic stir bar and condenser. Cold concentrated sulfuric acid (>98% w/w, $H_2SO_4$, 45 mL) was gradually added into the flask under stirring which consequently resulted in the formation of dark-red colored uniform slurry of resin. The slurry was heated at 95-100° C. under continuous stirring for 5 h. After completion of reaction, the cooled reaction mixture was filtered using fritted glass funnel under vacuum and then washed repeatedly with de-ionized water until the effluent was neutral, as determined by pH paper. The resin beads were finally washed with ethanol and air dried. The chemical functionalization of the polymer with sulfonic acid groups was determined to be 0.64 mmol/g, as determined by titrimetry following the procedure of Example A2.

Example A15

Preparation of poly[styrene-co-1-(4-vinylbenzyl)-pyridinium chloride-co-3-methyl-1-(4-vinylbenzyl)-3H-imidazol-1-ium chloride-co-divinylbenzene]

Poly(styrene-co-vinylbenzylchloride-co-divinylbenzene) ($Cl^-$ density=~4.0 mmol/g, 10 g, 40 mmol) was charged into a 100 mL flask equipped with a magnetic stir bar and condenser. Dry dimethylformamide (80 ml) was added into the flask (via cannula under $N_2$) while stirring which resulted in the formation of viscous slurry of polymer resin. Pyridine (1.6 mL, 19.82 mmol) and 1-methylimidazole (1.7 mL, 21.62 mmol) were then added to the resin slurry and the resulting reaction mixture was stirred at 95° C. for 18 h. After completion of reaction, the reaction mixture was cooled, filtered using fritted glass funnel under vacuum, washed sequentially with de-ionized water and ethanol, and finally air dried. The chemical functionalization of the polymer with pyridinium chloride and 1-methylimidazolium chloride groups was determined to be 3.79 mmol/g, as determined by titrimetry following the procedure of Example A2.

Example A16

Preparation of poly[styrene-co-4-vinylbenzene-sulfonic acid-co-1-(4-vinylbenzyl)-pyridiniumchloride-co-3-methyl-1-(4-vinylbenzyl)-3H-imidazol-1-ium bisulfate-co-divinylbenzene]

Poly[styrene-co-1-(4-vinylbenzyl)-pyridinium chloride-co-3-methyl-1-(4-vinylbenzyl)-3H-imidazol-1-ium chloride-co-divinylbenzene] (5 g) was charged into a 100 mL flask equipped with a magnetic stir bar and condenser. Cold concentrated sulfuric acid (>98% w/w, $H_2SO_4$, 75 mL) and fuming sulfuric acid (20% free $SO_3$, 2 mL) were then gradually added into the flask under stirring which consequently resulted in the formation of dark-red colored uniform slurry of resin. The slurry was heated at 95-100° C. under continuous stirring for 12 h. After completion of reaction, the cooled reaction mixture was filtered using fritted glass funnel under vacuum and then washed repeatedly with de-ionized water until the effluent was neutral, as determined by pH paper. The sulfonated resin beads were finally washed with ethanol and air dried. The chemical functionalization of the polymer resin with sulfonic acid groups was determined to be 1.16 mmol/g, as determined by titrimetry following the procedure of Example A2.

Example A17

Preparation of poly[styrene-co-4-methyl-4-(4-vinylbenzyl)-morpholin-4-ium chloride-co-divinylbenzene]

Poly(styrene-co-vinylbenzylchloride-co-divinylbenzene) ($Cl^-$ density=~4.0 mmol/g, 10 g, 40 mmol) was charged into a 100 mL flask equipped with a magnetic stir bar and condenser. Dry dimethylformamide (85 ml) was added into the flask (via cannula under $N_2$) while stirring which resulted in the formation of uniform viscous slurry of polymer resin. 1-Methylmorpholine (5.4 mL, 49.12 mmol) were then added to the resin slurry and the resulting reaction mixture was stirred at 95° C. for 18 h. After cooling, the reaction mixture was filtered using fritted glass funnel under vacuum, washed sequentially with de-ionized water and ethanol, and finally air dried. The chemical functionalization of the polymer with methylmorpholinium chloride groups was determined to be 3.33 mmol/g, as determined by titrimetry following the procedure of Example A2.

Example A18

Preparation of poly[styrene-co-4-vinylbenzene-sulfonic acid-co-4-methyl-4-(4-vinylbenzyl)-morpholin-4-ium bisulfate-co-divinylbenzene]

Poly[styrene-co-1-4-methyl-4-(4-vinylbenzyl)-morpholin-4-ium chloride-co-divinylbenzene] (8 g) was charged into a 100 mL flask equipped with a magnetic stir bar and condenser. Cold concentrated sulfuric acid (>98% w/w, $H_2SO_4$, 50 mL) was gradually added into the flask under stirring which consequently resulted in the formation of dark-red colored slurry. The slurry was stirred at 90° C. for 8 h. After cooling, the reaction mixture was filtered using fritted glass funnel under vacuum, washed repeatedly with de-ionized water until the effluent was neutral, as determined by pH paper. The sulfonated resin beads were finally washed with ethanol and air dried. The chemical functionalization of the polymer with sulfonic acid groups was determined to be 1.18 mmol/g, as determined by titrimetry following the procedure of Example A2.

Example A19

Preparation of [polystyrene-co-triphenyl-(4-vinylbenzyl)-phosphoniumchloride-co-divinylbenzene]

Poly(styrene-co-vinylbenzylchloride-co-divinylbenzene) ($Cl^-$ density=~4.0 mmol/g, 10 g, 40 mmol) was charged into a 100 mL flask equipped with a magnetic stir bar and condenser. Dry dimethylformamide (80 ml) was added into the flask (via cannula under $N_2$) while stirring and the uniform viscous slurry of polymer resin was obtained. Triphenylphosphine (11.6 g, 44.23 mmol) was then added to the resin slurry and the resulting reaction mixture was stirred at 95° C. for 18 h. After cooling, the reaction mixture was filtered using fritted glass funnel under vacuum, washed sequentially with de-ionized water and ethanol, and finally air dried. The chemical functionalization of the polymer with triphenylphosphonium chloride groups was determined to be 2.07 mmol/g, as determined by titrimetry following the procedure of Example A2.

Example A20

Preparation of poly[styrene-co-4-vinylbenzene-sulfonic acid-co-triphenyl-(4-vinylbenzyl)-phosphonium bisulfate-co-divinylbenzene]

Poly(styrene-co-triphenyl-(4-vinylbenzyl)-phosphonium chloride-co-divinylbenzene) (7 g) was charged into a 100 mL flask equipped with a magnetic stir bar and condenser. Cold concentrated sulfuric acid (>98% w/w, $H_2SO_4$, 40 mL) and fuming sulfuric acid (20% free $SO_3$, 15 mL) were gradually added into the flask under stirring which consequently resulted in the formation of dark-red colored slurry. The slurry was stirred at 95° C. for 8 h. After cooling, the reaction mixture was filtered using fritted glass funnel under vacuum, washed repeatedly with de-ionized water until the effluent was neutral, as determined by pH paper. The sulfonated resin beads were finally washed with ethanol and air dried. The chemical functionalization of the polymer with sulfonic acid groups was determined to be 2.12 mmol/g, as determined by titrimetry following the procedure of Example A2.

Example A21

Preparation of poly[styrene-co-1-(4-vinylbenzyl)-piperidine-co-divinylbenzene]

Poly(styrene-co-vinylbenzyl chloride-co-divinylbenzene) ($Cl^-$ density=~4.0 mmol/g, 10 g, 40 mmol) was charged into a 100 mL flask equipped with a magnetic stir bar and condenser. Dry dimethylformamide (50 ml) was added into the flask (via cannula under $N_2$) while stirring which resulted in the formation of uniform viscous slurry of polymer resin. Piperidine (4 g, 46.98 mmol) was then added to the resin slurry and the resulting reaction mixture was stirred at 95° C. for 16 h. After cooling, the reaction mixture was filtered using fritted glass funnel under vacuum, washed sequentially with de-ionized water and ethanol, and finally air dried.

Example A22

Preparation of poly[styrene-co-4-vinylbenzene-sulfonic acid-co-1-(4-vinylbenzyl)-piperidine-co-divinylbenzene]

Poly[styrene-co-1-(4-vinylbenzyl)-piperidine-co-divinylbenzene] (7 g) was charged into a 100 mL flask equipped with a magnetic stir bar and condenser. Cold concentrated sulfuric acid (>98% w/w, $H_2SO_4$, 45 mL) and fuming sulfuric acid (20% free $SO_3$, 12 mL) were gradually added into the flask under stirring which consequently resulted in the formation of dark-red colored slurry. The slurry was stirred at 95° C. for 8 h. After completion of reaction, the cooled reaction mixture was filtered using fritted glass funnel under vacuum and then washed repeatedly with de-ionized water until the effluent was neutral, as determined by pH paper. The resin beads were finally washed with ethanol and air dried. The chemical functionalization of the polymer with sulfonic acid groups was determined to be 0.72 mmol/g, as determined by titrimetry following the procedure of Example A2.

Example A23

Preparation of poly[styrene-co-4-vinylbenzene-sulfonic acid-co-1-methyl-1-(4-vinylbenzyl)-piperidin-1-ium chloride-co-divinylbenzene]

Poly(styrene-co-4-(1-piperidino)methylstyrene-co-divinylbenzene) (4 g) was charged into a 100 mL flask equipped with a magnetic stir bar and condenser. Dry dimethylformamide (40 ml) was added into the flask (via cannula under $N_2$) under stiffing to obtain uniform viscous slurry. Iodomethane (1.2 ml) and potassium iodide (10 mg) were then added into the flask. The reaction mixture was stirred at 95° C. for 24 h. After cooling, the reaction mixture was filtered using fritted glass funnel under vacuum and then washed multiple times with dilute HCl solution to ensure complete exchange of I$^-$ with Cl$^-$. The resin was finally washed with de-ionized water until the effluent was neutral, as determined by pH paper. The resin was finally air-dried.

Example A24

Preparation of poly[styrene-co-4-(4-vinylbenzyl)-morpholine-co-divinyl benzene]

Poly(styrene-co-vinylbenzylchloride-co-divinylbenzene) (Cl$^-$ density=~4.0 mmol/g, 10 g, 40 mmol) was charged into a 100 mL flask equipped with a magnetic stir bar and condenser. Dry dimethylformamide (50 ml) was added into the flask (via cannula under $N_2$) while stiffing and consequently, the uniform viscous slurry of polymer resin was obtained. Morpholine (4 g, 45.92 mmol) was then added to the resin slurry and the resulting reaction mixture was heated at 95° C. under continuous stirring for 16 h. After completion of reaction, the reaction mixture was cooled, filtered using fritted glass funnel under vacuum, washed sequentially with de-ionized water and ethanol, and finally air dried.

Example A25

Preparation of poly[styrene-co-4-vinylbenzene-sulfonic acid-co-4-(4-vinylbenzyl)-morpholine-co-divinylbenzene]

Poly[styrene-co-4-(4-vinylbenzyl)-morpholine-co-divinylbenzene] (10 g) was charged into a 200 mL flask equipped with a magnetic stir bar and condenser. Cold concentrated sulfuric acid (>98% w/w, $H_2SO_4$, 90 mL) and fuming sulfuric acid (20% free $SO_3$, 10 mL) were gradually added into the flask while stirring which consequently resulted in the formation of dark-red colored slurry. The slurry was stirred at 95° C. for 8 h. After cooling, the reaction mixture was filtered using fritted glass funnel under vacuum and then washed repeatedly with de-ionized water until the effluent was neutral, as determined by pH paper. The sulfonated resin beads were finally washed with ethanol and air dried. The chemical functionalization of the polymer with sulfonic acid groups was determined to be 0.34 mmol/g, as determined by titrimetry following the procedure of Example A2.

Example A26

Preparation of poly[styrene-co-4-vinylbenzene-sulfonic acid-co-4-(4-vinylbenzyl)-morpholine-4-oxide-co-divinylbenzene]

Poly[styrene-co-4-vinylbenzenesulfonic acid-co-4-(4-vinylbenzyl)-morpholine-co-divinyl benzene] (6 g) was charged into a 100 mL flask equipped with a magnetic stir bar and condenser. Methanol (60 mL) was then charged into the flask, followed by addition of hydrogen peroxide (30% solution in water, 8.5 mL). The reaction mixture was refluxed under continuous stirring for 8 h. After cooling, the reaction mixture was filtered, washed sequentially with de-ionized water and ethanol, and finally air dried.

Example A27

Preparation of poly[styrene-co-4-vinylbenzyl-triethylammonium chloride-co-divinylbenzene]

Poly(styrene-co-vinylbenzylchloride-co-divinylbenzene) (Cl$^-$ density=~4.0 mmol/g, 10 g, 40 mmol) was charged into a 100 mL flask equipped with a magnetic stir bar and condenser. Dry dimethylformamide (80 ml) was added into the flask (via cannula under $N_2$) while stiffing and consequently the uniform viscous slurry of polymer resin was obtained. Triethylamine (5 mL, 49.41 mmol) was then added to the resin slurry and the resulting reaction mixture was stirred at 95° C. for 18 h. After cooling, the reaction mixture was filtered using fritted glass funnel under vacuum, washed sequentially with de-ionized water and ethanol, and finally air dried. The chemical functionalization of the polymer resin with triethylammonium chloride groups was determined to be 2.61 mmol/g, as determined by titrimetry following the procedure of Example A2.

Example A28

Preparation of poly[styrene-co-4-vinylbenzene-sulfonic acid-co-triethyl-(4-vinylbenzyl)-ammonium chloride-co-divinylbenzene]

Poly[styrene-co-triethyl-(4-vinylbenzyl)-ammonium chloride-co-divinylbenzene](6 g) was charged into a 100 mL flask equipped with a magnetic stir bar and condenser. Cold concentrated sulfuric acid (>98% w/w, $H_2SO_4$, 60 mL) was gradually added into the flask under stirring which consequently resulted in the formation of dark-red colored uniform slurry of resin. The slurry was stirred at 95-100° C. for 8 h. After cooling, the reaction mixture was filtered using fritted glass funnel under vacuum and then washed repeatedly with de-ionized water until the effluent was neutral, as determined by pH paper. The sulfonated resin beads were finally washed with ethanol and air dried. The chemical functionalization of the polymer with sulfonic acid groups was determined to be 0.31 mmol/g, as determined by titrimetry following the procedure of Example A2.

Example A29

Preparation of poly[styrene-co-4-vinylbenzenesulfonic acid-co-vinylbenzylchloride-co-divinylbenzene]

Poly(styrene-co-vinylbenzyl chloride-co-divinylbenzene) (6 g) was charged into a 100 mL flask equipped with a magnetic stir bar and condenser. Fuming sulfuric acid (20% free $SO_3$, 25 mL) was gradually added into the flask under stirring which consequently resulted in the formation of dark-red colored slurry. The slurry was stirred at 90° C. for 5 h. After cooling, the reaction mixture was filtered using fritted glass funnel under vacuum, washed sequentially with de-ionized water and ethanol, and finally air dried. The chemical functionalization of the polymer with sulfonic acid groups was determined to be 0.34 mmol/g, as determined by titrimetry following the procedure of Example A2.

Example A30

Preparation of poly[styrene-co-4-vinylbenzenesulfonic acid-co-3-methyl-1-(4-vinylbenzyl)-3H-imidazol-1-ium chloride-co-divinylbenzene]

Poly[styrene-co-4-vinylbenzenesulfonic acid-co-vinylbenzylchloride-co-divinylbenzene] (5 g) was charged into a 100 mL flask equipped with a magnetic stir bar and condenser. Dry dimethylformamide (20 ml) was added into the flask (via cannula under $N_2$) while stirring and the uniform viscous slurry of polymer resin was obtained. 1-Methylimidazole (3 mL, 49.41 mmol) was then added to the resin slurry and the resulting reaction mixture was stirred at 95° C. for 18 h. After cooling, reaction mixture was filtered using fritted glass funnel under vacuum and then washed repeatedly with de-ionized water. The resin beads were finally washed with ethanol and air dried. The chemical functionalization of the polymer with sulfonic acid group and methylimidiazolium chloride groups was determined to be 0.23 mmol/g and 2.63 mmol/g, respectively, as determined by titrimetry following the procedure of Example A2.

Example A31

Preparation of poly[styrene-co-3-methyl-1-(4-vinylbenzyl)-3H-imidazol-1-ium chloride-co-4-boronyl-1-(4-vinylbenzyl)-pyridinium chloride-co-divinylbenzene]

Poly(styrene-co-vinylbenzylchloride-co-divinylbenzene) ($Cl^-$ density=~4.0 mmol/g, 10 g, 40 mmol) was charged into a 100 mL flask equipped with a magnetic stir bar and condenser. Dry dimethylformamide (80 ml) was added into the flask (via cannula under $N_2$) while stirring and consequently the uniform viscous slurry of polymer resin was obtained. 4-Pyridyl-boronic acid (1.8 g, 14.6 mmol) was then added to the resin slurry and the resulting reaction mixture was stirred at 95° C. for 2 days. 1-Methylimidazole (3 mL, 49.41 mmol) was then added to the reaction mixture and stirred further at 95° C. for 1 day. After cooling to room temperature, the reaction mixture was filtered using fritted glass funnel under vacuum, washed sequentially with de-ionized water and ethanol, and finally air dried. The chemical functionalization of the polymer with boronic acid group was determined to be 0.28 mmol/g respectively, as determined by titrimetry following the procedure of Example A2.

Example A32

Preparation of poly[styrene-co-3-methyl-1-(4-vinylbenzyl)-3H-imidazol-1-ium chloride-co-1-(4-vinylphenyl)methylphosphonic acid-co-divinylbenzene]

Poly[styrene-co-3-methyl-1-(4-vinylbenzyl)-3H-imidazol-1-ium chloride-co-divinylbenzene]($Cl^-$ density=~2.73 mmol/g, 5 g) was charged into a 100 mL flask equipped with a magnetic stir bar and condenser. Triethylphosphite (70 ml) was added into the flask and the resulting suspension was stirred at 120° C. for 2 days. The reaction mixture was filtered using fritted glass funnel and the resin beads were washed repeatedly with de-ionized water and ethanol. These resin beads were then suspended in concentrated HCl (80 ml) and refluxed at 115° C. under continuous stirring for 24 h. After cooling to room temperature, the reaction mixture was filtered using fritted glass funnel under vacuum and then washed repeatedly with de-ionized water. The resin beads were finally washed with ethanol and air dried. The chemical functionalization of the polymer with phosphonic acid group and methylimidiazolium chloride groups was determined to be 0.11 mmol/g and 2.81 mmol/g, respectively, as determined by titrimetry following the procedure of Example A2.

Example A33

Preparation of poly[styrene-co-4-vinylbenzenesulfonic acid-co-vinylbenzylchloride-co-vinyl-2-pyridine-co-divinylbenzene]

Poly(styrene-co-vinylbenzylchloride-co-vinyl-2-pyridine-co-divinylbenzene) (5 g) was charged into a 100 mL flask equipped with a magnetic stir bar and condenser. Cold concentrated sulfuric acid (>98% w/w, $H_2SO_4$, 80 mL) was gradually added into the flask under stirring which consequently resulted in the formation of dark-red colored slurry. The slurry was stirred at 95° C. for 8 h. After cooling to room temperature, the reaction mixture was filtered using fritted glass funnel under vacuum, washed repeatedly with de-ionized water until the effluent was neutral, as determined by pH paper. The sulfonated beads were finally washed with ethanol and air dried. The chemical functionalization of the polymer with sulfonic acid groups was determined to be 3.49 mmol/g, as determined by titrimetry following the procedure of Example A2.

Example A34

Preparation of poly[styrene-co-4-vinylbenzenesulfonic acid-co-vinylbenzylchloride-co-1-methyl-2-vinyl-pyridinium chloride-co-divinylbenzene]

Poly[styrene-co-4-vinylbenzenesulfonic acid-co-vinylbenzylchloride-co-vinyl-2-pyridine-co-divinylbenzene] (4 g) was charged into a 100 mL flask equipped with a magnetic stir bar and condenser. Dry dimethylformamide (80 ml) was added into the flask (via cannula under $N_2$) under stiffing to obtain uniform viscous slurry. Iodomethane (1.9 ml) was then gradually added into the flask followed by addition of potassium iodide (10 mg). The reaction mixture was stirred at 95° C. for 24 h. After cooling to room temperature, the cooled reaction mixture was filtered using fritted glass funnel under vacuum and then washed multiple times with dilute HCl solution to ensure complete exchange of I⁻ with Cl⁻. The resin beads were finally washed with de-ionized water until the effluent was neutral, as determined by pH paper and then air-dried.

Example A35

Preparation of poly[styrene-co-4-vinylbenzene-sulfonic acid-co-4-(4-vinylbenzyl)-morpholine-4-oxide-co-divinylbenzene]

Poly[styrene-co-4-(4-vinylbenzyl)-morpholine-4-oxide-co-divinylbenzene] (3 g) was charged into a 100 mL flask equipped with a magnetic stir bar and condenser. Cold concentrated sulfuric acid (>98% w/w, $H_2SO_4$, 45 mL) was gradually added into the flask under stirring which consequently resulted in the formation of dark-red colored slurry. The slurry was stirred at 95° C. for 8 h. After cooling to room temperature, the reaction mixture was filtered using fritted glass funnel under vacuum, washed repeatedly with de-ionized water until the effluent was neutral, as determined by pH paper. The sulfonated beads were finally washed with ethanol and air dried.

Example A36

Preparation of poly[styrene-co-4-vinylphenylphosphonic acid-co-3-methyl-1-(4-vinylbenzyl)-3H-imidazol-1-ium chloride-co-divinylbenzene]

Poly[styrene-co-3-methyl-1-(4-vinylbenzyl)-3H-imidazol-1-iumchloride-co-divinylbenzene](Cl⁻ density=~2.73 mmol/g, 5 g) was charged into a 100 mL flask equipped with a magnetic stir bar and condenser. Diethylphosphite (30 ml) and t-butylperoxide (3.2 ml) were added into the flask and the resulting suspension was stirred at 120° C. for 2 days. The reaction mixture was filtered using fritted glass funnel and the resin beads were washed repeatedly with de-ionized water and ethanol. These resin beads were then suspended in concentrated HCl (80 ml) and refluxed at 115° C. under continuous stirring for 2 days. After cooling to room temperature, the reaction mixture was filtered using fritted glass funnel under vacuum and then washed repeatedly with de-ionized water. The resin beads were finally washed with ethanol and air dried. The chemical functionalization of the polymer with aromatic phosphonic acid group was determined to be 0.15 mmol/g, as determined by titrimetry following the procedure of Example A2.

Example A37

Preparation of poly[styrene-co-3-carboxymethyl-1-(4-vinylbenzyl)-3H-imidazol-1-ium chloride-co-divinylbenzene]

Poly(styrene-co-vinylbenzylchloride-co-divinylbenzene) (Cl⁻ density=~4.0 mmol/g, 10 g, 40 mmol) was charged into a 100 mL flask equipped with a magnetic stir bar and condenser. Dimethylformamide (50 ml) was added into the flask and stirred to form a slurry of resin. Imidazole (2.8 g, 41.13 mmol) was then added to the resin slurry and stirred at 80° C. for 8 h. The reaction mixture was then cooled to 40° C. and t-butoxide (1.8 g) was added into the reaction mixture and stirred for 1 h. Bromoethylacetate (4 ml) was then added to and the reaction mixture was stirred at 80° C. for 6 h. After cooling to room temperature, the reaction mixture was filtered using fritted glass funnel under vacuum and then washed repeatedly with de-ionized water. The washed resin beads were suspended in the ethanolic sodium hydroxide solution and refluxed overnight. The resin beads were filtered and successively washed with deionized water multiple times and ethanol, and finally air dried. The chemical functionalization of the polymer with carboxylic acid group was determined to be 0.09 mmol/g, as determined by titrimetry following the procedure of Example A2.

Example A38

Preparation of poly[styrene-co-5-(4-vinylbenzylamino)-isophthalic acid-co-3-methyl-1-(4-vinylbenzyl)-3H-imidazol-1-ium chloride-co-divinylbenzene]

Poly(styrene-co-vinylbenzylchloride-co-divinylbenzene) (Cl⁻ density=~4.0 mmol/g, 10 g, 40 mmol) was charged into a 100 mL flask equipped with a magnetic stir bar and condenser. Dry dimethylformamide (80 ml) was added into the flask (via cannula under $N_2$) while stirring and consequently the uniform viscous slurry of polymer resin was obtained. Dimethyl aminoisophthalate (3.0 g, 14.3 mmol) was then added to the resin slurry and the resulting reaction mixture was stirred at 95° C. for 16 h. 1-Methylimidazole (2.3 mL, 28.4 mmol) was then added to the reaction mixture and stirred further at 95° C. for 1 day. After cooling to room temperature, the reaction mixture was filtered using fritted glass funnel under vacuum, washed sequentially with de-ionized water and ethanol. The washed resin beads were suspended in the ethanolic sodium hydroxide solution and refluxed overnight. The resin beads were filtered and successively washed with deionized water multiple times and ethanol, and finally air dried. The chemical functionalization of the polymer with carboxylic acid group was determined to be 0.16 mmol/g, as determined by titrimetry following the procedure of Example A2.

Example A39

Preparation of poly[styrene-co-(4-vinylbenzylamino)-acetic acid-co-3-methyl-1-(4-vinylbenzyl)-3H-imidazol-1-ium chloride-co-divinylbenzene]

Poly(styrene-co-vinylbenzylchloride-co-divinylbenzene) (Cl⁻ density=~4.0 mmol/g, 10 g, 40 mmol) was charged into a 100 mL flask equipped with a magnetic stir bar and condenser. Dry dimethylformamide (80 ml) was added into the flask (via cannula under $N_2$) while stirring and consequently the uniform viscous slurry of polymer resin was obtained. Glycine (1.2 g, 15.9 mmol) was then added to the resin slurry and the resulting reaction mixture was stirred at 95° C. for 2 days. 1-Methylimidazole (2.3 mL, 28.4 mmol) was then added to the reaction mixture and stirred further at 95° C. for 12 hours. After cooling to room temperature, the reaction mixture was filtered using fritted glass funnel under vacuum, washed sequentially with de-ionized water and ethanol, and finally air dried. The chemical functionalization of the polymer with carboxylic acid group was determined to be 0.05 mmol/g, as determined by titrimetry following the procedure of Example A2.

Example A40

Preparation of poly[styrene-co-(1-vinyl-1H-imidazole)-co-divinylbenzene]

To a 500 mL round bottom flask (RBF) containing a stirred solution of 1.00 g of poly(vinylalcohol) in 250.0 mL of deionized $H_2O$ at 0° C. is gradually added a solution containing 35 g (371 mmol) of 1-vinylimidazole, 10 g (96 mmol) of styrene, 1 g (7.7 mmol) of divinylbenzene (DVB) and 1.5 g (9.1 mmol) of azobisisobutyronitrile (AIBN) in 150 mL of a 1:1 (by volume) mixture of benzene/tetrahydrofuran (THF) at 0° C. After 2 hours of stiffing at 0° C. to homogenize the mixture, the reaction flask is transferred to an oil bath to increase the reaction temperature to 75° C., and the mixture is stirred vigorously for 24 hours. The resulting polymer is vacuum filtered using a fritted-glass funnel, washed repeatedly with 20% (by volume) methanol in water, THF, and MeOH, and then dried overnight at 50° C. under reduced pressure.

Example A41

Preparation of poly(styrene-co-vinylbenzylmethylimidazolium chloride-co-vinylbenzylmethylmorpholinium chloride-co-vinylbenzyltriphenylphosphonium chloride-co-divinylbenzene)

1-methylimidazole (4.61 g, 56.2 mmol), 4-methylmorpholine (5.65 g, 56.2 mmol), and triphenylphosphine (14.65, 55.9 mmol) were charged into a 500 mL flask equipped with a magnetic stir bar and a condenser. Acetone (100 ml) was added into the flask and mixture was stirred at 50° C. for 10 min. Poly(styrene-co-vinylbenzylchloride-co-divinylbenzene) (1% DVB, Cl⁻ density=4.18 mmol/g dry resin, 40.22 g, 168 mmol) was charged into the flask while stirring until a uniform polymer suspension was obtained. The resulting reaction mixture was refluxed for 24 h. After cooling, the reaction mixture was filtered using a fritted glass funnel under vacuum, washed sequentially with acetone and ethyl acetate, and dried overnight at 70° C. The chemical functionalization of the polymer resin with chloride groups was determined to be 2.61 mmol/g dry resin via titrimetry.

Example A42

Preparation of sulfonated poly(styrene-co-vinylbenzylmethylimidazolium bisulfate-co-vinylbenzylmethylmorpholinium bisulfate-co-vinylbenzyltriphenyl phosphonium bisulfate-co-divinylbenzene)

Poly(styrene-co-vinylbenzylmethylimidazolium chloride-co-vinylbenzylmethylmorpholinium chloride-co-vinylbenzyltriphenylphosphonium chloride-co-divinylbenzene) (35.02 g) was charged into a 500 mL flask equipped with a magnetic stir bar and condenser. Fuming sulfuric acid (20% free $SO_3$, 175 mL) was gradually added into the flask and stirred to form dark-red resin suspension. The mixture was stirred overnight at 90° C. After cooling to room temperature, the reaction mixture was filtered using fritted glass funnel under vacuum and then washed repeatedly with de-ionized water until the effluent was neutral, as determined by pH paper. The sulfonated polymer resin was air dried to a final moisture content of 56% g $H_2O$/g wet polymer. The chemical functionalization of the polymer resin with sulfonic acid groups was determined to be 3.65 mmol/g dry resin.

Example A43

Preparation of poly(styrene-co-vinylbenzylmethylimidazolium chloride-co-vinylbenzylmethylmorpholinium chloride-co-vinylbenzyltriphenylphosphonium chloride-co-divinylbenzene)

1-methylimidazole (7.02 g, 85.5 mmol), 4-methylmorpholine (4.37 g, 43.2 mmol) and triphenylphosphine (11.09, 42.3 mmol) were charged into a 500 mL flask equipped with a magnetic stir bar and condenser. Acetone (100 ml) was added into the flask and mixture was stirred at 50° C. for 10 min. Poly(styrene-co-vinylbenzylchloride-co-divinylbenzene) (1% DVB, Cl⁻ density=4.18 mmol/g dry resin, 40.38 g, 169 mmol) was charged into flask while stiffing until a uniform suspension was obtained. The resulting reaction mixture was refluxed for 18 h. After cooling, the reaction mixture was filtered using fritted glass funnel under vacuum, washed sequentially with acetone and ethyl acetate, and dried at 70° C. overnight. The chemical functionalization of the polymer resin with chloride groups was determined to be 2.36 mmol/g dry resin dry resin via titrimetry.

Example A44

Preparation of sulfonated poly(styrene-co-vinylbenzylmethylimidazolium bisulfate-co-vinylbenzylmethylmorpholinium bisulfate-co-vinylbenzyltriphenyl phosphonium bisulfate-co-divinylbenzene)

Poly(styrene-co-vinylbenzylmethylimidazolium chloride-co-vinylbenzylmethylmorpholinium chloride-co-vinylbenzyltriphenylphosphonium chloride-co-divinylbenzene) (35.12 g) was charged into a 500 mL flask equipped with a magnetic stir bar and condenser. Fuming sulfuric acid (20% free $SO_3$, 175 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were finally air dried. The chemical functionalization of the polymer resin with sulfonic acid groups was determined to be 4.38 mmol/g dry resin.

Example A45

Preparation of poly(styrene-co-vinylbenzylmethylmorpholinium chloride-co-vinylbenzyltriphenylphosphonium chloride-co-divinylbenzene)

4-methylmorpholine (8.65 g, 85.5 mmol) and triphenylphosphine (22.41, 85.3 mmol) were charged into a 500 mL flask equipped with a magnetic stir bar and condenser. Acetone (100 ml) was added into the flask and mixture was stirred at 50° C. for 10 min. Poly(styrene-co-vinylbenzylchloride-co-divinylbenzene) (1% DVB, Cl⁻ density=4.18 mmol/g dry resin, 40.12 g, 167 mmol) was charged into flask while stiffing until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight. The chemical functionalization of the polymer resin with chloride groups was determined to be 2.22 mmol/g dry resin via titrimetry.

Example A46

Preparation of sulfonated poly(styrene-co-vinylbenzylmethylmorpholinium bisulfate-co-vinylbenzyltriphenylphosphonium bisulfate-co-divinylbenzene)

Poly(styrene-co-vinylbenzylmethylimidazolium chloride-co-vinylbenzylmethylmorpholinium chloride-co-vinylbenzyltriphenylphosphonium chloride-co-divinylbenzene) (35.08 g) was charged into a 500 mL flask equipped with a magnetic stir bar and condenser. Fuming sulfuric acid (20% free $SO_3$, 175 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were dried under air to a final moisture content of 52% g $H_2O$/g wet resin. The chemical functionalization of the polymer resin with sulfonic acid groups was determined to be 4.24 mmol/g dry resin.

Example A47

Preparation of phenol-formaldehyde Resin

Phenol (12.87 g, 136.8 mmol) was dispensed into a 100 mL round bottom flask (RBF) equipped with a stir bar and condenser. De-ionized water (10 g) was charged into the flask. 37% Formalin solution (9.24 g, 110 mmol) and oxalic acid (75 mg) were added. The resulting reaction mixture was refluxed for 30 min. Additional oxalic acid (75 mg) was then added and refluxing was continued for another 1 hour. Chunk of solid resin was formed, which was ground to a coarse powder using a mortar and pestle. The resin was repeatedly washed with water and methanol and then dried at 70° C. overnight.

Example A48

Preparation of chloromethylated phenol-formaldehyde Resin

Phenol-formaldehyde resin (5.23 g, 44 mmol) was dispensed into a 100 mL three neck round bottom flask (RBF) equipped with a stir bar, condenser and nitrogen line. Anhydrous dichloroethane (DCE, 20 ml) was then charged into the flask. To ice-cooled suspension of resin in DCE, zinc chloride (6.83 g, 50 mmol) was added. Chloromethyl methyl ether (4.0 ml, 51 mmol) was then added dropwise into the reaction. The mixture was warmed to room temperature and stirred at 50° C. for 6 h. The product resin was recovered by vacuum filtration and washed sequentially with water, acetone and dichloromethane. The washed resin was dried at 40° C. overnight.

Example A49

Preparation of triphenylphosphine Functionalized phenol-formaldehyde Resin

Triphenylphosphine (10.12, 38.61 mmol) were charged into a 100 mL flask equipped with a magnetic stir bar and condenser. Acetone (30 ml) was added into the flask and mixture was stirred at 50° C. for 10 min. Chloromethylated phenol-formaldehyde resin (4.61 g, 38.03 mmol) was charged into flask while stiffing. The resulting reaction mixture was refluxed for 24 h. After cooling, the reaction mixture was filtered using fritted glass funnel under vacuum, washed sequentially with acetone and ethyl acetate, and dried at 70° C. overnight.

Example A50

Preparation of sulfonated triphenylphosphine-Functionalized phenol-formaldehyde Resin Triphenylphosphine-functionalized phenol-formaldeyde resin (5.12 g, 13.4 mmol) was charged into a 100 mL flask equipped with a magnetic stir bar and condenser. Fuming sulfuric acid (20% free $SO_3$, 25 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated resin was dried under air to a final moisture content of 49% g $H_2O$/g wet resin. The chemical functionalization of the polymer resin with sulfonic acid groups was determined to be 3.85 mmol/g dry resin.

Example A51

Preparation of poly(styrene-co-vinylimidazole-co-divinylbenzene)

De-ionized water (75 mL) was charged into flask into a 500 mL three neck round bottom flask equipped with a mechanical stirrer, condenser and $N_2$ line. Sodium chloride (1.18 g) and carboxymethylcellulose (0.61 g) were charged into the flask and stirred for 5 min. The solution of vinylimidazole (3.9 mL, 42.62 mmol), styrene (4.9 mL, 42.33 mmol) and divinylbenzene (0.9 mL, 4.0 mmol) in iso-octanol (25 mL) was charged into flask. The resulting emulsion was stirred at 500 rpm at room temperature for 1 h. Benzoyl peroxide (75%, 1.205 g) was added, and temperature was raised to 80° C. The reaction mixture was heated for 8 h at 80° C. with stirring rate of 500 rpm. The polymer product was recovered by vacuum filtration and washed with water and acetone multiple times. The isolated polymer was purified by soxhlet extraction with water and acetone. The resin was dried at 40° C. overnight.

Example A52

Preparation of poly(styrene-co-vinylmethylimidazolium iodide-co-divinylbenzene)

Poly(styrene-co-vinylimidazole-co-divinylbenzene) (3.49 g, 39 mmol) was dispensed into a 100 mL three neck round bottom flask (RBF) equipped with a stir bar, condenser and nitrogen line. Anhydrous tetrahydrofuran (20 ml) was then charged into the flask. To ice-cooled suspension of resin in tetrahydrofuran, potassium t-butoxide (5.62 g, 50 mmol) was added and stirred for 30 min. Iodomethane (3.2 ml, 51 mmol) was then added dropwise into the reaction. The mixture was warmed to room temperature and stirred at 50° C. for 6 h. The product resin was recovered by vacuum filtration and washed

Example A53

Preparation of sulfonated poly(styrene-co-vinylmethylimidazolium bisulfate-co-divinylbenzene)

Poly(styrene-co-vinylmethylimidazolium iodide-co-divinylbenzene) (3.89 g, 27.8 mmol) was charged into a 100 mL flask equipped with a magnetic stir bar and condenser. Fuming sulfuric acid (20% free $SO_3$, 20 mL) was gradually added into the flask and stirred to form dark-red colored slurry. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated polymer was dried under air to a final moisture content of 51% g $H_2O$/g wet resin.

Example A54

Preparation of poly(styrene-co-vinylbenzyltriphenylphosphonium chloride-co-divinylbenzene)

To a 250 mL flask equipped with a magnetic stir bar and condenser was charged triphenylphosphine (38.44 g, 145.1 mmol). Acetone (50 mL) was added into the flask and mixture was stirred at 50° C. for 10 min. Poly(styrene-co-vinylbenzylchloride-co-divinylbenzene) (8% DVB, Cl⁻ density=4.0 mmol/g dry resin, 30.12 g, 115.6 mmol) was charged into flask while stiffing until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight. The chemical functionalization of the polymer resin with triphenylphosphonium chloride groups was determined to be 1.94 mmol/g dry resin via titrimetry.

Example A55

Preparation of sulfonated poly(styrene-co-vinylbenzyltriphenyl phosphonium bisulfate-co-divinylbenzene)

Poly(styrene-co-vinylbenzyltriphenylphosphonium chloride-co-divinylbenzene) (40.12 g) was charged into a 500 mL flask equipped with a magnetic stir bar and condenser. Fuming sulfuric acid (20% free $SO_3$, 160 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were dried under air to a final moisture content of 54% g $H_2O$/g wet resin. The chemical functionalization of the polymer resin with sulfonic acid groups was determined to be 4.39 mmol/g dry resin.

Example A56

Preparation of poly(styrene-co-vinylbenzyltriphenylphosphonium chloride-co-divinylbenzene To a 250 mL flask equipped with a magnetic stir bar and condenser was charged triphenylphosphine (50.22 g, 189.6 mmol). Acetone (50 mL) was added into the flask and mixture was stirred at 50° C. for 10 min. Poly(styrene-co-vinylbenzylchloride-co-divinylbenzene) (4% DVB, Cl⁻ density=5.2 mmol/g dry resin, 30.06 g, 152.08 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight. The chemical functionalization of the polymer resin with triphenylphosphonium chloride groups was determined to be 2.00 mmol/g dry resin via titrimetry.

Example A57

Preparation of sulfonated poly(styrene-co-vinylbenzyltriphenyl phosphonium bisulfate-co-divinylbenzene)

Poly(styrene-co-vinylbenzyltriphenylphosphonium chloride-co-divinylbenzene) (40.04 g,) was charged into a 500 mL flask equipped with a magnetic stir bar and condenser. Fuming sulfuric acid (20% free $SO_3$, 160 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were dried under air to a final moisture content of 47% g $H_2O$/g wet resin. The chemical functionalization of the polymer resin with sulfonic acid groups was determined to be 4.36 mmol/g dry resin.

Example A58

Preparation of poly(styrene-co-vinylbenzylmethylimidazolium chloride-co-divinylbenzene)

To a 250 mL flask equipped with a magnetic stir bar and condenser was charged 1-methylimidazole (18 mL, 223.5 mmol). Acetone (75 mL) was added into the flask and mixture was stirred at 50° C. for 10 min. Poly(styrene-co-vinylbenzylchloride-co-divinylbenzene) (8% DVB, Cl⁻ density=4.0 mmol/g dry resin, 40.06, 153.7 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight. The chemical functionalization of the polymer resin with methylimidazolium chloride groups was determined to be 3.54 mmol/g dry resin via titrimetry.

Example A59

Preparation of sulfonated poly(styrene-co-vinylbenzylmethylimidazolium bisulfate-co-divinylbenzene)

Poly(styrene-co-vinylbenzylmethylimidazolium chloride-co-divinylbenzene) (30.08 g) was charged into a 500 mL flask equipped with a magnetic stir bar and condenser. Fuming sulfuric acid (20% free $SO_3$, 120 mL) was gradually added into the flask and stirred to form dark-red colored slurry of resin. The slurry was stirred at 90° C. overnight. After cooling, the reaction mixture was filtered using fritted glass funnel sequentially with water, acetone and dichloromethane. The washed resin was dried at 40° C. overnight.

under vacuum and then washed repeatedly with de-ionized water until the effluent was neutral, as determined by pH paper. The sulfonated beads were dried under air to a final moisture content of 50% g $H_2O$/g wet resin. The chemical functionalization of the polymer resin with sulfonic acid groups was determined to be 2.87 mmol/g dry resin.

Example A60

Preparation of poly(styrene-co-vinylbenzylmethylimidazolium chloride-co-divinylbenzene)

To a 250 mL flask equipped with a magnetic stir bar and condenser was charged 1-methylimidazole (20 mL, 248.4 mmol). Acetone (75 mL) was added into the flask and mixture was stirred at 50° C. for 10 min. Poly(styrene-co-vinylbenzylchloride-co-divinylbenzene) (4% DVB, $Cl^-$ density=5.2 mmol/g dry resin, 40.08, 203.8 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight. The chemical functionalization of the polymer resin with methylimidazolium chloride groups was determined to be 3.39 mmol/g dry resin via titrimetry.

Example A61

Preparation of sulfonated poly(styrene-co-vinylbenzylmethylimidazolium bisulfate-co-divinylbenzene)

Poly(styrene-co-vinylbenzylmethylimidazolium chloride-co-divinylbenzene) (30.14 g) was charged into a 500 mL flask equipped with a magnetic stir bar and condenser. Fuming sulfuric acid (20% free $SO_3$, 120 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were dried under air to a final moisture content of 55% g $H_2O$/g wet resin. The chemical functionalization of the polymer resin with sulfonic acid groups was determined to be 2.78 mmol/g dry resin.

Example A62

Preparation of poly(styrene-co-vinylbenzyltriphenylphosphonium chloride-co-divinylbenzene)

To a 250 mL flask equipped with a magnetic stir bar and condenser was charged triphenylphosphine (44.32 g, 163.9 mmol). Acetone (50 mL) was added into the flask and mixture was stirred at 50° C. for 10 min. Poly(styrene-co-vinylbenzylchloride-co-divinylbenzene) (13% DVB macroporous resin, $Cl^-$ density=4.14 mmol/g dry resin, 30.12 g, 115.6 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight.

Example A63

Preparation of sulfonated poly(styrene-co-vinylbenzyltriphenyl phosphonium bisulfate-co-divinylbenzene)

Poly(styrene-co-vinylbenzyltriphenylphosphonium chloride-co-divinylbenzene) (30.22 g) was charged into a 500 mL flask equipped with a magnetic stir bar and condenser. Fuming sulfuric acid (20% free $SO_3$, 90 mL) was gradually added into the flask and stirred to form dark-red colored slurry of resin. The slurry was stirred at 90° C. for 1 hour. After cooling, the reaction mixture was filtered using fritted glass funnel under vacuum and then washed repeatedly with de-ionized water until the effluent was neutral, as determined by pH paper. The sulfonated beads were dried under air to a final moisture content of 46% g $H_2O$/g wet resin. The chemical functionalization of the polymer resin with sulfonic acid groups was determined to be 2.82 mmol/g dry resin.

Example A64

Preparation of poly(styrene-co-vinylbenzyltriphenylphosphonium chloride-co-divinylbenzene)

To a 250 mL flask equipped with a magnetic stir bar and condenser was charged triphenylphosphine (55.02 g, 207.7 mmol). Acetone (50 mL) was added into the flask and mixture was stirred at 50° C. for 10 min. Poly(styrene-co-vinylbenzylchloride-co-divinylbenzene) (6.5% DVB macroporous resin, $Cl^-$ density=5.30 mmol/g dry resin, 30.12 g, 157.4 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight.

Example A65

Preparation of sulfonated poly(styrene-co-vinylbenzyltriphenyl phosphonium bisulfate-co-divinylbenzene)

Poly(styrene-co-vinylbenzyltriphenylphosphonium chloride-co-divinylbenzene) (30.12 g) was charged into a 500 mL flask equipped with a magnetic stir bar and condenser. Fuming sulfuric acid (20% free $SO_3$, 90 mL) was gradually added into the flask and stirred to form dark-red colored slurry of resin. The slurry was stirred at 90° C. for 1 hour. After cooling, the reaction mixture was filtered using fritted glass funnel under vacuum and then washed repeatedly with de-ionized water until the effluent was neutral, as determined by pH paper. The sulfonated beads were dried under air to a final moisture content of 49% g $H_2O$/g wet resin. The chemical functionalization of the polymer resin with sulfonic acid groups was determined to be 2.82 mmol/g dry resin.

Example A66

Preparation of poly(styrene-co-vinylbenzyltriphenylphosphonium chloride-co-divinylbenzene)

To a 250 mL flask equipped with a magnetic stir bar and condenser was charged triphenylphosphine (38.42 g, 145.0 mmol). Acetone (50 mL) was added into the flask and mixture was stirred at 50° C. for 10 min. Poly(styrene-co-vinylbenzylchloride-co-divinylbenzene) (4% DVB, Cl⁻ density=4.10 mmol/g dry resin, 30.12 g, 115.4 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight.

Example A67

Preparation of sulfonated poly(styrene-co-vinylbenzyltriphenylphosphonium bisulfate-co-divinylbenzene)

Poly(styrene-co-vinylbenzyltriphenylphosphonium chloride-co-divinylbenzene) (30.18 g) was charged into a 500 mL flask equipped with a magnetic stir bar and condenser. Fuming sulfuric acid (20% free $SO_3$, 120 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were dried under air to a final moisture content of 59% g $H_2O$/g wet resin. The chemical functionalization of the polymer resin with sulfonic acid groups was determined to be 3.03 mmol/g dry resin.

Example A68

Preparation of poly(styrene-co-vinylbenzyltriphenylphosphonium chloride-co-divinylbenzene)

To a 500 mL flask equipped with a magnetic stir bar and condenser was charged triphenylphosphine (44.22 g, 166.9 mmol). Acetone (70 mL) was added into the flask and mixture was stirred at 50° C. for 10 min. Poly(styrene-co-vinylbenzylchloride-co-divinylbenzene) (4% DVB, Cl⁻ density=3.9 mmol/g dry resin, 35.08 g, 130.4 mmol) was charged into flask while stirring until a uniform suspension was obtained. The resulting reaction mixture was refluxed for 24 h. After cooling, the reaction mixture was filtered using fritted glass funnel under vacuum, washed sequentially with acetone and ethyl acetate, and dried at 70° C. overnight.

Example A69

Preparation of sulfonated poly(styrene-co-vinylbenzyltriphenyl phosphonium bisulfate-co-divinylbenzene)

Poly(styrene-co-vinylbenzyltriphenylphosphonium chloride-co-divinylbenzene) (30.42 g) was charged into a 500 mL flask equipped with a magnetic stir bar and condenser. Fuming sulfuric acid (20% free $SO_3$, 120 mL) was gradually added into the flask and stirred to form dark-red colored slurry of resin. The slurry was stirred at 90° C. overnight. After cooling, the reaction mixture was filtered using fritted glass funnel under vacuum and then washed repeatedly with de-ionized water until the effluent was neutral, as determined by pH paper. The sulfonated beads were dried under air to a final moisture content of 57% g $H_2O$/g wet resin. The chemical functionalization of the polymer resin with sulfonic acid groups was determined to be 3.04 mmol/g dry resin.

Example A70

Preparation of poly(butyl-vinylimidazolium chloride-co-butylimidazolium chloride-co-styrene)

To a 500 mL flask equipped with a mechanical stirrer and reflux condenser is added 250 mL of acetone, 10 g of imidzole, 14 g of vinylimidazole, 15 g of styrene, 30 g of dichlorobutane and 1 g of azobisisobutyronitrile (AIBN). The solution is stirred under reflux conditions for 12 hours to produce a solid mass of polymer. The solid polymer is removed from the flask, washed repeatedly with acetone, and ground to a coarse powder using a mortar and pestle to yield the product.

Example A71

Preparation of sulfonated poly(butyl-vinylimidazolium bisulfate-co-butylimidazolium bisulfate-co-styrene)

Poly(butyl-vinylimidazolium chloride-co-butylimidazolium chloride-co-styrene) 30.42 g) is charged into a 500 mL flask equipped with a mechanical stirrer. Fuming sulfuric acid (20% free $SO_3$, 120 mL) is gradually added into the flask until the polymer is fully suspended. The resulting slurry is stirred at 90° C. for 5 hours. After cooling, the reaction mixture is filtered using fritted glass funnel under vacuum and then washed repeatedly with de-ionized water until the effluent is neutral, as determined by pH paper.

Preparation of Solid-Supported Catalysts

Example B1a

Preparation of the Carbon Support from *Populus tremuloides*

A carbon-containing starting material was obtained by milling 1.0 kg of commercially-sourced hardwood chips (input moisture content of 15% g $H_2O$/g wood; carbon content 45% g carbon/g wood) from the Aspen species *Populus tremuloides* using a 1 horsepower (HP) laboratory rotating knife mill equipped with a 2.0 mm output screen. The output hardwood milling-dust was dried at 70° C. to a moisture content below 5% g $H_2O$/g wood. 500 g of the resulting dry wood was charged into a 5 L glass reaction vessel equipped with an electric heating jacket, a nitrogen input line, an exhaust line directed to a scrubber with a water bubbler apparatus, and top and bottom thermocouples accurate to ±0.5° C. The atmosphere of the charged reaction vessel was purged with nitrogen for 10 minutes, after which the nitrogen flow was reduced to the minimum required to drive nitrogen through the scrubber apparatus and maintained at that minimum flow rate during the reaction. The temperature was increased gradually over 30 minutes to 350° C., maintained for 4.0 hours, and then decreased to room temperature over a 30-minute period. 175 g of a brown-black material was recovered from the reactor vessel. The product was ground gently into a coarse powder to yield a carbon support material.

Example B1b

Preparation of the Carbon Support from Coconut Shell

A carbon-containing starting material is obtained by milling 1.0 kg of commercially-sourced coconut shell chips (input moisture content of 10% g $H_2O$/g wood; carbon content 50% g carbon/g shells) using a 1 horsepower (HP) laboratory rotating knife mill equipped with a 2.0 mm output screen. The output milling-dust is dried at 70° C. to a moisture content below 5% g $H_2O$/g material. 500 g of the resulting dry material is charged into a 5 L glass reaction vessel equipped with an electric heating jacket, a nitrogen input line, an exhaust line directed to a scrubber with a water bubbler apparatus, and top and bottom thermocouples that are accurate to 0.5° C. The atmosphere of the charged reaction vessel is purged with nitrogen for 10 minutes, after which the nitrogen flow is reduced to the minimum required to drive nitrogen through the scrubber apparatus and maintained through the reaction. The temperature is increased gradually over 30 minutes to 350° C., maintained for 4.0 hours, and then decreased to room temperature over a 30-minute period. The powder recovered from the reactor vessel is ground gently into a coarse powder to yield the carbon support material.

Example B1c

Preparation of the Carbon Support from Shrimp Shell

A carbon-containing starting material was obtained by milling 100 g of commercially-sourced shrimp shells (input moisture content of 10% g $H_2O$/g wood; carbon content 40% g carbon/g shells and 5% g nitrogen/g shells) using a 1 horsepower (HP) laboratory rotating knife mill equipped with a 2.0 mm output screen. The output milling-dust was dried at 70° C. to a moisture content below 5% g $H_2O$/g material. 70 g of the resulting dry material was charged into a 1 L glass reaction vessel equipped with an electric heating jacket, a nitrogen input line, an exhaust line directed to a scrubber with a water bubbler apparatus, and top and bottom thermocouples that are accurate to 0.5° C. The atmosphere of the charged reaction vessel was purged with nitrogen for 10 minutes, after which the nitrogen flow was reduced to the minimum required to drive nitrogen through the scrubber apparatus and maintained through the reaction. The temperature was increased gradually over 30 minutes to 350° C., maintained for 4.0 hours, and then decreased to room temperature over a 30-minute period. The powder recovered from the reactor vessel was ground gently into a coarse powder to yield 35.2 g of the carbon support material.

Example B1d

Preparation of the Carbon Support from Chitosan

A carbon-containing starting material was obtained by milling 1.0 kg of commercially-available chitosan (input moisture content of 2% g $H_2O$/g chitosan; carbon content 40% g carbon/g shells and 8% g nitrogen/g shells) using a 1 horsepower (HP) laboratory rotating knife mill equipped with a 2.0 mm output screen. The output milling-dust was dried at 70° C. to a moisture content below 5% g $H_2O$/g material. 500 g of the resulting dry material was charged into a 5 L glass reaction vessel equipped with an electric heating jacket, a nitrogen input line, an exhaust line directed to a scrubber with a water bubbler apparatus, and top and bottom thermocouples that are accurate to 0.5° C. The atmosphere of the charged reaction vessel was purged with nitrogen for 10 minutes, after which the nitrogen flow was reduced to the minimum required to drive nitrogen through the scrubber apparatus and maintained through the reaction. The temperature was increased gradually over 30 minutes to 350° C., maintained for 4.0 hours, and then decreased to room temperature over a 30-minute period. The powder recovered from the reactor vessel was ground gently into a coarse powder to yield 214 g of the carbon support material.

Example B2a

Chloromethylation of the Carbon Support from Example B1a

To a 100 mL three-neck round bottom flask (RBF) equipped with a stir bar, a condenser and nitrogen line is suspended the carbon support from Example B1a in anhydrous dichloroethane (DCE). The stirred suspension is cooled to 0° C. using an ice-water bath with continuous nitrogen flow. To the stirred suspension is added anhydrous zinc chloride. Chloromethyl methylether is then added dropwise into the reaction over a period of 15 minutes. The mixture is warmed to room temperature and stirred at 50° C. for 6 hours. The product is recovered by vacuum filtration and washed sequentially with water, acetone and dichloromethane. The washed solid is dried at 40° C. under vacuum. The extent of chloromethylation is determined by elemental analysis and by gravimetry.

Example B2b

Chloroacylation of the Carbon Support from Example B1a

The carbon support from Example B1a was suspended in anhydrous dichloroethane (DCE) in a 100 mL three-neck round bottom flask (RBF) equipped with a stir bar, a condenser, and a nitrogen input line The stirred suspension was cooled to 0° C. using an ice-water bath with continuous nitrogen flow. To the stirred suspension was added anhydrous aluminum chloride. Chloroacetyl chloride was then added dropwise into the reaction over a period of 15 minutes. The mixture is warmed to room temperature and stirred at 50° C. for 12 hours. The product was recovered by vacuum filtration and washed sequentially with water, acetone and dichloromethane. The washed solid was dried at 40° C. under vacuum to yield the final product. The extent of chloroacylation was determined to be 3.0 mmol chloride per gram of dry material by elemental analysis and by gravimetry.

Example B2c

Chloromethylation of Biochar

The carbon support from Example B1a is suspended in anhydrous dichloroethane (DCE) in a 100 mL three-neck round bottom flask (RBF) equipped with a stir bar, a condenser and nitrogen line. The stirred suspension is cooled to 0° C. using an ice-water bath with continuous nitrogen flow. To the stirred suspension is added anhydrous zinc chloride. Chloromethyl methylether is then added dropwise into the reaction over a period of 15 minutes. The mixture is warmed to room temperature and stirred at 50° C. for 6 hours. The product is recovered by vacuum filtration and washed sequentially with water, acetone and dichloromethane. The washed solid is dried at 40° C. under vacuum. The extent of chloromethylation is determined by elemental analysis and by gravimetry.

Example B3a

Quaternization of the Alkylated Carbon Support from Example B2a

To a 500 mL flask equipped with a magnetic stir bar and a condenser was charged acetone (100 ml), 1-methylimidazole (4.6 g, 56 mmol), 4-methylmorpholine (5.7 g, 56 mmol), and triphenylphosphine (14.7, 56 mmol). The resulting mixture was stirred at 50° C. for 10 minutes. In the stirred solution was suspended 40 g of the chloromethylated carbon support obtained from Example B2a. The resulting reaction mixture was heated under reflux conditions for 24 hours. After cooling, the reaction mixture was filtered using a fritted glass funnel under vacuum, washed sequentially with acetone and ethyl acetate, and dried overnight at 70° C. The extent of quaternization was determined by ion exchange titrimetry of $Cl^-$ against $AgNO_3$.

Example B3b

Quaternization of the Alkylated Carbon Support from Example B2b

To a 500 mL flask equipped with a magnetic stir bar and a condenser was charged acetone (100 ml), 1-methylimidazole (4.6 g, 56 mmol), 4-methylmorpholine (5.7 g, 56 mmol), and triphenylphosphine (14.7, 56 mmol). The resulting mixture was stirred at 50° C. for 10 minutes. In the stirred solution was suspended 40 g of the chloroacylated carbon support obtained from Example B2b. The resulting reaction mixture was heated under reflux conditions for 24 hours. After cooling, the reaction mixture was filtered using a fritted glass funnel under vacuum, washed sequentially with acetone and ethyl acetate, and dried overnight at 70° C. The extent of quaternization was determined to be 1.7 mmol $Cl^-$ per gram of dry solid by ion exchange titrimetry of $Cl^-$ against $AgNO_3$.

Example B4a

Sulfonation of the Quaternized Carbon Support from Example B3a

To a 500 mL flask equipped with a magnetic stir bar and condenser is charged fuming sulfuric acid (20% free $SO_3$, 50 mL) and concentrated sulfuric acid (>95% w/w, ACS Reagent Grade, 50 mL). To the stirred acid is added 30 g of the quaternized carbon support obtained from Example B3a to form a dark black suspension. The mixture is stirred for 4 hours at 90° C. After cooling to room temperature, the reaction mixture is filtered using fritted glass funnel under vacuum, and then washed repeatedly with de-ionized water until the effluent is neutral, as determined by pH paper. The sulfonated support is air-dried to a final moisture content of 50% g $H_2O$/g wet polymer. The chemical functionalization of the support with sulfonic acid groups is determined by acid-base titration against sodium hydroxide.

Example B4b

Sulfonation of the Quaternized Carbon Support from Example B3b

To a 500 mL flask equipped with a magnetic stir bar and condenser was charged fuming sulfuric acid (20% free $SO_3$, 50 mL) and concentrated sulfuric acid (>95% w/w, ACS Reagent Grade, 50 mL). To the stirred acid was added 30 g of the quaternized carbon support from Example B3b to form a dark black suspension. The mixture was stirred for 4 hours at 90° C. After cooling to room temperature, the reaction mixture was filtered using fritted glass funnel under vacuum, and then washed repeatedly with de-ionized water until the effluent was neutral, as determined by pH paper. The sulfonated support was air-dried to a final moisture content of 56% g $H_2O$/g wet polymer. The chemical functionalization of the support resin with sulfonic acid groups was determined to be 3.65 mmol/g dry resin.

Production of Sugars from Biomass Feedstocks Using Exemplary Catalysts

Example C1

Digestion of Sugarcane Bagasse using Catalyst described in Example A3

Sugarcane bagasse (50% g $H_2O$/g wet bagasse, with a dry-matter composition of: 39.0% g glucan/g dry biomass, 17.3% g xylan/g dry biomass, 5.0% g arabinan/g dry biomass, 1.1% g galactan/g dry biomass, 5.5% g acetate/g dry biomass, 5.0% g soluble extractives/g dry biomass, 24.1% g lignin/g dry biomass, and 3.1% g ash/g dry biomass) was cut such that the maximum particle size was no greater than 1 cm. The composition of the lignocellulosic biomass was determined using a method based on the procedures known in the art. See R. Ruiz and T. Ehrman, "Determination of Carbohydrates in Biomass by High Performance Liquid Chromatography," NREL Laboratory Analytical Procedure LAP-002 (1996); D. Tempelton and T. Ehrman, "Determination of Acid-Insoluble Lignin in Biomass," NREL Laboratory Analytical Procedure LAP-003 (1995); T. Erhman, "Determination of Acid-Soluble Lignin in Biomass," NREL Laboratory Analytical Procedure LAP-004 (1996); and T. Ehrman, "Standard Method for Ash in Biomass," NREL Laboratory Analytical Procedure LAP-005 (1994).

To a 15 mL cylindrical glass reaction vial was added: 0.50 g of the cane bagasse sample, 0.30 g of Catalyst as prepared in Example A3 (initial moisture content: 12% g $H_2O$/g dispensed catalyst), and 800 L of deionized H2O. The reactants were mixed thoroughly with a glass stir rod to distribute the catalyst particles evenly throughout the biomass. The resulting mixture was gently compacted to yield a solid reactant cake. The glass reactor was sealed with a phenolic cap and incubated at 120° C. for four hours.

Example C2

Separation of Catalyst/Product Mixture from the Hydrolysis of Sugarcane Bagasse The cylindrical glass reactor from Example C1 was cooled to room temperature and unsealed. 5.0 mL of distilled $H_2O$ was added to the vial reactor and the resulting mixture of liquids and solids was agitated for 2 minutes by magnetic stirring. Following agitation, the solids were allowed to sediment for 30 seconds to produce the layered mixture. The solid catalyst formed a layer at the bottom of the vial reactor. Lignin and residual biomass formed a solid layer above the solid catalyst. The short-chained beta-glucans formed a layer of amorphous solids above the lignin and residual biomass. Finally, the soluble sugars formed a liquid layer above the short-chained beta-glucans.

Example C3

Recovery of Sugars and Soluble Carbohydrates from the Hydrolysis of Sugarcane Bagasse The supernatant and residual insoluble materials from Example C2 were separated by decantation. The soluble-sugar content of hydrolysis products was determined by a combination of high performance liquid chromatography (HPLC) and spectrophotometric methods. HPLC determination of soluble sugars and oligosaccharides was performed on a Hewlett-Packard 1050 Series instrument equipped with a refractive index (RI) detector using a 30 cm×7.8 mm Phenomenex HPB column with water as the mobile phase. The sugar column was protected by both a lead-exchanged sulfonated-polystyrene guard column and a tri-alkylammoniumhydroxide anionic-exchange guard column. All HPLC samples were microfiltered using a 0.2 m syringe filter prior to injection. Sample concentrations were determined by reference to a calibration generated from known standards.

The ability of the catalyst to hydrolyze the cellulose and hemicellulose components of the biomass to soluble sugars was measured by determining the effective first-order rate constant. The extent of reaction for a chemical species (e.g., glucan, xylan, arabinan) was determined by calculating the ratio of moles of the recovered species to the theoretical moles of the species that would be obtained as a result of complete conversion of the input reactant based on the known composition of the input biomass and the known molecular weights of the reactants and products and the known stoichiometries of the reactions under consideration.

For the digestion of sugarcane bagasse using catalyst as described in Example A3, the first-order rate constant for conversion of xylan to xylose was determined to be 0.3/hr. The first-order rate constant for conversion of glucan to soluble monosaccharides and oligosaccharides (including disaccharides) was determined to be 0.08/hr.

Example C4

Recovery of Insoluble Oligo-Glucans from Hydrolyzed Sugarcane Bagasse

An additional 5.0 mL of water was added to the residual solids from Example C3 and the mixture was gently agitated to suspend only the lightest particles. The suspension was decanted to remove the light particles from the residual lignin and residual catalyst, which remained in the solid sediment at the bottom of the reactor. The solid particles were concentrated by centrifugation.

The number average degree of polymerization ($DOP_N$) of residual water-insoluble glucans (including short-chain oligosaccharides) was determined by extracting the glucans into ice-cold phosphoric acid, precipitating the extracted carbohydrates into water, and measuring the ratio of terminal reducing sugars to the number of total sugar monomers the method of Zhang and Lynd. See Y.-H. Percival Zhang and Lee R. Lynd, "Determination of the Number-Average Degree of Polymerization of Cellodextrins and Cellulose with Application to Enzymatic Hydrolysis," *Biomacromolecules*, 6, 1510-1515 (2005). UV-Visible spectrophotometric analysis was performed on a Beckman DU-640 instrument. In cases where the digestion of hemicellulose was complete (as determined by HPLC), DOP determination of the residual cellulose was performed without the need for phosphoric acid extraction. In some cases, the number average degree of polymerization was verified by Gel Permeation Chromatography (GPC) analysis of cellulose was performed using a procedure adapted from the method of Evans et al. See R. Evans, R. Wearne, A. F. A. Wallis, "Molecular Weight Distribution of Cellulose as Its Tricarbanilate by High Performance Size Exclusion Chromatography," *J. Appl. Pol. Sci.*, 37, 3291-3303 (1989).

In a 20 mL reaction vial containing 3 mL of dry DMSO, was suspended an approximately 50 mg sample of cellulose (dried overnight at 50° C. under reduced pressure). The reaction vial was sealed with a PFTE septum, flushed with dry $N_2$, followed by addition of 1.0 mL phenylisocyanate via syringe. The reaction mixture was incubated at 60° C. for 4 hours with periodic mixing, until the majority of cellulose was dissolved. Excess isocyanate was quenched by addition of 1.0 mL of dry MeOH. Residual solids were pelletized by centrifugation, and a 1 mL aliquot of the supernatant was added to 5 mL of 30% v/v MeOH/$dH_2O$ to yield the carbanilated cellulose as an off-white precipitate. The product was recovered by centrifugation, and repeatedly washed with 30% v/v MeOH, followed by drying for 10 hours at 50° C. under reduced pressure. GPC was performed on a Hewlett-Packard 1050 Series HPLC using a series of TSK-Gel (G3000 Hhr, G4000 Hhr, G5000 Hhr) columns and tetrahydrofuran (THF) as the mobile phase with UV/Vis detection. The molecular weight distribution of the cellulose was determined using a calibration based on polystyrene standards of known molecular weight.

For the digestion of sugarcane bagasse using catalyst as shown in Example A3, the number average degree of polymerization of the oligo-glucans was determined to be 19±4 anhydroglucose (AHG) units. The observed reduction of the degree of polymerization of the residual cellulose to a value significantly lower than the degree of polymerization for the crystalline domains of the input cellulose (for which $DOP_N$>200 AHG units) indicates that the catalyst successfully hydrolyzed crystalline cellulose. The first order rate constant for conversion of β-glucan to short-chain oligo-glucans was determined to be 0.2/hr.

Example C5

Separation and Recovery of Lignin, Residual Unreacted Biomass and Catalyst from Hydrolyzed Sugarcane Bagasse An additional 10 mL of water was added to the residual solids in Example C4. The mixture was agitated to suspend the residual lignin (and residual unreacted biomass particles) without suspending the catalyst. The recovered catalyst was washed with water and then dried to constant mass at 110° C. in a gravity oven to yield 99.6% g/g recovery. The functional density of sulfonic acid groups on the recovered catalyst was determined to be 1.59±0.02 mmol/g by titration of the recovered catalyst indicating negligible loss of acid functionalization.

Example C6

Reuse of Recovered Catalyst

Some of the catalyst recovered from Example C5 (0.250 g dry basis) was returned to the 15 mL cylindrical vial reactor. 0.50 g of additional biomass (composition identical to that in Example C5) and 800 L of deionized $H_2O$ was added to the reactor, and the contents were mixed thoroughly, as described in Example C1. The reactor was sealed and incubated at 115° C. for four hours. Following the reaction, the product mixture was separated following the procedure described in Examples C2-C5. The first-order rate constant for conversion of xylan to xylose was determined to be 0.3/hr. The first-order rate constant for conversion of glucan to soluble monosaccharides and oligosaccharides (including disaccharides) was determined to be 0.1/hr. The number average degree of polymerization of residual cellulose was determined to be $DOP_N = 20 \pm 4$ AHG units, and the first order rate constant for conversion of β-glucan to short-chain oligo-glucans was determined to be 0.2/hr.

Example C7

Hydrolysis of Corn Stover using Catalyst as prepared in Example A34

Corn stover (7.2% g $H_2O$/g wet biomass, with a dry-matter composition of: 33.9% g glucan/g dry biomass, 24.1% g xylan/g dry biomass, 4.8% g arabinan/g dry biomass, 1.5% g galactan/g dry biomass, 4.0% g acetate/g dry biomass, 16.0% g soluble extractives/g dry biomass, 11.4% g lignin/g dry biomass, and 1.4% g ash/g dry biomass) was cut such that the maximum particle size was no greater than 1 cm. To a 15 mL cylindrical glass reaction vial was added: 0.45 g of the cane bagasse sample, 0.22 g of Catalyst as prepared in Example A34 (initial moisture content: 0.8% g $H_2O$/g dispensed catalyst), and 2.3 mL of deionized $H_2O$. The reactants were mixed thoroughly with a glass stir rod to distribute the catalyst particles evenly throughout the biomass. The resulting mixture was gently compacted to yield a solid reactant cake. The glass reactor was sealed with a phenolic cap and incubated at 110° C. for five hours. Following the reaction, the product mixture was separated following the procedure described in Examples C2-C5. The first-order rate constant for conversion of xylan to xylose was determined to be 0.1/hr. The first-order rate constant for conversion of glucan to soluble monosaccharides and oligosaccharides (including disaccharides) was determined to be 0.04/hr. The number average degree of polymerization of residual cellulose was determined to be $DOP_N = 20 \pm 4$ AHG units, and the first order rate constant for conversion of β-glucan to short-chain oligo-glucans was determined to be 0.06/hr.

Example C8

Hydrolysis of Oil Palm Empty Fruit Bunches Using Catalyst as Prepared in Example A20

Shredded oil palm empty fruit bunches (8.7% g $H_2O$/g wet biomass, with a dry-matter composition of: 35.0% g glucan/g dry biomass, 21.8% g xylan/g dry biomass, 1.8% g arabinan/g dry biomass, 4.8% g acetate/g dry biomass, 9.4% g soluble extractives/g dry biomass, 24.2% g lignin/g dry biomass, and 1.2% g ash/g dry biomass) was cut such that the maximum particle size was no greater than 1 cm. To a 15 mL cylindrical glass reaction vial was added: 0.46 g of the cane bagasse sample, 0.43 g of Catalyst as prepared in Example A20 (initial moisture content: 18.3% g $H_2O$/g dispensed catalyst), and 1.3 mL of deionized $H_2O$. The reactants were mixed thoroughly with a glass stir rod to distribute the catalyst particles evenly throughout the biomass. The resulting mixture was gently compacted to yield a solid reactant cake. The glass reactor was sealed with a phenolic cap and incubated at 110° C. for five hours. Following the reaction, the product mixture was separated following the procedure described in Examples C2-C5. The first-order rate constant for conversion of xylan to xylose was determined to be 0.4/hr. The first-order rate constant for conversion of glucan to soluble monosaccharides and oligosaccharides (including disaccharides) was determined to be 0.04/hr. The number average degree of polymerization of residual cellulose was determined to be $DOP_N = 20 \pm 4$ AHG units, and the first order rate constant for conversion of β-glucan to short-chain oligo-glucans was determined to be 0.06/hr.

Example C9

Hydrolysis of Sugarcane Bagasse Using Catalyst as Prepared in Example A32

Sugarcane bagasse (12.5% g $H_2O$/g wet bagasse, with a dry-matter composition of: 39.0% g glucan/g dry biomass, 17.3% g xylan/g dry biomass, 5.0% g arabinan/g dry biomass, 1.1% g galactan/g dry biomass, 5.5% g acetate/g dry biomass, 5.0% g soluble extractives/g dry biomass, 24.1% g lignin/g dry biomass, and 3.1% g ash/g dry biomass) was cut such that the maximum particle size was no greater than 1 cm. To a 15 mL cylindrical glass reaction vial was added: 0.53 g of the cane bagasse sample, 0.52 g of Catalyst as prepared in Example A32 (initial moisture content: 3.29% g $H_2O$/g dispensed catalyst), and 1.4 mL of deionized $H_2O$. The reactants were mixed thoroughly with a glass stir rod to distribute the catalyst particles evenly throughout the biomass. The resulting mixture was gently compacted to yield a solid reactant cake. The glass reactor was sealed with a phenolic cap and incubated at 115° C. for four hours. Following the reaction, the product mixture was separated following the procedure described in Examples C2-C5. The first-order rate constant for conversion of xylan to xylose was determined to be 0.59/hr. The first-order rate constant for conversion of glucan to soluble monosaccharides and oligosaccharides (including disaccharides) was determined to be 0.05/hr. The number average degree of polymerization of residual cellulose was determined to be $DOP_N = 23 \pm 4$ AHG units, and the first order rate constant for conversion of 3-glucan to short-chain oligo-glucans was determined to be 0.07/hr.

Example C10

Hydrolysis of Sugarcane Bagasse Using Catalyst as Prepared in Example A18

Sugarcane bagasse (12.5% g $H_2O$/g wet bagasse, with a dry-matter composition of: 39.0% g glucan/g dry biomass, 17.3% g xylan/g dry biomass, 5.0% g arabinan/g dry biomass, 1.1% g galactan/g dry biomass, 5.5% g acetate/g dry biomass, 5.0% g soluble extractives/g dry biomass, 24.1% g lignin/g dry biomass, and 3.1% g ash/g dry biomass) was cut such that the maximum particle size was no greater than 1 cm. To a 15 mL cylindrical glass reaction vial was added: 0.51 g of the cane bagasse sample, 0.51 g of Catalyst as prepared in Example A18 (initial moisture content: 7.9% g $H_2O$/g dispensed catalyst), and 1.4 mL of deionized $H_2O$. The reactants were mixed thoroughly with a glass stir rod to distribute the catalyst particles evenly throughout the biomass. The resulting mixture was gently compacted to yield a solid reactant cake. The glass reactor was sealed with a phenolic cap and incubated at 115° C. for four hours. Following the reaction, the product mixture was separated following the procedure described in Examples C2-C5. The first-order rate constant for conversion of xylan to xylose was determined to be 0.06/hr. The first-order rate constant for conversion of glucan to soluble oligo-, di-, and mono-saccharides was determined to be 0.05/hr. The number average degree of polymerization of residual cellulose was determined to be 20±4 AHG units, and the first order rate constant for conversion of β-glucan to short-chain oligo-glucans was determined to be 0.07/hr.

Example C11

High-Selectivity to Sugars

Shredded oil palm empty fruit bunches (8.7% g H$_2$O/g wet biomass, with a dry-matter composition of: 35.0% g glucan/g dry biomass, 21.8% g xylan/g dry biomass, 1.8% g arabinan/g dry biomass, 4.8% g acetate/g dry biomass, 9.4% g soluble extractives/g dry biomass, 24.2% g lignin/g dry biomass, and 1.2% g ash/g dry biomass) was cut such that the maximum particle size was no greater than 1 cm. To a 15 mL cylindrical glass reaction vial was added: 0.51 g of the cane bagasse sample, 0.51 g of Catalyst as prepared in Example A3 (initial moisture content: 8.9% g H$_2$O/g dispensed catalyst), and 2.6 mL of deionized H$_2$O. The reactants were mixed thoroughly with a glass stir rod to distribute the catalyst particles evenly throughout the biomass. The resulting mixture was gently compacted to yield a solid reactant cake. The glass reactor was sealed with a phenolic cap and incubated at 115° C. for four hours. Following the reaction, 10.0 mL of deionized H$_2$O was added to the product mixture to dissolve the soluble species and the solids were allowed to sediment. HPLC determination of sugar dehydration products and organic acids liberated from biomass samples was performed on an Agilent 1100 Series instrument using a 30 cm×7.8 mm Supelcogel™ H column (or a Phenomenex HOA column in some cases) with 0.005N sulfuric acid in water as the mobile phase. Quantitation of sugar degradation products: formic acid, levulinic acid, 5-hydroxymethylfurfural, and 2-furaldehyde, was performed by reference to a calibration curve generated from high-purity solutions of known concentration. The first order rate constant for the production of degradation products was found to be <0.001/hr, representing >99% mol sugars/mol degradation products.

Example C12

Fermentation of Cellulosic Sugars from Sugarcane Bagasse

Sugarcane bagasse (12.5% g H$_2$O/g wet bagasse, with a dry-matter composition of: 39.0% g glucan/g dry biomass, 17.3% g xylan/g dry biomass, 5.0% g arabinan/g dry biomass, 1.1% g galactan/g dry biomass, 5.5% g acetate/g dry biomass, 5.0% g soluble extractives/g dry biomass, 24.1% g lignin/g dry biomass, and 3.1% g ash/g dry biomass) was cut such that the maximum particle size was no greater than 1 cm. To a 15 mL cylindrical glass reaction vial was added: 1.6 g of the cane bagasse sample, 1.8 g of Catalyst as prepared in Example A3 (initial moisture content: 12.1% g H$_2$O/g dispensed catalyst), and 5.0 mL of deionized H$_2$O. The reactants were mixed thoroughly with a glass stir rod to distribute the catalyst particles evenly throughout the biomass. The resulting mixture was gently compacted to yield a solid reactant cake. The glass reactor was sealed with a phenolic cap and incubated at 110° C. for five hours. After five hours, an additional 1.0 mL of distilled H2O was added to the reaction mixture, which was then incubated at 105° C. for an additional 2 hours. The wet reactant cake was loaded into a syringe equipped with a 0.2 micrometer filter and the hydrolysate was pressed out of the product mixture into a sterile container. To a culture tube was added 2.5 mL of culture media (prepared by diluting 10 g of yeast extract and 20 g peptone to 500 mL in distilled water, followed by purification by sterile filtration), 2.5 mL of the hydrolysate, and 100 mL of yeast slurry (prepared by dissolving 500 mg of Alcotec 24 hour Turbo Super yeast into 5 mL of 30° C. of sterile H$_2$O. The culture was grown at 30° C. in shaking incubator, with 1 mL aliquots removed at 24, 48 and 72 hours. For each aliquot, the optical density of the culture was determined by spectrophotometer aliquot. The aliquot was purified by centrifugation and the supernatant was analyzed by HPLC to determine the concentrations of glucose, xylose, galactose, arabinose, ethanol, and glycerol. After 24 hours, ethanol and glycerol were found in the fermentation supernatant, indicating at least 65% fermentation yield on a molar basis relative to the initial glucose in the hydrolysate.

Example C13

Fermentation of Cellulosic Sugars from Cassava Stem

Cassava stem (2.0% g H$_2$O/g wet cassava stem, with a dry-matter composition of: 53.0% g glucan/g dry biomass, 6.0% g xylan/g dry biomass, 2.5% g arabinan/g dry biomass, 5.5% g acetate/g dry biomass, 5.9% g soluble extractives/g dry biomass, 24.2% g lignin/g dry biomass, and 2.1% g ash/g dry biomass) was shredded in a coffee-grinder such that the maximum particle size was no greater than 2 mm. To a 15 mL cylindrical glass reaction vial was added: 1.9 g of the shredded cassava stem, 2.0 g of Catalyst as prepared in Example A3 (initial moisture content: 12.0% g H$_2$O/g dispensed catalyst), and 8.0 mL of deionized H$_2$O. The reactants were mixed thoroughly with a glass stir rod to distribute the catalyst particles evenly throughout the biomass. The resulting mixture was gently compacted to yield a solid reactant cake. The glass reactor was sealed with a phenolic cap and incubated at 110° C. for five hours. After five hours, an additional 2.0 mL of distilled H2O was added to the reaction mixture, which was then incubated at 105° C. for an additional 2 hours. The wet reactant cake was loaded into a syringe equipped with a 0.2 micrometer filter and the hydrolysate was pressed out of the product mixture into a sterile container. To a culture tube was added 2.5 mL of culture media (prepared by diluting 10 g of yeast extract and 20 g peptone to 500 mL in distilled water, followed by purification by sterile filtration), 2.5 mL of the hydrolysate, and 100 mL of yeast slurry (prepared by dissolving 500 mg of Alcotec 24 hour Turbo Super yeast into 5 mL of 30° C. of sterile H$_2$O. The culture was grown at 30° C. in shaking incubator, with 1 mL aliquots removed at 24, 48 and 72 hours. For each aliquot, the optical density of the culture was determined by spectrophotometer aliquot. The aliquot was purified by centrifugation and the supernatant was analyzed by HPLC to determine the concentrations of glucose, xylose, galactose, arabinose, ethanol, and glycerol. After 24 hours, ethanol and glycerol were found in the fermentation supernatant, indicating at least 70% fermentation yield on a molar basis relative to the initial glucose in the hydrolysate.

Example C14

Fermentation of Glucose Obtained from Insoluble Starch

To 15 mL cylindrical glass reaction vial was added: 4.0 g of corn starch (3% g H$_2$O/g wet starch, with a dry-matter composition of: 98% g glucan/g dry biomass), 3.9 g of Catalyst as prepared in Example A3 (initial moisture content: 12.25% g H$_2$O/g dispensed catalyst), and 12.0 mL of deionized H$_2$O. The reactants were mixed thoroughly with a glass stir rod to distribute the catalyst particles evenly throughout the biomass. The resulting mixture was gently compacted to yield a solid reactant cake. The glass reactor was sealed with a phenolic cap and incubated at 110° C. for five hours. After five hours, an additional 2.0 mL of distilled H2O was added to the reaction mixture, which was then incubated at 105° C. for an additional 2 hours. The wet reactant cake was loaded into a syringe equipped with a 0.2 micrometer filter and the hydrolysate was pressed out of the product mixture into a sterile container. To a culture tube was added 2.5 mL of culture media (prepared by diluting 10 g of yeast extract and 20 g peptone to 500 mL in distilled water, followed by purification by sterile filtration), 2.5 mL of the hydrolysate, and 100 mL of yeast slurry (prepared by dissolving 500 mg of Alcotec 24 hour Turbo Super yeast into 5 mL of 30° C. of sterile $H_2O$. The culture was grown at 30° C. in shaking incubator, with 1 mL aliquots removed at 24, 48 and 72 hours. For each aliquot, the optical density of the culture was determined by spectrophotometer aliquot. The aliquot was purified by centrifugation and the supernatant was analyzed by HPLC to determine the concentrations of glucose, xylose, galactose, arabinose, ethanol, and glycerol. After 24 hours, ethanol and glycerol were found in the fermentation supernatant, indicating at least 88% fermentation yield on a molar basis relative to the initial glucose in the hydrolysate.

Example C15

Enzymatic Saccharification of Oligo-Glucans Obtained from Digestion of Sugarcane Bagasse with Catalyst as Prepared in Example A3

50.0 mg of the oligo-gucans obtained in Example C4 was suspended in 0.4 mL of 0.05 molar acetate buffer solution at pH 4.8 in a culture tube. The suspension was pre-warmed to 40° C., after which, 0.5 FPU of Celluclast® cellulase enzyme from *Trichoderma reesei* and 2 IU of cellobiase enzyme from *Aspergillus niger* (diluted in 0.1 mL of citrate buffer at 40° C.) was added. A 50.0 mL aliquot was sampled from the enzymatic reaction every hour for five hours. For each aliquot, the reaction was terminated by diluting the 50.0 mL sample to 0.7 mL in distilled water and adding 0.3 mL of DNS reagent (prepared by diluting 91 g of potassium sodium tartrate, 3.15 g dinitrosalicylic acid, 131 mL of 2 molar sodium hydroxide 2.5 g phenol and 2.5 g sodium sulfite to 500 mL with distilled $H_2O$). The 1 mL mixture was sealed in a microcentrifuge tube and boiled for exactly 5 minutes in water. The appearance of reducing sugars was measured by comparing the absorbance at 540 nm to a calibration curve generated from glucose samples of known concentration. The first order rate constant for reducing sugar liberation in the saccharification reaction was determined to be 0.15/hr.

Comparative Example C16

Attempted Hydrolysis of Sugarcane Bagasse with Cross-Linked, Sulfonated-Polystyrene (Negative Control 1)

The cellulose digestion capability of the catalysts described herein was compared to that of conventional acidified polymer-resins used for catalysis in organic and industrial chemistry (T. Okuhara, "Water-Tolerant Solid Acid Catalysts," *Chem. Rev.*, 102, 3641-3666 (2002)). Sugarcane bagasse (12.5% g $H_2O$/g wet bagasse, with a dry-matter composition of: 39.0% g glucan/g dry biomass, 17.3% g xylan/g dry biomass, 5.0% g arabinan/g dry biomass, 1.1% g galactan/g dry biomass, 5.5% g acetate/g dry biomass, 5.0% g soluble extractives/g dry biomass, 24.1% g lignin/g dry biomass, and 3.1% g ash/g dry biomass) was cut such that the maximum particle size was no greater than 1 cm. To a 15 mL cylindrical glass reaction vial was added: 0.51 g of the cane bagasse sample, 0.53 g of sulfonated polystyrene (Dowex® 50WX2 resin, acid functionalization: 4.8 mmol/g, initial moisture content: 19.6% g $H_2O$/g dispensed catalyst), and 1.4 mL of deionized $H_2O$. The reactants were mixed thoroughly with a glass stir rod to distribute the catalyst particles evenly throughout the biomass. The resulting mixture was gently compacted to yield a solid reactant cake. The glass reactor was sealed with a phenolic cap and incubated at 115° C. for six hours. Following the reaction, the product mixture was separated following the procedure described in Examples C2-C5. The first-order rate constant for conversion of xylan to xylose was determined to be 0.1/hr. The first-order rate constant for conversion of glucan to soluble oligo-, di-, and mono-saccharides was determined to be <0.01/hr. The number average degree of polymerization of residual cellulose was found to be $DOP_N>300AHG$ units, indicating little or no digestion of crystalline cellulose in the biomass sample. Short-chain oligosaccharides were not detected. Unlike the digestion products depicted in FIG. 1), the residual biomass exhibited little or no structural reduction in particle size.

Comparative Example C17

Attempted Hydrolysis of Sugarcane Bagasse with Sulfonated Polystyrene (Negative Control 2)

Sugarcane bagasse (12.5% g $H_2O$/g wet bagasse, with a dry-matter composition of: 39.0% g glucan/g dry biomass, 17.3% g xylan/g dry biomass, 5.0% g arabinan/g dry biomass, 1.1% g galactan/g dry biomass, 5.5% g acetate/g dry biomass, 5.0% g soluble extractives/g dry biomass, 24.1% g lignin/g dry biomass, and 3.1% g ash/g dry biomass) was cut such that the maximum particle size was no greater than 1 cm. To a 15 mL cylindrical glass reaction vial was added: 0.52 g of the cane bagasse sample, 0.55 g of sulfonated polystyrene (Amberlyst® 15, acid functionalization: 4.6 mmol/g, initial moisture content: 10.8% g $H_2O$/g dispensed catalyst), and 1.8 mL of deionized $H_2O$. The reactants were mixed thoroughly with a glass stir rod to distribute the catalyst particles evenly throughout the biomass. The resulting mixture was gently compacted to yield a solid reactant cake. The glass reactor was sealed with a phenolic cap and incubated at 115° C. for six hours. Following the reaction, the product mixture was separated following the procedure described in Examples C2-C5. The first-order rate constant for conversion of xylan to xylose was determined to be 0.1/hr. The first-order rate constant for conversion of glucan to soluble oligo-, di-, and mono-saccharides was determined to be <0.01/hr. The number average degree of polymerization of residual cellulose was determined to be $DOP_N>300$ AHG units, indicating little or no digestion of crystalline cellulose in the biomass sample. Short-chain oligosaccharides were not detected. Unlike the digestion products depicted in FIG. 1), the residual biomass exhibited little or no structural reduction in particle size.

Comparative Example C18

Attempted Hydrolysis of Sugarcane Bagasse with Cross-Linked Polyacrylic Acid (Negative Control 3)

Sugarcane bagasse (12.5% g $H_2O$/g wet bagasse, with a dry-matter composition of: 39.0% g glucan/g dry biomass, 17.3% g xylan/g dry biomass, 5.0% g arabinan/g dry biomass, 1.1% g galactan/g dry biomass, 5.5% g acetate/g dry biomass, 5.0% g soluble extractives/g dry biomass, 24.1% g lignin/g dry biomass, and 3.1% g ash/g dry biomass) was cut such that the maximum particle size was no greater than 1 cm. To a 15 mL cylindrical glass reaction vial was added: 0.50 g of the cane bagasse sample, 0.50 g of polyacrylic acid beads (Amberlite® IRC86 resin, acid functionalization: 10.7 mmol/g, initial moisture content: 5.2% g $H_2O$/g dispensed catalyst), and 1.8 mL of deionized $H_2O$. The reactants were mixed thoroughly with a glass stir rod to distribute the catalyst particles evenly throughout the biomass. The resulting mixture was gently compacted to yield a solid reactant cake. The glass reactor was sealed with a phenolic cap and incubated at 115° C. for six hours. Following the reaction, the product mixture was separated following the procedure described in Examples C2-C5. The first-order rate constant for conversion of xylan to xylose was determined to be <0.05/hr. The first-order rate constant for conversion of glucan to soluble oligo-, di-, and mono-saccharides was determined to be <0.001/hr. The number average degree of polymerization of residual cellulose was determined to be $DOP_N$>300 AHG units, indicating little or no digestion of crystalline cellulose in the biomass sample. Short-chain oligosaccharides were not detected. The residual biomass exhibited little or no structural reduction in particle size.

Comparative Example C19

Attempted Hydrolysis of Sugarcane Bagasse with a Non-Acidic Ionomer as Prepared in Example A2 (Negative Control 4)

Sugarcane bagasse (12.5% g $H_2O$/g wet bagasse, with a dry-matter composition of: 39.0% g glucan/g dry biomass, 17.3% g xylan/g dry biomass, 5.0% g arabinan/g dry biomass, 1.1% g galactan/g dry biomass, 5.5% g acetate/g dry biomass, 5.0% g soluble extractives/g dry biomass, 24.1% g lignin/g dry biomass, and 3.1% g ash/g dry biomass) was cut such that the maximum particle size was no greater than 1 cm. To a 15 mL cylindrical glass reaction vial was added: 0.50 g of the cane bagasse sample, 0.50 g of poly[styrene-co-3-methyl-1-(4-vinylbenzyl)-3H-imidazol-1-ium chloride-co-divinylbenzene] (Catalyst as described in Example A2, Acid functionalization: 0.0 mmol/g, initial moisture content: 4.0% g $H_2O$/g dispensed polymer), and 1.8 mL of deionized $H_2O$. The reactants were mixed thoroughly with a glass stir rod to distribute the catalyst particles evenly throughout the biomass. The resulting mixture was gently compacted to yield a solid reactant cake. The glass reactor was sealed with a phenolic cap and incubated at 115° C. for six hours. Following the reaction, the product mixture was separated following the procedure described in Examples C2-C5. The first-order rate constant for conversion of xylan to xylose was determined to be <0.001/hr. No detectable amounts of soluble oligo-, di-, and mono-saccharides were observed. It was determined that the number average degree of polymerization of the residual cellulose was $DOP_N$>300 AHG units, indicating little or no digestion of crystalline cellulose in the biomass sample. Short-chain oligosaccharides were not detected. Unlike the digestion products depicted in FIG. 1), the residual biomass appeared physically unchanged from the input form.

Example D1

Digestion of Sugarcane Bagasse Using Catalyst Described in Example B4a

Sugarcane bagasse was milled using a 1 horsepower rotating-knive laboratory mill equipped with a 2 mm screen. The bagasse had the following composition: 50% g $H_2O$/g wet bagasse, with a dry-matter composition of: 39.0% g glucan/g dry biomass, 17.3% g xylan/g dry biomass, 5.0% g arabinan/g dry biomass, 1.1% g galactan/g dry biomass, 5.5% g acetate/g dry biomass, 5.0% g soluble extractives/g dry biomass, 24.1% g lignin/g dry biomass, and 3.1% g ash/g dry biomass. The composition of the bagasse was determined using a method based on the procedures known in the art. See R. Ruiz and T. Ehrman, "Determination of Carbohydrates in Biomass by High Performance Liquid Chromatography," NREL Laboratory Analytical Procedure LAP-002 (1996); D. Templeton and T. Ehrman, "Determination of Acid-Insoluble Lignin in Biomass," NREL Laboratory Analytical Procedure LAP-003 (1995); T. Erhman, "Determination of Acid-Soluble Lignin in Biomass," NREL Laboratory Analytical Procedure LAP-004 (1996); and T. Ehrman, "Standard Method for Ash in Biomass," NREL Laboratory Analytical Procedure LAP-005 (1994).

To a 20 mL serum vial was added: 1.0 g of the cane bagasse sample, 1.0 g of the catalyst as prepared according to the procedure in Example B4a (initial moisture content: 12% g $H_2O$/g dispensed catalyst), and 1600 L of deionized $H_2O$. The reactants were mixed thoroughly with a glass stir rod to distribute the catalyst particles evenly throughout the biomass. The resulting mixture was gently compacted to yield a solid reactant cake. The reaction vial was sealed with a rubber stopper and crimp-top and incubated at 105° C. for 4 hours.

Example D2

Separation of Catalyst/Product Mixture from the Hydrolysis of Sugarcane Bagasse

The serum vial reactor from Example D1 was cooled to room temperature and unsealed. 15.0 mL of distilled $H_2O$ was added to the vial reactor and the resulting mixture of liquids and solids was mixed gently. Following agitation, the solids were allowed to sediment for 30 seconds to produce a layered mixture with catalyst on the bottom and lignin and unreacted biomass on top. Short-chained beta-glucans remained suspended in the liquid layer above the lignin and residual biomass.

Example D3

Recovery of Sugars and Soluble Carbohydrates from the Hydrolysis of Sugarcane Bagasse The supernatant and suspended glucans from Example D2 were separated by decantation. The soluble-sugar content of hydrolysis products was determined by a combination of high performance liquid chromatography (HPLC) and spectrophotometric methods. HPLC determination of soluble sugars and oligosaccharides was performed on a Hewlett-Packard 1100 Series instrument equipped with a refractive index (RI) detector using a 30 cm×7.8 mm BioRad Aminex HPX-87P column with water as the mobile phase. The sugar column was protected by both a lead-exchanged sulfonated-polystyrene guard column and a tri-alkylammoniumhydroxide anionic-exchange guard column. All HPLC samples were microfiltered using a 0.2 m syringe filter prior to injection. Sample concentrations were determined by reference to a calibration generated from known standards.

The ability of the catalyst to hydrolyze the cellulose and hemicellulose components of the biomass to soluble sugars was measured by determining the effective first-order rate constant. The extent of reaction for a chemical species (e.g., glucan, xylan, arabinan) was determined by calculating the ratio of moles of the recovered species to the theoretical moles of the species that would be obtained as a result of complete conversion of the input reactant based on the known composition of the input biomass and the known molecular weights of the reactants and products and the known stoichiometries of the reactions under consideration.

For the digestion of sugarcane bagasse using catalyst prepared according to the procedure in Example B4a, the first-order rate constant for conversion of xylan to xylose was determined to be 0.5/hr. The first-order rate constant for conversion of glucan to soluble monosaccharides and oligosaccharides (including disaccharides) was determined to be 0.1/hr.

Example D4

Separation and Recovery of Lignin, Residual Unreacted Biomass and Catalyst from Hydrolyzed Sugarcane Bagasse An additional 10 mL of water was added to the residual solids in Example D3. The mixture was agitated to suspend the residual lignin and residual unreacted biomass particles without suspending the catalyst, and the lignin and residual biomass were removed by decantation. The recovered catalyst was washed with water and then dried to constant mass at 110° C. in a gravity oven to yield >99% g/g recovery.

Example D5

Reuse of Recovered Catalyst

Some of the catalyst recovered from Example D4 (0.250 g dry material) was returned to the serum-vial reactor. 0.25 g of additional biomass (composition identical to that in Example D1) and 800 L of deionized $H_2O$ was added to the reactor, and the contents were mixed thoroughly, as described in Example D1. The reactor was sealed and incubated at 105° C. for four hours. Following the reaction, the product mixture was separated following the procedure described in Examples D2-D3. The first-order rate constant for conversion of xylan to xylose was determined to be 0.5/hr. The first-order rate constant for conversion of glucan to soluble monosaccharides and oligosaccharides (including disaccharides) was determined to be 0.1/hr.

Example E1

Comparison of Sugar Production from Various Feedstocks with Catalyst of A20

Each feedstock in Table 2 below was milled using a 1 horsepower rotating-knive laboratory mill equipped with a 2 mm screen. The composition of each feedstock was determined according to procedures known in the art. See e.g., R. Ruiz and T. Ehrman, "Determination of Carbohydrates in Biomass by High Performance Liquid Chromatography," NREL Laboratory Analytical Procedure LAP-002 (1996); D. Tempelton and T. Ehrman, "Determination of Acid-Insoluble Lignin in Biomass," NREL Laboratory Analytical Procedure LAP-003 (1995); T. Erhman, "Determination of Acid-Soluble Lignin in Biomass," NREL Laboratory Analytical Procedure LAP-004 (1996); and T. Ehrman, "Standard Method for Ash in Biomass," NREL Laboratory Analytical Procedure LAP-005 (1994). Conversion rates are shown in Table 3.

TABLE 2

Summary of Feedstock Composition Before Hydroslysis

| Biomass | glucan (g/g) | xylan (g/g) | galactan (g/g) | arabinan (g/g) | acetyl-glycosides (g/g) | lignin & insoluble (g/g) | extractive solubles (g/g) | Other (g/g) |
|---|---|---|---|---|---|---|---|---|
| Sugarcane Bagasse | 35.0% | 24.4% | 0.0% | 2.5% | 3.4% | 22.8% | 11.2% | 0.8% |
| Corn Stover | 29.3% | 23.9% | 0.0% | 2.3% | 3.8% | 12.0% | 23.4% | 5.5% |
| Cassava Stem | 41.4% | 16.2% | 0.0% | 0.0% | 3.8% | 34.8% | 0.0% | 3.9% |
| Hardwood (*Eucalyptus*) | 40.7% | 11.8% | 0.0% | 1.2% | 3.6% | 22.1% | 15.7% | 4.9% |
| Sorted Food Waste | 10.7% | 2.6% | 0.0% | 0.6% | 1.9% | 32.2% | 0.0% | 52.1% |
| Oil Palm (Empty Fruit Bunch) | 33.9% | 22.6% | 0.0% | 3.0% | 5.4% | 17.7% | 17.3% | 0.1% |
| Oil Palm (Mesocarp Fibre) | 18.8% | 21.2% | 0.0% | 3.0% | 2.5% | 34.0% | 16.8% | 3.8% |
| Softwood (Loblolly, Jack, and Red pine) | 41.5% | 6.2% | 1.9% | 11.5% | 1.8% | 27.0% | 8.5% | 1.7% |
| Pine bark | 19.6% | 3.5% | 2.6% | 5.0% | 0.3% | 31.6% | 30.1% | 7.4% |
| Hardwood (Birch, Aspen) | 33.6% | 23.5% | 2.3% | 6.0% | 0.0% | 24.4% | 4.6% | 5.6% |
| Hardwood (Maple) | 39.8% | 15.8% | 1.5% | 4.1% | 0.0% | 22.8% | 12.8% | 3.4% |
| Foodwaste sorted | 7.0% | 2.0% | 0.0% | 0.0% | 2.0% | 31.0% | 59.0% | 0.0% |
| Bamboo | 35.0% | 18.0% | 0.0% | 0.0% | 0.0% | 22.0% | 15.0% | 10.0% |
| BeetPulp | 18.0% | 3.0% | 5.0% | 16.0% | 4.0% | 23.0% | 22.0% | 9.0% |

TABLE 2-continued

Summary of Feedstock Composition Before Hydroslysis

| Biomass | glucan (g/g) | xylan (g/g) | galactan (g/g) | arabinan (g/g) | acetyl-glycosides (g/g) | lignin & insoluble (g/g) | extractive solubles (g/g) | Other (g/g) |
|---|---|---|---|---|---|---|---|---|
| PaperSludge | 14.0% | 3.0% | 0.0% | 0.0% | 0.0% | 13.0% | 22.0% | 48.0% |
| KenafFibers (grain fibers) | 38.0% | 17.0% | 0.0% | 0.0% | 0.0% | 25.0% | 9.0% | 11.0% |
| BagasseStraw | 28.0% | 18.0% | 3.0% | 0.0% | 0.0% | 13.0% | 29.0% | 9.0% |
| BirchBrk (hardwood) | 34.0% | 23.0% | 2.0% | 6.0% | 0.0% | 24.0% | 5.0% | 6.0% |
| Birch (hardwood) | 34.0% | 21.0% | 1.0% | 3.0% | 0.0% | 22.0% | 6.0% | 13.0% |
| AspenBrk (hardwood) | 49.0% | 17.0% | 2.0% | 3.0% | 0.0% | 27.0% | 3.0% | 0.0% |
| Aspen (hardwood) | 51.0% | 18.0% | 1.4% | 4.0% | 0.0% | 32.0% | 3.0% | 0.0% |
| JackPine WoodBrk (hardwood) | 39.0% | 8.0% | 4.0% | 14.0% | 0.0% | 27.0% | 8.0% | 0.0% |
| JackPine Wood (hardwood) | 39.0% | 8.0% | 4.0% | 12.0% | 0.0% | 28.0% | 8.0% | 1.0% |
| RedPineBrk (hardwood) | 42.0% | 7.0% | 3.0% | 13.0% | 0.0% | 25.0% | 8.0% | 2.0% |
| RedPine (hardwood) | 42.0% | 7.0% | 3.0% | 14.0% | 0.0% | 26.0% | 8.0% | 0.0% |
| MapleBrk (hardwood) | 40.0% | 16.0% | 2.0% | 4.0% | 0.0% | 23.0% | 13.0% | 2.0% |
| MapleB (hardwood) | 45.0% | 17.0% | 1.0% | 4.0% | 0.0% | 25.0% | 8.0% | 0.0% |

TABLE 3

Summary of Overall Conversion Rate

| Lignocellulosic Feedstock | Biomass Conversion Rate (1/hr) |
|---|---|
| Sugarcane Bagasse | 0.19 |
| Corn Stover | 0.22 |
| Cassava Stem | 0.41 |
| Hardwood (*Eucalyptus*) | 0.04 |
| Sorted Food Waste | 0.48 |
| Oil Palm (Empty Fruit Bunch) | 0.18 |
| Oil Palm (Mesocarp Fibre) | 0.12 |
| Softwood (Loblolly, Jack, and Red pine) | 0.07 |
| Pine bark | 0.08 |
| Hardwood (Birch, Aspen) | 0.11 |
| Hardwood (Maple) | 0.08 |
| Foodwaste sorted | 1.15 |
| Bamboo | 0.32 |
| BeetPulp | 0.64 |
| PaperSludge | 0.08 |
| KenafFibers (grain fibers) | 0.42 |
| BagasseStraw | 0.61 |
| BirchBrk (hardwood) | 0.60 |
| Birch (hardwood) | 0.53 |
| AspenBrk (hardwood) | 0.22 |
| Aspen (hardwood) | 0.14 |
| JackPineWoodBrk(hardwood) | 0.15 |
| JackPineWood(hardwood) | 0.13 |
| RedPineBrk (hardwood) | 0.18 |
| RedPine (hardwood) | 0.18 |
| MapleBrk (hardwood) | 0.40 |
| MapleB(hardwood) | 0.39 |

To a 20 mL serum vial was added: 1.0 g of the milled feedstock, 1.0 g of Catalyst A20 and 2 mL of dionized water. The reactants were mixed thoroughly with a glass stir rod to distribute the catalyst particles evenly throughout the feedstock. The resulting mixture was gently compacted to yield a solid reactant cake. The reaction vial was sealed with a rubber stopper and crimp-top and incubated at 105° C. for four hours.

Following reaction, the serum vial was cooled to room temperature and unsealed. 15.0 mL of distilled $H_2O$ was added to the vial reactor and the resulting mixture of liquids and solids was mixed by vortexing for 2 minutes. Following agitation, the solids were allowed to sediment for 30 seconds to produce a layered mixture with catalyst on the bottom and lignin and unreacted biomass on top. Short-chained beta-glucans remained suspended in the liquid layer above the lignin and residual biomass.

The supernatant and suspended beta-glucans were separated by decantation. The soluble-sugar content of hydrolysis products was determined by a combination of high performance liquid chromatography (HPLC) and spectrophotometric methods. HPLC determination of soluble sugars and oligosaccharides was performed on a Hewlett-Packard 1100 Series instrument equipped with a refractive index (RI) detector using a 30 cm×7.8 mm BioRad Aminex HPX-87P column with water as the mobile phase. The sugar column was protected by both a lead-exchanged sulfonated-polystyrene guard column and a tri-alkylammoniumhydroxide anionic-exchange guard column. All HPLC samples were microfiltered using a 0.2 mm syringe filter prior to injection. Sample concentrations were determined by reference to a calibration generated from known standards.

The ability of the catalyst to hydrolyze the cellulose and hemicellulose components of each feedstock to soluble sugars was measured by determining the effective first-order rate constant as summarized in Table 2 above. The extent of reaction for a chemical species (e.g., glucan, xylan, arabinan) was determined by calculating the ratio of moles of the recovered species to the theoretical moles of the species that would be obtained as a result of complete conversion of the input reactant based on the known composition of the input biomass and the known molecular weights of the reactants and products and the known stoichiometries of the reactions under consideration.

What is claimed is:

1. A method of producing one or more sugars from feedstock, comprising:
   combining feedstock and a polymeric catalyst to form a reaction mixture,
      wherein the feedstock is selected from the group consisting of softwood, hardwood, sugarbeet pulp, food waste, enzymatic digestion residuals, and beer bottoms, or any combination thereof, and
      wherein the polymeric catalyst comprises acidic monomers and ionic monomers connected to form a polymeric backbone, wherein a plurality of acidic monomers independently comprises at least one Bronsted-Lowry acid, and wherein a plurality of ionic monomers independently comprises at least one nitrogen-containing cationic group, at least one phosphorous-containing cationic group, or a combination thereof; and
   degrading the feedstock in the reaction mixture to produce a liquid phase and a solid phase, wherein the liquid phase comprises one or more sugars, and the solid phase comprises residual feedstock.

2. The method of claim 1, wherein the feedstock and the polymeric catalyst are further combined with a solvent to form the reaction mixture.

3. The method of claim 1, wherein the one or more sugars are selected from one or more monosaccharides, one or more oligosaccharides, or a combination thereof.

4. The method of claim 1, further comprising pretreating the feedstock before combining the feedstock with the polymeric catalyst.

5. The method of claim 1, further comprising
   d) isolating at least a portion of the liquid phase from the solid phase; and
   e) recovering the one or more sugars from the isolated liquid phase.

6. The method of claim 2, wherein isolating the at least a portion of the liquid phase from the solid phase in step (d) produces a residual feedstock mixture, and the method further comprises:
   i) providing additional feedstock;
   ii) combining the additional feedstock with the residual feedstock mixture;
   iii) degrading the additional feedstock and the residual feedstock mixture to produce a second liquid phase and a second solid phase, wherein the second liquid phase comprises one or more additional sugars, and wherein the second solid phase comprises additional residual feedstock;
   iv) isolating at least a portion of the second liquid phase from the second solid phase; and
   v) recovering the one or more additional sugars from the isolated second liquid phase.

7. The method of claim 6, wherein the feedstock and the additional feedstock are the same type of feedstock.

8. The method of claim 6, wherein the one or more additional sugars are selected from one or more monosaccharides, one or more oligosaccharides, or a combination thereof.

9. The method of claim 6, further comprising pretreating the additional feedstock before combining the additional feedstock with the residual feedstock mixture.

10. A method of producing one or more sugars from feedstock, comprising:
   combining feedstock and a solid-supported catalyst to form a reaction mixture,
      wherein the feedstock is selected from the group consisting of softwood, hardwood, cassava, bagasse, sugarbeet pulp, straw, paper sludge, oil palm, corn stover, food waste, enzymatic digestion residuals, and beer bottoms, or any combination thereof, and
      wherein the solid-supported catalyst comprises a solid support, acidic moieties attached to the solid support, and ionic moieties attached to the solid support,
         wherein the solid support is selected from the group consisting of biochar, amorphous carbon, activated carbon, silica, silica gel, alumina, magnesia, titania, zirconia, clay, magnesium silicate, silicon carbide, zeolite, ceramic, and any combinations thereof,
         wherein a plurality of acidic moieties independently comprises at least one Bronsted-Lowry acid, and wherein a plurality of ionic moieties independently comprises at least one nitrogen-containing cationic group, at least one phosphorous-containing cationic group, or a combination thereof, and
         wherein at least a portion of the acidic moieties are directly attached to the solid support, or at least a portion of the acidic moieties are attached to the solid support by a linker, or a combination thereof, and
         wherein at least a portion of the ionic moieties are directly attached to the solid support, or at least a portion of the ionic moieties are attached to the solid support by a linker, or a combination thereof; and
   degrading the feedstock in the reaction mixture to produce a liquid phase and a solid phase, wherein the liquid phase comprises one or more sugars, and the solid phase comprises residual feedstock.

11. The method of claim 10, wherein the feedstock and the solid-supported catalyst are further combined with a solvent to form the reaction mixture.

12. The method of claim 10, wherein the one or more sugars are selected from one or more monosaccharides, one or more oligosaccharides, or a combination thereof.

13. The method of claim 10, further comprising pretreating the feedstock before combining the feedstock with the solid-supported catalyst.

14. The method of claim 10, further comprising
   d) isolating at least a portion of the liquid phase from the solid phase; and
   e) recovering the one or more sugars from the isolated liquid phase.

15. The method of claim 14, wherein isolating the at least a portion of the liquid phase from the solid phase in step (d) produces a residual feedstock mixture, and the method further comprises:
   i) providing additional feedstock;
   ii) combining the additional feedstock with the residual feedstock mixture;
   iii) degrading the additional feedstock and the residual feedstock mixture to produce a second liquid phase and a second solid phase, wherein the second liquid phase comprises one or more additional sugars, and wherein the second solid phase comprises additional residual feedstock;
   iv) isolating at least a portion of the second liquid phase from the second solid phase; and
   v) recovering the one or more additional sugars from the isolated second liquid phase.

16. The method of claim 15, wherein the feedstock and the additional feedstock are the same type of feedstock.

17. The method of claim 15, wherein the one or more additional sugars are selected from one or more monosaccharides, one or more oligosaccharides, or a combination thereof.

18. The method of claim 15, further comprising pretreating the additional feedstock before combining the additional feedstock with the residual feedstock mixture.

* * * * *